US012590129B2

(12) United States Patent
Roberts et al.

(10) Patent No.: US 12,590,129 B2
(45) Date of Patent: **\*Mar. 31, 2026**

(54) LIVER-SPECIFIC REGULATORY NUCLEIC ACID SEQUENCES

(71) Applicant: ASKBIO INC., Research Triangle Park, NC (US)

(72) Inventors: Michael Roberts, Midlothian (GB); Juan Manuel Iglesias, Midlothian (GB); Jorge Omar Yanez-Cuna, Midlothian (GB); Nicolle Kippen, Midlothian (GB); Ross Fraser, Midlothian (GB); Katie Baker, Midlothian (GB)

(73) Assignee: ASKBIO INC.

( * ) Notice: Subject to any disclaimer, the term of this patent is extended or adjusted under 35 U.S.C. 154(b) by 1162 days.

This patent is subject to a terminal disclaimer.

(21) Appl. No.: 17/295,208

(22) PCT Filed: Nov. 19, 2019

(86) PCT No.: PCT/GB2019/053267
§ 371 (c)(1),
(2) Date: May 19, 2021

(87) PCT Pub. No.: WO2020/104782
PCT Pub. Date: May 28, 2020

(65) Prior Publication Data
US 2022/0009981 A1      Jan. 13, 2022

(30) Foreign Application Priority Data
Nov. 19, 2018     (GB) ...................................... 1818816

(51) Int. Cl.
C07K 14/47          (2006.01)
A61K 48/00          (2006.01)
(Continued)

(52) U.S. Cl.
CPC ...... *C07K 14/4705* (2013.01); *A61K 48/0058* (2013.01); *C12N 5/067* (2013.01); *C12N 15/86* (2013.01); *C12N 2830/008* (2013.01)

(58) Field of Classification Search
CPC .............. C07K 14/435; C07K 14/4705; A61K 48/0058; C12N 15/86; C12N 2830/008; C61K 48/0058
See application file for complete search history.

(56) References Cited

U.S. PATENT DOCUMENTS 5,721,096 A * 2/1998 Karathanasis ....... C12Q 1/6897
                                                435/7.1
6,521,225 B1     2/2003 Srivastava et al.
(Continued)

FOREIGN PATENT DOCUMENTS

CN          102628041 A     8/2012
CN          102634515 A     8/2012
(Continued)

OTHER PUBLICATIONS

Database accession No. ABK29876. "Wild type hepatitis B virus (HBV) X promoter." Geneseq Apr. 23, 2002 (Apr. 23, 2002), retrieved from EBI accession No. GSN: ABK29876.
(Continued)

*Primary Examiner* — Terra C Gibbs
(74) *Attorney, Agent, or Firm* — NIXON PEABODY LLP; Ronald I. Eisenstein; Jeanne N. Jodoin

(57) ABSTRACT

The present invention relates to regulatory nucleic acid sequences, in particular liver-specific cis-regulatory elements, cis-regulatory modules, promoters and other such nucleic acid sequences, that are capable of enhancing liver-specific expression of genes. The invention also relates to expression constructs, vectors and cells comprising such liver-specific regulatory nucleic acid sequences, and to methods of their use. The liver-specific regulatory nucleic
(Continued)

acid sequences are of particular utility for gene therapy applications, but also find utility in other areas such as bioprocessing and biotechnology.

22 Claims, 28 Drawing Sheets

Specification includes a Sequence Listing.

(51) Int. Cl.
    *C12N 5/071*        (2010.01)
    *C12N 15/86*      (2006.01)

(56)            References Cited

U.S. PATENT DOCUMENTS

| | | | |
|---|---|---|---|
| 7,351,813 B2 | 4/2008 | Miao et al. | |
| 9,617,548 B2 | 4/2017 | Chuah et al. | |
| 11,161,890 B2 * | 11/2021 | Wong | C12N 15/81 |
| 11,535,866 B2 * | 12/2022 | Wilson | C12N 9/93 |
| 2002/0076798 A1 | 6/2002 | Miao et al. | |
| 2003/0077812 A1 | 4/2003 | McArthur et al. | |
| 2003/0124530 A1 | 7/2003 | Edwards et al. | |
| 2011/0065100 A1 * | 3/2011 | Aldred | C12Q 1/6886 506/14 |
| 2020/0199582 A1 | 6/2020 | Roberts | |

FOREIGN PATENT DOCUMENTS

| | | |
|---|---|---|
| CN | 108588097 A | 9/2018 |
| JP | 2001500376 A | 1/2001 |
| JP | 2004500880 A | 1/2004 |
| JP | 2011517955 A | 6/2011 |
| JP | 2014506456 A | 3/2014 |
| WO | WO-2009130208 A1 * | 10/2009 .......... A61K 3/4846 |
| WO | WO-2016146757 A1 * | 9/2016 ............. A61K 38/37 |
| WO | WO-2017180857 A1 * | 10/2017 ............ A61K 38/37 |
| WO | WO-2018215613 A1 * | 11/2018 .......... A01K 7/0275 |

OTHER PUBLICATIONS

Database accession No. ABX09226. "Arteriosclerosis-detecting probe from PROC #4." Geneseq Jan. 22, 2003 (Jan. 22, 2003), retrieved from EBI accession No. GSN: ABX09226.

Database accession No. ADE80458. "Duplex oligonucleotide for DNA protein binding assay seq id 428." Geneseq Jan. 29, 2004 (Jan. 29, 2004), retrieved from EBI accession No. GSN: ADE80458.

Database accession No. BDS84014. "Micro RNA mutation detecting probe H2." Geneseq May 18, 2017 (May 18, 2017), retrieved from EBI accession No. GSN: BDS84014.

Database accession No. BFJ18268. "HBV enhancer DNA sequence (Enhl)." Geneseq Jul. 26, 2018 (Jul. 26, 2018), retrieved from EBI accession No. GSN: BFJ18268.

Nair et al. "Computationally designed liver-specific transcriptional modules and hyperactive factor IX improve hepatic gene therapy." Blood, The Journal of the American Society of Hematology 123(20): 3195-3199 (2014).

Rouet et al. "A potent enhancer made of clustered liver-specific elements in the transcription control sequences of human alpha 1-microglobulin/bikunin gene." Journal of Biological Chemistry 267(29): 20765-20773 (1992).

Lv et al. "Progress in the molecular biology of apolipoprotein CI." Chinese Journal of Arteriosclerosis, vol. 6, Issue 4: 356-362 (1998) [English Translation Provided].

Li et al. "A small regulatory element from chromosome 19 enhances liver-specific gene expression." Gene Therapy 16 (1): 43-51 (2009).

* cited by examiner

SEQUENCE LISTING

<160> NUMBER OF SEQ ID NOS: 288

<210> SEQ ID NO 1
<211> LENGTH: 103
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: CRE0018

<400> SEQUENCE: 1
caggctttca ctttctcgcc aacttacaag gcctttctgt gtaaacaata cctgaacctt      60
taccccgttg cccggcaacg gccaggtctg tgccaagtgt ttg                        103

-continued

```
<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0042

<400> SEQUENCE: 2
ccctgttcaa acatgtccta atactctgtc tctgcaaggg tcatcagtag ttttccatct        60
tactcaacat cctcccagtg                                                    80

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0051

<400> SEQUENCE: 3
aggttaattt ttaaaaagca gtcaaaagtc caagtggccc ttggcagcat ttactctctc        60
tgtttgctct ggttaataat ctcaggagca caaacattcc                            100

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0058

<400> SEQUENCE: 4
ggcccgggag gcgccctttg gaccttttgc aatcctggcg                              40

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0065

<400> SEQUENCE: 5
cactgaaccc ttgacccctg ccctgcagcc cccgcagctt gctgtttgcc cactctattt        60
gcccagcccc ag                                                           72

<210> SEQ ID NO 6
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0065.1

<400> SEQUENCE: 6
```

```
cactgaaccc ttgacccctg ccctgcagcc cccgcagctt gctgtttgcc cactctattt      60
gcccagcccc agggacagag ctgatccttg aactcttaag ttccac                     106
```

```
<210> SEQ ID NO 7
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0066

<400> SEQUENCE: 7
ccctggagag tcctttagca gggcaaagtg caacataggc agaccttaag ggatgactca      60
gtaacagata agctttgtgt gcctgca                                          87
```

```
<210> SEQ ID NO 8
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0066.2

<400> SEQUENCE: 8
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctg                  168
```

```
<210> SEQ ID NO 9
<211> LENGTH: 241
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0066.1

<400> SEQUENCE: 9
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctgct ctgctcagcc     180
agtcagccct gcctcccttg tttaggacca cacagcactg ctgggtgtct gcctttcctt     240
g                                                                     241
```

```
<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0068

<400> SEQUENCE: 10
cctccccgtg ttcctgctct ttgtccctct gtcctactta gactaatatt tgccttgggt      60
actgcaaaca ggaaatgggg gagggacagg agtagggcgg                            100
```

-continued

```
<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0074

<400> SEQUENCE: 11
agaatgaaca ttgaactttg gactatacct gaggggtgag gtaaacaaca ggactataaa      60
t                                                                     61

<210> SEQ ID NO 12
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0001

<400> SEQUENCE: 12
gctggtttct tataaaactg atggaagata caaacactat taaagaactg tttgcatgtt      60
gcaaatgatg tccaaagtcc aaacattgtt aataattaat actccaataa acatcatgtc     120
agaatttctg ttttcttttc cctttgaacc tttgcaggat tgccacatca tcaggaccac     180
accttcatca ggaatgaata t                                              201

<210> SEQ ID NO 13
<211> LENGTH: 232
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0005

<400> SEQUENCE: 13
attggcatct tctattgctt ttcctggtga cttcattttt cactcttggc taaaaatggg      60
tctctgatga tttattctat cctgggtgtt gacaagctga agaagttgtg tggggcctgc     120
tgccagtaac cctgggtgac gaagcgtgac tcaccactcc gaggtcagtg gggggatgga     180
aggcagggga gtcagctgac aagatctgct gctttgtcac caggccttct gc            232

<210> SEQ ID NO 14
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0012

<400> SEQUENCE: 14
tgaaatgcct gccatatatt agtgccctga agtccaaagg tagaggaacc gagtgtttaa      60
aaattactgt ggctgtggag tcaacatgat gtaaaaaaac aaacatttgg ataacaccaa     120
gaagccagat atggttgaaa tgttgactgg ttgacaaaaa taatttgggt tgcttaatgg     180
```

```
tgcacaaagg taatgcaaaa                                                      200

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0047

<400> SEQUENCE: 15
ctgtttgctg cttgcaatgt ttgcccattt taggg                                     35

<210> SEQ ID NO 16
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0048

<400> SEQUENCE: 16
tgctctctga caaagatacg gtgggtccca ctgatgaact gtgctgccac agtaaatgta         60
gccactatgc ctatctccat tctgaagatg tg                                       92

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0056

<400> SEQUENCE: 17
ccgcccccac tgaacccttg acccctgccc tgcagccccc gcagcttgct gtttgcccac         60
tctatttgcc cagccccag                                                       79

<210> SEQ ID NO 18
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0062

<400> SEQUENCE: 18
aagctttctg aacagccaaa cagagattcc aaagttcagg caccaaagtt cagaccctaa         60
cagttattta caagggtcag ttaac                                                85

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0077
```

<400> SEQUENCE: 19
aagcaaatat ttgtggttat ggattaactc gaactgtttg cccactctat ttgccc          56

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0078

<400> SEQUENCE: 20
ggcgcccttt ggacctttg caatcctgga gcaaacagca aacac                       45

<210> SEQ ID NO 21
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0083.1

<400> SEQUENCE: 21
tttggagaag acagagccaa tgaggccctc gttccaggga aacagaatat gctcagcatg       60
acgcagcact ccctgaactt tccggttaca tcacccaata gctgagatca ga             112

<210> SEQ ID NO 22
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0089

<400> SEQUENCE: 22
ttggtggaat atctttatgt cttttgctag ccacttgtca catgttatca tatttggttt       60
aatgagaagt cagatatacc ttaatgataa cttatgtctg ga                        102

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0052

<400> SEQUENCE: 23
gggcatataa aacaggggca aggcacagac tcatagcaga gcaatcacca ccaagcctgg       60
aataactgca gccacc                                                     76

<210> SEQ ID NO 24
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: CRE0079

<400> SEQUENCE: 24
ctcttttgtt ttacatgaag ggtctggcag ccaaagcaat cactcaaagt tcaaacctta      60
tcattttttg ctttgttcct cttggccttg gttttgtaca tcagctttga aaataccatc     120
ccagggttaa tgctgggggtt aatttataac taagagtgct ctagttttgc aatacaggac    180
atgctataaa aatggaaaga tgttgctttc tgagagatgc                            220

<210> SEQ ID NO 25
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0006

<400> SEQUENCE: 25
ccgatgacct aatgattctg agcttggcaa aggtcttatc tcccagctcg cccaggccca      60
gtgttccagg aatgtgacct ttgctgcagc agccgctgga ggggggcagag gggatgggct    120 ggaggttgag caaacagagc agcagaaaag gcagttcctc ttctccagtg ccctccttcc    180
ctgtctctgc ctctccctcc cttcctcagg catcagagcg gagacttcag ggagaccaga    240
gcccagcttg ccaggcactg agctagaagc cctgccatg                             279

<210> SEQ ID NO 26
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRE0059

<400> SEQUENCE: 26
agtcatatgt ttgctcactg aaggttacta gttaacaggc atcccttaaa caggatataa      60
aaggacttca gcaggactgc tcgaaacatc ccact                                 95

<210> SEQ ID NO 27
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0073

<400> SEQUENCE: 27
gggcgactca gatcccagcc agtggactta gccctgtttt gctcctccga taactggggt      60
gaccttggtt aatattcacc agcagcctcc cccgttgccc ctctggatcc actgcttaaa    120
tacggacgag gacagggccc tgtctcctca gcttcaggca ccaccactga cctgggacag    180
tgaatc                                                                 186

<210> SEQ ID NO 28
<211> LENGTH: 164
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: CRE0073.1

<400> SEQUENCE: 28
tggacttagc ccctgtttgc tcctccgata actggggtga ccttggttaa tattcaccag      60
cagcctcccc cgttgcccct ctggatccac tgcttaaata cggacgagga cagggccctg     120
tctcctcagc ttcaggcacc accactgacc tgggacagtg aatc                      164

<210> SEQ ID NO 29
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRE0040

<400> SEQUENCE: 29
cctttgcaac agcttatcgg aagcaaacaa gctgagggga attgagcaag aatttctggg      60
ataccaacag cataggagga acaaaggacg tagagggagg gttgactgtc tacacaggac     120
aaagccaatg attaaccaaa cctcttgcag atttaaatag gatgggaact aggagtggca     180
gcaatccttt ctttcagctg gagtgctcct caggagccag ccccaccctt agaaaagatg     240

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LVR_CRE0080_PROC

<400> SEQUENCE: 30
aagcaaatat ttgtggttat ggattaactc gaa                                   33

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LVR_CRE0081_APOA1

<400> SEQUENCE: 31
ctgtttgccc actctatttg ccc                                              23

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LVR_CRE0061_APOB

<400> SEQUENCE: 32
ggcgcccttt ggaccttttg caatcctgg                                        29

-continued

```
<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LVR_CRE0082_APOC4

<400> SEQUENCE: 33
agcaaacagc aaacac                                                       16

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IRF TFBS in CRE0018

<400> SEQUENCE: 34
ctttcacttt c                                                            11

<210> SEQ ID NO 35
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NF1 TFBS in CRE0018

<400> SEQUENCE: 35 tcgccaa                                                                  7

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0018

<400> SEQUENCE: 36
tgtgtaaaca                                                              10

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HBLF TFBS in CRE0018

<400> SEQUENCE: 37
tgtaaacaat a                                                            11

<210> SEQ ID NO 38
<211> LENGTH: 14
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RXRa TFBS in CRE0018

<400> SEQUENCE: 38
ctgaaccttt accc                                                          14

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EF-C TFBS in CRE0018

<400> SEQUENCE: 39
gttgcccggc aac                                                           13

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NF1 TFBS in CRE0018

<400> SEQUENCE: 40
caggtctgtg ccaag                                                         15

<210> SEQ ID NO 41
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c/EBP TFBS in CRE0018

<400> SEQUENCE: 41
tgccaagtgt ttg                                                           13

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0042

<400> SEQUENCE: 42
gttcaaacat g                                                             11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: C/EBP TFBS in CRE0042

<400> SEQUENCE: 43
ctaatactct g                                                        11

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0042

<400> SEQUENCE: 44
tgcaagggtc at                                                       12

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0042

<400> SEQUENCE: 45
ttactcaaca                                                          10

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0051

<400> SEQUENCE: 46
gttaattttt aaa                                                      13

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0051

<400> SEQUENCE: 47
gtggcccttg g                                                        11

<210> SEQ ID NO 48
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0051

<400> SEQUENCE: 48
```

-continued

```
tgtttgc                                                          7

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0051

<400> SEQUENCE: 49
tggttaataa tctca                                                 15

<210> SEQ ID NO 50
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0051

<400> SEQUENCE: 50 acaaaca                                                          7

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0058

<400> SEQUENCE: 51
cgccctttgg acc                                                   13

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c/EBP TFBS in CRE0058

<400> SEQUENCE: 52
gaccttttgc aatcctgg                                              18

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RXR Alpha TFBS in CRE0065

<400> SEQUENCE: 53
actgaaccct tgacccctgc cct                                        23
```

-continued

```
<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0065

<400> SEQUENCE: 54
ctgtttgccc                                                         10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0065

<400> SEQUENCE: 55
ctatttgccc                                                         10

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RXR Alpha TFBS in CRE0065.1

<400> SEQUENCE: 56
actgaaccct tgacccctgc cct                                          23

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0065.1

<400> SEQUENCE: 57
ctgtttgccc                                                         10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0065.1

<400> SEQUENCE: 58
ctatttgccc                                                         10

<210> SEQ ID NO 59
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0065.1

<400> SEQUENCE: 59
tgatccttga actct                                                      15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4G TFBS in CRE0066

<400> SEQUENCE: 60
gcagggcaaa gtgca                                                      15

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FOS::JUN TFBS in CRE0066

<400> SEQUENCE: 61
gatgactcag                                                            10

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0068

<400> SEQUENCE: 62
ttcctgctct ttgtccc                                                    17

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-1/HNF-3 TFBS in CRE0068

<400> SEQUENCE: 63
agactaatat ttgcc                                                      15

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: SP1 TFBS in CRE0068

<400> SEQUENCE: 64
atgggggagg gacag                                                                       15

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0074

<400> SEQUENCE: 65
aacattgaac tttggacta                                                                   19

<210> SEQ ID NO 66
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FoxO1a TFBS in CRE0074

<400> SEQUENCE: 66 gtaaacaa                                                                                8

<210> SEQ ID NO 67
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0001

<400> SEQUENCE: 67
tccaaagtcc aaa                                                                         13

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-1 TFBS in CRE0001

<400> SEQUENCE: 68
tgttaataat taata                                                                       15

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0001

<400> SEQUENCE: 69

-continued

```
caataaacat ca                                                    12

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0001

<400> SEQUENCE: 70
ttccctttga acctt                                                 15

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0012

<400> SEQUENCE: 71
aagtccaaag gtaga                                                 15

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0012

<400> SEQUENCE: 72
gagtcaacat ga                                                    12

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0012

<400> SEQUENCE: 73
aaatgttgac tg                                                    12

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0012

<400> SEQUENCE: 74
ggttgcttaa t                                                     11

<210> SEQ ID NO 75
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0047

<400> SEQUENCE: 75
gcaatgtttg cccat                                                           15

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0047

<400> SEQUENCE: 76
tgtttgccca t                                                               11

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0056

<400> SEQUENCE: 77
actgaaccct tgacccctgc cct                                                  23

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0056

<400> SEQUENCE: 78
tgcccactct atttgcccag cc                                                   22

<210> SEQ ID NO 79
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-4 TFBS in CRE0062

<400> SEQUENCE: 79
agattccaaa gttca                                                           15

<210> SEQ ID NO 80
<211> LENGTH: 13
<212> TYPE: DNA
<213> ORGANISM: Artificial Sequence
<220> FEATURE:
```

-continued

<223> OTHER INFORMATION: Description of Artificial Sequence: Synthetic
      oligonucleotide
<220> FEATURE:
<223> OTHER INFORMATION: HNF-4 TFBS in CRE0062

<400> SEQUENCE: 80
accaaagttc aga                                                             13

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF-3 TFBS in CRE0062

<400> SEQUENCE: 81
gttatttaca a                                                               11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0077

<400> SEQUENCE: 82
agcaaatatt t                                                               11

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0077

<400> SEQUENCE: 83
aaatatttgt gg                                                              12

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0077

<400> SEQUENCE: 84
ggttatggat taact                                                           15

<210> SEQ ID NO 85
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0077

-continued

```
<400> SEQUENCE: 85
ctgtttgccc                                                              10

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0077

<400> SEQUENCE: 86
ctatttgccc                                                              10

<210> SEQ ID NO 87
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0078

<400> SEQUENCE: 87
cgccctttgg acc                                                          13

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c/EBP TFBS in CRE0078

<400> SEQUENCE: 88
gaccttttgc aatcctgg                                                     18

<210> SEQ ID NO 89
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0078

<400> SEQUENCE: 89 ctgtttgct                                                               9

<210> SEQ ID NO 90
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0078

<400> SEQUENCE: 90
gtgtttgctg                                                              10
```

<210> SEQ ID NO 91
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0006

<400> SEQUENCE: 91
tggcaaaggt ctt                                                      13

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RXRa TFBS in CRE0006

<400> SEQUENCE: 92
tgtgaccttt g                                                        11

<210> SEQ ID NO 93
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0006

<400> SEQUENCE: 93
gtgacctttg ctg                                                      13

<210> SEQ ID NO 94
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c/EBP TFBS in CRE0006

<400> SEQUENCE: 94
aggttgagca aaca                                                     14

<210> SEQ ID NO 95
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0006

<400> SEQUENCE: 95 agcaaacag                                                            9

<210> SEQ ID NO 96
<211> LENGTH: 31

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0006

<400> SEQUENCE: 96
ggagaggcag agacagggaa ggagggcact g                                        31

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF4 TFBS in CRE0079

<400> SEQUENCE: 97
ctcaaagttc aaa                                                            13

<210> SEQ ID NO 98
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0079

<400> SEQUENCE: 98
gttaatttat aac                                                            13

<210> SEQ ID NO 99
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0079

<400> SEQUENCE: 99
tagttttgca atac                                                           14

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0079

<400> SEQUENCE: 100
ctttctgaga gatg                                                           14

<210> SEQ ID NO 101
<211> LENGTH: 13
<212> TYPE: DNA
<213> ORGANISM: Artificial Sequence
<220> FEATURE:
<223> OTHER INFORMATION: Description of Artificial Sequence: Synthetic
```

-continued oligonucleotide
<220> FEATURE:
<223> OTHER INFORMATION: HNF1 TFBS in CRE0059

<400> SEQUENCE: 101
gttactagtt aac                                                              13

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0059

<400> SEQUENCE: 102
gctcgaaaca tccca                                                            15

<210> SEQ ID NO 103
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0073

<400> SEQUENCE: 103 tgtttgc                                                                      7

<210> SEQ ID NO 104
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0073

<400> SEQUENCE: 104
tttgctcctc cg                                                               12

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0073

<400> SEQUENCE: 105
tggttaatat tcaccagc                                                         18

<210> SEQ ID NO 106
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0073

-continued

```
<400> SEQUENCE: 106
ttcaccagca gc                                                    12

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0073

<400> SEQUENCE: 107
ccctgtctcc tcagcttc                                              18

<210> SEQ ID NO 108
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF3 TFBS in CRE0073.1

<400> SEQUENCE: 108 tgtttgc                                                          7

<210> SEQ ID NO 109
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0073.1

<400> SEQUENCE: 109
tttgctcctc cg                                                    12

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0073.1

<400> SEQUENCE: 110
tggttaatat tcaccagc                                              18

<210> SEQ ID NO 111
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0073.1

<400> SEQUENCE: 111
ttcaccagca gc                                                    12
```

-continued

```
<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0073.1

<400> SEQUENCE: 112
ccctgtctcc tcagcttc                                                        18

<210> SEQ ID NO 113
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C/EBP TFBS in CRE0040

<400> SEQUENCE: 113
gaattgagca agaa                                                            14

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HNF1 TFBS in CRE0040

<400> SEQUENCE: 114
caaagccaat gattaaccaa a                                                    21

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TSS in CRE0040

<400> SEQUENCE: 115
ggagtggcag caatcctttc tttcagctgg                                           30

<210> SEQ ID NO 116
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0107

<400> SEQUENCE: 116
ccctggagag tcctttagca gggcaaagtg caacataggc agaccttaag ggatgactca         60
gtaacagata agctttgtgt gcctgcaggg ggatgggaag agggtggggc aggagaggga        120
cataaaaggg ctctgaggca ttgtactgtg aattccttca gtctcctgtt tggagaagac        180
```

-continued

```
agagccaatg aggccctcgt tccagggaaa cagaatatgc tcagcatgac gcagcactcc     240
ctgaactttc cggttacatc acccaatagc tgagatcaga                          280

<210> SEQ ID NO 117
<211> LENGTH: 241
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0109

<400> SEQUENCE: 117
ccctggagag tcctttagca gggcaaagtg caacataggc agaccttaag ggatgactca      60
gtaacagata agctttgtgt gcctgcaggg ggatgggaag agggtggggc aggagagggga    120 cataaaaggg ctctgaggca ttgtactgtg aattccttca gtctcctgct ctgctcagcc    180
agtcagccct gcctcccttg tttaggacca cacagcactg ctgggtgtct gcctttcctt    240
g                                                                    241

<210> SEQ ID NO 118
<211> LENGTH: 212
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0111

<400> SEQUENCE: 118
aggttaattt ttaaaaagca gtcaaaagtc caagtggccc ttggcagcat ttactctctc      60
tgtttgctct ggttaataat ctcaggagca caaacattcc tttggagaag acagagccaa     120
tgaggccctc gttccaggga aacagaatat gctcagcatg acgcagcact ccctgaactt     180
tccggttaca tcacccaata gctgagatca ga                                  212

<210> SEQ ID NO 119
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0112

<400> SEQUENCE: 119
cactgaaccc ttgacccctg ccctgcagcc cccgcagctt gctgtttgcc cactctattt      60
gcccagcccc agaggttaat ttttaaaaag cagtcaaaag tccaagtggc ccttggcagc     120
atttactctc tctgtttgct ctggttaata atctcaggag cacaaacatt cctttggaga     180
agacagagcc aatgaggccc tcgttccagg gaaacagaat atgctcagca tgacgcagca    240
ctccctgaac tttccggtta catcacccaa tagctgagat caga                     284

<210> SEQ ID NO 120
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: CRM_SP0113

<400> SEQUENCE: 120
cactgaaccc ttgacccctg ccctgcagcc cccgcagctt gctgtttgcc cactctattt      60
gcccagcccc agccctggag agtcctttag cagggcaaag tgcaacatag gcagacctta     120
agggatgact cagtaacaga taagctttgt gtgcctgcag ggggatggga agagggtggg     180
gcaggagagg gacataaaag ggctctgagg cattgtactg tgaattcctt cagtctcctg     240

<210> SEQ ID NO 121
<211> LENGTH: 241
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0115

<400> SEQUENCE: 121
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctgct ctgctcagcc     180
agtcagccct gcctcccttg tttaggacca cacagcactg ctgggtgtct gcctttcctt     240
g                                                                     241

<210> SEQ ID NO 122
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0116

<400> SEQUENCE: 122
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctg                  168

<210> SEQ ID NO 123
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0121

<400> SEQUENCE: 123
ccctggagag tcctttagca gggcaaagtg caacataggc agaccttaag ggatgactca      60
gtaacagata agctttgtgt gcctgcaccc tggagagtcc tttagcaggg caaagtgcaa     120
cataggcaga ccttaaggga tgactcagta acagataagc tttgtgtgcc tgca           174

<210> SEQ ID NO 124
<211> LENGTH: 159
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<223> OTHER INFORMATION: CRM_SP0124

<400> SEQUENCE: 124
cactgaaccc ttgacccctg ccctgcagcc cccgcagctt gctgtttgcc cactctattt          60
gcccagcccc agccctggag agtcctttag cagggcaaag tgcaacatag gcagacctta         120
agggatgact cagtaacaga taagctttgt gtgcctgca                                 159

<210> SEQ ID NO 125
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0127 (CRM_LVR_127)

<400> SEQUENCE: 125
agaatgaaca ttgaactttg dactatacct gaggggtgag gtaaacaaca ggactataaa          60
tggcccggga ggcgcccttt ggaccttttg caatcctggc gcactgaacc cttgacccct         120
gccctgcagc ccccgcagct tgctgtttgc ccactctatt tgcccagccc cagggacaga         180
gctgatcctt gaactcttaa gttccac                                             207

<210> SEQ ID NO 126
<211> LENGTH: 313
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0127A1 (CRM_LVR_127_A1)

<400> SEQUENCE: 126
aggttaattt ttaaaaagca gtcaaaagtc caagtggccc ttggcagcat ttactctctc          60
tgtttgctct ggttaataat ctcaggagca caaacattcc tgtaccagaa tgaacattga         120
actttggact atacctgagg ggtgaggtaa acaacaggac tataaatggc ccgggaggcg         180
ccctttggac cttttgcaat cctggcgcac tgaacccttg accctgccc tgcagccccc          240 gcagcttgct gtttgcccac tctatttgcc cagccccagg dacagagctg atccttgaac         300
tcttaagttc cac                                                             313

<210> SEQ ID NO 127
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0127V1 (CRM_LVR_127_V1)

<400> SEQUENCE: 127
aagcaaatat ttgtggttat ggattaactc gaactgtttg cccactctat ttgccctgta          60
ccagaatgaa cattgaactt tggactatac ctgaggggtg aggtaaacaa caggactata         120
aatggcccgg gaggcgccct ttggaccttt tgcaatcctg gcgcactgaa cccttgaccc         180
```

-continued

```
ctgccctgca gcccccgcag cttgctgttt gcccactcta tttgcccagc cccagggaca      240
gagctgatcc ttgaactctt aagttccac                                        269

<210> SEQ ID NO 128
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0127V2 (CRM_LVR_127_V2)

<400> SEQUENCE: 128
ggcgcccttt ggaccttttg caatcctgga gcaaacagca aacactgtac cagaatgaac       60
attgaacttt ggactatacc tgaggggtga ggtaaacaac aggactataa atggcccggg      120
aggcgccctt tggacctttt gcaatcctgg cgcactgaac ccttgacccc tgccctgcag      180
cccccgcagc ttgctgtttg cccactctat ttgcccagcc ccaggacag agctgatcct       240 tgaactctta agttccac                                                    258

<210> SEQ ID NO 129
<211> LENGTH: 194
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0128

<400> SEQUENCE: 129
agaatgaaca ttgaactttg gactatacct gaggggtgag gtaaacaaca ggactataaa       60
tagaatgaac attgaacttt ggactatacc tgaggggtga ggtaaacaac aggactataa      120
atcactgaac ccttgacccc tgccctgcag cccccgcagc ttgctgtttg cccactctat      180
ttgcccagcc ccag                                                        194

<210> SEQ ID NO 130
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0131 (CRM_LVR_131)

<400> SEQUENCE: 130
ggcccgggag gcgccctttg dacctttttgc aatcctggcg cactgaaccc ttgacccctg      60
ccctgcagcc cccgcagctt gctgtttgcc cactctattt gcccagcccc agccctggag      120
agtcctttag cagggcaaag tgcaacatag gcagaccttta agggatgact cagtaacaga      180
taagctttgt gtgcctgca                                                    199

<210> SEQ ID NO 131
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0132 (CRM_LVR_132)
```

<400> SEQUENCE: 131
agaatgaaca ttgaactttg gactatacct gaggggtgag gtaaacaaca ggactataaa     60
tggcccggga ggcgcccttt ggaccttttg caatcctggc gcactgaacc cttgaccct    120 gccctgcagc ccccgcagct tgctgtttgc ccactctatt tgcccagccc cagccctgga    180
gagtccttta gcagggcaaa gtgcaacata ggcagacctt aagggatgac tcagtaacag    240
ataagctttg tgtgcctgca                                                260

<210> SEQ ID NO 132
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0133 (CRM_LVR_133)

<400> SEQUENCE: 132
agaatgaaca ttgaactttg gactatacct gaggggtgag gtaaacaaca ggactataaa     60
tggcccggga ggcgcccttt ggaccttttg caatcctggc g                        101

<210> SEQ ID NO 133
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0155

<400> SEQUENCE: 133
gctggtttct tataaaactg atggaagata caaacactat taaagaactg tttgcatgtt     60
gcaaatgatg tccaaagtcc aaacattgtt aataattaat actccaataa acatcatgtc    120
agaatttctg ttttcttttc cctttgaacc tttgcaggat tgccacatca tcaggaccac    180
accttcatca ggaatgaata t                                              201

<210> SEQ ID NO 134
<211> LENGTH: 232
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0158

<400> SEQUENCE: 134
attggcatct tctattgctt ttcctggtga cttcattttt cactcttggc taaaaatggg     60
tctctgatga tttattctat cctgggtgtt gacaagctga agaagttgtg tggggcctgc    120
tgccagtaac cctgggtgac gaagcgtgac tcaccactcc gaggtcagtg gggggatgga    180
aggcagggga gtcagctgac aagatctgct gctttgtcac caggccttct gc            232

<210> SEQ ID NO 135
<211> LENGTH: 200
<212> TYPE: DNA
<213> ORGANISM: Artificial Sequence
<220> FEATURE:
<223> OTHER INFORMATION: Description of Artificial Sequence: Synthetic -continued

```
          polynucleotide
<220> FEATURE:
<223> OTHER INFORMATION: CRM_SP0163

<400> SEQUENCE: 135
tgaaatgcct gccatatatt agtgccctga agtccaaagg tagaggaacc gagtgtttaa      60
aaattactgt ggctgtggag tcaacatgat gtaaaaaaac aaacatttgg ataacaccaa     120
gaagccagat atggttgaaa tgttgactgg ttgacaaaaa taatttgggt tgcttaatgg     180
tgcacaaagg taatgcaaaa                                                  200

<210> SEQ ID NO 136
<211> LENGTH: 103
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: CRM_SP0236

<400> SEQUENCE: 136
caggctttca ctttctcgcc aacttacaag gcctttctgt gtaaacaata cctgaacctt      60
taccccgttg cccggcaacg gccaggtctg tgccaagtgt ttg                       103

<210> SEQ ID NO 137
<211> LENGTH: 402
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: CRM_SP0239

<400> SEQUENCE: 137
caggctttca ctttctcgcc aacttacaag gcctttctgt gtaaacaata cctgaacctt      60
taccccgttg cccggcaacg gccaggtctg tgccaagtgt ttgaggttaa tttttaaaaa     120
gcagtcaaaa gtccaagtgg cccttggcag catttactct ctctgtttgc tctggttaat     180
aatctcagga gcacaaacat tccggcccgg gaggcgccct ttggaccttt tgcaatcctg     240
gcgcactgaa cccttgaccc ctgccctgca gcccccgcag cttgctgttt gcccactcta     300
tttgcccagc cccagccctg gagagtcctt tagcagggca aagtgcaaca taggcagacc     360
ttaagggatg actcagtaac agataagctt tgtgtgcctg ca                       402

<210> SEQ ID NO 138
<211> LENGTH: 103
<212> TYPE: DNA
<213> ORGANISM: Artificial Sequence
<220> FEATURE:
<223> OTHER INFORMATION: Description of Artificial Sequence: Synthetic
          polynucleotide
<220> FEATURE:
<223> OTHER INFORMATION: CRM_SP0240

<400> SEQUENCE: 138
caggctttca ctttctcgcc aacttacaag gcctttctgt gtaaacaata cctgaacctt      60
taccccgttg cccggcaacg gccaggtctg tgccaagtgt ttg                       103

<210> SEQ ID NO 139
<211> LENGTH: 299
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0241

<400> SEQUENCE: 139
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg cactgaaccc ttgacccctg ccctgcagcc cccgcagctt     180
gctgtttgcc cactctattt gcccagcccc agccctggag agtcctttag cagggcaaag     240
tgcaacatag gcagacctta agggatgact cagtaacaga taagctttgt gtgcctgca      299

<210> SEQ ID NO 140
<211> LENGTH: 212
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0242

<400> SEQUENCE: 140
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg cactgaaccc ttgacccctg ccctgcagcc cccgcagctt     180
gctgtttgcc cactctattt gcccagcccc ag                                   212

<210> SEQ ID NO 141
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0243

<400> SEQUENCE: 141
tgaaatgcct gccatatatt agtgccctga agtccaaagg tagaggaacc gagtgtttaa      60
aaattactgt ggctgtggag tcaacatgat gtaaaaaaac aaacatttgg ataacaccaa     120
gaagccagat atggttgaaa tgttgactgg ttgacaaaaa taatttgggt tgcttaatgg     180
tgcacaaagg taatgcaaaa aggttaattt ttaaaaagca gtcaaaagtc caagtggccc     240
ttggcagcat ttactctctc tgtttgctct ggttaataat ctcaggagca caaacattcc     300
ggcccgggag gcgccctttg gaccttttgc aatcctggcg cactgaaccc ttgacccctg     360
ccctgcagcc cccgcagctt gctgtttgcc cactctattt gcccagcccc agccctggag     420
agtcctttag cagggcaaag tgcaacatag gcagacctta agggatgact cagtaacaga     480
taagctttgt gtgcctgca                                                  499

<210> SEQ ID NO 142
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide -continued

```
<220> FEATURE:
<223> OTHER INFORMATION: CRM_SP0244

<400> SEQUENCE: 142
ctttggacct tttgcaatcc tggcgcactg aacccttgac ccctgccctg cagccccgc        60 agcttgctgt ttgcccactc tatttgccca gccccagtga aatgcctgcc atatattagt       120
gccctgaagt ccaaaggtag aggaaccgag tgtttaaaaa ttactgtggc tgtggagtca      180
acatgatgta aaaaaacaaa catttggata acaccaagaa gccagatatg gttgaaatgt      240
tgactggttg acaaaaataa tttgggttgc ttaatggtgc acaaaggtaa tgcaaaa        297

<210> SEQ ID NO 143
<211> LENGTH: 212
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0246

<400> SEQUENCE: 143
aggttaattt ttaaaaagca gtcaaaagtc caagtggccc ttggcagcat ttactctctc        60
tgtttgctct ggttaataat ctcaggagca caaacattcc ggcccgggag gcgccctttg      120 gacctttgc aatcctggcg cactgaaccc ttgaccccctg ccctgcagcc cccgcagctt      180
gctgtttgcc cactctattt gcccagcccc ag                                     212

<210> SEQ ID NO 144
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0247

<400> SEQUENCE: 144
gctggtttct tataaaactg atggaagata caaacactat taaagaactg tttgcatgtt        60
gcaaatgatg tccaaagtcc aaacattgtt aataattaat actccaataa acatcatgtc      120
agaatttctg ttttcttttc cctttgaacc tttgcaggat tgccacatca tcaggaccac      180
accttcatca ggaatgaata tcaggctttc actttctcgc caacttacaa ggcctttctg      240
tgtaaacaat acctgaacct ttaccccgtt gcccggcaac ggccaggtct gtgccaagtg      300
tttg                                                                    304

<210> SEQ ID NO 145
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0248

<400> SEQUENCE: 145
aggttaattt ttaaaaagca gtcaaaagtc caagtggccc ttggcagcat ttactctctc        60
tgtttgctct ggttaataat ctcaggagca caaacattcc ggcccgggag gcgccctttg      120 gacctttgc aatcctggcg cactgaaccc ttgaccccctg ccctgcagcc cccgcagctt      180
```

-continued

```
gctgtttgcc cactctattt gcccagcccc agcaggcttt cactttctcg ccaacttaca      240
aggcctttct gtgtaaacaa tacctgaacc tttaccccgt tgcccggcaa cggccaggtc      300
tgtgccaagt gtttg                                                        315

<210> SEQ ID NO 146
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0249

<400> SEQUENCE: 146
aggttaattt ttaaaaagca gtcaaaagtc caagtggccc ttggcagcat ttactctctc       60
tgtttgctct ggttaataat ctcaggagca caaacattcc ggcccgggag gcgccctttg      120
gaccttttgc aatcctggcg cactgaaccc ttgacccctg ccctgcagcc cccgcagctt      180
gctgtttgcc cactctattt gcccagcccc agcaggcttt cactttctcg ccaacttaca      240
aggcctttct gtgtaaacaa tacctgaacc tttaccccgt tgcccggcaa cggccaggtc      300
tgtgccaagt gtttg                                                        315

<210> SEQ ID NO 147
<211> LENGTH: 413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0250

<400> SEQUENCE: 147
aggttaattt ttaaaaagca gtcaaaagtc caagtggccc ttggcagcat ttactctctc       60
tgtttgctct ggttaataat ctcaggagca caaacattcc ggcccgggag gcgccctttg      120
gaccttttgc aatcctggcg cactgaaccc ttgacccctg ccctgcagcc cccgcagctt      180
gctgtttgcc cactctattt gcccagcccc aggctggttt cttataaaac tgatggaaga      240
tacaaacact attaaagaac tgtttgcatg ttgcaaatga tgtccaaagt ccaaacattg      300
ttaataatta atactccaat aaacatcatg tcagaatttc tgttttcttt tccctttgaa      360
cctttgcagg attgccacat catcaggacc acaccttcat caggaatgaa tat            413

<210> SEQ ID NO 148
<211> LENGTH: 268
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0251

<400> SEQUENCE: 148
aggttaattt ttaaaaagca gtcaaaagtc caagtggccc ttggcagcat ttactctctc       60
tgtttgctct ggttaataat ctcaggagca caaacattcc ggcccgggag gcgccctttg      120
gaccttttgc aatcctggcg cactgaaccc ttgacccctg ccctgcagcc cccgcagctt      180
gctgtttgcc cactctattt gcccagcccc agaagcaaat atttgtggtt atggattaac      240
```

-continued

```
tcgaactgtt tgcccactct atttgccc                                              268

<210> SEQ ID NO 149
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0252

<400> SEQUENCE: 149
aagcaaatat ttgtggttat ggattaactc gaactgtttg cccactctat ttgccccagg     60
ctttcacttt ctcgccaact tacaaggcct ttctgtgtaa acaatacctg aacctttacc     120
ccgttgcccg gcaacggcca ggtctgtgcc aagtgtttg                            159

<210> SEQ ID NO 150
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0253

<400> SEQUENCE: 150
aagcaaatat ttgtggttat ggattaactc gaactgtttg cccactctat ttgccccagg     60
ctttcacttt ctcgccaact tacaaggcct ttctgtgtaa acaatacctg aacctttacc     120
ccgttgcccg gcaacggcca ggtctgtgcc aagtgtttg                            159

<210> SEQ ID NO 151
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0254

<400> SEQUENCE: 151
aggttaattt ttaaaaagca gtcaaaagtc caagtggccc ttggcagcat ttactctctc     60
tgtttgctct ggttaataat ctcaggagca caaacattcc ggcccgggag gcgccctttg     120
gaccttttgc aatcctggcg caggctttca ctttctcgcc aacttacaag gcctttctgt     180
gtaaacaata cctgaacctt taccccgttg cccggcaacg gccaggtctg tgccaagtgt     240
ttg                                                                   243

<210> SEQ ID NO 152
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0255

<400> SEQUENCE: 152
aggttaattt ttaaaaagca gtcaaaagtc caagtggccc ttggcagcat ttactctctc     60
```

-continued

_____ tgtttgctct ggttaataat ctcaggagca caaacattcc ggcccgggag gcgccctttg      120 gacctttgc aatcctggcg caggctttca ctttctcgcc aacttacaag gcctttctgt       180
gtaaacaata cctgaacctt taccccgttg cccggcaacg gccaggtctg tgccaagtgt      240
ttg                                                                   243

<210> SEQ ID NO 153
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0256

<400> SEQUENCE: 153
attggcatct tctattgctt ttcctggtga cttcattttt cactcttggc taaaaatggg       60
tctctgatga tttattctat cctgggtgtt gacaagctga agaagttgtg tggggcctgc      120
tgccagtaac cctgggtgac gaagcgtgac tcaccactcc gaggtcagtg gggggatgga     180
aggcagggga gtcagctgac aagatctgct gctttgtcac caggccttct gccaggcttt      240
cactttctcg ccaacttaca aggcctttct gtgtaaacaa tacctgaacc tttaccccgt      300
tgcccggcaa cggccaggtc tgtgccaagt gtttg                                335

<210> SEQ ID NO 154
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0257

<400> SEQUENCE: 154
caggctttca ctttctcgcc aacttacaag gcctttctgt gtaaacaata cctgaacctt       60
taccccgttg cccggcaacg gccaggtctg tgccaagtgt ttggctggtt tcttataaaa      120
ctgatggaag atacaaacac tattaaagaa ctgtttgcat gttgcaaatg atgtccaaag      180
tccaaacatt gttaataatt aatactccaa taaacatcat gtcagaattt ctgtttttctt     240 ttccctttga acctttgcag gattgccaca tcatcaggac cacaccttca tcaggaatga      300
atat                                                                  304

<210> SEQ ID NO 155
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0258

<400> SEQUENCE: 155
ctgtttgctg cttgcaatgt ttgcccattt tagggaggtt aatttttaaa aagcagtcaa       60
aagtccaagt ggcccttggc agcatttact ctctctgttt gctctggtta ataatctcag      120
gagcacaaac attccggccc gggaggcgcc ctttggacct tttgcaatcc tggcgcactg      180 aaccccttgac ccctgccctg cagcccccgc agcttgctgt ttgcccactc tatttgccca     240

```
gccccagccc tggagagtcc tttagcaggg caaagtgcaa cataggcaga ccttaaggga      300
tgactcagta acagataagc tttgtgtgcc tgca                                   334

<210> SEQ ID NO 156
<211> LENGTH: 236
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0259

<400> SEQUENCE: 156
ctgtttgctg cttgcaatgt ttgcccattt taggggctgg tttcttataa aactgatgga       60
agatacaaac actattaaag aactgtttgc atgttgcaaa tgatgtccaa agtccaaaca      120
ttgttaataa ttaatactcc aataaacatc atgtcagaat ttctgttttc ttttcccttt      180
gaacctttgc aggattgcca catcatcagg accacacctt catcaggaat gaatat         236

<210> SEQ ID NO 157
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0264

<400> SEQUENCE: 157
caggctttca ctttctcgcc aacttacaag gcctttctgt gtaaacaata cctgaacctt       60
taccccgttg cccggcaacg gccaggtctg tgccaagtgt ttg                       103

<210> SEQ ID NO 158
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0265 (CRM_LVR_131_A1)

<400> SEQUENCE: 158
aggttaattt ttaaaaagca gtcaaaagtc caagtggccc ttggcagcat ttactctctc       60
tgtttgctct ggttaataat ctcaggagca caaacattcc tgtaccggcc cgggaggcgc      120
cctttggacc ttttgcaatc ctggcgcact gaacccttga ccctgccct gcagcccccg      180 cagcttgctg tttgcccact ctatttgccc agccccagcc ctggagagtc ctttagcagg      240
gcaaagtgca acataggcag accttaaggg atgactcagt aacagataag ctttgtgtgc      300
ctgca                                                                   305

<210> SEQ ID NO 159
<211> LENGTH: 261
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0266 (CRM_LVR_131_V1)

<400> SEQUENCE: 159
```

-continued

```
aagcaaatat ttgtggttat ggattaactc gaactgtttg cccactctat ttgccctgta      60
ccggcccggg aggcgccctt tggacctttt gcaatcctgg cgcactgaac ccttgacccc     120
tgccctgcag cccccgcagc ttgctgtttg cccactctat ttgcccagcc ccagccctgg     180
agagtccttt agcagggcaa agtgcaacat aggcagacct taagggatga ctcagtaaca     240
gataagcttt gtgtgcctgc a                                               261
```

```
<210> SEQ ID NO 160
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0267 (CRM_LVR_131_V2)

<400> SEQUENCE: 160
ggcgcccttt ggaccttttg caatcctgga gcaaacagca aacactgtac cggcccggga      60
ggcgcccttt ggaccttttg caatcctggc gcactgaacc cttgacccct gccctgcagc     120
ccccgcagct tgctgtttgc ccactctatt tgcccagccc cagccctgga gagtccttta     180
gcagggcaaa gtgcaacata ggcagacctt aagggatgac tcagtaacag ataagctttg     240
tgtgcctgca                                                           250
```

```
<210> SEQ ID NO 161
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0268 (CRM_LVR_132_A1)

<400> SEQUENCE: 161
aggttaattt ttaaaaagca gtcaaaagtc caagtggccc ttggcagcat ttactctctc      60
tgtttgctct ggttaataat ctcaggagca caaacattcc tgtaccagaa tgaacattga     120
actttggact atacctgagg ggtgaggtaa acaacaggac tataaatggc ccgggaggcg     180 cccttttggac cttttgcaat cctggcgcac tgaacccttg accctgccc tgcagccccc     240 gcagcttgct gtttgcccac tctatttgcc cagccccagc cctggagagt cctttagcag     300
ggcaaagtgc aacataggca gaccttaagg gatgactcag taacagataa gctttgtgtg     360
cctgca                                                               366
```

```
<210> SEQ ID NO 162
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0269 (CRM_LVR_132_V1)

<400> SEQUENCE: 162
aagcaaatat ttgtggttat ggattaactc gaactgtttg cccactctat ttgccctgta      60
ccagaatgaa cattgaactt tggactatac ctgaggggtg aggtaaacaa caggactata     120
aatggcccgg gaggcgccct ttggaccttt tgcaatcctg gcgcactgaa cccttgaccc     180
```

```
ctgccctgca gcccccgcag cttgctgttt gcccactcta tttgcccagc cccagccctg       240
gagagtcctt tagcagggca aagtgcaaca taggcagacc ttaagggatg actcagtaac       300
agataagctt tgtgtgcctg ca                                                322
```

<210> SEQ ID NO 163
<211> LENGTH: 311
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0270 (CRM_LVR_132_V2)

<400> SEQUENCE: 163

```
ggcgcccttt ggacctttg caatcctgga gcaaacagca aacactgtac cagaatgaac       60
attgaacttt ggactatacc tgaggggtga ggtaaacaac aggactataa atggcccggg     120
aggcgccctt tggacctttt gcaatcctgg cgcactgaac ccttgacccc tgccctgcag     180
cccccgcagc ttgctgtttg cccactctat ttgcccagcc ccagccctgg agagtccttt     240
agcagggcaa agtgcaacat aggcagacct taagggatga ctcagtaaca gataagcttt     300
gtgtgcctgc a                                                          311
```

<210> SEQ ID NO 164
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0271 (CRM_LVR_133_A1)

<400> SEQUENCE: 164

```
aggttaattt ttaaaaagca gtcaaaagtc caagtggccc ttggcagcat ttactctctc       60
tgtttgctct ggttaataat ctcaggagca caaacattcc tgtaccagaa tgaacattga     120
actttggact atacctgagg ggtgaggtaa acaacaggac tataaatggc ccgggaggcg     180 cccttggac cttttgcaat cctggcg                                          207
```

<210> SEQ ID NO 165
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0272 (CRM_LVR_133_V1)

<400> SEQUENCE: 165

```
aagcaaatat ttgtggttat ggattaactc gaactgtttg cccactctat ttgccctgta       60
ccagaatgaa cattgaactt tggactatac ctgaggggtg aggtaaacaa caggactata     120
aatggcccgg gaggcgccct ttggaccttt tgcaatcctg gcg                       163
```

<210> SEQ ID NO 166
<211> LENGTH: 152
<212> TYPE: DNA
<213> ORGANISM: Artificial Sequence
<220> FEATURE:
<223> OTHER INFORMATION: Description of Artificial Sequence: Synthetic -continued polynucleotide
<220> FEATURE:
<223> OTHER INFORMATION: CRM_SP0273 (CRM_LVR_133_V2)

<400> SEQUENCE: 166 ggcgccctttt ggacctttg caatcctgga gcaaacagca aacactgtac cagaatgaac        60
attgaacttt ggactatacc tgaggggtga ggtaaacaac aggactataa atggcccggg       120
aggcgccctt tggaccttttt gcaatcctgg cg                                    152

<210> SEQ ID NO 167
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0368

<400> SEQUENCE: 167
aggttaattt ttaaaaagca gtcaaaagtc caagtggccc ttggcagcat ttactctctc        60
tgtttgctct ggttaataat ctcaggagca caaacattcc                             100

<210> SEQ ID NO 168
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0373

<400> SEQUENCE: 168
aggttaattt ttaaaaagca gtcaaaagtc caagtggccc ttggcagcat ttactctctc        60
tgtttgctct ggttaataat ctcaggagca caaacattcc tgtaccggcc cgggaggcgc       120
cctttggacc ttttgcaatc ctggcg                                            146

<210> SEQ ID NO 169
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0378

<400> SEQUENCE: 169
tgctctctga caaagatacg gtgggtccca ctgatgaact gtgctgccac agtaaatgta        60
gccactatgc ctatctccat tctgaagatg tgccctgttc aaacatgtcc taatactctg       120
tctctgcaag ggtcatcagt agttttccat cttactcaac atcctcccag tg               172

<210> SEQ ID NO 170
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0379

<400> SEQUENCE: 170
cctccccgtg ttcctgctct ttgtccctct gtcctactta gactaatatt tgccttgggt      60
actgcaaaca ggaaatgggg gagggacagg agtagggcgg ccctgttcaa acatgtccta     120
atactctgtc tctgcaaggg tcatcagtag ttttccatct tactcaacat cctcccagtg     180

<210> SEQ ID NO 171
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0380

<400> SEQUENCE: 171
ccgcccccac tgaacccttg accctgccc tgcagccccc gcagcttgct gtttgcccac      60
tctatttgcc cagccccagc cctgttcaaa catgtcctaa tactctgtct ctgcaagggt     120
catcagtagt tttccatctt actcaacatc ctcccagtg                            159

<210> SEQ ID NO 172
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0381

<400> SEQUENCE: 172
aagctttctg aacagccaaa cagagattcc aaagttcagg caccaaagtt cagaccctaa      60
cagttattta caagggtcag ttaacccctg ttcaaacatg tcctaatact ctgtctctgc     120
aagggtcatc agtagttttc catcttactc aacatcctcc cagtg                     165

<210> SEQ ID NO 173
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0384

<400> SEQUENCE: 173
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg                                                 140

<210> SEQ ID NO 174
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0388

<400> SEQUENCE: 174
aggttaattt ttaaaaagca gtcaaaagtc caagtggccc ttggcagcat ttactctctc      60

-continued tgtttgctct ggttaataat ctcaggagca caaacattcc                               100

<210> SEQ ID NO 175
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0396

<400> SEQUENCE: 175
aggttaattt ttaaaaagca gtcaaaagtc caagtggccc ttggcagcat ttactctctc         60
tgtttgctct ggttaataat ctcaggagca caaacattcc tgtaccggcc cgggaggcgc        120
cctttggacc ttttgcaatc ctggcgccct ggagagtcct ttagcagggc aaagtgcaac        180
ataggcagac cttaagggat gactcagtaa cagataagct ttgtgtgcct gca               233

<210> SEQ ID NO 176
<211> LENGTH: 265
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0397

<400> SEQUENCE: 176
aggttaattt ttaaaaagca gtcaaaagtc caagtggccc ttggcagcat ttactctctc         60
tgtttgctct ggttaataat ctcaggagca caaacattcc tgtacccact gaacccttga        120
cccctgccct gcagccccg cagcttgctg tttgcccact ctatttgccc agccccagcc         180
ctggagagtc ctttagcagg gcaaagtgca acataggcag accttaaggg atgactcagt        240
aacagataag ctttgtgtgc ctgca                                              265

<210> SEQ ID NO 177
<211> LENGTH: 469
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0398

<400> SEQUENCE: 177
caggctttca ctttctcgcc aacttacaag gcctttctgt gtaaacaata cctgaacctt         60
taccccgttg cccggcaacg gccaggtctg tgccaagtgt ttgaggttaa tttttaaaaa        120
gcagtcaaaa gtccaagtgg cccttggcag catttactct ctctgtttgc tctggttaat        180
aatctcagga gcacaaacat tcctgtacca gaatgaacat tgaactttgg actatacctg        240
aggggtgagg taaacaacag gactataaat ggcccgggag gcgcccttg gaccttttgc         300 aatcctggcg cactgaaccc ttgacccctg ccctgcagcc cccgcagctt gctgtttgcc        360
cactctattt gcccagcccc agccctggag agtcctttag cagggcaaag tgcaacatag        420
gcagacctta aggatgact cagtaacaga taagctttgt gtgcctgca                     469

<210> SEQ ID NO 178
<211> LENGTH: 61
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CRM_SP0399

<400> SEQUENCE: 178
agaatgaaca ttgaactttg gactatacct gaggggtgag gtaaacaaca ggactataaa      60
t                                                                      61

<210> SEQ ID NO 179
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0403

<400> SEQUENCE: 179
caggctttca ctttctcgcc aacttacaag gcctttctgt gtaaacaata cctgaacctt      60
taccccgttg cccggcaacg gccaggtctg tgccaagtgt ttgaagcaaa tatttgtggt     120
tatggattaa ctcgaactgt ttgcccactc tatttgccct gtaccggccc gggaggcgcc     180
ctttggacct tttgcaatcc tggcgcactg aacccttgac ccctgccctg cagccccgc      240 agcttgctgt ttgcccactc tatttgccca gccccagccc tggagagtcc tttagcaggg     300
caaagtgcaa cataggcaga ccttaaggga tgactcagta acagataagc tttgtgtgcc     360
tgca                                                                  364

<210> SEQ ID NO 180
<211> LENGTH: 425
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0404

<400> SEQUENCE: 180
caggctttca ctttctcgcc aacttacaag gcctttctgt gtaaacaata cctgaacctt      60
taccccgttg cccggcaacg gccaggtctg tgccaagtgt ttgaagcaaa tatttgtggt     120
tatggattaa ctcgaactgt ttgcccactc tatttgccct gtaccagaat gaacattgaa     180
ctttggacta tacctgaggg gtgaggtaaa caacaggact ataaatggcc cgggaggcgc     240
cctttggacc ttttgcaatc ctggcgcact gaacccttga ccctgccct gcagcccccg      300 cagcttgctg tttgcccact ctatttgccc agccccagcc ctggagagtc ctttagcagg     360
gcaaagtgca acataggcag accttaaggg atgactcagt aacagataag ctttgtgtgc     420
ctgca                                                                 425

<210> SEQ ID NO 181
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0405

-continued

<400> SEQUENCE: 181
caggctttca ctttctcgcc aacttacaag gcctttctgt gtaaacaata cctgaacctt        60
taccccgttg cccggcaacg gccaggtctg tgccaagtgt ttgaagcaaa tatttgtggt       120
tatggattaa ctcgaactgt ttgcccactc tatttgccct gtaccagaat gaacattgaa       180
ctttggacta tacctgaggg gtgaggtaaa caacaggact ataaatggcc cgggaggcgc       240
cctttggacc ttttgcaatc ctggcgcact gaacccttga cccctgccct gcagcccccg       300
cagcttgctg tttgcccact ctatttgccc agccccag                               338

<210> SEQ ID NO 182
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0406

<400> SEQUENCE: 182
aggttaattt ttaaaaagca gtcaaaagtc caagtggccc ttggcagcat ttactctctc        60
tgtttgctct ggttaataat ctcaggagca caaacattcc ggcccgggag gcgccctttg       120
gaccttttgc aatcctggcg                                                   140

<210> SEQ ID NO 183
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0407

<400> SEQUENCE: 183
aggttaattt ttaaaaagca gtcaaaagtc caagtggccc ttggcagcat ttactctctc        60
tgtttgctct ggttaataat ctcaggagca caaacattcc caggctttca ctttctcgcc       120
aacttacaag gcctttctgt gtaaacaata cctgaacctt taccccgttg cccggcaacg       180
gccaggtctg tgccaagtgt ttg                                               203

<210> SEQ ID NO 184
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0409

<400> SEQUENCE: 184
aggttaattt ttaaaaagca gtcaaaagtc caagtggccc ttggcagcat ttactctctc        60
tgtttgctct ggttaataat ctcaggagca caaacattcc ccctgttcaa acatgtccta       120
atactctgtc tctgcaaggg tcatcagtag ttttccatct tactcaacat cctcccagtg       180

<210> SEQ ID NO 185
<211> LENGTH: 80
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: CRM_SP0411

<400> SEQUENCE: 185
ccctgttcaa acatgtccta atactctgtc tctgcaaggg tcatcagtag ttttccatct     60
tactcaacat cctcccagtg                                                 80

<210> SEQ ID NO 186
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0412

<400> SEQUENCE: 186
aggttaattt ttaaaaagca gtcaaaagtc caagtggccc ttggcagcat ttactctctc     60
tgtttgctct ggttaataat ctcaggagca caaacattcc ccctgttcaa acatgtccta    120
atactctgtc tctgcaaggg tcatcagtag ttttccatct tactcaacat cctcccagtg    180

<210> SEQ ID NO 187
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CRM_SP0413

<400> SEQUENCE: 187
aggttaattt ttaaaaagca gtcaaaagtc caagtggccc ttggcagcat ttactctctc     60
tgtttgctct ggttaataat ctcaggagca caaacattcc tgtaccggcc cgggaggcgc    120
cctttggacc ttttgcaatc ctggcg                                        146

<210> SEQ ID NO 188
<211> LENGTH: 356
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0107

<400> SEQUENCE: 188
ccctggagag tcctttagca gggcaaagtg caacataggc agaccttaag ggatgactca     60
gtaacagata agctttgtgt gcctgcaggg ggatgggaag agggtggggc aggagaggga    120
cataaaaggg ctctgaggca ttgtactgtg aattccttca gtctcctgtt tggagaagac    180
agagccaatg aggccctcgt tccagggaaa cagaatatgc tcagcatgac gcagcactcc    240
ctgaactttc cggttacatc acccaatagc tgagatcaga gggcatataa aacagggggca    300 aggcacagac tcatagcaga gcaatcacca ccaagcctgg aataactgca gccacc        356

<210> SEQ ID NO 189
<211> LENGTH: 453
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0109

<400> SEQUENCE: 189
cctggagagt cctttagcag ggcaaagtgc aacataggca gaccttaagg gatgactcag        60
taacagataa gctttgtgtg cctgcagggg gatgggaaga gggtggggca ggagagggac       120
ataaaagggc tctgaggcat tgtactgtga attccttcag tctcctgctc tgctcagcca       180
gtcagccctg cctcccttgt ttaggaccac acagcactgc tgggtgtctg cctttccttg       240
ggtaattttt ttttctggtt aatatttagc aagaattctg cagagtgatc aaaaaaatca       300
aatactcagt atttcagaaa tagattaaat aggttacttt tttactgata atgtgaaaga       360
atgatataaa aacttgattt tcctcaacaa cattactttc ttttgtaaat gtggtttcta       420
caaagatgaa actactaaaa cttacaggcc acc                                    453

<210> SEQ ID NO 190
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0111

<400> SEQUENCE: 190
aggttaattt ttaaaaagca gtcaaaagtc caagtggccc ttggcagcat ttactctctc        60
tgtttgctct ggttaataat ctcaggagca caaacattcc tttggagaag acagagccaa       120
tgaggccctc gttccaggga aacagaatat gctcagcatg acgcagcact ccctgaactt       180
tccggttaca tcacccaata gctgagatca gagggcatat aaaacagggg caaggcacag       240
actcatagca gagcaatcac caccaagcct ggaataactg cagccacc                    288

<210> SEQ ID NO 191
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0112

<400> SEQUENCE: 191
cactgaaccc ttgacccctg ccctgcagcc cccgcagctt gctgtttgcc cactctattt        60
gcccagcccc agaggttaat tttaaaaag cagtcaaaag tccaagtggc ccttggcagc       120
atttactctc tctgtttgct ctggttaata atctcaggag cacaaacatt cctttggaga       180
agacagagcc aatgaggccc tcgttccagg gaaacagaat atgctcagca tgacgcagca       240
ctccctgaac tttccggtta catcacccaa tagctgagat cagagggcat ataaaacagg       300
ggcaaggcac agactcatag cagagcaatc accaccaagc ctggaataac tgcagccacc       360

<210> SEQ ID NO 192
<211> LENGTH: 316
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: SP0113

<400> SEQUENCE: 192
cactgaaccc ttgacccctg ccctgcagcc cccgcagctt gctgtttgcc cactctattt      60
gcccagcccc agccctggag agtcctttag cagggcaaag tgcaacatag gcagacctta     120
agggatgact cagtaacaga taagctttgt gtgcctgcag ggggatggga agagggtggg     180
gcaggagagg gacataaaag ggctctgagg cattgtactg tgaattcctt cagtctcctg     240
gggcatataa aacaggggca aggcacagac tcatagcaga gcaatcacca ccaagcctgg     300
aataactgca gccacc                                                     316

<210> SEQ ID NO 193
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0115

<400> SEQUENCE: 193
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctgct ctgctcagcc     180
agtcagccct gcctcccttg tttaggacca cacagcactg ctgggtgtct gcctttcctt     240
gtggacttag cccctgtttg ctcctccgat aactggggtg accttggtta atattccacca    300 gcagcctccc ccgttgcccc tctggatcca ctgcttaaat acggacgagg acagggccct     360
gtctcctcag cttcaggcac caccactgac ctgggacagt gaatcgccac c              411

<210> SEQ ID NO 194
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0116

<400> SEQUENCE: 194
ccctggagag tcctttagca gggcaaagtg caacataggc agaccttaag ggatgactca      60
gtaacagata agctttgtgt gcctgcaggg ggatgggaag agggtggggc aggagaggga     120
cataaaaggg ctctgaggca ttgtactgtg aattccttca gtctcctgtg gacttagccc     180
ctgtttgctc ctccgataac tggggtgacc ttggttaata ttcaccagca gcctcccccg     240
ttgcccctct ggatccactg cttaaatacg gacgaggaca gggccctgtc tcctcagctt     300
caggcaccac cactgacctg ggacagtgaa tcgccacc                             338

<210> SEQ ID NO 195
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide -continued

```
<220> FEATURE:
<223> OTHER INFORMATION: SP0121

<400> SEQUENCE: 195
ccctggagag tcctttagca gggcaaagtg caacataggc agaccttaag ggatgactca      60
gtaacagata agctttgtgt gcctgcaccc tggagagtcc tttagcaggg caaagtgcaa     120
cataggcaga ccttaaggga tgactcagta acagataagc tttgtgtgcc tgcagggcat     180
ataaaacagg ggcaaggcac agactcatag cagagcaatc accaccaagc ctggaataac     240
tgcagccacc                                                           250

<210> SEQ ID NO 196
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0124

<400> SEQUENCE: 196
cactgaaccc ttgacccctg ccctgcagcc cccgcagctt gctgtttgcc cactctattt      60
gcccagcccc agccctggag agtcctttag cagggcaaag tgcaacatag gcagacctta     120
agggatgact cagtaacaga taagctttgt gtgcctgcac tcttttgttt tacatgaagg     180
gtctggcagc caaagcaatc actcaaagtt caaaccttat cattttttgc tttgttcctc     240
ttggccttgg ttttgtacat cagctttgaa aataccatcc cagggttaat gctggggtta     300
atttataact aagagtgctc tagttttgca atacaggaca tgctataaaa atggaaagat     360
gttgctttct gagagatgcg ccacc                                          385

<210> SEQ ID NO 197
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0127 (LVR_SP127)

<400> SEQUENCE: 197
agaatgaaca ttgaactttg gactatacct gaggggtgag gtaaacaaca ggactataaa      60
tggcccggga ggcgcccttt ggaccttttg caatcctggc gcactgaacc cttgacccct     120
gccctgcagc ccccgcagct tgctgtttgc ccactctatt tgcccagccc cagggacaga     180
gctgatcctt gaactcttaa gttccacggg catataaaac aggggcaagg cacagactca     240
tagcagagca atcaccacca agcctggaat aactgcagcc acc                       283

<210> SEQ ID NO 198
<211> LENGTH: 389
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0127A1 (LVR_SP127_A1)

<400> SEQUENCE: 198
aggttaattt ttaaaaagca gtcaaaagtc caagtggccc ttggcagcat ttactctctc      60
```

-continued

```
tgtttgctct ggttaataat ctcaggagca caaacattcc tgtaccagaa tgaacattga       120
actttggact atacctgagg ggtgaggtaa acaacaggac tataaatggc ccgggaggcg       180
ccctttggac cttttgcaat cctggcgcac tgaacccttg acccctgccc tgcagccccc       240
gcagcttgct gtttgcccac tctatttgcc cagccccagg gacagagctg atccttgaac       300
tcttaagttc cacgggcata taaaacaggg gcaaggcaca gactcatagc agagcaatca       360
ccaccaagcc tggaataact gcagccacc                                         389

<210> SEQ ID NO 199
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0127V1 (LVR_SP127_V1)

<400> SEQUENCE: 199
aagcaaatat ttgtggttat ggattaactc gaactgtttg cccactctat ttgccctgta        60
ccagaatgaa cattgaactt tggactatac ctgaggggtg aggtaaacaa caggactata       120
aatggcccgg gaggcgccct ttggaccttt tgcaatcctg gcgcactgaa cccttgaccc       180
ctgccctgca gccccgcag cttgctgttt gcccactcta tttgcccagc cccagggaca       240
gagctgatcc ttgaactctt aagttccacg ggcatataaa acaggggcaa ggcacagact       300
catagcagag caatcaccac caagcctgga ataactgcag ccacc                      345

<210> SEQ ID NO 200
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0127V2 (LVR_SP127_V2)

<400> SEQUENCE: 200
ggcgcccttt ggacctttg caatcctgga gcaaacagca aacactgtac cagaatgaac        60 attgaactt ggactatacc tgaggggtga ggtaaacaac aggactataa atggcccggg       120
aggcgcccct tggacctttt gcaatcctgg cgcactgaac ccttgacccc tgccctgcag       180
cccccgcagc ttgctgtttg cccactctat ttgcccagcc ccaggacag agctgatcct       240 tgaactctta agttccacgg gcatataaaa caggggcaag gcacagactc atagcagagc       300
aatcaccacc aagcctggaa taactgcagc cacc                                  334

<210> SEQ ID NO 201
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0128

<400> SEQUENCE: 201
agaatgaaca ttgaactttg gactatacct gaggggtgag gtaaacaaca ggactataaa        60
tagaatgaac attgaacttt ggactatacc tgaggggtga ggtaaacaac aggactataa       120
```

-continued

```
atcactgaac ccttgacccc tgccctgcag cccccgcagc ttgctgtttg cccactctat      180
ttgcccagcc ccaggggcat ataaaacagg ggcaaggcac agactcatag cagagcaatc      240
accaccaagc ctggaataac tgcagccacc                                      270

<210> SEQ ID NO 202
<211> LENGTH: 275
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0131 (LVR_SP131)

<400> SEQUENCE: 202
ggcccgggag gcgccctttg dacctttttgc aatcctggcg cactgaaccc ttgacccctg       60
ccctgcagcc cccgcagctt gctgtttgcc cactctattt gcccagcccc agccctggag      120
agtcctttag cagggcaaag tgcaacatag gcagacctta aggatgact cagtaacaga      180 taagctttgt gtgcctgcag ggcatataaa acaggggcaa ggcacagact catagcagag      240
caatcaccac caagcctgga ataactgcag ccacc                                275

<210> SEQ ID NO 203
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0132 (LVR_SP132)

<400> SEQUENCE: 203
agaatgaaca ttgaactttg gactatacct gaggggtgag gtaaacaaca ggactataaa       60
tggcccggga ggcgcccttt ggaccttttg caatcctggc gcactgaacc cttgacccct      120
gccctgcagc ccccgcagct tgctgtttgc ccactctatt tgcccagccc cagccctgga      180
gagtccttta gcagggcaaa gtgcaacata ggcagacctt aagggatgac tcagtaacag      240
ataagctttg tgtgcctgca gggcatataa acaggggca aggcacagac tcatagcaga      300
gcaatcacca ccaagcctgg aataactgca gccacc                                336

<210> SEQ ID NO 204
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0133 (LVR_SP133)

<400> SEQUENCE: 204
agaatgaaca ttgaactttg gactatacct gaggggtgag gtaaacaaca ggactataaa       60
tggcccggga ggcgcccttt ggaccttttg caatcctggc gctctttgt tttacatgaa      120 gggtctggca gccaaagcaa tcactcaaag ttcaaacctt atcatttttt gctttgttcc      180
tcttggcctt ggttttgtac atcagctttg aaaataccat cccagggtta atgctggggt      240
taatttataa ctaagagtgc tctagttttg caatacagga catgctataa aaatggaaag      300
atgttgcttt ctgagagatg cgccacc                                          327
```

<210> SEQ ID NO 205
<211> LENGTH: 480
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0155

<400> SEQUENCE: 205
gctggtttct tataaaactg atggaagata caaacactat taaagaactg tttgcatgtt     60
gcaaatgatg tccaaagtcc aaacattgtt aataattaat actccaataa acatcatgtc    120
agaatttctg ttttctttc cctttgaacc tttgcaggat tgccacatca tcaggaccac     180
accttcatca ggaatgaata tccgatgacc taatgattct gagcttggca aaggtcttat    240
ctcccagctc gcccaggccc agtgttccag gaatgtgacc tttgctgcag cagccgctgg    300 aggggggcaga ggggatgggc tggaggttga gcaaacagag cagcagaaaa ggcagttcct    360
cttctccagt gccctccttc cctgtctctg cctctccctc ccttcctcag gcatcagagc    420
ggagacttca gggagaccag agcccagctt gccaggcact gagctagaag ccctgccatg    480

<210> SEQ ID NO 206
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0158

<400> SEQUENCE: 206
attggcatct tctattgctt ttcctggtga cttcattttt cactcttggc taaaaatggg     60
tctctgatga tttattctat cctgggtgtt gacaagctga agaagttgtg tggggcctgc    120
tgccagtaac cctgggtgac gaagcgtgac tcaccactcc gaggtcagtg ggggatgga     180 aggcagggga gtcagctgac aagatctgct gctttgtcac caggccttct gcccgatgac    240
ctaatgattc tgagcttggc aaaggtctta tctcccagct cgcccaggcc cagtgttcca    300
ggaatgtgac ctttgctgca gcagccgctg gagggggcag aggggatggg ctggaggttg    360
agcaaacaga gcagcagaaa aggcagttcc tcttctccag tgccctcctt ccctgtctct    420
gcctctccct cccttcctca ggcatcagag cggagacttc agggagacca gagcccagct    480
tgccaggcac tgagctagaa gccctgccat g                                   511

<210> SEQ ID NO 207
<211> LENGTH: 479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0163

<400> SEQUENCE: 207
tgaaatgcct gccatatatt agtgccctga agtccaaagg tagaggaacc gagtgtttaa     60
aaattactgt ggctgtggag tcaacatgat gtaaaaaaac aaacatttgg ataacaccaa    120
gaagccagat atggttgaaa tgttgactgg ttgacaaaaa taatttgggt tgcttaatgg    180

```
tgcacaaagg taatgcaaaa ccgatgacct aatgattctg agcttggcaa aggtcttatc      240
tcccagctcg cccaggccca gtgttccagg aatgtgacct ttgctgcagc agccgctgga      300
gggggcagag gggatgggct ggaggttgag caaacagagc agcagaaaag gcagttcctc      360
ttctccagtg ccctccttcc ctgtctctgc ctctccctcc cttcctcagg catcagagcg      420
gagacttcag ggagaccaga gcccagcttg ccaggcactg agctagaagc cctgccatg       479
```

```
<210> SEQ ID NO 208
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0236

<400> SEQUENCE: 208
caggctttca ctttctcgcc aacttacaag gcctttctgt gtaaacaata cctgaacctt       60
taccccgttg cccggcaacg gccaggtctg tgccaagtgt ttgcctttgc aacagcttat      120
cggaagcaaa caagctgagg ggaattgagc aagaatttct gggataccaa cagcatagga      180
ggaacaaagg acgtagaggg agggttgact gtctacacag gacaaagcca atgattaacc      240
aaacctcttg cagatttaaa taggatggga actaggagtg gcagcaatcc tttctttcag      300
ctggagtgct cctcaggagc cagccccacc cttagaaaag                           340
```

```
<210> SEQ ID NO 209
<211> LENGTH: 478
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0239

<400> SEQUENCE: 209
caggctttca ctttctcgcc aacttacaag gcctttctgt gtaaacaata cctgaacctt       60
taccccgttg cccggcaacg gccaggtctg tgccaagtgt ttgaggttaa tttttaaaaa      120
gcagtcaaaa gtccaagtgg cccttggcag catttactct ctctgtttgc tctggttaat      180
aatctcagga gcacaaacat tccggcccgg gaggcgccct ttggaccttt tgcaatcctg      240
gcgcactgaa cccttgaccc ctgccctgca gcccccgcag cttgctgttt gcccactcta      300
tttgcccagc cccagccctg gagagtcctt tagcagggca aagtgcaaca taggcagacc      360
ttaagggatg actcagtaac agataagctt tgtgtgcctg cagggcatat aaaacagggg      420
caaggcacag actcatagca gagcaatcac caccaagcct ggaataactg cagccacc       478
```

```
<210> SEQ ID NO 210
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0240

<400> SEQUENCE: 210
caggctttca ctttctcgcc aacttacaag gcctttctgt gtaaacaata cctgaacctt       60
```

-continued

```
taccccgttg cccggcaacg gccaggtctg tgccaagtgt ttgccgatga cctaatgatt    120
ctgagcttgg caaaggtctt atctcccagc tcgcccaggc ccagtgttcc aggaatgtga    180
cctttgctgc agcagccgct ggaggggca gaggggatgg gctggaggtt gagcaaacag     240
agcagcagaa aaggcagttc ctcttctcca gtgccctcct tccctgtctc tgcctctccc    300
tcccttcctc aggcatcaga gcggagactt cagggagacc agagcccagc ttgccaggca    360
ctgagctaga agccctgcc                                                 379

<210> SEQ ID NO 211
<211> LENGTH: 575
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0241

<400> SEQUENCE: 211
aggttaattt ttaaaaagca gtcaaaagtc caagtggccc ttggcagcat ttactctctc     60
tgtttgctct ggttaataat ctcaggagca caaacattcc ggcccgggag gcgccctttg    120
gaccttttgc aatcctggcg cactgaaccc ttgacccctg ccctgcagcc ccgcagcttc    180
gctgtttgcc cactctattt gcccagcccc agcctggag agtcctttag cagggcaaag     240
tgcaacatag gcagaccta agggatgact cagtaacaga taagctttgt gtgcctgcac     300
cgatgaccta atgattctga gcttggcaaa ggtcttatct cccagctcgc ccaggcccag    360
tgttccagga atgtgacctt tgctgcagca gccgctggag ggggcagagg ggatgggctg    420
gaggttgagc aaacagagca gcagaaaagg cagttcctct tctccagtgc cctccttccc    480
tgtctctgcc tctccctccc ttcctcaggc atcagagcgg agacttcagg gagaccagag    540
cccagcttgc caggcactga gctagaagcc ctgcc                               575

<210> SEQ ID NO 212
<211> LENGTH: 488
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0242

<400> SEQUENCE: 212
aggttaattt ttaaaaagca gtcaaaagtc caagtggccc ttggcagcat ttactctctc     60
tgtttgctct ggttaataat ctcaggagca caaacattcc ggcccgggag gcgccctttg    120
gaccttttgc aatcctggcg cactgaaccc ttgacccctg ccctgcagcc ccgcagcttc    180
gctgtttgcc cactctattt gcccagcccc agccgatgac ctaatgattc tgagcttggc    240
aaaggtctta tctcccagct cgcccaggcc cagtgttcca ggaatgtgac ctttgctgca    300
gcagccgctg gaggggcag aggggatggg ctggaggttg agcaaacaga gcagcagaaa     360
aggcagttcc tcttctccag tgccctcctt ccctgtctct gcctctccct cccttcctca    420
ggcatcagag cggagacttc agggagacca gagcccagct tgccaggcac tgagctagaa    480
gccctgcc                                                             488

<210> SEQ ID NO 213
```

```
<211> LENGTH: 575
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0243

<400> SEQUENCE: 213
tgaaatgcct gccatatatt agtgccctga agtccaaagg tagaggaacc gagtgtttaa        60
aaattactgt ggctgtggag tcaacatgat gtaaaaaaac aaacatttgg ataacaccaa       120
gaagccagat atggttgaaa tgttgactgg ttgacaaaaa taatttgggt tgcttaatgg       180
tgcacaaagg taatgcaaaa aggttaattt ttaaaaagca gtcaaaagtc caagtggccc       240
ttggcagcat ttactctctc tgtttgctct ggttaataat ctcaggagca caaacattcc       300
ggcccgggag gcgccctttg gacctttgc aatcctggcg cactgaaccc ttgacccctg        360
ccctgcagcc cccgcagctt gctgtttgcc cactctattt gcccagcccc agccctggag       420
agtcctttag cagggcaaag tgcaacatag gcagacctta agggatgact cagtaacaga       480
taagctttgt gtgcctgcag ggcatataaa acaggggcaa ggcacagact catagcagag       540
caatcaccac caagcctgga ataactgcag ccacc                                 575

<210> SEQ ID NO 214
<211> LENGTH: 688
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0244

<400> SEQUENCE: 214
aggttaattt ttaaaaagca gtcaaaagtc caagtggccc ttggcagcat ttactctctc        60
tgtttgctct ggttaataat ctcaggagca caaacattcc ggcccgggag gcgccctttg       120 gacctttgc aatcctggcg cactgaaccc ttgacccctg ccctgcagcc cccgcagctt        180
gctgtttgcc cactctattt gcccagcccc agtgaaatgc ctgccatata ttagtgccct       240
gaagtccaaa ggtagaggaa ccgagtgttt aaaaaattact gtggctgtgg agtcaacatg      300
atgtaaaaaa acaaacattt ggataacacc aagaagccag atatggttga aatgttgact      360
ggttgacaaa ataatttggg ttgcttaat ggtgcacaaa ggtaatgcaa aaccgatgac       420
ctaatgattc tgagcttggc aaaggtctta tctcccagct cgcccaggcc cagtgttcca      480
ggaatgtgac ctttgctgca gcagccgctg gaggggcag aggggatggg ctggaggttg        540
agcaaacaga gcagcagaaa aggcagttcc tcttctccag tgccctcctt ccctgtctct      600
gcctctccct cccttcctca ggcatcagag cggagacttc agggagacca gagcccagct      660
tgccaggcac tgagctagaa gccctgcc                                         688

<210> SEQ ID NO 215
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0246
```

-continued

```
<400> SEQUENCE: 215
aggttaattt ttaaaaagca gtcaaaagtc caagtggccc ttggcagcat ttactctctc      60
tgtttgctct ggttaataat ctcaggagca caaacattcc ggcccgggag gcgccctttg     120 gacctttgc aatcctggcg cactgaaccc ttgaccccctg ccctgcagcc cccgcagctt     180
gctgtttgcc cactctattt gcccagcccc aggggcatat aaaacagggg caaggcacag     240
actcatagca gagcaatcac caccaagcct ggaataactg cagccacc                 288

<210> SEQ ID NO 216
<211> LENGTH: 580
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0247

<400> SEQUENCE: 216
gctggtttct tataaaactg atggaagata caaacactat taaagaactg tttgcatgtt      60
gcaaatgatg tccaaagtcc aaacattgtt aataattaat actccaataa acatcatgtc     120
agaatttctg ttttcttttc cctttgaacc tttgcaggat tgccacatca tcaggaccac     180
accttcatca ggaatgaata tcaggctttc actttctcgc caacttacaa ggcctttctg     240
tgtaaacaat acctgaacct ttaccccgtt gcccggcaac ggccaggtct gtgccaagtg     300
tttgccgatg acctaatgat tctgagcttg gcaaaggtct tatctcccag ctcgcccagg     360
cccagtgttc caggaatgtg acctttgctg cagcagccgc tggaggggc agaggggatg       420 ggctggaggt tgagcaaaca gagcagcaga aaaggcagtt cctcttctcc agtgccctcc     480
ttccctgtct ctgcctctcc ctcccttcct caggcatcag agcggagact tcagggagac     540
cagagcccag cttgccaggc actgagctag aagccctgcc                          580

<210> SEQ ID NO 217
<211> LENGTH: 391
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0248

<400> SEQUENCE: 217
aggttaattt ttaaaaagca gtcaaaagtc caagtggccc ttggcagcat ttactctctc      60
tgtttgctct ggttaataat ctcaggagca caaacattcc ggcccgggag gcgccctttg     120 gacctttgc aatcctggcg cactgaaccc ttgaccccctg ccctgcagcc cccgcagctt     180
gctgtttgcc cactctattt gcccagcccc agcaggcttt cactttctcg ccaacttaca     240
aggcctttct gtgtaaacaa tacctgaacc tttaccccgt tgcccggcaa cggccaggtc     300
tgtgccaagt gtttggggca tataaaacag gggcaaggca cagactcata gcagagcaat     360
caccaccaag cctggaataa ctgcagccac c                                   391

<210> SEQ ID NO 218
<211> LENGTH: 507
<212> TYPE: DNA
<213> ORGANISM: Artificial Sequence
<220> FEATURE:
<223> OTHER INFORMATION: Description of Artificial Sequence: Synthetic
```

-continued

```
          polynucleotide
<220> FEATURE:
<223> OTHER INFORMATION: SP0249

<400> SEQUENCE: 218
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg cactgaaccc ttgacccctg ccctgcagcc cccgcagctt     180
gctgtttgcc cactctattt gcccagcccc agcaggcttt cactttctcg ccaacttaca     240
aggcctttct gtgtaaacaa tacctgaacc tttaccccgt tgcccggcaa cggccaggtc     300
tgtgccaagt gtttggggcg actcagatcc cagccagtgg acttagcccc tgtttgctcc     360
tccgataact ggggtgacct tggttaatat tcaccagcag cctcccccgt tgcccctctg     420
gatccactgc ttaaatacgg acgaggacag ggccctgtct cctcagcttc aggcaccacc     480
actgacctgg gacagtgaat cgccacc                                        507

<210> SEQ ID NO 219
<211> LENGTH: 689
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0250

<400> SEQUENCE: 219
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg cactgaaccc ttgacccctg ccctgcagcc cccgcagctt     180
gctgtttgcc cactctattt gcccagcccc aggctggttt cttataaaac tgatggaaga     240
tacaaacact attaaagaac tgtttgcatg ttgcaaatga tgtccaaagt ccaaacattg     300
ttaataatta atactccaat aaacatcatg tcagaatttc tgttttcttt tccctttgaa     360
cctttgcagg attgccacat catcaggacc acaccttcat caggaatgaa tatccgatga     420
cctaatgatt ctgagcttgg caaaggtctt atctcccagc tcgcccaggc ccagtgttcc     480
aggaatgtga cctttgctgc agcagccgct ggaggggggca gaggggatgg gctggaggtt     540
gagcaaacag agcagcagaa aaggcagttc ctcttctcca gtgccctcct tccctgtctc     600
tgcctctccc tcccttcctc aggcatcaga gcggagactt cagggagacc agagcccagc     660
ttgccaggca ctgagctaga agccctgcc                                      689

<210> SEQ ID NO 220
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0251

<400> SEQUENCE: 220
aggttaattt ttaaaaagca gtcaaaagtc caagtggccc ttggcagcat ttactctctc      60
tgtttgctct ggttaataat ctcaggagca caaacattcc ggcccgggag gcgccctttg     120
gaccttttgc aatcctggcg cactgaaccc ttgacccctg ccctgcagcc cccgcagctt     180
```

-continued

```
gctgtttgcc cactctattt gcccagcccc agaagcaaat atttgtggtt atggattaac      240
tcgaactgtt tgcccactct atttgcccgg gcatataaaa caggggcaag gcacagactc      300
atagcagagc aatcaccacc aagcctggaa taactgcagc cacc                      344
```

<210> SEQ ID NO 221
<211> LENGTH: 401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0252

<400> SEQUENCE: 221

```
aagcaaatat ttgtggttat ggattaactc gaactgtttg cccactctat ttgccccagg       60
ctttcacttt ctcgccaact tacaaggcct ttctgtgtaa acaatacctg aacctttacc      120
ccgttgcccg gcaacggcca ggtctgtgcc aagtgtttgc ctttgcaaca gcttatcgga      180
agcaaacaag ctgaggggaa ttgagcaaga atttctggga taccaacagc ataggaggaa      240
caaaggacgt agagggaggg ttgactgtct acacaggaca aagccaatga ttaaccaaac      300
ctcttgcaga tttaaatagg atgggaacta ggagtggcag caatcctttc tttcagctgg      360
agtgctcctc aggagccagc cccacccttq gaaaaqccac c                         401
```

<210> SEQ ID NO 222
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0253

<400> SEQUENCE: 222

```
aagcaaatat ttgtggttat ggattaactc gaactgtttg cccactctat ttgccccagg       60
ctttcacttt ctcgccaact tacaaggcct ttctgtgtaa acaatacctg aacctttacc      120
ccgttgcccg gcaacggcca ggtctgtgcc aagtgtttgc cgatgaccta atgattctga      180
gcttggcaaa ggtcttatct cccagctcgc ccaggcccag tgttccagga atgtgacctt      240
tgctgcagca gccgctggag ggggcagagg ggatgggctg gaggttgagc aaacagagca      300
gcagaaaagg cagttcctct tctccagtgc cctccttccc tgtctctgcc tctccctccc      360
ttcctcaggc atcagagcgg agacttcagg gagaccagag cccagcttgc caggcactga      420
gctagaagcc ctgcc                                                     435
```

<210> SEQ ID NO 223
<211> LENGTH: 485
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0254

<400> SEQUENCE: 223

```
aggttaattt ttaaaaagca gtcaaaagtc caagtggccc ttggcagcat ttactctctc       60
tgtttgctct ggttaataat ctcaggagca caaacattcc ggcccgggag gcgccctttg      120
```

```
gacctttgc aatcctggcg caggctttca ctttctcgcc aacttacaag gcctttctgt      180
gtaaacaata cctgaacctt tacccccgttg cccggcaacg gccaggtctg tgccaagtgt     240
ttgcctttgc aacagcttat cggaagcaaa caagctgagg ggaattgagc aagaatttct     300
gggataccaa cagcatagga ggaacaaagg acgtagaggg agggttgact gtctacacag     360
gacaaagcca atgattaacc aaacctcttg cagatttaaa taggatggga actaggagtg     420
gcagcaatcc tttctttcag ctggagtgct cctcaggagc cagccccacc cttagaaaag     480
ccacc                                                                  485

<210> SEQ ID NO 224
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0255

<400> SEQUENCE: 224
aggttaattt ttaaaaagca gtcaaaagtc caagtggccc ttggcagcat ttactctctc       60
tgtttgctct ggttaataat ctcaggagca caaacattcc ggcccgggag gcgccctttg      120 gacctttgc aatcctggcg caggctttca ctttctcgcc aacttacaag gcctttctgt      180
gtaaacaata cctgaacctt tacccccgttg cccggcaacg gccaggtctg tgccaagtgt     240
ttgccgatga cctaatgatt ctgagcttgg caaaggtctt atctcccagc tcgcccaggc     300
ccagtgttcc aggaatgtga cctttgctgc agcagccgct ggaggggca gaggggatgg      360 gctggaggtt gagcaaacag agcagcagaa aaggcagttc ctcttctcca gtgccctcct     420
tccctgtctc tgcctctccc tcccttcctc aggcatcaga gcggagactt cagggagacc     480
agagcccagc ttgccaggca ctgagctaga agccctgcc                            519

<210> SEQ ID NO 225
<211> LENGTH: 611
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0256

<400> SEQUENCE: 225
attggcatct tctattgctt ttcctggtga cttcattttt cactcttggc taaaaatggg       60
tctctgatga tttattctat cctgggtgtt gacaagctga agaagttgtg tggggcctgc      120
tgccagtaac cctgggtgac gaagcgtgac tcaccactcc gaggtcagtg gggggatgga     180
aggcagggga gtcagctgac aagatctgct gctttgtcac caggccttct gccaggcttt     240
cactttctcg ccaacttaca aggcctttct gtgtaaacaa tacctgaacc tttacccccgt     300 tgccccggcaa cggccaggtc tgtgccaagt gtttgccgat gacctaatga ttctgagctt     360
ggcaaaggtc ttatctccca gctcgcccag gcccagtgtt ccaggaatgt gacctttgct     420
gcagcagccg ctggaggggg cagaggggat gggctggagg ttgagcaaac agagcagcag     480
aaaaggcagt tcctcttctc cagtgccctc cttccctgtc tctgcctctc cctcccttcc     540
tcaggcatca gagcggagac ttcagggaga ccagagcccag gcttgccagg cactgagcta     600
```

-continued

```
gaagccctgc c                                                           611
```

```
<210> SEQ ID NO 226
<211> LENGTH: 580
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0257

<400> SEQUENCE: 226
caggctttca ctttctcgcc aacttacaag gcctttctgt gtaaacaata cctgaacctt        60
taccccgttg cccggcaacg gccaggtctg tgccaagtgt ttggctggtt tcttataaaa       120
ctgatggaag atacaaacac tattaaagaa ctgtttgcat gttgcaaatg atgtccaaag       180
tccaaacatt gttaataatt aatactccaa taaacatcat gtcagaattt ctgttttctt       240
ttccctttga acctttgcag gattgccaca tcatcaggac cacaccttca tcaggaatga       300
atatccgatg acctaatgat tctgagcttg gcaaaggtct tatctcccag ctcgcccagg       360
cccagtgttc caggaatgtg acctttgctg cagcagccgc tggaggggggc agaggggatg       420 ggctggaggt tgagcaaaca gagcagcaga aaaggcagtt cctcttctcc agtgccctcc       480
ttccctgtct ctgcctctcc ctcccttcct caggcatcag agcggagact tcagggagac       540
cagagcccag cttgccaggc actgagctag aagccctgcc                             580
```

```
<210> SEQ ID NO 227
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0258

<400> SEQUENCE: 227
ctgtttgctg cttgcaatgt ttgcccattt tagggaggtt aatttttaaa aagcagtcaa        60
aagtccaagt ggcccttggc agcatttact ctctctgttt gctctggtta ataatctcag       120
gagcacaaac attccggccc gggaggcgcc ctttggacct tttgcaatcc tggcgcactg       180
aacccttgac ccctgccctg cagcccccgc agcttgctgt ttgcccactc tatttgccca       240
gccccagccc tggagagtcc tttagcaggg caaagtgcaa cataggcaga ccttaaggga       300
tgactcagta acagataagc tttgtgtgcc tgcagggcat ataaaacagg ggcaaggcac       360
agactcatag cagagcaatc accaccaagc ctggaataac tgcagccacc                  410
```

```
<210> SEQ ID NO 228
<211> LENGTH: 512
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0259

<400> SEQUENCE: 228
ctgtttgctg cttgcaatgt ttgcccattt taggggctgg tttcttataa aactgatgga        60
agatacaaac actattaaag aactgtttgc atgttgcaaa tgatgtccaa agtccaaaca       120
```
ttgttaataa ttaatactcc aataaacatc atgtcagaat ttctgttttc ttttcccttt    180
gaacctttgc aggattgcca catcatcagg accacacctt catcaggaat gaatatccga    240
tgacctaatg attctgagct tggcaaaggt cttatctccc agctcgccca ggcccagtgt    300
tccaggaatg tgacctttgc tgcagcagcc gctggagggg gcagagggga tgggctggag    360
gttgagcaaa cagagcagca gaaaaggcag ttcctcttct ccagtgccct ccttccctgt    420
ctctgcctct ccctcccttc ctcaggcatc agagcggaga cttcagggag accagagccc    480
agcttgccag gcactgagct agaagccctg cc    512

<210> SEQ ID NO 229
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0264

<400> SEQUENCE: 229
caggctttca ctttctcgcc aacttacaag gcctttctgt gtaaacaata cctgaacctt    60
taccccgttg cccggcaacg gccaggtctg tgccaagtgt ttgcctttgc aacagcttat    120
cggaagcaaa caagctgagg ggaattgagc aagaatttct gggataccaa cagcatagga    180
ggaacaaagg acgtagaggg agggttgact gtctacacag gacaaagcca atgattaacc    240
aaacctcttg cagatttaaa taggatggga actaggagtg gcagcaatcc tttctttcag    300
ctggagtgct cctcaggagc cagccccacc cttagaaaag ccacc    345

<210> SEQ ID NO 230
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0265(LVR_SP131_A1)

<400> SEQUENCE: 230
aggttaattt ttaaaaagca gtcaaaagtc caagtggccc ttggcagcat ttactctctc    60
tgtttgctct ggttaataat ctcaggagca caaacattcc tgtaccggcc cgggaggcgc    120
cctttggacc ttttgcaatc ctggcgcact gaacccttga cccctgccct gcagcccccg    180
cagcttgctg tttgcccact ctatttgccc agccccagcc ctggagagtc ctttagcagg    240
gcaaagtgca acataggcag accttaaggg atgactcagt aacagataag ctttgtgtgc    300
ctgcagggca tataaaacag gggcaaggca cagactcata gcagagcaat caccaccaag    360
cctggaataa ctgcagccac c    381

<210> SEQ ID NO 231
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0266(LVR_SP131_V1)

<400> SEQUENCE: 231

-continued

```
aagcaaatat ttgtggttat ggattaactc gaactgtttg cccactctat ttgccctgta      60
ccggcccggg aggcgccctt tggacctttt gcaatcctgg cgcactgaac ccttgacccc     120
tgccctgcag cccccgcagc ttgctgtttg cccactctat ttgcccagcc ccagccctgg     180
agagtccttt agcagggcaa agtgcaacat aggcagacct taagggatga ctcagtaaca     240
gataagcttt gtgtgcctgc agggcatata aaacaggggc aaggcacaga ctcatagcag     300
agcaatcacc accaagcctg gaataactgc agccacc                              337
```

```
<210> SEQ ID NO 232
<211> LENGTH: 326
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0267(LVR_SP131_V2)

<400> SEQUENCE: 232
```

```
ggcgccctt tggacctttg caatcctgga gcaaacagca aacactgtac cggcccggga      60
ggcgcccttt ggacctttg caatcctggc gcactgaacc cttgacccct gccctgcagc     120
ccccgcagct tgctgtttgc ccactctatt tgcccagccc cagccctgga gagtccttta     180
gcagggcaaa gtgcaacata ggcagacctt aagggatgac tcagtaacag ataagctttg     240
tgtgcctgca gggcatataa aacaggggca aggcacagac tcatagcaga gcaatcacca     300
ccaagcctgg aataactgca gccacc                                         326
```

```
<210> SEQ ID NO 233
<211> LENGTH: 442
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0268 (LVR_132_A1)

<400> SEQUENCE: 233
```

```
aggttaattt ttaaaaagca gtcaaaagtc caagtggccc ttggcagcat ttactctctc      60
tgtttgctct ggttaataat ctcaggagca caaacattcc tgtaccagaa tgaacattga     120
actttggact atacctgagg ggtgaggtaa acaacaggac tataaatggc ccgggaggcg     180
ccctttggac cttttgcaat cctggcgcac tgaacccttg accctgccc tgcagccccc     240 gcagcttgct gtttgcccac tctatttgcc cagccccagc cctggagagt cctttagcag     300
ggcaaagtgc aacataggca gaccttaagg gatgactcag taacagataa gctttgtgtg     360
cctgcagggc atataaaaca ggggcaaggc acagactcat agcagagcaa tcaccaccaa     420
gcctggaata actgcagcca cc                                             442
```

```
<210> SEQ ID NO 234
<211> LENGTH: 398
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0269 (LVR_132_V1)

<400> SEQUENCE: 234
```

```
aagcaaatat ttgtggttat ggattaactc gaactgtttg cccactctat ttgccctgta         60
ccagaatgaa cattgaactt tggactatac ctgaggggtg aggtaaacaa caggactata        120
aatggcccgg gaggcgccct ttggaccttt tgcaatcctg gcgcactgaa cccttgaccc        180
ctgccctgca gcccccgcag cttgctgttt gcccactcta tttgcccagc cccagccctg        240
gagagtcctt tagcagggca aagtgcaaca taggcagacc ttaagggatg actcagtaac        300
agataagctt tgtgtgcctg cagggcatat aaaacagggg caaggcacag actcatagca        360
gagcaatcac caccaagcct ggaataactg cagccacc                                398
```

```
<210> SEQ ID NO 235
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0270 (LVR_132_V2)

<400> SEQUENCE: 235
ggcgcccttt ggacctttg caatcctgga gcaaacagca aacactgtac cagaatgaac          60
attgaacttt ggactatacc tgaggggtga ggtaaacaac aggactataa atggcccggg        120
aggcgccctt tggacctttt gcaatcctgg cgcactgaac ccttgacccc tgccctgcag        180
cccccgcagc ttgctgtttg cccactctat ttgcccagcc ccagccctgg agagtccttt        240
agcagggcaa agtgcaacat aggcagacct taagggatga ctcagtaaca gataagcttt        300
gtgtgcctgc agggcatata aaacaggggc aaggcacaga ctcatagcag agcaatcacc        360
accaagcctg gaataactgc agccacc                                            387
```

```
<210> SEQ ID NO 236
<211> LENGTH: 433
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0271 (LVR_133_A1)

<400> SEQUENCE: 236
aggttaattt ttaaaaagca gtcaaaagtc caagtggccc ttggcagcat ttactctctc         60
tgtttgctct ggttaataat ctcaggagca caaacattcc tgtaccagaa tgaacattga        120
actttggact atacctgagg ggtgaggtaa acaacaggac tataaatggc ccgggaggcg        180
ccctttggac cttttgcaat cctggcgctc ttttgtttta catgaagggt ctggcagcca        240
aagcaatcac tcaaagttca aaccttatca ttttttgctt tgttcctctt ggccttggtt        300
ttgtacatca gctttgaaaa taccatccca gggttaatgc tggggttaat ttataactaa        360
gagtgctcta gttttgcaat acaggacatg ctataaaaat ggaaagatgt tgctttctga        420
gagatgcgcc acc                                                            433
```

```
<210> SEQ ID NO 237
<211> LENGTH: 389
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

-continued

<223> OTHER INFORMATION: SP0272 (LVR_133_V1)

<400> SEQUENCE: 237
aagcaaatat ttgtggttat ggattaactc gaactgtttg cccactctat ttgccctgta        60
ccagaatgaa cattgaactt tggactatac ctgaggggtg aggtaaacaa caggactata       120
aatggcccgg gaggcgccct ttggaccttt tgcaatcctg gcgctctttt gttttacatg       180
aagggtctgg cagccaaagc aatcactcaa agttcaaacc ttatcatttt ttgctttgtt       240
cctcttggcc ttggttttgt acatcagctt tgaaaatacc atcccagggt taatgctggg       300
gttaatttat aactaagagt gctctagttt tgcaatacag gacatgctat aaaaatggaa       360
agatgttgct ttctgagaga tgcgccacc                                        389

<210> SEQ ID NO 238
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0273 (LVR_133_V2)

<400> SEQUENCE: 238
ggcgcccttt ggaccttttg caatcctgga gcaaacagca aacactgtac cagaatgaac        60
attgaacttt ggactatacc tgaggggtga ggtaaacaac aggactataa atggcccggg       120
aggcgccctt tggacctttt gcaatcctgg cgctcttttg ttttacatga agggtctggc       180
agccaaagca atcactcaaa gttcaaacct tatcattttt tgctttgttc ctcttggcct       240
tggttttgta catcagcttt gaaaatacca tcccagggtt aatgctgggg ttaatttata       300
actaagagtg ctctagtttt gcaatacagg acatgctata aaaatggaaa gatgttgctt       360
tctgagagat gcgccacc                                                    378

<210> SEQ ID NO 239
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0368

<400> SEQUENCE: 239
aggttaattt ttaaaaagca gtcaaaagtc caagtggccc ttggcagcat ttactctctc        60
tgtttgctct ggttaataat ctcaggagca caaacattcc agtcatatgt ttgctcactg       120
aaggttacta gttaacaggc atcccttaaa caggatataa aaggacttca gcaggactgc       180
tcgaaacatc ccactcagcc acc                                              203

<210> SEQ ID NO 240
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0373

<400> SEQUENCE: 240

-continued

```
aggttaattt ttaaaaagca gtcaaaagtc caagtggccc ttggcagcat ttactctctc      60
tgtttgctct ggttaataat ctcaggagca caaacattcc tgtaccggcc cgggaggcgc     120
cctttggacc ttttgcaatc ctggcggggc atataaaaca ggggcaaggc acagactcat     180
agcagagcaa tcaccaccaa gcctggaata actgcagcca cc                        222
```

```
<210> SEQ ID NO 241
<211> LENGTH: 275
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0378

<400> SEQUENCE: 241
tgctctctga caaagatacg gtgggtccca ctgatgaact gtgctgccac agtaaatgta      60
gccactatgc ctatctccat tctgaagatg tgccctgttc aaacatgtcc taatactctg     120
tctctgcaag ggtcatcagt agttttccat cttactcaac atcctcccag tgagtcatat     180
gtttgctcac tgaaggttac tagttaacag gcatccctta aacaggatat aaaaggactt     240
cagcaggact gctcgaaaca tcccactcag ccacc                                 275
```

```
<210> SEQ ID NO 242
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0379

<400> SEQUENCE: 242
cctccccgtg ttcctgctct ttgtccctct gtcctactta gactaatatt tgccttgggt      60
actgcaaaca ggaaatgggg gagggacagg agtagggcgg ccctgttcaa acatgtccta     120
atactctgtc tctgcaaggg tcatcagtag ttttccatct tactcaacat cctcccagtg     180
agtcatatgt ttgctcactg aaggttacta gttaacaggc atcccttaaa caggatataa     240
aaggacttca gcaggactgc tcgaaacatc ccactcagcc acc                        283
```

```
<210> SEQ ID NO 243
<211> LENGTH: 262
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0380

<400> SEQUENCE: 243
ccgcccccac tgaacccttg acccctgccc tgcagccccc gcagcttgct gtttgcccac      60
tctatttgcc cagccccagc cctgttcaaa catgtcctaa tactctgtct ctgcaagggt     120
catcagtagt tttccatctt actcaacatc ctcccagtga gtcatatgtt tgctcactga     180
aggttactag ttaacaggca tcccttaaac aggatataaa aggacttcag caggactgct     240
cgaaacatcc cactcagcca cc                                               262
```

```
<210> SEQ ID NO 244
```

```
<211> LENGTH: 268
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0381

<400> SEQUENCE: 244
aagctttctg aacagccaaa cagagattcc aaagttcagg caccaaagtt cagaccctaa      60
cagttattta caagggtcag ttacccctg ttcaaacatg tcctaatact ctgtctctgc      120
aagggtcatc agtagttttc catcttactc aacatcctcc cagtgagtca tatgtttgct      180
cactgaaggt tactagttaa caggcatccc ttaaacagga tataaaagga cttcagcagg      240
actgctcgaa acatcccact cagccacc                                        268

<210> SEQ ID NO 245
<211> LENGTH: 422
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0384

<400> SEQUENCE: 245
aggttaattt ttaaaaagca gtcaaaagtc caagtggccc ttggcagcat ttactctctc      60
tgtttgctct ggttaataat ctcaggagca caaacattcc ggcccgggag cgcccctttg     120
gaccttttgc aatcctggcg ccgatgacct aatgattctg agcttggcaa aggtcttatc     180
tcccagctcg cccaggccca gtgttccagg aatgtgacct ttgctgcagc agccgctgga     240
gggggcagag gggatgggct ggaggttgag caaacagagc agcagaaaag gcagttcctc     300
ttctccagtg ccctccttcc ctgtctctgc ctctccctcc cttcctcagg catcagagcg     360
gagacttcag ggagaccaga gcccagcttg ccaggcactg agctagaagc cctgccgcca     420
cc                                                                    422

<210> SEQ ID NO 246
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0388

<400> SEQUENCE: 246
aggttaattt ttaaaaagca gtcaaaagtc caagtggccc ttggcagcat ttactctctc      60
tgtttgctct ggttaataat ctcaggagca caaacattcc gggcatataa aacaggggca     120
aggcacagac tcatagcaga gcaatcacca ccaagcctgg aataactgca gccacc         176

<210> SEQ ID NO 247
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0396
```

<400> SEQUENCE: 247

```
aggttaattt ttaaaaagca gtcaaaagtc caagtggccc ttggcagcat ttactctctc      60
tgtttgctct ggttaataat ctcaggagca caaacattcc tgtaccggcc cgggaggcgc     120
cctttggacc ttttgcaatc ctggcgccct ggagagtcct ttagcagggc aaagtgcaac     180
ataggcagac cttaagggat gactcagtaa cagataagct ttgtgtgcct gcagggcata     240
taaaacaggg gcaaggcaca gactcatagc agagcaatca ccaccaagcc tggaataact     300
gcagccacc                                                             309
```

<210> SEQ ID NO 248
<211> LENGTH: 341
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: SP0397

<400> SEQUENCE: 248

```
aggttaattt ttaaaaagca gtcaaaagtc caagtggccc ttggcagcat ttactctctc      60
tgtttgctct ggttaataat ctcaggagca caaacattcc tgtacccact gaacccttga     120
cccctgccct gcagccccg cagcttgctg tttgcccact ctatttgccc agccccagcc     180
ctggagagtc ctttagcagg gcaaagtgca acataggcag accttaaggg atgactcagt     240
aacagataag ctttgtgtgc ctgcagggca tataaaacag gggcaaggca cagactcata     300
gcagagcaat caccaccaag cctggaataa ctgcagccac c                         341
```

<210> SEQ ID NO 249
<211> LENGTH: 545
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: SP0398

<400> SEQUENCE: 249

```
caggctttca ctttctcgcc aacttacaag gcctttctgt gtaaacaata cctgaacctt      60
taccccgttg cccggcaacg gccaggtctg tgccaagtgt ttgaggttaa tttttaaaaa     120
gcagtcaaaa gtccaagtgg cccttggcag catttactct ctctgtttgc tctggttaat     180
aatctcagga gcacaaacat tcctgtacca gaatgaacat tgaactttgg actatacctg     240
aggggtgagg taaacaacag gactataaat ggcccgggag gcgcccctttg gaccttttgc     300 aatcctggcg cactgaaccc ttgaccctg ccctgcagcc cccgcagctt gctgtttgcc     360
cactctattt gcccagcccc agccctggag agtcctttag cagggcaaag tgcaacatag     420
gcagacctta agggatgact cagtaacaga taagctttgt gtgcctgcag ggcatataaa     480 acagggggcaa ggcacagact catagcagag caatcaccac caagcctgga ataactgcag     540
ccacc                                                                 545
```

<210> SEQ ID NO 250
<211> LENGTH: 137
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: SP0399

<400> SEQUENCE: 250
agaatgaaca ttgaactttg gactatacct gaggggtgag gtaaacaaca ggactataaa        60
tgggcatata aaacaggggc aaggcacaga ctcatagcag agcaatcacc accaagcctg       120
gaataactgc agccacc                                                      137

<210> SEQ ID NO 251
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0403

<400> SEQUENCE: 251
caggctttca ctttctcgcc aacttacaag gcctttctgt gtaaacaata cctgaacctt        60
taccccgttg cccggcaacg gccaggtctg tgccaagtgt ttgaagcaaa tatttgtggt       120
tatggattaa ctcgaactgt ttgcccactc tatttgccct gtaccggccc gggaggcgcc       180
ctttggacct tttgcaatcc tggcgcactg aacccttgac ccctgccctg cagccccgc       240 agcttgctgt ttgcccactc tatttgccca gccccagccc tggagagtcc tttagcaggg       300
caaagtgcaa cataggcaga ccttaaggga tgactcagta acagataagc tttgtgtgcc       360
tgcagggcat ataaaacagg ggcaaggcac agactcatag cagagcaatc accaccaagc       420
ctggaataac tgcagccacc                                                   440

<210> SEQ ID NO 252
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0404

<400> SEQUENCE: 252
caggctttca ctttctcgcc aacttacaag gcctttctgt gtaaacaata cctgaacctt        60
taccccgttg cccggcaacg gccaggtctg tgccaagtgt ttgaagcaaa tatttgtggt       120
tatggattaa ctcgaactgt ttgcccactc tatttgccct gtaccagaat gaacattgaa       180
ctttggacta tacctgaggg gtgaggtaaa caacaggact ataaatggcc gggaggcgc       240 cctttggacc ttttgcaatc ctggcgcact gaacccttga cccctgccct gcagccccg       300 cagcttgctg tttgcccact ctatttgccc agccccagcc ctggagagtc ctttagcagg       360
gcaaagtgca acataggcag accttaaggg atgactcagt aacagataag ctttgtgtgc       420
ctgcagggca tataaaacag gggcaaggca cagactcata gcagagcaat caccaccaag       480
cctggaataa ctgcagccac c                                                 501

<210> SEQ ID NO 253
<211> LENGTH: 414
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: SP0405

<400> SEQUENCE: 253
caggctttca ctttctcgcc aacttacaag gcctttctgt gtaaacaata cctgaacctt        60
taccccgttg cccggcaacg gccaggtctg tgccaagtgt ttgaagcaaa tatttgtggt       120
tatggattaa ctcgaactgt ttgcccactc tatttgccct gtaccagaat gaacattgaa       180
ctttggacta tacctgaggg gtgaggtaaa caacaggact ataaatggcc cgggaggcgc       240
cctttggacc ttttgcaatc ctggcgcact gaacccttga cccctgccct gcagcccccg       300
cagcttgctg tttgcccact ctatttgccc agccccaggg gcatataaaa caggggcaag       360
gcacagactc atagcagagc aatcaccacc aagcctggaa taactgcagc cacc            414

<210> SEQ ID NO 254
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0406

<400> SEQUENCE: 254
aggttaattt ttaaaaagca gtcaaaagtc caagtggccc ttggcagcat ttactctctc        60
tgtttgctct ggttaataat ctcaggagca caaacattcc ggcccgggag gcgccctttg       120 gacctttgc aatcctggcg agtcatatgt ttgctcactg aaggttacta gttaacaggc       180
atcccttaaa caggatataa aaggacttca gcaggactgc tcgaaacatc ccactcagcc       240
acc                                                                     243

<210> SEQ ID NO 255
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0407

<400> SEQUENCE: 255
aggttaattt ttaaaaagca gtcaaaagtc caagtggccc ttggcagcat ttactctctc        60
tgtttgctct ggttaataat ctcaggagca caaacattcc caggctttca ctttctcgcc       120
aacttacaag gcctttctgt gtaaacaata cctgaacctt taccccgttg cccggcaacg       180
gccaggtctg tgccaagtgt ttggggcata taaaacaggg gcaaggcaca gactcatagc       240
agagcaatca ccaccaagcc tggaataact gcagccacc                              279

<210> SEQ ID NO 256
<211> LENGTH: 256
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0409

<400> SEQUENCE: 256

```
aggttaattt ttaaaaagca gtcaaaagtc caagtggccc ttggcagcat ttactctctc       60
tgtttgctct ggttaataat ctcaggagca caaacattcc ccctgttcaa acatgtccta      120
atactctgtc tctgcaaggg tcatcagtag ttttccatct tactcaacat cctcccagtg      180
gggcatataa aacaggggca aggcacagac tcatagcaga gcaatcacca ccaagcctgg      240
aataactgca gccacc                                                       256
```

<210> SEQ ID NO 257
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0411

<400> SEQUENCE: 257

```
ccctgttcaa acatgtccta atactctgtc tctgcaaggg tcatcagtag ttttccatct       60
tactcaacat cctcccagtg agtcatatgt ttgctcactg aaggttacta gttaacaggc      120
atcccttaaa caggatataa aaggacttca gcaggactgc tcgaaacatc ccactcagcc      180
acc                                                                     183
```

<210> SEQ ID NO 258
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0412

<400> SEQUENCE: 258

```
aggttaattt ttaaaaagca gtcaaaagtc caagtggccc ttggcagcat ttactctctc       60
tgtttgctct ggttaataat ctcaggagca caaacattcc ccctgttcaa acatgtccta      120
atactctgtc tctgcaaggg tcatcagtag ttttccatct tactcaacat cctcccagtg      180
agtcatatgt ttgctcactg aaggttacta gttaacaggc atcccttaaa caggatataa      240
aaggacttca gcaggactgc tcgaaacatc ccactcagcc acc                        283
```

<210> SEQ ID NO 259
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SP0413

<400> SEQUENCE: 259

```
aggttaattt ttaaaaagca gtcaaaagtc caagtggccc ttggcagcat ttactctctc       60
tgtttgctct ggttaataat ctcaggagca caaacattcc tgtaccggcc cgggaggcgc      120
cctttggacc ttttgcaatc ctggcgagtc atatgtttgc tcactgaagg ttactagtta      180
acaggcatcc cttaaacagg atataaaagg acttcagcag gactgctcga aacatcccac      240
tcagccacc                                                               249
```

```
<210> SEQ ID NO 260
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: LP1

<400> SEQUENCE: 260
ccctaaaatg ggcaaacatt gcaagcagca aacagcaaac acacagccct ccctgcctgc        60
tgaccttgga gctggggcag aggtcagaga cctctctggg cccatgccac ctccaacatc       120
cactcgaccc cttggaattt cggtggagag gagcagaggt tgtcctggcg tggtttaggt       180
agtgtgagag gggaatgact cctttcggta agtgcagtgg aagctgtaca ctgcccaggc       240
aaagcgtccg ggcagcgtag gcgggcgact cagatcccag ccagtggact tagcccctgt       300
ttgctcctcc gataactggg gtgaccttgg ttaatattca ccagcagcct ccccgttgc        360 ccctctggat ccactgctta aatacggacg aggacagggc cctgtctcct cagcttcagg       420
caccaccact gacctgggac agtgaatccg gactctaagg taaatataaa atttttaagt       480
gtataatgtg ttaaactact gattctaatt gtttctctct tttagattcc aacctttgga       540
actgaattct agaccacc                                                      558

<210> SEQ ID NO 261
<211> LENGTH: 580
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CMV-IE

<400> SEQUENCE: 261
atagtaatca attacggggt cattagttca tagcccatat atggagttcc gcgttacata        60
acttacggta aatggcccgc ctggctgacc gcccaacgac ccccgcccat tgacgtcaat       120
aatgacgtat gttcccatag taacgccaat agggactttc cattgacgtc aatgggtgga       180
gtatttacgg taaactgccc acttggcagt acatcaagtg tatcatatgc caagtacgcc       240
ccctattgac gtcaatgacg gtaaatggcc cgcctggcat tatgcccagt acatgacctt       300
atgggacttt cctacttggc agtacatcta cgtattagtc atcgctatta ccatggtgat       360
gcggttttgg cagtacatca atgggcgtgg atagcggttt gactcacggg gatttccaag       420
tctccacccc attgacgtca atgggagttt gttttggcac caaaatcaac gggactttcc       480
aaaatgtcgt aacaactccg ccccattgac gcaaatgggc ggtaggcgtg tacggtggga       540
ggtctatata agcagagctg gtttagtgaa ccgtcagatc                             580

<210> SEQ ID NO 262
<211> LENGTH: 1775
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CBA

<400> SEQUENCE: 262
agatctgaat tcggtaccta gttattaata gtaatcaatt acggggtcat tagttcatag        60
```

```
cccatatatg gagttccgcg ttacataact tacggtaaat ggcccgcctg gctgaccgcc        120
caacgacccc cgcccattga cgtcaataat gacgtatgtt cccatagtaa cgccaatagg        180
gactttccat tgacgtcaat gggtggagta tttacggtaa actgcccact tggcagtaca        240
tcaagtgtat catatgccaa gtacgccccc tattgacgtc aatgacggta aatggcccgc        300
ctggcattat gcccagtaca tgaccttatg ggactttcct acttggcagt acatctacgt        360
attagtcatc gctattacca tggtcgaggt gagccccacg ttctgcttca ctctccccat        420
ctcccccccc tccccacccc caattttgta tttatttatt ttttaattat tttgtgcagc        480 gatggggggcg gggggggggg ggggcgcgc gccaggcggg gcggggcggg gcgaggggcg        540
gggcggggcg aggcggagag gtgcggcggc agccaatcag agcggcgcgc tccgaaagtt        600
tccttttatg gcgaggcggc ggcggcggcg gccctataaa aagcgaagcg cgcggcgggc        660
gggagtcgct gcgcgctgcc ttcgccccgt gccccgctcc gccgccgcct cgcgccgccc        720
gccccggctc tgactgaccg cgttactccc acaggtgagc gggcgggacg gcccttctcc        780
tccgggctgt aattagcgct tggtttaatg acggcttgtt tctttctgtg gctgcgtga         840 aagccttgag gggctccggg agggcccttt gtgcgggggg agcggctcgg ggggtgcgtg        900
cgtgtgtgtg tgcgtgggga gcgccgcgtg cggctccgcg ctgcccggcg gctgtgagcg        960
ctgcgggcgc ggcgcggggc tttgtgcgct ccgcagtgtg cgcgagggga gcgcggccgg       1020
gggcggtgcc ccgcggtgcg ggggggctg cgaggggaac aaaggctgcg tgcggggtgt       1080
gtgcgtgggg gggtgagcag ggggtgtggg cgcgtcggtc gggctgcaac ccccctgca        1140 ccccctccc cgagttgctg agcacggccc ggcttcgggt gcggggctcc gtacggggcg       1200
tggcgcgggg ctcgccgtgc cgggcggggg gtggcggcag gtggggggtgc cgggcggggc      1260 ggggccgcct cgggccgggg agggctcggg ggaggggcgc ggcggccccc ggagcgccgg      1320
cggctgtcga ggcgcggcga ccgcagcca ttgcctttta tggtaatcgt gcgagagggc       1380
gcagggactt cctttgtccc aaatctgtgc ggagccgaaa tctgggaggc gccgccgcac      1440
cccctctagc gggcgcgggg cgaagcggtg cggcgccggc aggaaggaaa tgggcggggga     1500 gggccttcgt gcgtcgccgc gccgccgtcc ccttctccct ctccagcctc ggggctgtcc      1560
gcggggggac ggctgccttc ggggggggacg gggcagggcg gggttcggct tctggcgtgt     1620
gaccggcggc tctagagcct ctgctaacca tgttcatgcc ttcttctttt tcctacagct      1680
cctgggcaac gtgctggtta ttgtgctgtc tcatcatttt ggcaaagaat tcctcgaaga      1740
tctaggcaac gcgtctcgag gcggccgccg ccacc                                 1775
```

```
<210> SEQ ID NO 263
<211> LENGTH: 890
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TBG

<400> SEQUENCE: 263 aggttaatttt ttaaaaagca gtcaaaagtc caagtggccc ttggcagcat ttactctctc         60
tgtttgctct ggttaataat ctcaggagca caaacattcc agatccaggt taattttttaa        120 aaagcagtca aaagtccaag tggcccttgg cagcatttac tctctctgtt tgctctggtt        180
aataatctca ggagcacaaa cattccagat ccggcgcgcc agggctggaa gctacctttg        240
```

-continued

```
acatcatttc ctctgcgaat gcatgtataa tttctacaga acctattaga aaggatcacc      300
cagcctctgc ttttgtacaa ctttcccttaa aaaaactgcc aattccactg ctgtttggcc      360
caatagtgag aacttttttcc tgctgcctct tggtgctttt gcctatggcc cctattctgc      420
ctgctgaaga cactcttgcc agcatggact aaaccccctc cagctctgac aatcctcttt      480
ctcttttgtt ttacatgaag ggtctggcag ccaaagcaat cactcaaagt tcaaaccttta      540 tcatttttttg ctttgttcct cttggccttg gttttgtaca tcagctttga aaataccatc      600
ccagggttaa tgctgggggtt aatttataac taagagtgct ctagttttgc aatacaggac      660
atgctataaa aatggaaaga tgttgctttc tgagagactg cagaagttgg tcgtgaggca      720
ctgggcaggt aagtatcaag gttacaagac aggtttaagg agaccaatag aaactgggct      780
tgtcgagaca gagaagactc ttgcgtttct gataggcacc tattggtctt actgacatcc      840
actttgcctt tctctccaca gggcaatccg gtactgttgg taaagccacc      890
```

<210> SEQ ID NO 264
<211> LENGTH: 6178
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: pAAV_SYNP_Luc_2A_GFP

<400> SEQUENCE: 264

```
agcgcccaat acgcaaaccg cctctccccg cgcgttggcc gattcattaa tgcagctggc       60
acgacaggtt tcccgactgg aaagcgggca gtgagcgcaa cgcaattaat gtgagttagc      120
tcactcatta ggcaccccag gctttacact ttatgcttcc ggctcgtatg ttgtgtggaa      180
ttgtgagcgg ataacaattt cacacaggaa acagctatga ccatgattac gaattgcctg      240
caggcagctg cgcgctcgct cgctcactga ggccgcccgg gcaaagcccg ggcgtcgggc      300
gacctttggt cgcccggcct cagtgagcga gcgagcgcgc agagagggag tggccaactc      360
catcactagg ggttcctatc gatatcaagc ttggtaccga gtctgatcgt agcggccgcc      420
accatggaag atgccaaaaa cattaagaag ggcccagcgc cattctaccc actcgaagac      480
gggaccgccg gcgagcagct gcacaaagcc atgaagcgct acgccctggt gcccggcacc      540
atcgccttta ccgacgcaca tatcgaggtg gacattacct acgccgagta cttcgagatg      600
agcgttcggc tggcagaagc tatgaagcgc tatgggctga atacaaacca tcggatcgtg      660
gtgtgcagcg agaatagctt gcagttcttc atgcccgtgt tgggtgccct gttcatcggt      720
gtggctgtgg ccccagctaa cgacatctac aacgagcgcg agctgctgaa cagcatgggc      780
atcagccagc ccaccgtcgt attcgtgagc aagaaagggc tgcaaaagat cctcaacgtg      840
caaaagaagc taccgatcat acaaaagatc atcatcatgg atagcaagac cgactaccag      900
ggcttccaaa gcatgtacac cttcgtgact tcccatttgc cacccggctt caacgagtac      960
gacttcgtgc ccgagagctt cgaccgggac aaaaccatcg ccctgatcat gaacagtagt     1020
ggcagtaccg gattgcccaa gggcgtagcc ctaccgcacc gcaccgcttg tgtccgattc     1080
agtcatgccc gcgaccccat cttcggcaac cagatcatcc ccgacaccgc tatcctcagc     1140
gtggtgccat tcaccacgg cttcggcatg ttcaccacgc tgggctactt gatctgcggc     1200
tttcgggtcg tgctcatgta ccgcttcgag gaggagctat tcttgcgcag cttgcaagac     1260
tataagattc aatctgccct gctggtgccc acactattta gcttcttcgc taagagcact     1320
```

-continued

```
ctcatcgaca agtacgacct aagcaacttg cacgagatcg ccagcggcgg ggcgccgctc    1380
agcaaggagg taggtgaggc cgtggccaaa cgcttccacc taccaggcat ccgccagggc    1440
tacggcctga cagaaacaac cagcgccatt ctgatcaccc ccgaaggggga cgacaagcct   1500 ggcgcagtag gcaaggtggt gcccttcttc gaggctaagg tggtggactt ggacaccggt    1560
aagacactgg gtgtgaacca gcgcggcgag ctgtgcgtcc gtggccccat gatcatgagc    1620
ggctacgtta acaaccccga ggctacaaac gctctcatcg acaaggacgg ctggctgcac     1680
agcggcgaca tcgcctactg ggacgaggac gagcacttct tcatcgtgga ccggctgaag    1740
agcctgatca aatacaaggg ctaccaggta gccccagccg aactggagag catcctgctg    1800
caacacccca acatcttcga cgccggggtc gccggcctgc ccgacgacga tgccggcgag    1860
ctgcccgccg cagtcgtcgt gctggaacac ggtaaaacca tgaccgagaa ggagatcgtg    1920
gactatgtgg ccagccaggt tacaaccgcc aagaagctgc gcggtggtgt tgtgttcgtg    1980
gacgaggtgc ctaaaggact gaccggcaag ttggacgccc gcaagatccg cgagattctc    2040
attaaggcca agaagggcgg caagatcgcc gtgggatccg gagagggcag aggaagtctt    2100
ctaacatgcg gtgacgtgga ggagaatccc ggccctatgg tgagcaaggg cgaggagctg    2160
ttcaccgggg tggtgcccat cctggtcgag ctggacggcg acgtaaacgg ccacaagttc    2220
agcgtgtccg gcgagggcga gggcgatgcc acctacggca agctgaccct gaagttcatc    2280
tgcaccaccg gcaagctgcc cgtgccctgg cccaccctcg tgaccaccct gacctacggc    2340
gtgcagtgct tcagccgcta ccccgaccac atgaagcagc acgacttctt caagtccgcc    2400
atgcccgaag gctacgtcca ggagcgcacc atcttcttca aggacgacgg caactacaag    2460
acccgcgccg aggtgaagtt cgagggcgac accctggtga accgcatcga gctgaagggc    2520
atcgacttca aggaggacgg caacatcctg gggcacaagc tggagtacaa ctacaacagc    2580
cacaacgtct atatcatggc cgacaagcag aagaacggca tcaaggtgaa cttcaagatc    2640
cgccacaaca tcgaggacgg cagcgtgcag ctcgccgacc actaccagca gaacacccccc   2700 atcggcgacg gccccgtgct gctgcccgac aaccactacc tgagcaccca gtccaagctg    2760
agcaaagacc ccaacgagaa gcgcgatcac atggtcctgc tggagttcgt gaccgccgcc    2820
gggatcactc tcggcatgga cgagctgtac aagtaatgaa tcgatggtct ctacgagtaa    2880
tagacgccca gttgaattcc ttcgagcaga catgataaga tacattgatg agtttggaca    2940
aaccacaact agaatgcagt gaaaaaaatg ctttatttgt gaaatttgtg atgctattgc    3000
tttatttgta accattataa gctgcaataa acaagttaac aacaacaatt gcattcattt    3060
tatgtttcag gttcaggggg aggtgtggga ggttttttaa agcaagtaaa acctctacaa    3120
atgtggtaaa atcgataagg atccgtcgac agatctagga cccctagtg atggagttgg     3180 ccactccctc tctgcgcgct cgctcgctca ctgaggccgg gcgaccaaag gtcgcccgac    3240
gcccgggctt tgcccgggcg gcctcagtga gcgagcgagc gcgcagctgc ctgcaggcag    3300
cttggcactg gccgtcgttt tacaacgtcg tgactgggaa aaccctggcg ttacccaact    3360
taatcgcctt gcagcacatc cccctttcgc cagctggcgt aatagcgaag aggcccgcac    3420
cgatcgccct tcccaacagt tgcgcagcct gaatggcgaa tggcgcctga tgcggtattt    3480
tctccttacg catctgtgcg gtatttcaca ccgcatacgt caaagcaacc atagtacgcg    3540
ccctgtagcg gcgcattaag cgcggcgggt gtggtggtta cgcgcagcgt gaccgctaca    3600
cttgccagcg ccctagcgcc cgctcctttc gctttcttcc cttcctttct cgccacgttc    3660
```

-continued

```
gccggctttc cccgtcaagc tctaaatcgg gggctccctt tagggttccg atttagtgct    3720
ttacggcacc tcgaccccaa aaaacttgat ttgggtgatg gttcacgtag tgggccatcg    3780
ccctgataga cggttttttcg ccctttgacg ttggagtcca cgttctttaa tagtggactc    3840
ttgttccaaa ctggaacaac actcaaccct atctcgggct attcttttga tttataaggg    3900
attttgccga tttcggccta ttggttaaaa aatgagctga tttaacaaaa atttaacgcg    3960
aattttaaca aaatattaac gtttacaatt ttatggtgca ctctcagtac aatctgctct    4020
gatgccgcat agttaagcca gccccgacac ccgccaacac ccgctgacgc gccctgacgg    4080
gcttgtctgc tcccggcatc cgcttacaga caagctgtga ccgtctccgg gagctgcatg    4140
tgtcagaggt tttcaccgtc atcaccgaaa cgcgcgagac gaaagggcct cgtgatacgc    4200
ctatttttat aggttaatgt catgataata atggtttctt agacgtcagg tggcactttt    4260
cggggaaatg tgcgcggaac ccctatttgt ttatttttct aaatacattc aaatatgtat    4320
ccgctcatga caataaacc ctgataaatg cttcaataat attgaaaaag gaagagtatg    4380
agtattcaac atttccgtgt cgcccttatt ccctttttg cggcattttg ccttcctgtt    4440
tttgctcacc cagaaacgct ggtgaaagta aaagatgctg aagatcagtt gggtgcacga    4500
gtgggttaca tcgaactgga tctcaacagc ggtaagatcc ttgagagttt tcgccccgaa    4560
gaacgttttc caatgatgag cacttttaaa gttctgctat gtggcgcggt attatcccgt    4620
attgacgccg ggcaagagca actcggtcgc cgcatacact attctcagaa tgacttggtt    4680
gagtactcac cagtcacaga aaagcatctt acggatggca tgacagtaag agaattatgc    4740
agtgctgcca taaccatgag tgataacact gcggccaact tacttctgac aacgatcgga    4800
ggaccgaagg agctaaccgc ttttttgcac aacatggggg atcatgtaac tcgccttgat    4860
cgttgggaac cggagctgaa tgaagccata ccaaacgacg agcgtgacac cacgatgcct    4920
gtagcaatgg caacaacgtt gcgcaaacta ttaactggcg aactacttac tctagcttcc    4980
cggcaacaat taatagactg gatggaggcg gataaagttg caggaccact tctgcgctcg    5040
gcccttccgg ctggctggtt tattgctgat aaatctggag ccggtgagcg tgggtctcgc    5100
ggtatcattg cagcactggg gccagatggt aagccctccc gtatcgtagt tatctacacg    5160
acggggagtc aggcaactat ggatgaacga aatagacaga tcgctgagat aggtgcctca    5220
ctgattaagc attggtaact gtcagaccaa gtttactcat atatacttta gattgattta    5280
aaacttcatt tttaatttaa aaggatctag gtgaagatcc ttttttgataa tctcatgacc    5340 aaaatccctt aacgtgagtt ttcgttccac tgagcgtcag accccgtaga aaagatcaaa    5400
ggatcttctt gagatccttt ttttctgcgc gtaatctgct gcttgcaaac aaaaaaacca    5460
ccgctaccag cggtggtttg tttgccggat caagagctac caactctttt tccgaaggta    5520
actggcttca gcagagcgca gataccaaat actgttcttc tagtgtagcc gtagttaggc    5580
caccacttca agaactctgt agcaccgcct acatacctcg ctctgctaat cctgttacca    5640
gtggctgctg ccagtggcga taagtcgtgt cttaccgggt tggactcaag acgatagtta    5700
ccggataagg cgcagcggtc gggctgaacg gggggttcgt gcacacagcc cagcttggag    5760
cgaacgacct acaccgaact gagatacccta cagcgtgagc tatgagaaag cgccacgctt    5820
cccgaaggga gaaaggcgga caggtatccg gtaagcggca gggtcggaac aggagagcgc    5880
acgagggagc ttccaggggg aaacgcctgg tatctttata gtcctgtcgg gtttcgccac    5940
ctctgacttg agcgtcgatt tttgtgatgc tcgtcagggg ggcggagcct atggaaaaac    6000
gccagcaacg cggcctttttt acggttcctg gccttttgct ggccttttgc tcacatgttc    6060
```

-continued

```
tttcctgcgt tatcccctga ttctgtggat aaccgtatta ccgcctttga gtgagctgat     6120
accgctcgcc gcagccgaac gaccgagcgc agcgagtcag tgagcgagga agcggaag       6178

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: forward primer

<400> SEQUENCE: 265
acgctgggct acttgatc                                                      18

<210> SEQ ID NO 266
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: reverse primer

<400> SEQUENCE: 266
cgaggaggag ctattcttg                                                     19

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: probe

<400> SEQUENCE: 267
tttcgggtcg tgctcatg                                                      18

<210> SEQ ID NO 268
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: the functional variant of CRE0018
<220> FEATURE:
<221> NAME/KEY: modified_base
<222> LOCATION: (19)..(38)
<223> OTHER INFORMATION: a, c, t, g, unknown or other
<220> FEATURE:
<221> NAME/KEY: misc_feature
<222> LOCATION: (19)..(38)
<223> OTHER INFORMATION: This region may encompass 10 to 20 nucleotides
<220> FEATURE:
<221> NAME/KEY: modified_base
<222> LOCATION: (52)..(61)
<223> OTHER INFORMATION: a, c, t, g, unknown or other
<220> FEATURE:
<221> NAME/KEY: misc_feature
<222> LOCATION: (52)..(61)
<223> OTHER INFORMATION: This region may encompass 1 to 10 nucleotides
<220> FEATURE:
<221> NAME/KEY: modified_base
<222> LOCATION: (76)..(85)
```

```
<223> OTHER INFORMATION: a, c, t, g, unknown or other
<220> FEATURE:
<221> NAME/KEY: misc_feature
<222> LOCATION: (76)..(85)
<223> OTHER INFORMATION: This region may encompass 1 to 10 nucleotides
<220> FEATURE:
<221> NAME/KEY: modified_base
<222> LOCATION: (99)..(108)
<223> OTHER INFORMATION: a, c, t, g, unknown or other
<220> FEATURE:
<221> NAME/KEY: misc_feature
<222> LOCATION: (99)..(108)
<223> OTHER INFORMATION: This region may encompass 1 to 10 nucleotides
<220> FEATURE:
<223> OTHER INFORMATION: See specification as filed for detailed
      description of substitutions and preferred embodiments

<400> SEQUENCE: 268
ctttcacttt ctcgccaann nnnnnnnnnn nnnnnnnntg tgtaaacaat annnnnnnnn      60
nctgaacctt tacccnnnnn nnnnngttgc ccggcaacnn nnnnnnnnca ggtctgtgcc     120
aagtgtttg                                                            129

<210> SEQ ID NO 269
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0042
<220> FEATURE:
<221> NAME/KEY: modified_base
<222> LOCATION: (12)..(21)
<223> OTHER INFORMATION: a, c, t, g, unknown or other
<220> FEATURE:
<221> NAME/KEY: misc_feature
<222> LOCATION: (12)..(21)
<223> OTHER INFORMATION: This region may encompass 1 to 10 nucleotides
<220> FEATURE:
<221> NAME/KEY: modified_base
<222> LOCATION: (33)..(42)
<223> OTHER INFORMATION: a, c, t, g, unknown or other
<220> FEATURE:
<221> NAME/KEY: misc_feature
<222> LOCATION: (33)..(42)
<223> OTHER INFORMATION: This region may encompass 1 to 10 nucleotides
<220> FEATURE:
<221> NAME/KEY: modified_base
<222> LOCATION: (55)..(77)
<223> OTHER INFORMATION: a, c, t, g, unknown or other
<220> FEATURE:
<221> NAME/KEY: misc_feature
<222> LOCATION: (55)..(77)
<223> OTHER INFORMATION: This region may encompass 8 to 23 nucleotides
<220> FEATURE:
<223> OTHER INFORMATION: See specification as filed for detailed
      description of substitutions and preferred embodiments

<400> SEQUENCE: 269
gttcaaacat gnnnnnnnnn nctaatactc tgnnnnnnnn nntgcaaggg tcatnnnnnn      60
nnnnnnnnnn nnnnnnntta ctcaaca                                         87

<210> SEQ ID NO 270
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: functional variant of CRE0051
```

-continued

```
<220> FEATURE:
<221> NAME/KEY: modified_base
<222> LOCATION: (14)..(39)
<223> OTHER INFORMATION: a, c, t, g, unknown or other
<220> FEATURE:
<221> NAME/KEY: misc_feature
<222> LOCATION: (14)..(39)
<223> OTHER INFORMATION: This region may encompass 10 to 26 nucleotides
<220> FEATURE:
<221> NAME/KEY: modified_base
<222> LOCATION: (51)..(72)
<223> OTHER INFORMATION: a, c, t, g, unknown or other
<220> FEATURE:
<221> NAME/KEY: misc_feature
<222> LOCATION: (51)..(72)
<223> OTHER INFORMATION: This region may encompass 8 to 22 nucleotides
<220> FEATURE:
<221> NAME/KEY: modified_base
<222> LOCATION: (80)..(89)
<223> OTHER INFORMATION: a, c, t, g, unknown or other
<220> FEATURE:
<221> NAME/KEY: misc_feature
<222> LOCATION: (80)..(89)
<223> OTHER INFORMATION: This region may encompass 1 to 10 nucleotides
<220> FEATURE:
<221> NAME/KEY: modified_base
<222> LOCATION: (105)..(117)
<223> OTHER INFORMATION: a, c, t, g, unknown or other
<220> FEATURE:
<221> NAME/KEY: misc_feature
<222> LOCATION: (105)..(117)
<223> OTHER INFORMATION: This region may encompass 1 to 13 nucleotides
<220> FEATURE:
<223> OTHER INFORMATION: See specification as filed for detailed
      description of substitutions and preferred embodiments

<400> SEQUENCE: 270
gttaattttt aaannnnnnn nnnnnnnnnn nnnnnnnnng tggcccttgg nnnnnnnnnn      60
nnnnnnnnnn nntgtttgcn nnnnnnnnnt ggttaataat ctcannnnnn nnnnnnnaca     120
aaca                                                                124

<210> SEQ ID NO 271
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0058

<400> SEQUENCE: 271
gcgccctttg gaccttttgc aatcctgg                                       28

<210> SEQ ID NO 272
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0065
<220> FEATURE:
<221> NAME/KEY: modified_base
<222> LOCATION: (19)..(48)
<223> OTHER INFORMATION: a, c, t, g, unknown or other
<220> FEATURE:
<221> NAME/KEY: misc_feature
<222> LOCATION: (19)..(48)
<223> OTHER INFORMATION: This region may encompass 14 to 30 nucleotides
<220> FEATURE:
<221> NAME/KEY: modified_base
```

```
<222> LOCATION: (59)..(68)
<223> OTHER INFORMATION: a, c, t, g, unknown or other
<220> FEATURE:
<221> NAME/KEY: misc_feature
<222> LOCATION: (59)..(68)
<223> OTHER INFORMATION: This region may encompass 1 to 10 nucleotides
<220> FEATURE:
<223> OTHER INFORMATION: See specification as filed for detailed
      description of substitutions and preferred embodiments

<400> SEQUENCE: 272
actgaaccct tgacccctnn nnnnnnnnnn nnnnnnnnnn nnnnnnnnct gtttgcccnn      60
nnnnnnnnta tttgccc                                                    77

<210> SEQ ID NO 273
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: functional variant of CRE0065.1
<220> FEATURE:
<221> NAME/KEY: modified_base
<222> LOCATION: (19)..(48)
<223> OTHER INFORMATION: a, c, t, g, unknown or other
<220> FEATURE:
<221> NAME/KEY: misc_feature
<222> LOCATION: (19)..(48)
<223> OTHER INFORMATION: This region may encompass 14 to 30 nucleotides
<220> FEATURE:
<221> NAME/KEY: modified_base
<222> LOCATION: (59)..(68)
<223> OTHER INFORMATION: a, c, t, g, unknown or other
<220> FEATURE:
<221> NAME/KEY: misc_feature
<222> LOCATION: (59)..(68)
<223> OTHER INFORMATION: This region may encompass 1 to 10 nucleotides
<220> FEATURE:
<221> NAME/KEY: modified_base
<222> LOCATION: (78)..(102)
<223> OTHER INFORMATION: a, c, t, g, unknown or other
<220> FEATURE:
<221> NAME/KEY: misc_feature
<222> LOCATION: (78)..(102)
<223> OTHER INFORMATION: This region may encompass 9 to 25 nucleotides
<220> FEATURE:
<223> OTHER INFORMATION: See specification as filed for detailed
      description of substitutions and preferred embodiments

<400> SEQUENCE: 273
actgaaccct tgacccctnn nnnnnnnnnn nnnnnnnnnn nnnnnnnnct gtttgcccnn      60
nnnnnnnnta tttgcccnnn nnnnnnnnnn nnnnnnnnnn nntgatcctt gaactct       117

<210> SEQ ID NO 274
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0066
<220> FEATURE:
<221> NAME/KEY: modified_base
<222> LOCATION: (16)..(43)
<223> OTHER INFORMATION: a, c, t, g, unknown or other
<220> FEATURE:
<221> NAME/KEY: misc_feature
<222> LOCATION: (16)..(43)
<223> OTHER INFORMATION: This region may encompass 10 to 28 nucleotides
<220> FEATURE:
```

<223> OTHER INFORMATION: See specification as filed for detailed
      description of substitutions and preferred embodiments

<400> SEQUENCE: 274
gcagggcaaa gtgcannnnn nnnnnnnnnn nnnnnnnnnn nnngatgact cag          53

<210> SEQ ID NO 275
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0068
<220> FEATURE:
<221> NAME/KEY: modified_base
<222> LOCATION: (18)..(37)
<223> OTHER INFORMATION: a, c, t, g, unknown or other
<220> FEATURE:
<221> NAME/KEY: misc_feature
<222> LOCATION: (18)..(37)
<223> OTHER INFORMATION: This region may encompass 4 to 20 nucleotides
<220> FEATURE:
<221> NAME/KEY: modified_base
<222> LOCATION: (53)..(82)
<223> OTHER INFORMATION: a, c, t, g, unknown or other
<220> FEATURE:
<221> NAME/KEY: misc_feature
<222> LOCATION: (53)..(82)
<223> OTHER INFORMATION: This region may encompass 10 to 30 nucleotides
<220> FEATURE:
<223> OTHER INFORMATION: See specification as filed for detailed
      description of substitutions and preferred embodiments

<400> SEQUENCE: 275
ttcctgctct ttgtcccnnn nnnnnnnnnn nnnnnnnaga ctaatatttg ccnnnnnnnn     60
nnnnnnnnnn nnnnnnnnnn nnatggggga gggacag                              97

<210> SEQ ID NO 276
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0074
<220> FEATURE:
<221> NAME/KEY: modified_base
<222> LOCATION: (20)..(42)
<223> OTHER INFORMATION: a, c, t, g, unknown or other
<220> FEATURE:
<221> NAME/KEY: misc_feature
<222> LOCATION: (20)..(42)
<223> OTHER INFORMATION: This region may encompass 7 to 23 nucleotides
<220> FEATURE:
<223> OTHER INFORMATION: See specification as filed for detailed
      description of substitutions and preferred embodiments

<400> SEQUENCE: 276
aacattgaac tttggactan nnnnnnnnnn nnnnnnnnnn nngtaaacaa              50

<210> SEQ ID NO 277
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: functional variant of CRE0051

```
<220> FEATURE:
<221> NAME/KEY: modified_base
<222> LOCATION: (14)..(23)
<223> OTHER INFORMATION: a, c, t, g, unknown or other
<220> FEATURE:
<221> NAME/KEY: misc_feature
<222> LOCATION: (14)..(23)
<223> OTHER INFORMATION: This region may encompass 1 to 10 nucleotides
<220> FEATURE:
<221> NAME/KEY: modified_base
<222> LOCATION: (39)..(48)
<223> OTHER INFORMATION: a, c, t, g, unknown or other
<220> FEATURE:
<221> NAME/KEY: misc_feature
<222> LOCATION: (39)..(48)
<223> OTHER INFORMATION: This region may encompass 1 to 10 nucleotides
<220> FEATURE:
<221> NAME/KEY: modified_base
<222> LOCATION: (61)..(91)
<223> OTHER INFORMATION: a, c, t, g, unknown or other
<220> FEATURE:
<221> NAME/KEY: misc_feature
<222> LOCATION: (61)..(91)
<223> OTHER INFORMATION: This region may encompass 11 to 31 nucleotides
<220> FEATURE:
<223> OTHER INFORMATION: See specification as filed for detailed
      description of substitutions and preferred embodiments

<400> SEQUENCE: 277
tccaaagtcc aaannnnnnn nnntgttaat aattaatann nnnnnnnnca ataaacatca      60
nnnnnnnnnn nnnnnnnnnn nnnnnnnnnn nttccctttg aacctt                    106

<210> SEQ ID NO 278
<211> LENGTH: 179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: functional variant of CRE0012
<220> FEATURE:
<221> NAME/KEY: modified_base
<222> LOCATION: (16)..(58)
<223> OTHER INFORMATION: a, c, t, g, unknown or other
<220> FEATURE:
<221> NAME/KEY: misc_feature
<222> LOCATION: (16)..(58)
<223> OTHER INFORMATION: This region may encompass 23 to 43 nucleotides
<220> FEATURE:
<221> NAME/KEY: modified_base
<222> LOCATION: (71)..(128)
<223> OTHER INFORMATION: a, c, t, g, unknown or other
<220> FEATURE:
<221> NAME/KEY: misc_feature
<222> LOCATION: (71)..(128)
<223> OTHER INFORMATION: This region may encompass 38 to 58 nucleotides
<220> FEATURE:
<221> NAME/KEY: modified_base
<222> LOCATION: (141)..(168)
<223> OTHER INFORMATION: a, c, t, g, unknown or other
<220> FEATURE:
<221> NAME/KEY: misc_feature
<222> LOCATION: (141)..(168)
<223> OTHER INFORMATION: This region may encompass 8 to 28 nucleotides
<220> FEATURE:
<223> OTHER INFORMATION: See specification as filed for detailed
      description of substitutions and preferred embodiments

<400> SEQUENCE: 278
aagtccaaag gtagannnnn nnnnnnnnnn nnnnnnnnnn nnnnnnnnnn nnnnnnnnga      60
gtcaacatga nnnnnnnnnn nnnnnnnnnn nnnnnnnnnn nnnnnnnnnn nnnnnnnnnn     120
nnnnnnnnaa atgttgactg nnnnnnnnnn nnnnnnnnnn nnnnnnnngg ttgcttaat      179
```

```
<210> SEQ ID NO 279
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0047

<400> SEQUENCE: 279
gcaatgtttg cccat                                                      15

<210> SEQ ID NO 280
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0056
<220> FEATURE:
<221> NAME/KEY: modified_base
<222> LOCATION: (24)..(55)
<223> OTHER INFORMATION: a, c, t, g, unknown or other
<220> FEATURE:
<221> NAME/KEY: misc_feature
<222> LOCATION: (24)..(55)
<223> OTHER INFORMATION: This region may encompass 12 to 32 nucleotides
<220> FEATURE:
<223> OTHER INFORMATION: See specification as filed for detailed
      description of substitutions and preferred embodiments

<400> SEQUENCE: 280
actgaaccct tgacccctgc cctnnnnnnn nnnnnnnnnn nnnnnnnnnn nnnnntgccc      60
actctatttg cccagcc                                                    77

<210> SEQ ID NO 281
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: the functional variant of CRE0062
<220> FEATURE:
<221> NAME/KEY: modified_base
<222> LOCATION: (18)..(30)
<223> OTHER INFORMATION: a, c, t, g, unknown or other
<220> FEATURE:
<221> NAME/KEY: misc_feature
<222> LOCATION: (18)..(30)
<223> OTHER INFORMATION: This region may encompass 1 to 13 nucleotides
<220> FEATURE:
<221> NAME/KEY: modified_base
<222> LOCATION: (44)..(61)
<223> OTHER INFORMATION: a, c, t, g, unknown or other
<220> FEATURE:
<221> NAME/KEY: misc_feature
<222> LOCATION: (44)..(61)
<223> OTHER INFORMATION: This region may encompass 1 to 18 nucleotides
<220> FEATURE:
<223> OTHER INFORMATION: See specification as filed for detailed
      description of substitutions and preferred embodiments

<400> SEQUENCE: 281
agagattcca aagttcannn nnnnnnnnnn accaaagttc agannnnnnn nnnnnnnnnn      60
ngttatttac aa                                                         72
```

-continued

```
<210> SEQ ID NO 282
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: the functional variant of CRE0077
<220> FEATURE:
<221> NAME/KEY: modified_base
<222> LOCATION: (29)..(38)
<223> OTHER INFORMATION: a, c, t, g, unknown or other
<220> FEATURE:
<221> NAME/KEY: misc_feature
<222> LOCATION: (29)..(38)
<223> OTHER INFORMATION: This region may encompass 0 to 10 nucleotides
<220> FEATURE:
<221> NAME/KEY: modified_base
<222> LOCATION: (49)..(58)
<223> OTHER INFORMATION: a, c, t, g, unknown or other
<220> FEATURE:
<221> NAME/KEY: misc_feature
<222> LOCATION: (49)..(58)
<223> OTHER INFORMATION: This region may encompass 0 to 10 nucleotides
<220> FEATURE:
<223> OTHER INFORMATION: See specification as filed for detailed
      description of substitutions and preferred embodiments

<400> SEQUENCE: 282
agcaaatatt tgtggttatg gattaactnn nnnnnnnnct gtttgcccnn nnnnnnnnct        60
atttgccc                                                                68

<210> SEQ ID NO 283
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: functional variant of CRE0078

<400> SEQUENCE: 283
cgccctttgg accttttgca atcctggagc aaacagcaaa cac                         43

<210> SEQ ID NO 284
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence not comprised in CRM or synthetic
      liver-specific

<400> SEQUENCE: 284
ggacttagcc cctgtttgct cctccgataa ctggggtgac cttggttaat attcacca        58

<210> SEQ ID NO 285
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence not comprised in CRM or synthetic
      liver-specific
```

-continued

```
<400> SEQUENCE: 285
gcccctgttt gctcctccga taactggggt gaccttggtt aatattcacc a          51

<210> SEQ ID NO 286
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
aagcaaatat ttgtggttat ggattaactc gaactgtttg cccactctat ttgccctgta    60
cc                                                                   62

<210> SEQ ID NO 287
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggcgcccttt ggacctttg caatcctgga gcaaacagca aacactgtac c            51

<210> SEQ ID NO 288
<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
ctcttttgtt ttacatgaag ggtctggcag ccaaagcaat cactcaaagt tcaaacctta    60
tcattttttg ctttgttcct cttggccttg gttttgtaca tcagctttga aaataccatc   120
ccagggttaa tgctgggggtt aatttataac taagagtgct ctagttttgc aatacaggac  180
atgctataaa aatggaaaga tgttgctttc tgagagatgc gccacc                  226
```

LIVER-SPECIFIC REGULATORY NUCLEIC ACID SEQUENCES

CROSS REFERENCE TO RELATED APPLICATIONS

This Application is a 35 U.S.C. § 371 National Phase Entry of International Patent Application No. PCT/GB2019/053267 filed Nov. 19, 2019, which designates the U.S. and claims benefit of foreign priority under 35 U.S.C. § 119(b) of GB Application Number 1818816.9 filed Nov. 19, 2018, the contents of which are incorporated herein in their entireties by reference.

SEQUENCE LISTING

The instant application contains a Sequence Listing which has been submitted electronically in ASCII format and is hereby incorporated by reference in its entirety. Said ASCII copy, created on Jul. 14, 2021, is named 046192-096150US-PX_SL.txt and is 154,438 bytes in size.

FIELD OF THE INVENTION

The present invention relates to regulatory nucleic acid sequences, in particular liver-specific cis-regulatory elements, cis-regulatory modules, promoters and other such nucleic acid sequences, that are capable of enhancing liver-specific expression of genes. The invention also relates to expression constructs, vectors and cells comprising such liver-specific regulatory nucleic acid sequences, and to methods of their use. The liver-specific regulatory nucleic acid sequences are of particular utility for gene therapy applications, but also find utility in other areas such as bioprocessing and biotechnology.

BACKGROUND OF THE INVENTION

The following discussion is provided to aid the reader in understanding the disclosure and does not constitute any admission as to the contents or relevance of the prior art.

In many areas, including gene therapy, it is desirable to provide regulatory nucleic acid sequences that are capable of driving expression of a gene to produce a protein or nucleic acid expression product within a desired cell, tissue or organ.

Expression in the liver is of particular interest as it is involved in a wide range of essential functions in the body, including the synthesis of many proteins involved in metabolism, haemostasis, and protection against infection. Given that many diseases are linked to disruption of gene expression in the liver, there is a significant interest in developing gene therapy strategies that allow expression of a transgene in the liver to produce a therapeutic expression product. Examples of diseases of the liver associated with abnormal expression of genes include haemophilia (including haemophilia A or B), familial hypercholesterolemia, ornithine transcarbamylase deficiency, a-antitrypsin deficiency, hepatitis virus infection, non-viral hepatitis, liver cancer, and various other liver diseases (such as non-alcoholic fatty liver disease (NAFLD), and alcohol-related liver disease (ARLD).

A significant challenge in using gene therapy to treat liver diseases is the ability to provide liver-specific (also known as hepato-specific) therapeutic gene expression. It is known to target of mammalian hepatocytes by injecting DNA or viral vectors into the liver parenchyma, hepatic artery or portal vein. Adenoviral vectors have also been reported to primarily target the liver in mice. However, they also infect other tissues, in particular lung and skeletal muscle, leading to "off-target" effects. Some forms of adeno-associated viral vectors (AAV) or lentiviral vectors preferentially transduce hepatocytes, but off-target effects do again arise.

It is therefore desirable to provide systems to regulate gene expression in a liver-specific manner. Ideally, such systems are highly-specific to the liver (thereby avoiding or minimising off-target expression in non-target tissues) and are also powerful, i.e. they drive high expression levels in the liver. The use of cis-acting regulatory elements has been proposed to provide both specificity and activity. Typically, this concerns cis-regulatory enhancer sequences, i.e. nucleic acid sequences that act in cis to increase the activity of a promoter. Enhancers are typically active regardless of their orientation, and they can act over distances of up to several kilobases away from the promoter in some cases, though they typically also act when much closer to the promoter.

Various enhancer sequences for liver-specific expression of genes have been described in the literature. WO95/011308 and WO01/098482 describe a gene therapy vector comprising a hepatocyte-specific apolipoprotein E-Hepatocyte Control Region enhancer linked to a promoter and a transgene. Other liver-specific constructs have also been proposed in the literature, e.g. with the AAT promoter and the albumin or hepatitis B enhancers, or the alcohol dehydrogenase 6 (ADH6) basal promoter linked to two tandem copies of the apolipoprotein E enhancer element. WO2009/130208 describes various liver-specific regulatory elements, which are described as advantageous because of their comparatively short length. Regulatory sequences of short length are desirable to minimise the proportion of a gene therapy vector taken up by regulatory sequences; this is particularly important for gene therapy vectors with limited capacity (payload) such as AAV vectors.

There remains a need in the art for regulatory nucleic acids which are able to drive liver-specific gene expression. In particular, there is a need for liver-specific regulatory sequences (e.g. cis-regulatory elements and minimal or proximal promoter elements), and for liver-specific cis-regulatory modules and promoters comprising such elements, which can be incorporated in expression constructs and vectors for liver-specific expression of a desired gene (e.g. a therapeutic transgene in a gene therapy context).

BRIEF SUMMARY OF THE INVENTION

In a first aspect of the present invention, there is provided a synthetic liver-specific cis-regulatory module (CRM) comprising two or more operably linked cis-regulatory elements (GREs) selected from the group consisting of:

CRE0018 (SEQ ID NO: 1) or a functional variant thereof;

CRE0042 (SEQ ID NO: 2) or a functional variant thereof;

CRE0051 (SEQ ID NO: 3) or a functional variant thereof;

CRE0058 (SEQ ID NO: 4) or a functional variant thereof;

CRE0065 (SEQ ID NO: 5) or a functional variant thereof;

CRE0066 (SEQ ID NO: 7) or a functional variant thereof;

CRE0068 (SEQ ID NO: 10) or a functional variant thereof; and

CRE0074 (SEQ ID NO: 11) or a functional variant thereof.

In some embodiments the synthetic liver-specific CRM comprises three or more, four or more, five or more, or six or more of said GREs. As discussed in more detail below, these GREs have been found to contribute to the activity of CRMs present in synthetic liver-specific promoters.

In some embodiments, the synthetic liver-specific CRM of the present invention comprises a combination of GREs, or functional variants thereof, selected from the group consisting of:

CRE0051 and CRE0058;
CRE0051 and CRE0042;
CRE0051, CRE0058 and CRE0065;
CRE0051, CRE0058 and CRE0066;
CRE0051, CRE0058, CRE0065 and CRE0066;
CRE0018, CRE0051, CRE0058, CRE0065 and CRE0066
CRE0051, CRE0065 and CRE0066;
CRE0051, CRE0074 and CRE0058;
CRE0051, CRE0074, CRE0058 and CRE0065;
CRE0058 and CRE0065;
CRE0068 and CRE0042;
CRE0058, CRE0065 and CRE0066;
CRE0074, CRE0058 and CRE0065;
CRE0051, CRE0074, CRE0058, CRE0065 and CRE0066; and
CRE0074, CRE0058, CRE0065 and CRE0066.

In any of the combinations of CREs, or functional variants thereof, disclosed herein, the recited CREs may be present in any order. In some embodiments, which in some cases are preferred, the CREs are present in the recited order (i.e. in an upstream to downstream order, with reference to their position with respect to an operably linked promoter element or gene).

In any of the combinations of CREs, or functional variants thereof, disclosed herein, some or all of the recited CREs may suitably be positioned adjacent to one other in the CRM (i.e. without any intervening CREs or other regulatory elements). The CREs may be contiguous or non-contiguous (i.e. they can be positioned immediately adjacent to one another or they can be separated by a spacer or other sequence). In some preferred embodiments, the CREs, or functional variants thereof, are provided in the recited order and are adjacent to one another. For example, the synthetic liver-specific regulatory nucleic acid may comprise CRE0051 immediately upstream of CRE0058, and so forth. The CREs may be contiguous or non-contiguous. In some embodiments it is preferred that some or all of the CREs are contiguous.

CRMs comprising the abovementioned combinations CREs have been found to provide significant liver-specific enhancer activity when combined with a suitable promoter element. Particularly high levels of activity have been observed when the CREs are present in the recited order and adjacent to one another. Thus, these represent some preferred CRE "motifs", which typically correlate to high levels of liver-specific promoter activity.

In some embodiments, a synthetic liver-specific CRM of the present invention comprises two, three, four or more CREs selected from the group consisting of:

CRE0051 or a functional variant thereof;
CRE0058 or a functional variant thereof;
CRE0065 or a functional variant thereof;
CRE0066 or a functional variant thereof; and
CRE0074 or a functional variant thereof.

In some embodiments, a synthetic liver-specific CRM of the present invention further comprises one or more CREs selected from the group consisting of:

CRE0001 (SEQ ID NO: 12) or a functional variant thereof;
CRE0005 (SEQ ID NO: 13) or a functional variant thereof;
CRE0012 (SEQ ID NO: 14) or a functional variant thereof;

CRE0047 (SEQ ID NO: 15) or a functional variant thereof;
CRE0048 (SEQ ID NO: 16) or a functional variant thereof;
CRE0056 (SEQ ID NO: 17) or a functional variant thereof;
CRE0062 (SEQ ID NO: 18) or a functional variant thereof;
CRE0077 (SEQ ID NO: 19) or a functional variant thereof;
CRE0078 (SEQ ID NO: 20) or a functional variant thereof;
CRE0083.1 (SEQ ID NO: 21) or a functional variant thereof; and
CRE0089 (SEQ ID NO: 22) or a functional variant thereof.

In some preferred embodiments of the present invention, the synthetic liver-specific CRM comprises a combination of CREs, or functional variants thereof, selected from the group consisting of:

CRE0051, CRE0058;
CRE0018, CRE0077, CRE0074, CRE0058, CRE0065;
CRE0068, CRE0042;
CRE0051, CRE0042;
CRE0065, CRE0051, CRE0083.1;
CRE0018, CRE0051, CRE0058, CRE0065, CRE0066;
CRE0012, CRE0051, CRE0058, CRE0065, CRE0066;
CRE0051, CRE0058, CRE0065, CRE0066;
CRE0051, CRE0058, CRE0018;
CRE0051, CRE0058, CRE0065, CRE0018;
CRE0051, CRE0058, CRE0065, CRE0012;
CRE0047, CRE0051, CRE0058, CRE0065, CRE0066;
CRE0051, CRE0074, CRE0058, CRE0065, CRE0066;
CRE0051, CRE0058, CRE0065, CRE0001;
CRE0051, CRE0058, CRE0065;
CRE0051, CRE0066.2; and
CRE0047, CRE0001.

Preferably said CREs are present in the synthetic liver-specific CRM in the recited order. As above, in such a synthetic liver-specific CRM, some or all of the recited CREs, or functional variants thereof, may suitably be adjacent to one other. The CREs may be contiguous or non-contiguous. CRMs comprising these combinations of CREs have been found to provide high levels of liver-specific enhancer activity when combined with a suitable promoter element.

In some preferred embodiments of the present invention the synthetic liver-specific CRM comprises a combination of CREs, or functional variants thereof, selected from the group consisting of:

CRE0018, CRE0051, CRE0058, CRE0065, CRE0066 (i.e. the CREs from SP0239);
CRE0051 CRE0058, CRE0065, CRE0012 (i.e. the CREs from SP0244);
CRE0051, CRE0058, CRE0065, CRE0066 (i.e. the CREs from SP0265); and
CRE0051, CRE0042 (i.e. the CREs from SP0412).

Again, the CREs are preferably present in the recited order, and are preferably positioned adjacent to one another. They may also be contiguous. CRMs comprising these combinations of CREs have been found to provide high levels of liver-specific enhancer activity when combined with a suitable promoter element and are of particular interest.

In some embodiments of the present invention, the synthetic liver-specific CRM comprises a CRM selected from the group consisting of: CRM_SP0109, CRM_SP0112, CRM_SP0113, CRM_SP0121, CRM_SP0124, CRM_SP0127, CRM_SP0127A1, CRM_SP0127V1, CRM_SP0127V2, CRM_SP0128, CRM_SP0131, CRM_SP0132, CRM_SP0133, CRM_SP0239, CRM_SP0240, CRM_SP0241, CRM_SP0242, CRM_SP0243, CRM_SP0244, CRM_SP0246, CRM_SP0247, CRM_SP0248, CRM_SP0249, CRM_SP0250, CRM_SP0251, CRM_SP0253, CRM_SP0254, CRM_SP0255, CRM_SP0256, CRM_SP0257, CRM_SP0258, CRM_SP0265, CRM_SP0266, CRM_SP0267, CRM_SP0268, CRM_SP0269, CRM_SP0270, CRM_SP0271, CRM_SP0272, CRM_SP0273, CRM_SP0368, CRM_SP0373, CRM_SP0378, CRM_SP0379, CRM_SP0380, CRM_SP0381, CRM_SP0384, CRM_SP0396, CRM_SP0397, CRM_SP0398, CRM_SP0403, CRM_SP0404, CRM_SP0405, CRM_SP0406, CRM_SP0407, CRM_SP0409, CRM_SP0411, CRM_SP0412, CRM_SP0413, CRM_SP0107, CRM_SP0111, CRM_SP0115, CRM_SP0116, CRM_SP0155, CRM_SP0158, CRM_SP0163, CRM_SP0236, CRM_SP0252, CRM_SP0259, CRM_SP0264, CRM_SP0388 and CRM_SP0399, or a functional variant of any thereof. Suitably the functional variant of any of said CRMs comprises a sequence that is at least 70% identical to the reference synthetic liver-specific CRM, more preferably at least 80%, 90%, 95% or 99% identical to the reference synthetic liver-specific CRM. The sequences and SEQ ID NOs corresponding to these CRMs are set out in Example 1.

In some embodiments of the invention, the synthetic liver-specific CRM comprises a CRM selected from the group consisting of: CRM_SP0399, CRM_SP0405, CRM_SP0379, CRM_SP0381, CRM_SP0384, CRM_SP0412, CRM_SP0112, CRM_SP0239, CRM_SP0243, CRM_SP0413, CRM_SP0163, CRM_SP0382, CRM_SP0383, CRM_SP0241, CRM_SP0255, CRM_SP0249, CRM_SP0247, CRM_SP0265, CRM_SP0406, CRM_SP0373, CRM_SP0155, CRM_SP0380, CRM_SP0244, CRM_SP0111, CRM_SP0258, CRM_SP0268, CRM_SP0250, CRM_SP0242, CRM_SP0109, and CRM_SP0259 or a functional variant of any thereof. Suitably the functional variant of any of said CRMs comprises a sequence that is at least 70% identical to the reference synthetic liver-specific CRM, more preferably at least 80%, 90%, 95% or 99% identical to the reference synthetic liver-specific CRM. This group comprises synthetic liver-specific CRMs exhibiting very high levels of activity.

In some embodiments of the invention, the synthetic liver-specific CRM comprises a CRM selected from the group consisting of: CRM_SP0239, CRM_SP0244, CRM_SP0259 CRM_SP0265 and CRM_SP0412, or a functional variant of any thereof. This group comprises a preferred subset of CRMs from synthetic liver-specific promoters exhibiting very high levels of activity. Suitably the functional variant of any of said CRMs comprises a sequence that is at least 70% identical to the reference synthetic liver-specific CRM, more preferably at least 80%, 90%, 95% or 99% identical to the reference synthetic liver-specific CRM.

In a second aspect of the present invention, there is provided a synthetic liver-specific promoter comprising:
a) a CRM according to the first aspect operably linked to a promoter element (preferably a minimal promoter or liver-specific proximal promoter); or
b) at least one of the following CREs or functional variants thereof:
CRE0018 or a functional variant thereof;
CRE0042 or a functional variant thereof;
CRE0051 or a functional variant thereof;
CRE0058 or a functional variant thereof;
CRE0065 or a functional variant thereof;
CRE0066 or a functional variant thereof;
CRE0068 or a functional variant thereof; and
CRE0074 or a functional variant thereof,
operably linked to a promoter element selected from CRE0059, or a functional variant thereof, or CRE0006, or a functional variant thereof.

Suitable promoter elements for use in the synthetic liver-specific promoter of group a) are discussed herein. By way of non-limiting example, the promoter element can be selected from CRE0006, CRE0059, CRE0052, CRE0079, CRE0073, and CRE0073.1, or a functional variant of any thereof.

In some embodiments, the synthetic liver-specific promoter of b) comprises at least two of the recited cis-regulatory elements, or functional variants thereof, operably linked to a promoter element selected from CRE0059 or a functional variant thereof or CRE0006 or a functional variant. In other words, the synthetic liver-specific promoter of b) can comprise a CRM according to the first aspect operably linked to a promoter element selected from CRE0059 or CRE0006 (or functional variants thereof).

In some embodiments a synthetic liver-specific promoter of the present invention comprises one the combinations of CREs, or functional variants thereof, as set out in Table 1 operably linked to a promoter element:

TABLE 1

| CRE0051 | CRE0066.2 | | | |
|---|---|---|---|---|
| CRE0065 | CRE0051 | CRE0083.1 | | |
| CRE0065 | CRE0066.2 | | | |
| CRE0066 | CRE0066 | | | |
| CRE0065 | CRE0066 | | | |
| CRE0074 | CRE0058 | CRE0065.1 | | |
| CRE0051 | CRE0074 | CRE0058 | CRE0065.1 | |
| CRE0077 | CRE0074 | CRE0058 | CRE0065.1 | |
| CRE0078 | CRE0074 | CRE0058 | CRE0065.1 | |
| CRE0074 | CRE0074 | CRE0065 | | |
| CRE0058 | CRE0065 | CRE0066 | | |
| CRE0074 | CRE0058 | CRE0065 | CRE0066 | |
| CRE0074 | CRE0058 | | | |
| CRE0018 | CRE0051 | CRE0058 | CRE0065 | CRE0066 |
| CRE0051 | CRE0058 | CRE0065 | CRE0066 | |
| CRE0051 | CRE0058 | CRE0065 | | |
| CRE0012 | CRE0051 | CRE0058 | CRE0065 | CRE0066 |
| CRE0051 | CRE0058 | CRE0065 | CRE0012 | |

TABLE 1-continued

| | | | | | |
|---|---|---|---|---|---|
| CRE0051 | CRE0058 | CRE0065 | CRE0018 | | |
| CRE0051 | CRE0058 | CRE0065 | CRE0001 | | |
| CRE0051 | CRE0058 | CRE0065 | CRE0077 | | |
| CRE0051 | CRE0058 | CRE0018 | | | |
| CRE0047 | CRE0051 | CRE0058 | CRE0065 | CRE0066 | |
| CRE0051 | CRE0058 | CRE0065 | CRE0066 | | |
| CRE0077 | CRE0058 | CRE0065 | CRE0066 | | |
| CRE0078 | CRE0058 | CRE0065 | CRE0066 | | |
| CRE0051 | CRE0074 | CRE0058 | CRE0065 | CRE0066 | |
| CRE0077 | CRE0074 | CRE0058 | CRE0065 | CRE0066 | |
| CRE0078 | CRE0074 | CRE0058 | CRE0065 | CRE0066 | |
| CRE0051 | CRE0074 | CRE0058 | | | |
| CRE0077 | CRE0074 | CRE0058 | | | |
| CRE0078 | CRE0074 | CRE0058 | | | |
| CRE0051 | CRE0058 | | | | |
| CRE0068 | CRE0042 | | | | |
| CRE0051 | CRE0058 | CRE0066 | | | |
| CRE0051 | CRE0065 | CRE0066 | | | |
| CRE0018 | CRE0051 | CRE0074 | CRE0058 | CRE0065 | CRE0066 |
| CRE0018 | CRE0077 | CRE0058 | CRE0065 | CRE0066 | |
| CRE0018 | CRE0077 | CRE0074 | CRE0058 | CRE0065 | CRE0066 |
| CRE0018 | CRE0077 | CRE0074 | CRE0058 | CRE0065 | |
| CRE0051 | CRE0042 | | | | |
| CRE0001 | CRE0018 | | | | |
| CRE0077 | CRE0018 | | | | |
| CRE0005 | CRE0018 | | | | |
| CRE0018 | CRE0001 | | | | |
| CRE0048 | CRE0042 | | | | |
| CRE0056 | CRE0042 | | | | |
| CRE0062 | CRE0042 | | | | |

Again, the CREs are preferably present in the recited order, and are preferably positioned adjacent to one another. They may also be contiguous.

Table 1 sets out combinations of two or more CREs selected from CRE0018, CRE0042, CRE0051, CRE0058, CRE0065, CRE0066, CRE0068, and CRE0074 that have been found to provide high levels of liver-specific activity when combined with a suitable promoter element (e.g. a minimal promoter or liver-specific proximal promoter). These combinations of CREs, or functional variants thereof, also represent some preferred embodiments of CRMs according to the first aspect of the invention. Combinations of at least two CREs comprising at least one CRE selected from CRE0018, CRE0042, CRE0051, CRE0058, CRE0065, CRE0066, CRE0068, and CRE0074 that have been found to provide high levels of liver-specific activity when combined with promoter element CRE0059 or CRE0006 are set out in the final 7 rows. These represent additional preferred of CRMs according to the invention.

In some embodiments, the synthetic liver-specific promoter comprises one the individual CREs, or functional variants thereof, or combinations of CREs, or functional variants thereof, as set out in Table 2 operably linked to a promoter element selected from CRE0006, or a functional variant thereof, or CRE0059, or a functional variant thereof:

TABLE 2

| | | | | |
|---|---|---|---|---|
| CRE0051 | CRE0066.2 | | | |
| CRE0065 | CRE0051 | CRE0083.1 | | |
| CRE0065 | CRE0066.2 | | | |
| CRE0066 | CRE0066 | | | |
| CRE0065 | CRE0066 | | | |
| CRE0074 | CRE0058 | CRE0065.1 | | |
| CRE0051 | CRE0074 | CRE0058 | CRE0065.1 | |
| CRE0077 | CRE0074 | CRE0058 | CRE0065.1 | |
| CRE0078 | CRE0074 | CRE0058 | CRE0065.1 | |
| CRE0074 | CRE0074 | CRE0065 | | |
| | CRE0058 | CRE0065 | CRE0066 | |
| CRE0074 | CRE0058 | CRE0065 | CRE0066 | |
| CRE0074 | CRE0058 | | | |
| CRE0018 | CRE0051 | CRE0058 | CRE0065 | CRE0066 |
| CRE0018 | | | | |
| CRE0051 | CRE0058 | CRE0065 | CRE0066 | |
| CRE0051 | CRE0058 | CRE0065 | | |
| CRE0012 | CRE0051 | CRE0058 | CRE0065 | CRE0066 |
| CRE0051 | CRE0058 | CRE0065 | CRE0012 | |
| CRE0001 | CRE0018 | | | |
| CRE0051 | CRE0058 | CRE0065 | CRE0018 | |
| CRE0051 | CRE0058 | CRE0065 | CRE0001 | |
| CRE0051 | CRE0058 | CRE0065 | CRE0077 | |
| CRE0077 | CRE0018 | | | |
| CRE0051 | CRE0058 | CRE0018 | | |
| CRE0005 | CRE0018 | | | |
| CRE0018 | CRE0001 | | | |
| CRE0047 | CRE0051 | CRE0058 | CRE0065 | CRE0066 |

TABLE 2-continued

| | | | | | |
|---|---|---|---|---|---|
| CRE0051 | CRE0058 | CRE0065 | CRE0066 | | |
| CRE0077 | CRE0058 | CRE0065 | CRE0066 | | |
| CRE0078 | CRE0058 | CRE0065 | CRE0066 | | |
| CRE0051 | CRE0074 | CRE0058 | CRE0065 | CRE0066 | |
| CRE0077 | CRE0074 | CRE0058 | CRE0065 | CRE0066 | |
| CRE0078 | CRE0074 | CRE0058 | CRE0065 | CRE0066 | |
| CRE0051 | CRE0074 | CRE0058 | | | |
| CRE0077 | CRE0074 | CRE0058 | | | |
| CRE0078 | CRE0074 | CRE0058 | | | |
| CRE0051 | | | | | |
| CRE0051 | CRE0058 | | | | |
| CRE0048 | CRE0042 | | | | |
| CRE0068 | CRE0042 | | | | |
| CRE0056 | CRE0042 | | | | |
| CRE0062 | CRE0042 | | | | |
| CRE0051 | CRE0058 | CRE0066 | | | |
| CRE0051 | CRE0065 | CRE0066 | | | |
| CRE0018 | CRE0051 | CRE0074 | CRE0058 | CRE0065 | CRE0066 |
| CRE0018 | CRE0077 | CRE0058 | CRE0065 | CRE0066 | |
| CRE0018 | CRE0077 | CRE0074 | CRE0058 | CRE0065 | CRE0066 |
| CRE0018 | CRE0077 | CRE0074 | CRE0058 | CRE0065 | |
| CRE0051 | CRE0018 | | | | |
| CRE0051 | CRE0042 | | | | |
| CRE0042 | | | | | |

Again, the CREs are preferably present in the recited order, and are preferably adjacent to one another. They may also be contiguous. The promoter element lies downstream of the CREs, and it is typically adjacent to the proximal CRE. The promoter element can be contiguous with the adjacent CRE, or it can be separated by a spacer.

Table 2 sets out various individual CREs, or combinations of CREs, selected from CRE0018, CRE0051, CRE0058, CRE0065, CRE0066, CRE0042, CRE0068, and CRE0074 (or functional variants thereof) that can suitably be provided operably linked to with promoter elements CRE0006 or CRE0059 (or functional variants thereof) in accordance with some embodiments of the present invention.

In some embodiments the synthetic liver-specific promoter comprises one of the combinations of CREs, or functional variants thereof, operably linked to a promoter element, or functional variant thereof, as set out in Table 3 below:

TABLE 3

| Promoter Name | CREs | | | | | Promoter Element |
|---|---|---|---|---|---|---|
| SP0109 | CRE0051 | CRE0066.2 | | | | CRE0052 |
| SP0112 | CRE0065 | CRE0051 | CRE0083.1 | | | CRE0052 |
| SP0113 | CRE0065 | CRE0066.2 | | | | CRE0052 |
| SP0121 | CRE0066 | CRE0066 | | | | CRE0052 |
| SP0124 | CRE0065 | CRE0066 | | | | CRE0079 |
| SP0127 | CRE0074 | CRE0058 | CRE0065.1 | | | CRE0052 |
| SP0127A1 | CRE0051 | CRE0074 | CRE0058 | CRE0065.1 | | CRE0052 |
| SP0127V1 | CRE0077 | CRE0074 | CRE0058 | CRE0065.1 | | CRE0052 |
| SP0127V2 | CRE0078 | CRE0074 | CRE0058 | CRE0065.1 | | CRE0052 |
| SP0128 | CRE0074 | CRE0074 | CRE0065 | | | CRE0052 |
| SP0131 | CRE0058 | CRE0065 | CRE0066 | | | CRE0052 |
| SP0132 | CRE0074 | CRE0058 | CRE0065 | CRE0066 | | CRE0052 |
| SP0133 | CRE0074 | CRE0058 | | | | CRE0079 |
| SP0239 | CRE0018 | CRE0051 | CRE0058 | CRE0065 | CRE0066 | CRE0052 |
| SP0240 | CRE0018 | | | | | CRE0006 |
| SP0241 | CRE0051 | CRE0058 | CRE0065 | CRE0066 | | CRE0006 |
| SP0242 | CRE0051 | CRE0058 | CRE0065 | | | CRE0006 |
| SP0243 | CRE0012 | CRE0051 | CRE0058 | CRE0065 | CRE0066 | CRE0052 |
| SP0244 | CRE0051 | CRE0058 | CRE0065 | CRE0012 | | CRE0006 |
| SP0246 | CRE0051 | CRE0058 | CRE0065 | | | CRE0052 |
| SP0247 | CRE0001 | CRE0018 | | | | CRE0006 |
| SP0248 | CRE0051 | CRE0058 | CRE0065 | CRE0018 | | CRE0052 |
| SP0249 | CRE0051 | CRE0058 | CRE0065 | CRE0018 | | CRE0073 |
| SP0250 | CRE0051 | CRE0058 | CRE0065 | CRE0001 | | CRE0006 |
| SP0251 | CRE0051 | CRE0058 | CRE0065 | CRE0077 | | CRE0052 |
| SP0253 | CRE0077 | CRE0018 | | | | CRE0006 |
| SP0254 | CRE0051 | CRE0058 | CRE0018 | | | CRE0040 |
| SP0255 | CRE0051 | CRE0058 | CRE0018 | | | CRE0006 |
| SP0256 | CRE0005 | CRE0018 | | | | CRE0006 |
| SP0257 | CRE0018 | CRE0001 | | | | CRE0006 |
| SP0258 | CRE0047 | CRE0051 | CRE0058 | CRE0065 | CRE0066 | CRE0052 |
| SP0265 | CRE0051 | CRE0058 | CRE0065 | CRE0066 | | CRE0052 |
| SP0266 | CRE0077 | CRE0058 | CRE0065 | CRE0066 | | CRE0052 |
| SP0267 | CRE0078 | CRE0058 | CRE0065 | CRE0066 | | CRE0052 |
| SP0268 | CRE0051 | CRE0074 | CRE0058 | CRE0065 | CRE0066 | CRE0052 |
| SP0269 | CRE0077 | CRE0074 | CRE0058 | CRE0065 | CRE0066 | CRE0052 |

TABLE 3-continued

| Promoter Name | | CREs | | | | Promoter Element |
|---|---|---|---|---|---|---|
| SP0270 | CRE0078 | CRE0074 | CRE0058 | CRE0065 | CRE0066 | CRE0052 |
| SP0271 | CRE0051 | CRE0074 | CRE0058 | | | CRE0079 |
| SP0272 | CRE0077 | CRE0074 | CRE0058 | | | CRE0079 |
| SP0273 | CRE0078 | CRE0074 | CRE0058 | | | CRE0079 |
| SP0368 | CRE0051 | | | | | CRE0059 |
| SP0373 | CRE0051 | CRE0058 | | | | CRE0052 |
| SP0378 | CRE0048 | CRE0042 | | | | CRE0059 |
| SP0379 | CRE0068 | CRE0042 | | | | CRE0059 |
| SP0380 | CRE0056 | CRE0042 | | | | CRE0059 |
| SP0381 | CRE0062 | CRE0042 | | | | CRE0059 |
| SP0384 | CRE0051 | CRE0058 | | | | CRE0006 |
| SP0396 | CRE0051 | CRE0058 | CRE0066 | | | CRE0052 |
| SP0397 | CRE0051 | CRE0065 | CRE0066 | | | CRE0052 |
| SP0398 | CRE0018 | CRE0051 | CRE0074 | CRE0058 | CRE0065 | CRE0066 | CRE0052 |
| SP0403 | CRE0018 | CRE0077 | CRE0058 | CRE0065 | CRE0066 | CRE0052 |
| SP0404 | CRE0018 | CRE0077 | CRE0074 | CRE0058 | CRE0065 | CRE0066 | CRE0052 |
| SP0405 | CRE0018 | CRE0077 | CRE0074 | CRE0058 | CRE0065 | | CRE0052 |
| SP0406 | CRE0051 | CRE0058 | | | | CRE0059 |
| SP0407 | CRE0051 | CRE0018 | | | | CRE0052 |
| SP0409 | CRE0051 | CRE0042 | | | | CRE0052 |
| SP0411 | CRE0042 | | | | | CRE0059 |
| SP0412 | CRE0051 | CRE0042 | | | | CRE0059 |
| SP0413 | CRE0051 | CRE0058 | | | | CRE0059 |

Again, the CREs are preferably present in the recited order, and are preferably adjacent to one another. They may also be contiguous. The promoter element lies downstream of the CREs, and it is typically adjacent to the proximal CRE. The promoter element can be contiguous with the adjacent CRE, or it can be separated by a spacer.

In a further aspect, there is provided a synthetic liver-specific promoter comprising one of the following CREs or functional variants thereof, or combinations of CREs or functional variants thereof, operably linked to a promoter element or functional variant thereof as set out in Table 4:

TABLE 4

| Promoter Name | | CREs | Promoter Element |
|---|---|---|---|
| SP0107 | CRE0066.2 | CRE0083.1 | CRE0052 |
| SP0111 | CRE0051 | CRE0083.1 | CRE0052 |
| SP0115 | CRE0066.1 | | CRE0073.1 |
| SP0116 | CRE0066.2 | | CRE0073.1 |
| SP0155 | CRE0001 | | CRE0006 |
| SP0158 | CRE0005 | | CRE0006 |
| SP0163 | CRE0012 | | CRE0006 |
| SP0236 | CRE0018 | | CRE0040 |
| SP0252 | CRE0077 | CRE0018 | CRE0040 |
| SP0259 | CRE0047 | CRE0001 | CRE0006 |
| SP0264 | CRE0018 | | CRE0040 |
| SP0388 | CRE0051 | | CRE0052 |
| SP0399 | CRE0074 | | CRE0052 |

Again, the CREs are preferably present in the recited order, and are preferably adjacent to one another. They may also be contiguous. The promoter element lies downstream of the CREs, and it is typically adjacent to the proximal CRE. The promoter element can be contiguous with the adjacent CRE, or it can be separated by a spacer.

Table 4 provides further exemplary combinations of CREs and promoter elements that have been found to provide high levels of liver-specific activity. Thus, they represent additional synthetic liver-specific promoters of interest.

In some embodiments of the present invention, the synthetic liver-specific promoter comprises a promoter selected from the group consisting of: SP0109, SP0112, SP0113, SP0121, SP0124, SP0127, SP0127A1, SP0127V1, SP0127V2, SP0128, SP0131, SP0132, SP0133, SP0239, SP0240, SP0241, SP0242, SP0243, SP0244, SP0246, SP0247, SP0248, SP0249, SP0250, SP0251, SP0253, SP0254, SP0255, SP0256, SP0257, SP0258, SP0265, SP0266, SP0267, SP0268, SP0269, SP0270, SP0271, SP0272, SP0273, SP0368, SP0373, SP0378, SP0379, SP0380, SP0381, SP0384, SP0396, SP0397, SP0398, SP0403, SP0404, SP0405, SP0406, SP0407, SP0409, SP0411, SP0412, SP0413, SP0107, SP0111, SP0115, SP0116, SP0155, SP0158, SP0163, SP0236, SP0252, SP0259, SP0264, SP0388 and SP0399, or a functional variant of any thereof. Suitably the functional variant of any of said promoters comprises a sequence that is at least 70% identical to the reference synthetic liver-specific promoter, more preferably at least 80%, 90%, 95% or 99% identical to the reference synthetic liver-specific promoter. The sequences and SEQ ID NOs corresponding to these promoters are set out in Example 1.

In some embodiments of the present invention, the synthetic liver-specific promoter comprises a promoter selected from the group consisting of: SP0109, SP0112, SP0113, SP0121, SP0124, SP0127, SP0127A1, SP0127V1, SP0127V2, SP0128, SP0131, SP0132, SP0133, SP0239, SP0240, SP0241, SP0242, SP0243, SP0244, SP0246, SP0247, SP0248, SP0249, SP0250, SP0251, SP0253, SP0254, SP0255, SP0256, SP0257, SP0258, SP0265, SP0266, SP0267, SP0268, SP0269, SP0270, SP0271, SP0272, SP0273, SP0368, SP0373, SP0378, SP0379, SP0380, SP0381, SP0384, SP0396, SP0397, SP0398, SP0403, SP0404, SP0405, SP0406, SP0407, SP0409, SP0411, SP0412, SP0413, SP0107, SP0111, SP0115, SP0116, SP0155, SP0158, SP0163, SP0236, SP0252, SP0259, SP0264, SP0388 and SP0399, or a functional variant of any thereof. Suitably the functional variant of any of said promoters comprises a sequence that is at least 70% identical to the reference synthetic liver-specific promoter, more preferably at least 80%, 90%, 95% or 99% identical to the reference synthetic liver-specific promoter. The sequences and SEQ ID NOs corresponding to these promoters are set out in Example 1.

In some embodiments of the invention, the synthetic liver-specific promoter comprises a promoter selected from the group consisting of: SP0399, SP0405, SP0379, SP0381, SP0384, SP0412, SP0112, SP0239, SP0243, SP0413, SP0163, SP0382, SP0383, SP0241, SP0255, SP0249, SP0247, SP0265, SP0406, SP0373, SP0155, SP0380, SP0244, SP0111, SP0258, SP0268, SP0250, SP0242, SP0109, SP0259, SP0266, SP0158, SP0398, SP0253, SP0254, SP0257, SP0269, SP0409, SP0127A1, SP0270, SP0378, SP0403, SP0236, SP0248, SP0251, SP0411, SP0271, SP0132, SP0368, SP0246, SP0404 and SP0116, or a functional variant of any thereof. Suitably the functional variant of any of said promoters comprises a sequence that is at least 70% identical to the reference synthetic liver-specific promoter, more preferably at least 80%, 90%, 95% or 99% identical to the reference synthetic liver-specific promoter. This group comprises synthetic liver-specific promoters having relatively high levels of activity.

In some embodiments of the invention, the synthetic liver-specific promoter comprises a promoter selected from the group consisting of: SP0399, SP0405, SP0379, SP0381, SP0384, SP0412, SP0112, SP0239, SP0243, SP0413, SP0163, SP0382, SP0383, SP0241, SP0255, SP0249, SP0247, SP0265, SP0406, SP0373, SP0155, SP0380, SP0244, SP0111, SP0258, SP0268, SP0250, SP0242, SP0109 and SP0259 or a functional variant of any thereof. Suitably the functional variant of any of said promoters comprises a sequence that is at least 70% identical to the reference synthetic liver-specific promoter, more preferably at least 80%, 90%, 95% or 99% identical to the reference synthetic liver-specific promoter. This group comprises synthetic liver-specific promoters having high levels of activity.

In some embodiments of the invention the synthetic liver-specific promoter comprises a promoter selected from the group consisting of: SP0239, SP0244, SP0259, SP0265 and SP0412, or a functional variant of any thereof. This group comprises a particularly preferred subset of synthetic liver-specific promoters having high levels of activity. SP0412 and SP0265 (or a functional variant of either thereof) are of particular interest given their short length (283 and 381 nucleotides, respectively). In vivo activity for SP0239 and SP0244 has also been confirmed to be high compared to the LP1 promoter.

According in some embodiments, the synthetic liver-specific promoter comprises a combination of CREs (or functional variants of any thereof) and a promoter elements (or functional variants of any thereof) selected from the following:

CRE0018, CRE0051, CRE0058, CRE0065, CRE0066, CRE0052 (i.e. the CREs and promoter element from SP0239);

CRE0051 CRE0058, CRE0065, CRE0012, CRE0006 (i.e. the CREs and promoter element CREs from SP0244);

CRE0047, CRE0001, CRE0006 (i.e. the CREs and promoter element from SP0265);

CRE0051, CRE0058, CRE0065, CRE0066, CRE0052 (i.e. the CREs and promoter element from SP0265); and CRE0051, CRE0042, CRE0059 (i.e. the CREs and promoter element from SP0412).

The synthetic liver-specific promoters SP0109, SP0121, SP0113, and SP0380 have been found to have somewhat higher expression in non-liver (HEK293) cells than other synthetic liver-specific promoters disclosed herein. Accordingly, in some embodiments, where low levels of expression in non-liver cells are particularly import, there promoters or functional variants thereof may be less desirable. In such cases, the synthetic liver-specific promoters which show very low expression in non-liver (HEK293) cells may be particularly preferred.

In some embodiments of the present invention the synthetic liver-specific promoter has length of 700 or fewer nucleotides, for example, 600, 500, 450, 400, 350, 300, 250, 200, 150, 100, 75, 70, 68 or fewer nucleotides.

In a further aspect, the present invention provides a synthetic liver-specific promoter comprising CRE0006, or a functional variant thereof. CRE0006 can be provided without any operably linked CREs (i.e. the synthetic liver-specific promoter consists essentially of CRE0006), or it can be provided with operatively linked CREs. It has surprisingly been found that CRE0006 is an active liver-specific promoter in its own right (i.e. absent any operably linked regulatory sequences; see results for SP0154 in Example 3) as well as providing high levels of activity when combined with one or more liver-specific CREs (e.g. as discussed above). The present invention thus also provides a synthetic liver-specific promoter consisting of CRE0006, or a functional variant thereof. The invention also provides a promoter element comprising CRE0006 or a functional variant thereof, optionally wherein the promoter element has a length of 400 or fewer nucleotides, preferably 350 or fewer nucleotides, more preferably 300 or fewer nucleotides, more preferably 280 or fewer nucleotides. The invention also provides a promoter element consisting of CRE0006 or a functional variant thereof.

In a further aspect, the present invention provides a synthetic liver-specific promoter comprising CRE0059, or a functional variant thereof. CRE0059 has surprisingly been found to provide high levels of activity when combined with one or more liver-specific CREs (e.g. as discussed above). The invention also provides a promoter element comprising CRE0059 or a functional variant thereof, wherein the promoter element has a length of 350 or fewer nucleotides, more preferably 300 or fewer nucleotides, more preferably 250 or fewer nucleotides, more preferably 230 or fewer nucleotides. The invention also provides a promoter element consisting of CRE0059 or a functional variant thereof.

In a further aspect, the present invention provides a synthetic liver-specific promoter comprising CRE0079, or a functional variant thereof. CRE0079 has surprisingly been found to provide high levels of activity when combined with one or more liver-specific CREs (e.g. as discussed above). The invention also provides a promoter element comprising CRE0079 or a functional variant thereof, wherein the promoter element has a length of 200 or fewer nucleotides, preferably 150 or fewer nucleotides, more preferably 100 or fewer nucleotides. The invention also provides a promoter element consisting of CRE0079 or a functional variant thereof.

In a further aspect, the present invention provides a synthetic liver-specific promoter comprising CRE0073, or a functional variant thereof. CRE0073 has surprisingly been found to provide high levels of activity when combined with one or more liver-specific CREs (e.g. as discussed above). The invention also provides a promoter element comprising CRE0073 or a functional variant thereof, wherein the promoter element has a length of 300 or fewer nucleotides, more preferably 250 or fewer nucleotides, more preferably 200 or fewer nucleotides, more preferably 190 or fewer nucleotides. The invention also provides a promoter element consisting of CRE0073 or a functional variant thereof.

In a further aspect, the present invention provides a synthetic liver-specific promoter comprising CRE0073.1, or a functional variant thereof. CRE0073.1 has surprisingly been found to provide high levels of activity when combined with one or more liver-specific CREs (e.g. as discussed above). The invention also provides a promoter element comprising CRE0073.1 or a functional variant thereof, wherein the promoter element has a length of 180 or fewer nucleotides, more preferably 170 or fewer nucleotides. The invention also provides a promoter element consisting of CRE0073.1 or a functional variant thereof.

In a further aspect, the present invention provides a synthetic liver-specific promoter comprising CRE0040, or a functional variant thereof. CRE0040 has surprisingly been found to provide high levels of activity when combined with one or more liver-specific CREs (e.g. as discussed above). The invention also provides a promoter element comprising CRE0040 or a functional variant thereof, wherein the promoter element has a length of 400 or fewer nucleotides, more preferably 325 or fewer nucleotides, more preferably 275 or fewer nucleotides, more preferably 250 or fewer nucleotides. The invention also provides a promoter element consisting of CRE0040 or a functional variant thereof.

In some embodiments of the invention, the synthetic liver-specific CRM and/or synthetic liver-specific promoter of the present invention does not comprise CR0077, or a functional variant thereof, or CR0078, or a functional variant thereof.

In some embodiments of the invention, the synthetic liver-specific CRM and/or synthetic liver-specific promoter of the present invention does not comprise CRE0052 or a functional variant thereof.

In a further aspect of the invention, there is provided a CRE selected from the group consisting of: CRE0018, CRE0042, CRE0058, CRE0065, CRE0066, CRE0068, CRE0074, CRE0001, CRE0005, CRE0012, CRE0047, CRE0048, CRE0056, CRE0062, CRE0077, CRE0078, CRE0083.1, and CRE0089, or a functional variant of any thereof. In some preferred embodiments there is provided a CRE selected from the group consisting of: CRE0018, CRE0042, CRE0058, CRE0065, CRE0066, CRE0068, and CRE0074, or a functional variant of any thereof. In a further aspect, there is provided a synthetic liver-specific CRM or synthetic liver-specific promoter comprising any one or more of said CREs, or functional variants of thereof.

In a further aspect of the invention, there is provided an expression cassette comprising a synthetic liver-specific promoter of the present invention operably linked to a sequence encoding an expression product, suitably a gene, e.g. a transgene.

In a further aspect, there is provided a vector comprising a synthetic liver-specific CRM, a synthetic liver-specific promoter, or an expression cassette according to the present invention. In some embodiments the vector is an expression vector. In some embodiments the vector is a viral vector. In some embodiments the vector is a gene therapy vector, suitably an AAV vector, an adenoviral vector, a retroviral vector or a lentiviral vector. AAV vectors are particular interest.

In a further aspect, there is provided a virion (viral particle) comprising a vector, suitably a viral vector, according to the present invention.

In a further aspect, there is provided a pharmaceutical composition comprising a synthetic liver-specific CRM, synthetic liver-specific promoter, expression cassette, vector or virion according to the present invention.

In a further aspect, there is provided a synthetic liver-specific regulatory CRM, synthetic liver-specific promoter, expression cassette, vector, virion or pharmaceutical composition according to the present invention for use in therapy, i.e. the prevention or treatment of a medical condition or disease. Suitably the condition or disease associated with aberrant gene expression, optionally aberrant gene expression in the liver. Suitably the use is for gene therapy, preferably for use in treatment of a disease involving aberrant gene expression. Suitably the gene therapy involves expression of a therapeutic expression product in the liver.

In a further aspect, there is provided a cell comprising a synthetic liver-specific CRM, synthetic liver-specific promoter, expression cassette, vector, or virion as described herein. In some embodiments the cell is a eukaryotic cell, optionally a mammalian cell, optionally a human cell. Suitably the cell can be a liver cell, optionally wherein the cell is a human liver cell. The synthetic liver-specific CRM, synthetic liver-specific promoter, expression cassette can be in a vector or can be in the genome of the cell.

In a further aspect, there is provided a synthetic liver-specific CRM, synthetic liver-specific promoter, expression cassette, vector, virion or pharmaceutical composition as described herein for use in the manufacture of a pharmaceutical composition for the treatment of a medical condition or disease as discussed herein.

In a further aspect, there is provided a method for producing an expression product, the method comprising providing a synthetic liver-specific expression cassette of the present invention in a liver cell and expressing the gene present in the synthetic liver-specific expression cassette. The method can be in vitro or ex vivo, or it can be in vivo. In some embodiments the method is bioprocessing method.

In a further aspect, there is provided a method of expressing a therapeutic transgene in a liver cell, the method comprising introducing into the liver cell a synthetic liver-specific expression cassette, vector or virion as described herein.

In a further aspect, there is provided a method of therapy of a subject, preferably a human, in need thereof, the method comprising:

administering to the subject an expression cassette, vector, virion or pharmaceutical composition as described herein, which comprises a sequence encoding a therapeutic product operably linked to a promoter according to the present invention; and expressing a therapeutic amount of the therapeutic product in the liver of said subject.

In some embodiments the method comprises:

introducing into the liver of the subject an expression cassette, vector, virion or pharmaceutical composition as described herein, which comprises a gene encoding a therapeutic product; and expressing a therapeutic amount of the therapeutic product in the liver of said subject.

Suitably the method comprises administering a vector, virion or pharmaceutical composition as described herein to the subject. In some preferred embodiments the vector is a viral gene therapy vector, preferably an AAV vector.

The CBA (chicken beta actin) promoter as used herein comprises the CMV immediate early enhancer +chicken beta actin proximal promoter +intron.

Figure 3:
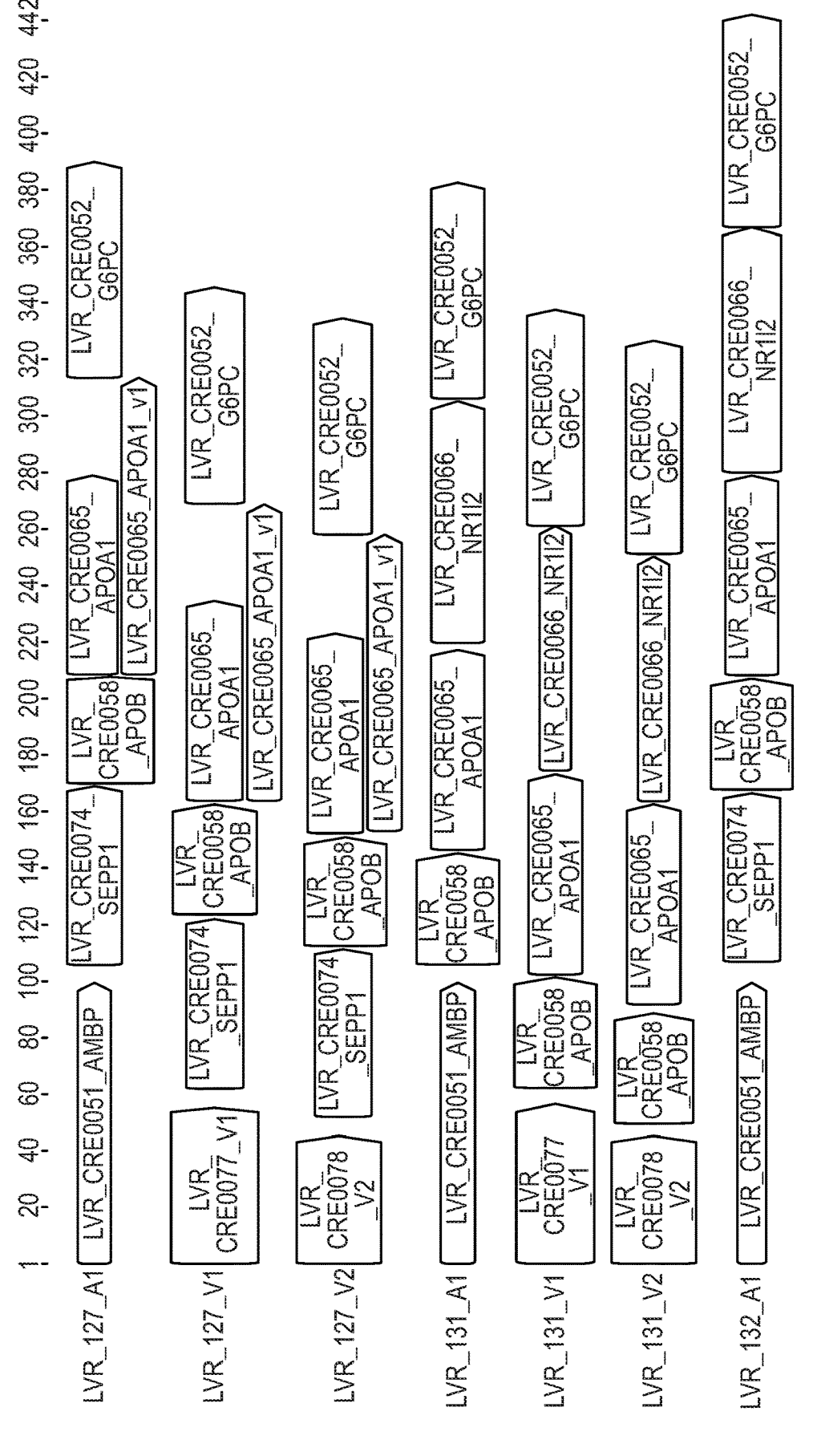
Figure 3:
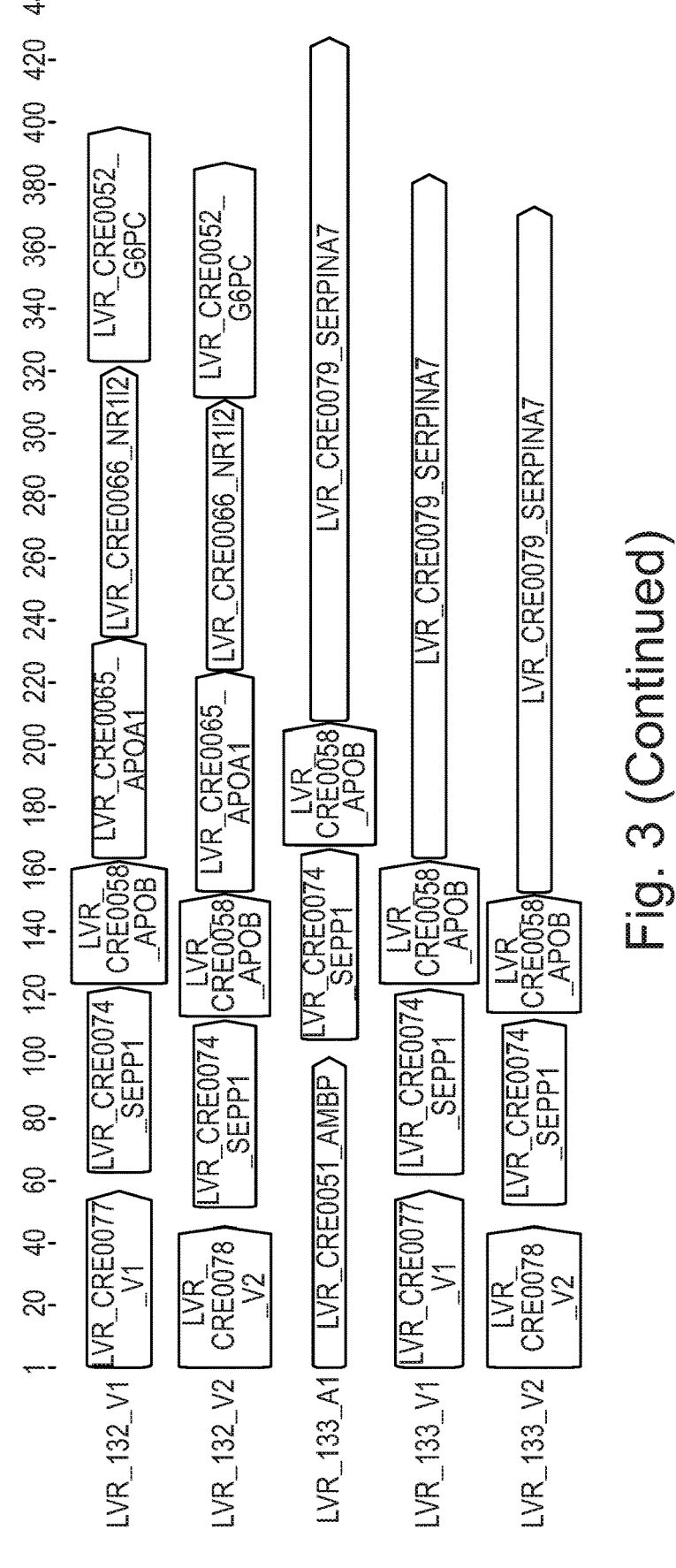

FIG. 3 shows a schematic illustration of further synthetic promoters according to the present invention, with the CRE enhancer elements indicated. These promoters correspond to the promoters of FIG. 1, but with the addition of the "V1" (LVR_CRE0077_V1), "V2" (or LVR_CRE0078_V2) and "V1" (or LVR_CRE0051_AMBP) CRE enhancers.

Figure 4A:
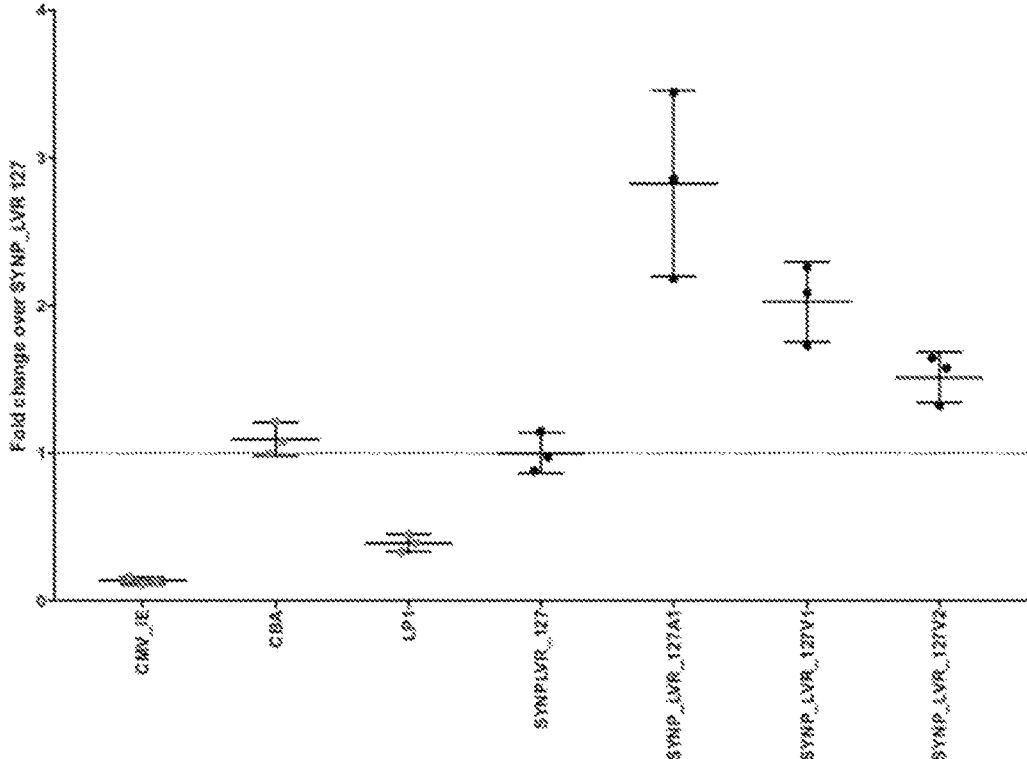

FIG. 4a shows a graph of expression levels of luciferase reporter protein driven by variants of the LVR_127 synthetic liver-specific promoter in Huh7 cells, i.e. LVR_127 alone, and with the A1, V1 and V2 CRE enhancer elements added immediately upstream of the LVR_127 promoter. Again, a comparison with the LP1, CMV-IE and CBA promoters is shown.

Figure 4B:
Figure 4B:
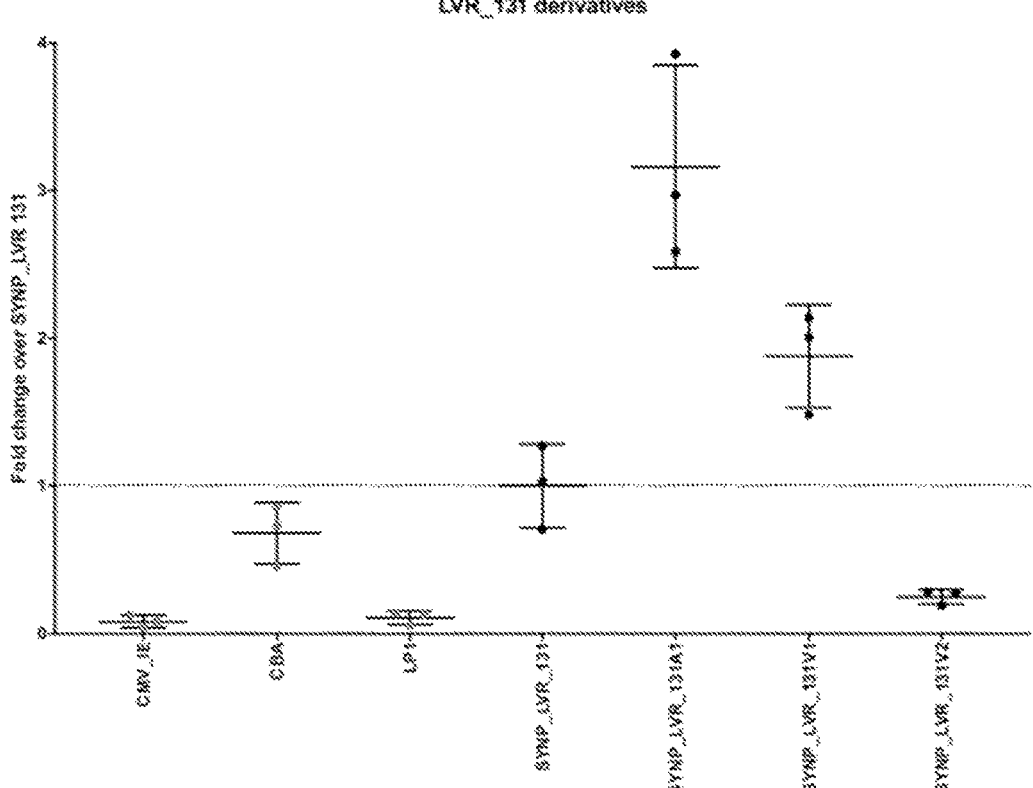

FIG. 4b shows a graph of expression levels of luciferase reporter protein driven by variants of the LVR_131 synthetic liver-specific promoter in Huh7 cells, i.e. LVR_131 alone, and with the A1, V1 and V2 CRE enhancer elements added immediately upstream of the LVR_131 promoter. Again, a comparison with the LP1, CMV-IE and CBA promoters is shown.

Figure 4C:
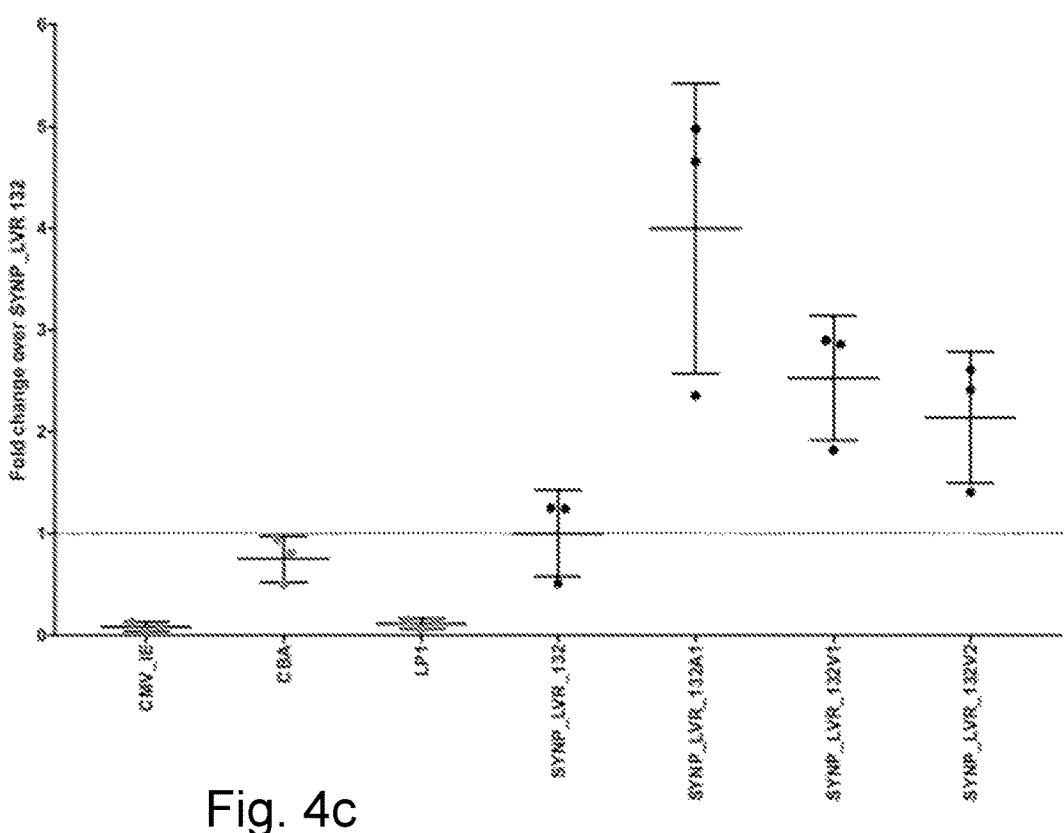

FIG. 4c shows a graph of expression levels of luciferase reporter protein driven by variants of the LVR_132 synthetic liver-specific promoter in Huh7 cells, i.e. LVR_132 alone, and with the A1, V1 and V2 CRE enhancer elements added immediately upstream of the LVR_132 promoter. Again, a comparison with the LP1, CMV-IE and CBA promoters is shown.

Figure 4D:
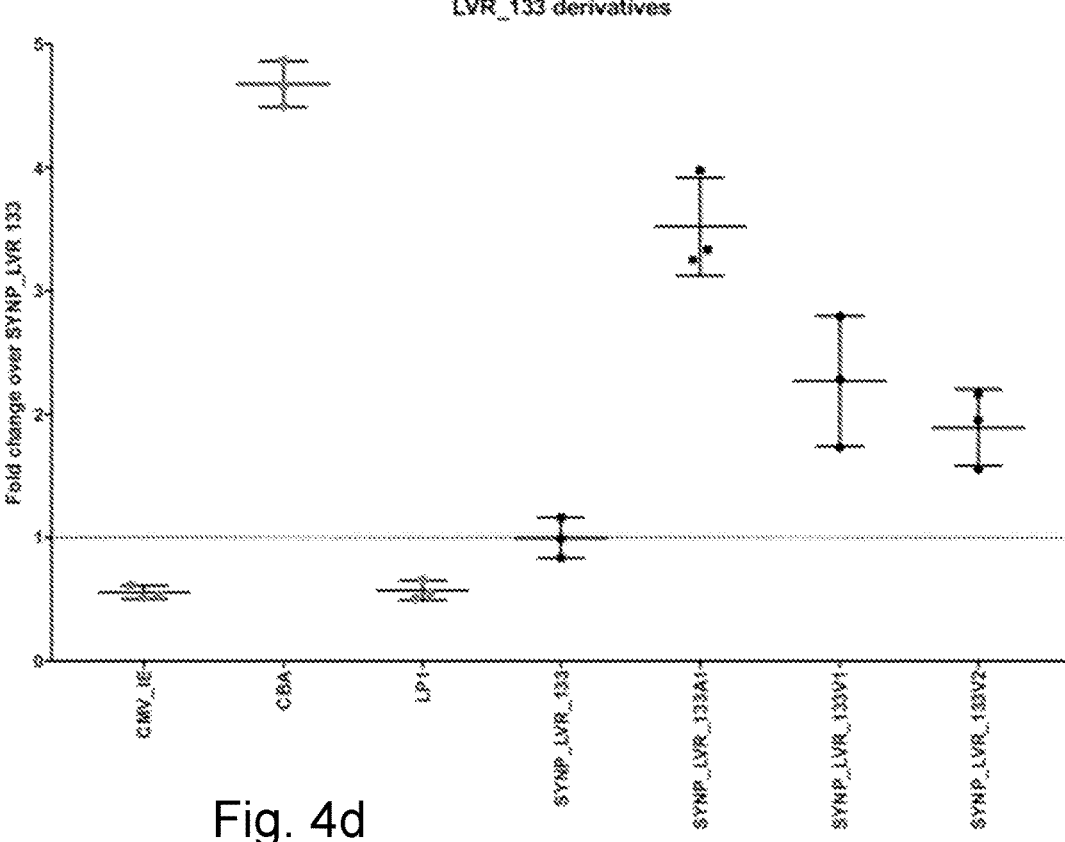

FIG. 4d shows a graph of expression levels of luciferase reporter protein driven by variants of the LVR_133 synthetic liver-specific promoter in Huh7 cells, i.e. LVR_133 alone, and with the A1, V1 and V2 CRE enhancer elements added immediately upstream of the LVR_133 promoter. Again, a comparison with the LP1, CMV-IE and CBA promoters is shown.

Figure 5:
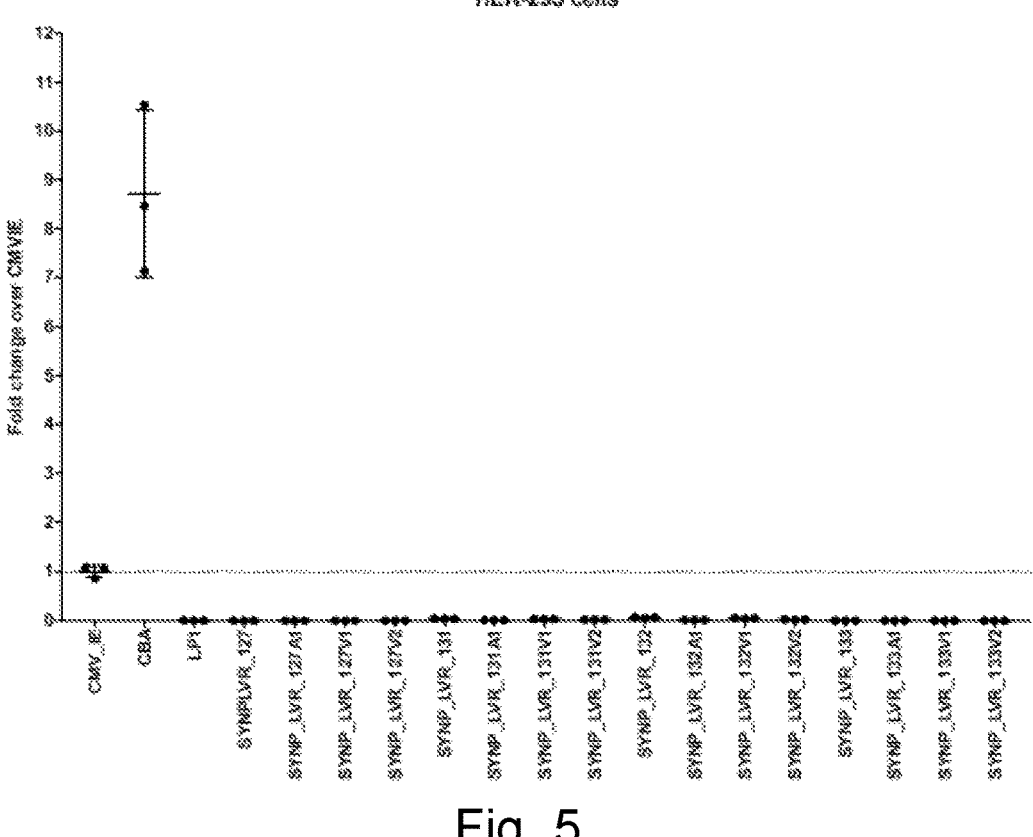

FIG. 5 shows a graph of expression levels of luciferase reporter protein in HEK-293 cells (i.e. non-liver-derived cells) driven by the LVR_127, LVR_131, LVR_132 and LVR_133 synthetic liver-specific promoters, and the variants thereof as set out in respect of FIGS. 4a-4d. Again, a comparison with the LP1, CMV-IE and CBA promoters is shown.

Figure 6:
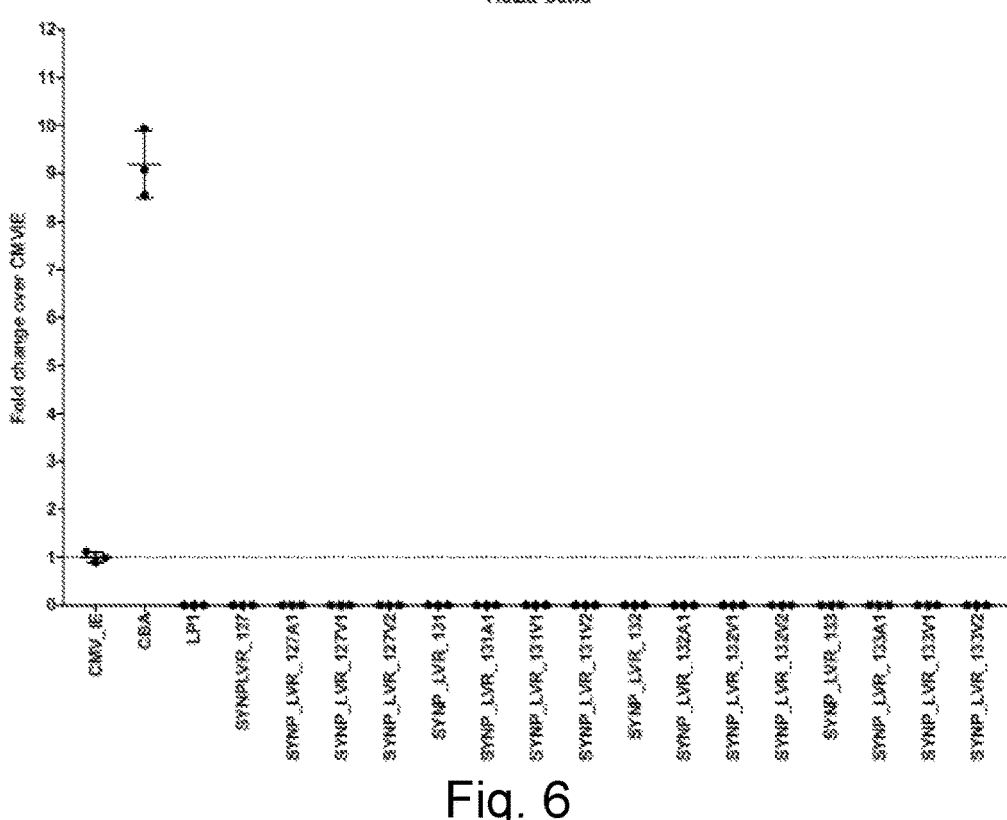

FIG. 6 shows a graph of expression levels of luciferase reporter protein in HeLa cells (i.e. non-liver-derived cells) driven by the LVR_127, LVR_131, LVR_132 and LVR_133 synthetic liver-specific promoters, and the variants thereof as set out in respect of FIGS. 4a-4d. Again, a comparison with the LP1, CMV-IE and CBA promoters is shown.

Figure 7A:
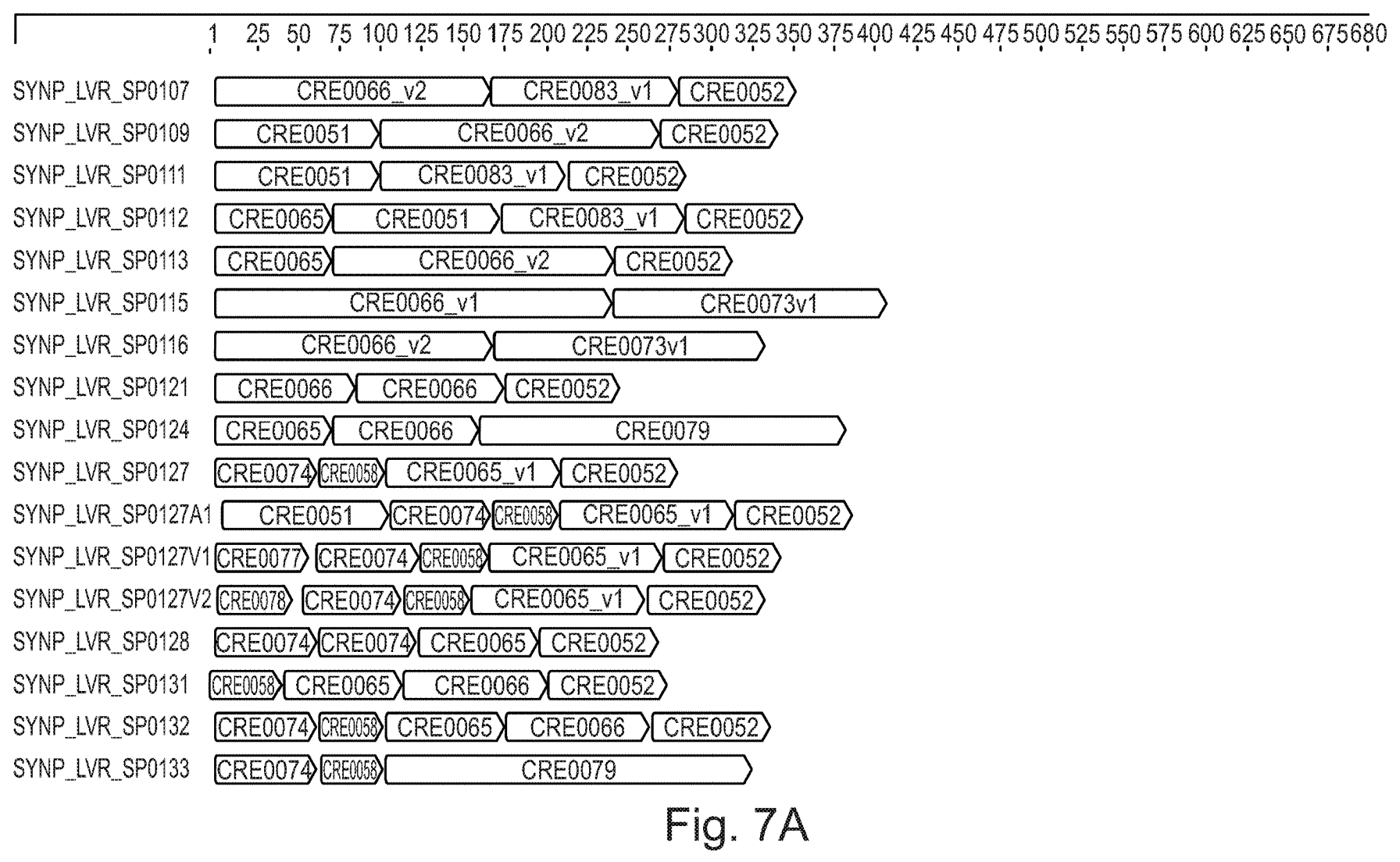
Figure 7B:
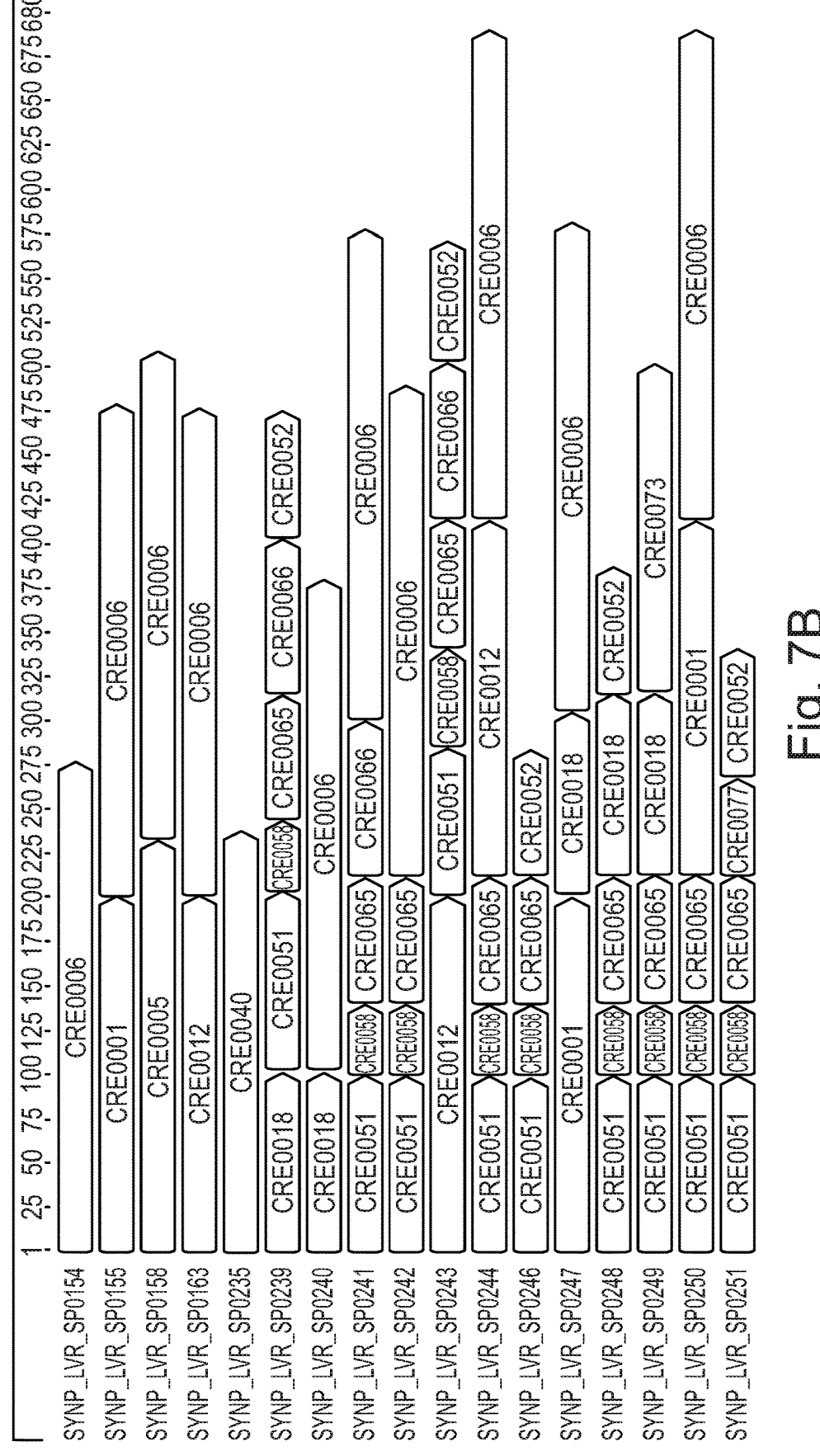
Figure 7B:
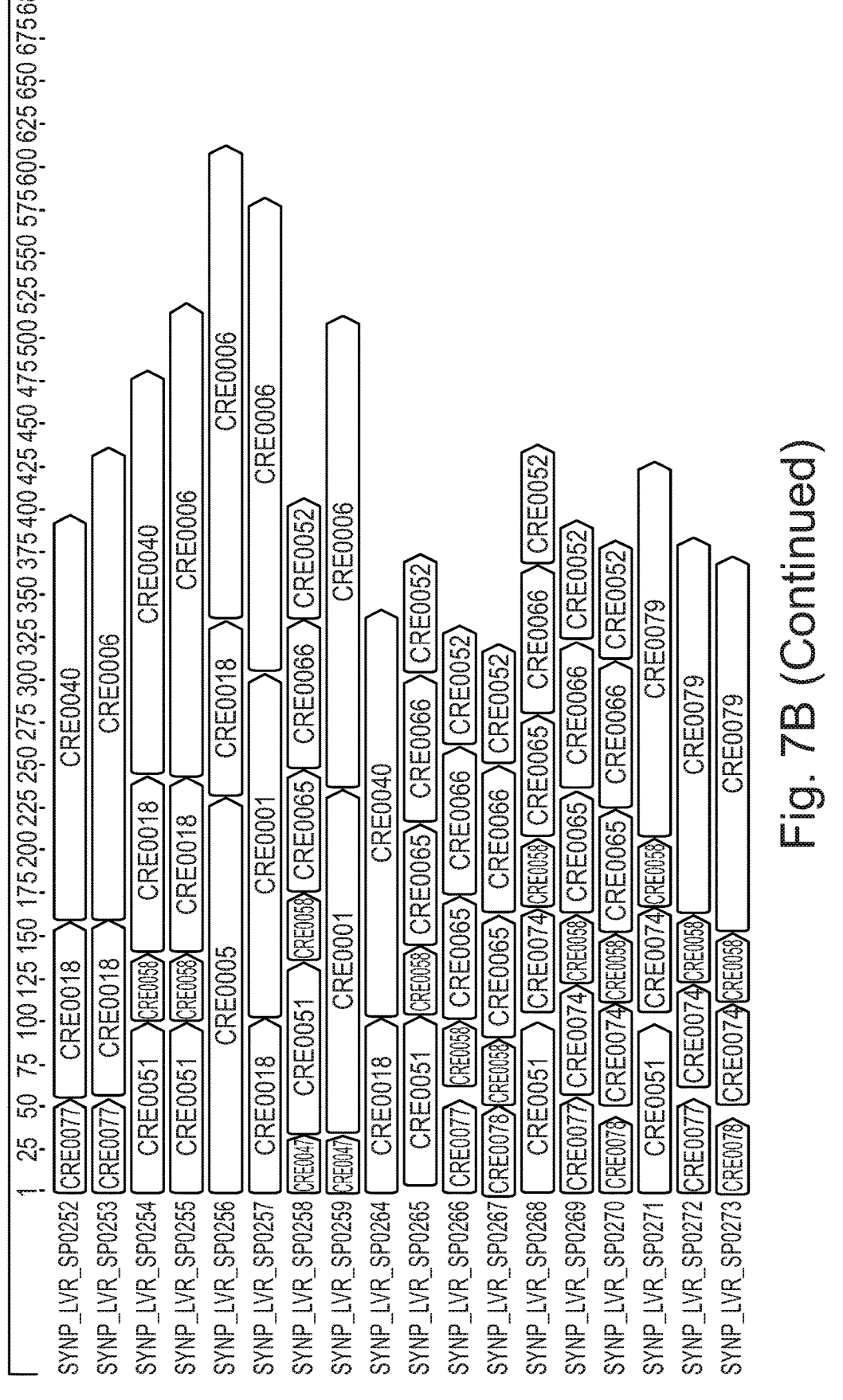
Figure 7C:
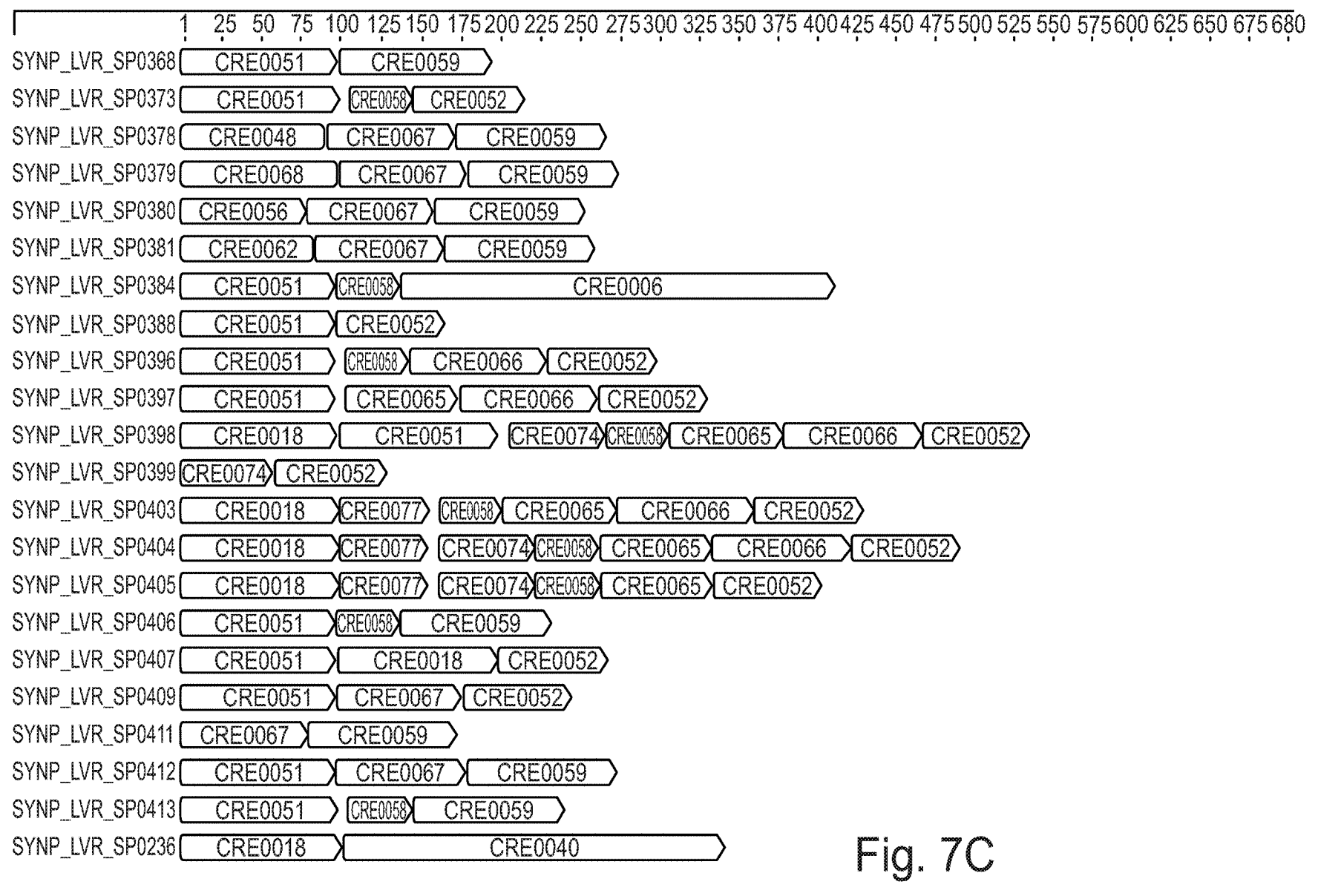

FIG. 7A, FIG. 7B and FIG. 7C show a schematic illustration of synthetic liver-specific promoters according to embodiments of the present invention, with the CRE enhancer elements indicated.

Figure 8A:
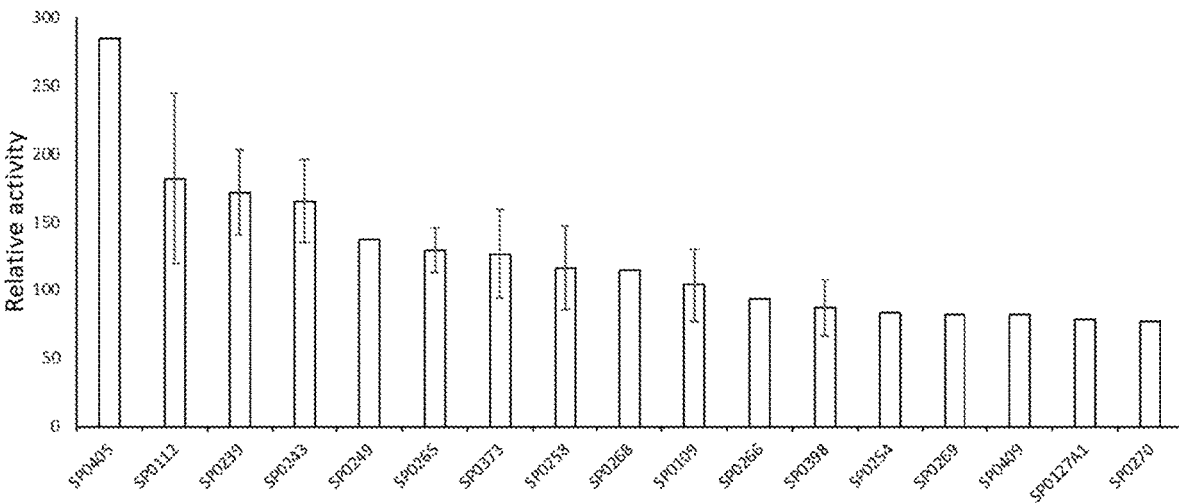
Figure 8B:
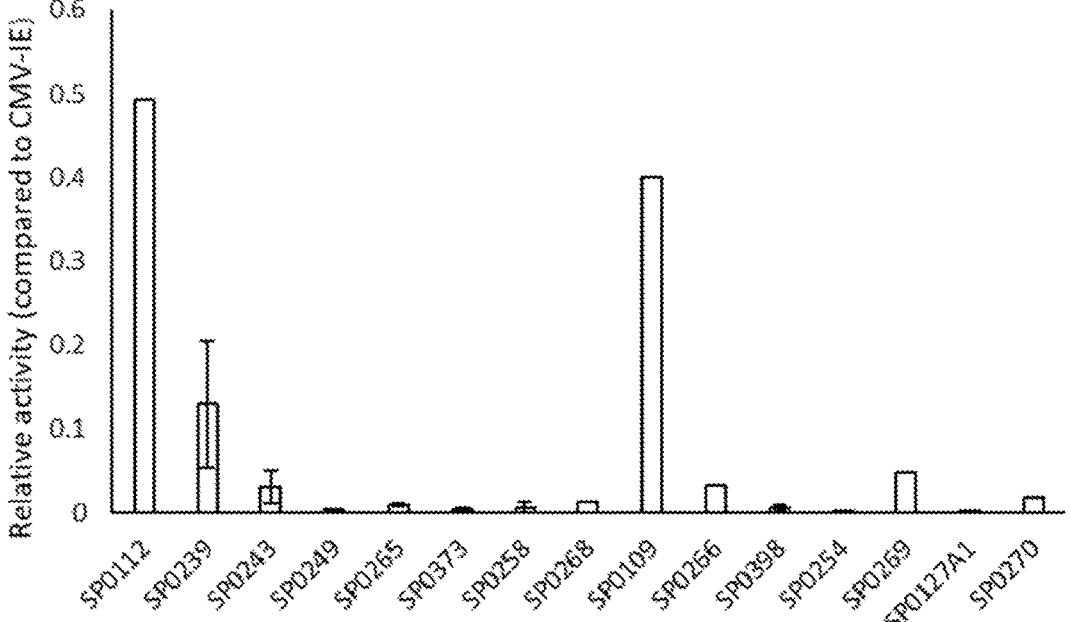
Figure 9A:
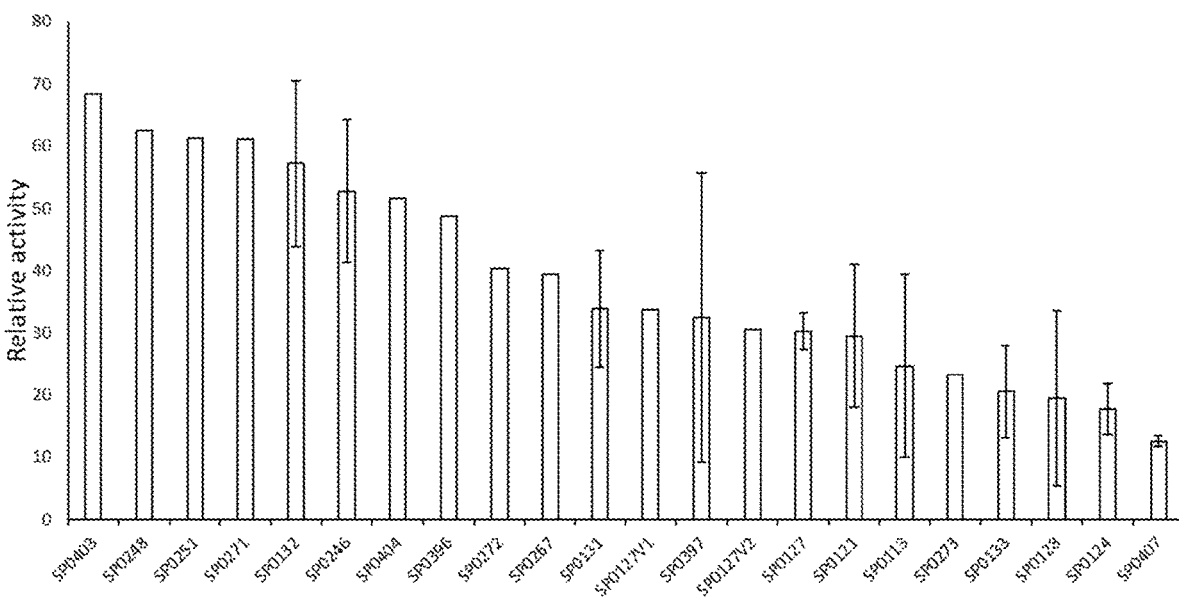
Figure 9B:
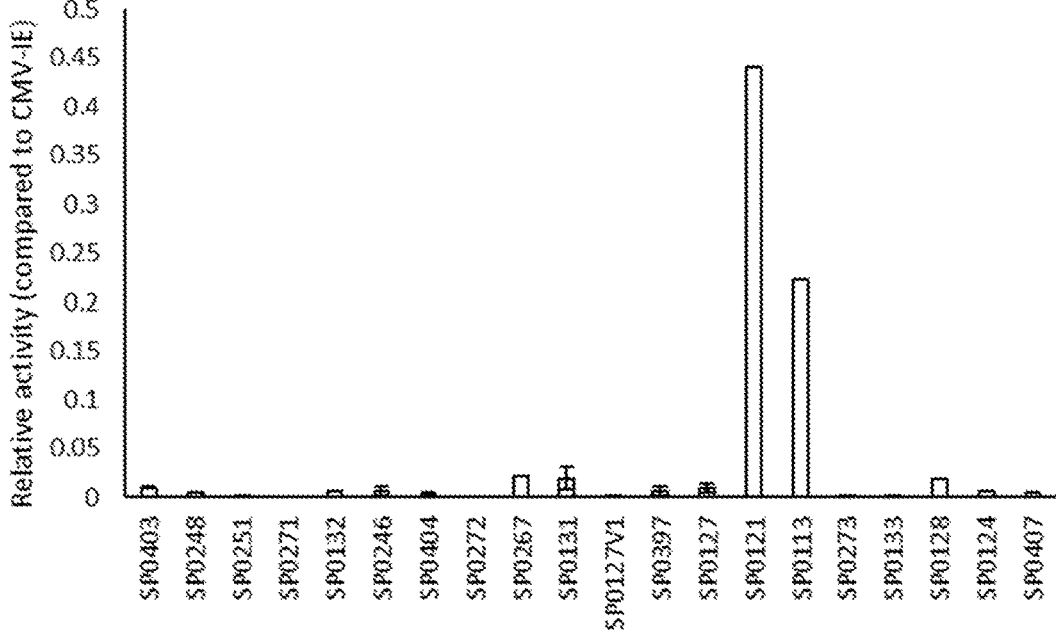
Figure 10A:
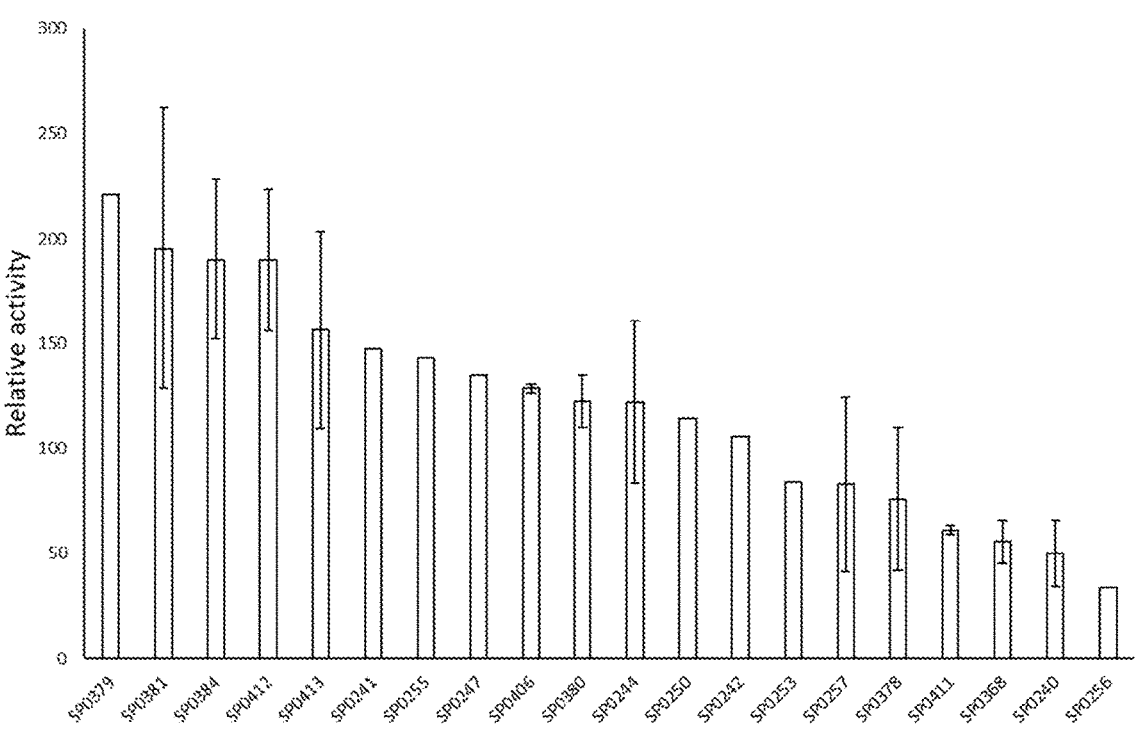
Figure 10B:
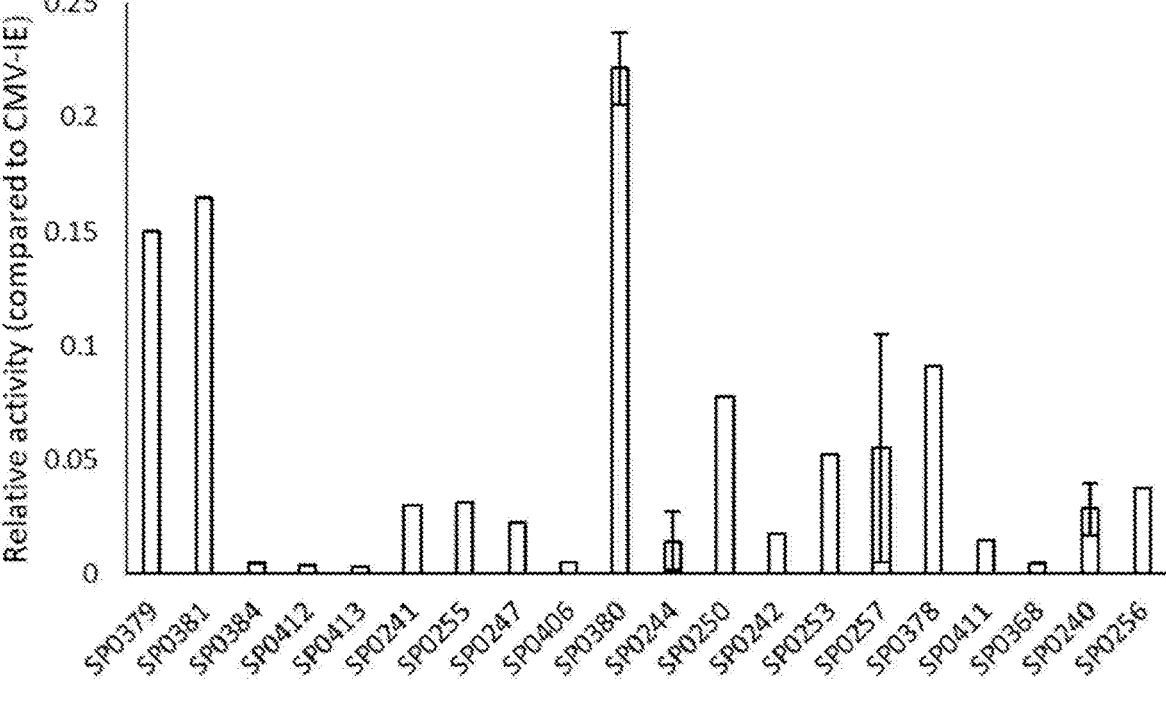

FIG. 8A, FIG. 9A, FIG. 10A and FIG. 11A show the average activity of the promoters according to embodiments of this invention in Huh7 cell normalised to the activity of TBG. A relative activity of 100 is equal to the activity of TBG. The error bar is a standard error of the mean. If no error bar is present, the results come from a single experiment. In FIG. 8A, FIG. 9A and FIG. 10A, the promoters have been arranged in terms of relative activity with the promoters with the highest relative activity first. Promoters in FIG. 10A are members of 'Group 2' as defined in Example 3. Some of the promoters in FIG. 10A are also members of 'Group 1' as defined in Example 3. Promoters in FIG. 8A and FIG. 9A are members of 'Group 1' as defined in Example 3.

FIG. 8B, FIG. 9B, FIG. 10B and FIG. 11C show the average expression in HEK293 of the promoters presented in FIG. 8A, FIG. 9A, FIG. 10A and FIG. 11A, respectively. The mean relative activity of different experiments is shown for each promoter. If no error bar is present, the results come from a single experiment. Specificity has been tested and confirmed for the majority, but not all, of the promoters presented in FIG. 8A, FIG. 9A, FIG. 10A and FIG. 11A.

Figure 11A:
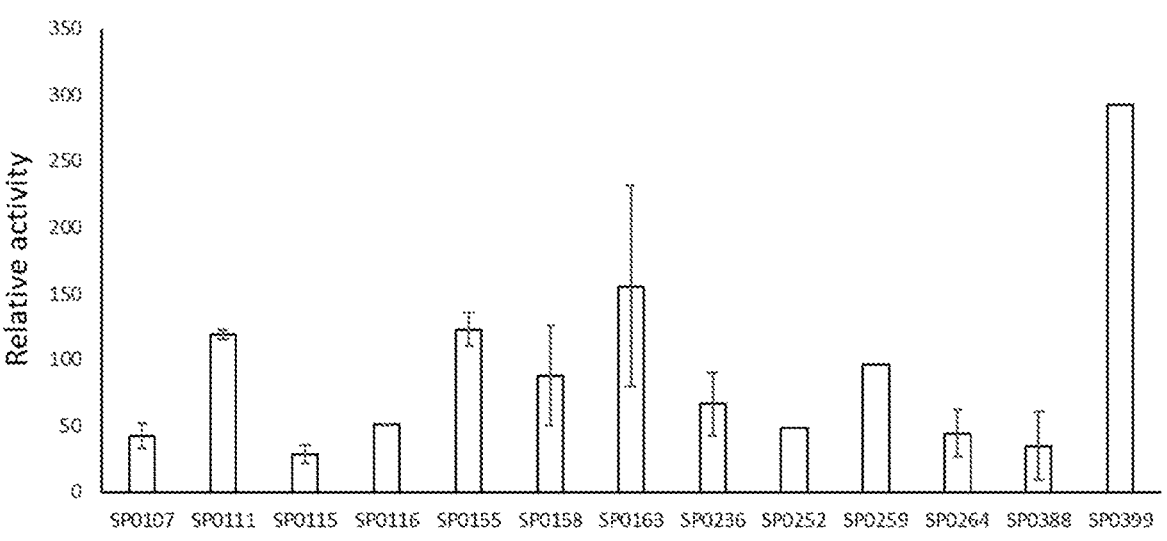
Figure 11B:
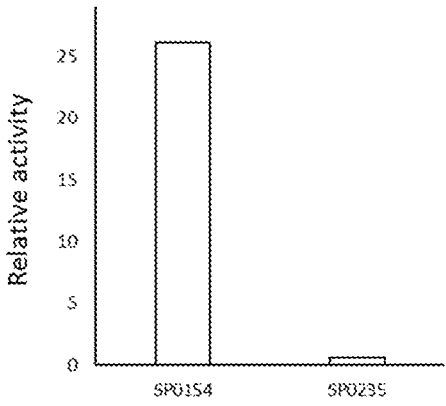
Figure 11C:
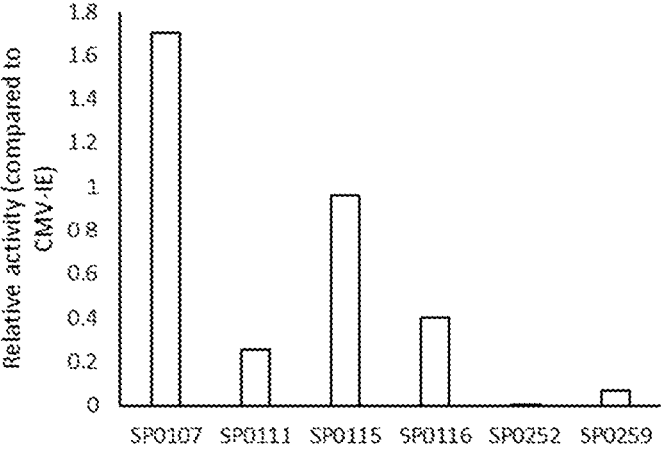

FIG. 11B shows the average activity of two promoters containing only promoter elements CRE0006 (SP0154) and CRE0040 (SP0235).

Figure 12A:
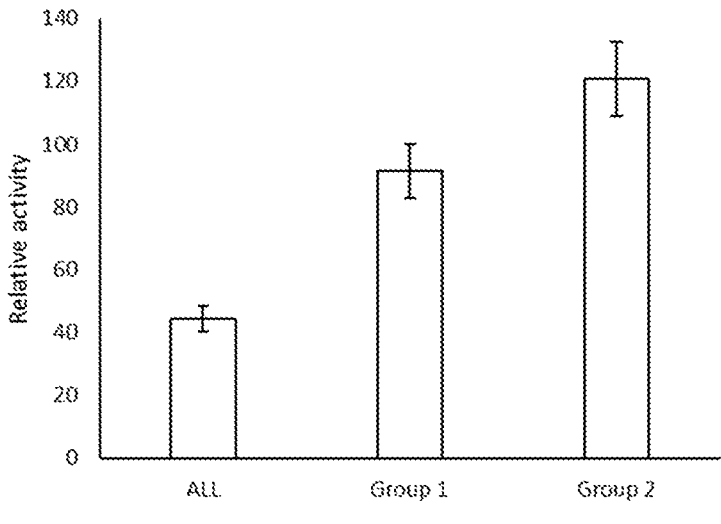

FIG. 12A shows the average relative activity of a large pool of liver-specific promoters (group 'ALL), promoters which comprise at least two "Core" CREs ('Group 1') and promoters which comprise at least one "Core" CRE operably linked to a promoter element selected from CRE0059 or CRE0006 ('Group 2'). The average relative activity of 'Group 1' (n=49) is around two times higher than the average relative activity of group 'ALL' (n=217). Additionally, the average relative activity of 'Group 2' (n=20) is around three times higher than the average relative activity of group 'ALL' (n=217). Error bars are standard error of the mean.

Figure 12B:
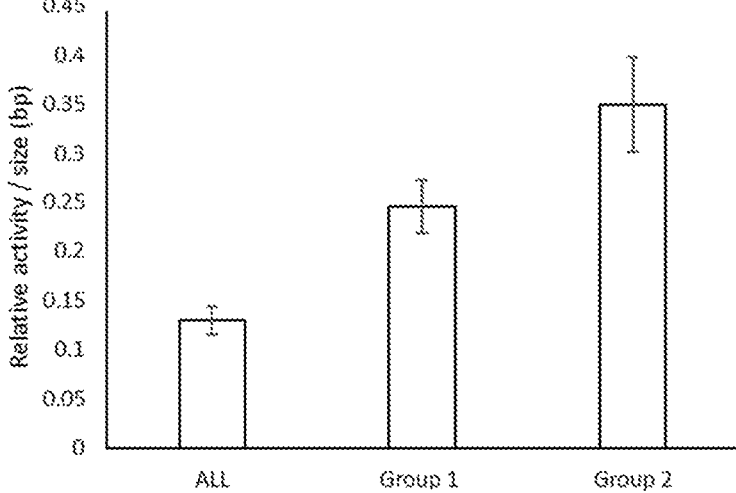

FIG. 12B presents the mean value of the relative activity of each promoter divided by its size (in base pairs) per each of groups 'ALL', 'Group 1' and 'Group 2'. The increased performance of 'Group 1' and 'Group 2' compared to group 'ALL' persists even when size of the promoters is taken into account. This indicates that the superior performance of 'Group 1' and 'Group 2' compared to group 'ALL' is not due to differences in promoter size between the groups.

Figure 13A:
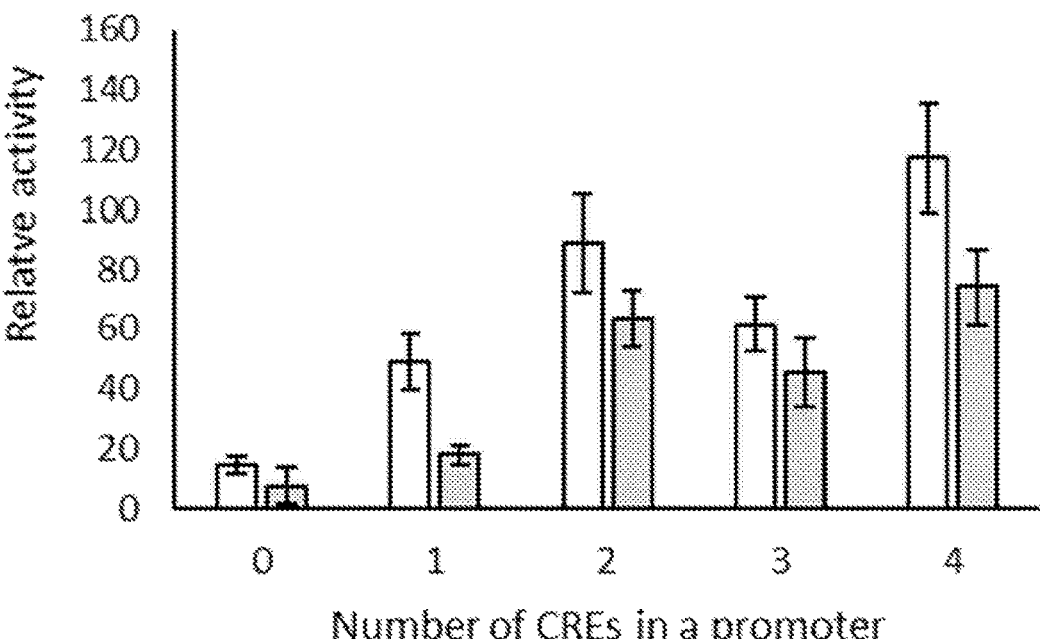

FIG. 13A shows the mean activity of promoters which have a specific number of core CREs compared to the mean activity of promoters which have the specific number of CREs (any CREs). The presence of 1, 2, 3 or 4 of the core CRE elements is associated with increased activity compared to promoters which have 1, 2, 3 or 4 of any CRE elements. The core CREs are the group consisting of CRE0018 (SEQ ID NO: 1), CRE0042 (SEQ ID NO: 2), CRE0051 (SEQ ID NO: 3), CRE0058 (SEQ ID NO: 4), CRE0065 (SEQ ID NO: 5), CRE0066 (SEQ ID NO: 7), CRE0068 (SEQ ID NO: 10) and CRE0074 (SEQ ID NO: 11).

Figure 13B:
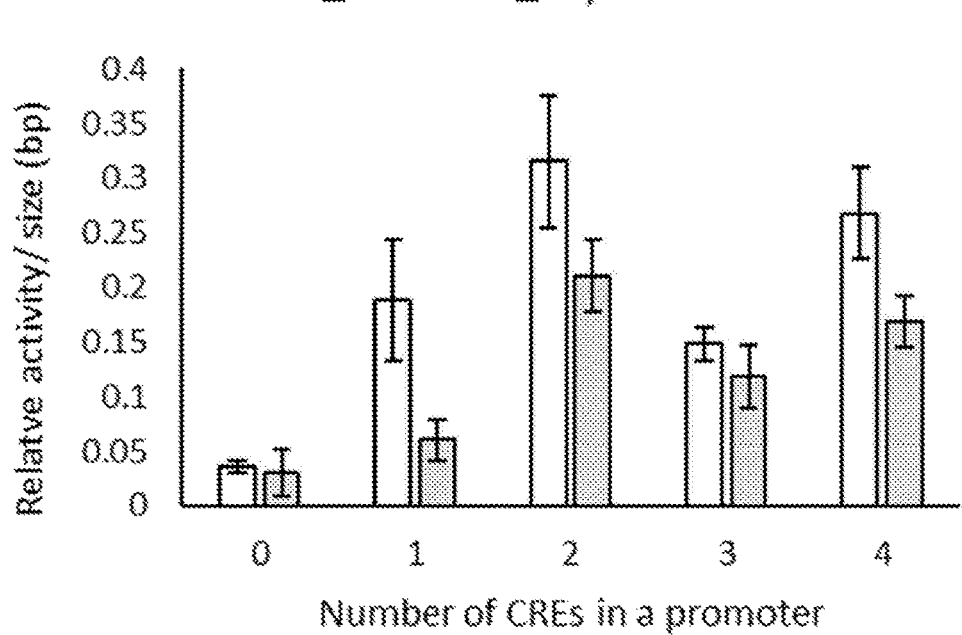

FIG. 13B shows the mean activity over size (in base pairs) of promoters which have a specific number of core CREs compared to the mean activity over size of promoters which have the specific number of CREs (any CREs). The presence of 1, 2, 3 or 4 of the core CRE elements is associated with increased activity over size (bp) compared to promoters which have 1, 2 3 or 4 of any CRE elements. This indicates that the higher activity of promoters comprising the specified number of core CREs compared to promoters comprising the specified number of any CRE is not due to differences in promoter size.

Figure 14:
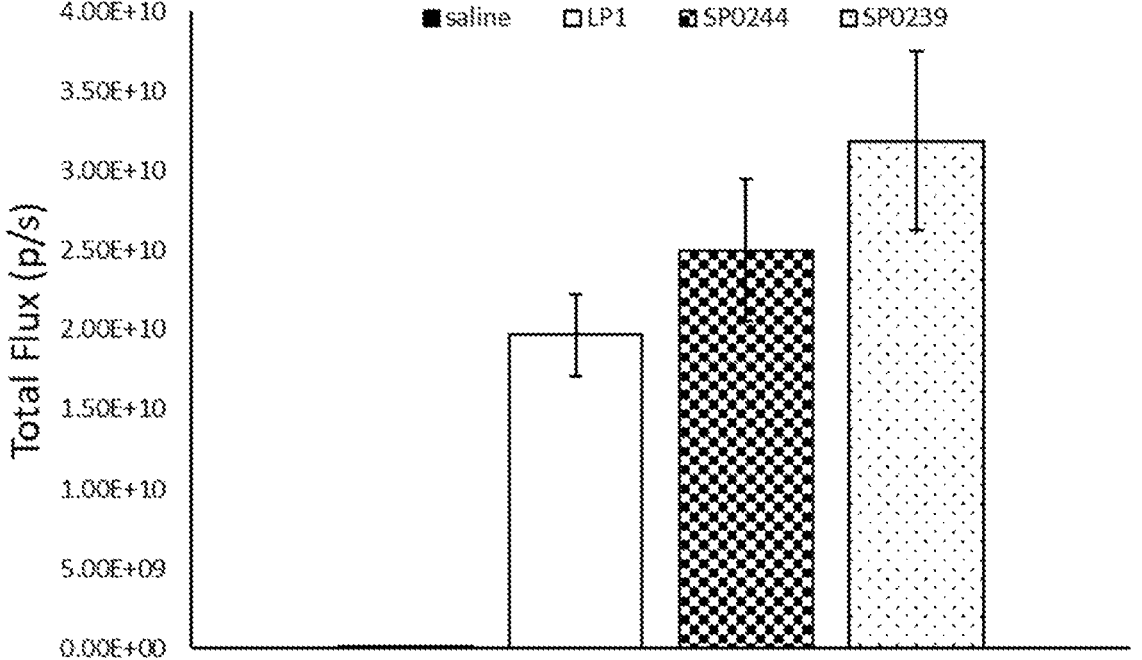

FIG. 14 shows the mean in vivo luciferase expression in mice driven by the different promoters. The expression level is shown as the mean bioluminescence intensity total flux (in photons per second). Error bars are standard error of the mean. When animals are injected with saline only (n=10), no luciferase bioluminescence is detected. When animals are injected with a construct comprising luciferase operably linked to the LP1 promoter (n=9), luciferase bioluminescence is detected. To test the activity of some of the liver-specific promoters, animals are injected with an equivalent construct comprising luciferase operably inked to the SP0244 promoter (n=8) and the SP0239 promoter (n=10). Promoters SP0244 and SP0239 showed higher luciferase expression than the control LP1.

Figure 15A:
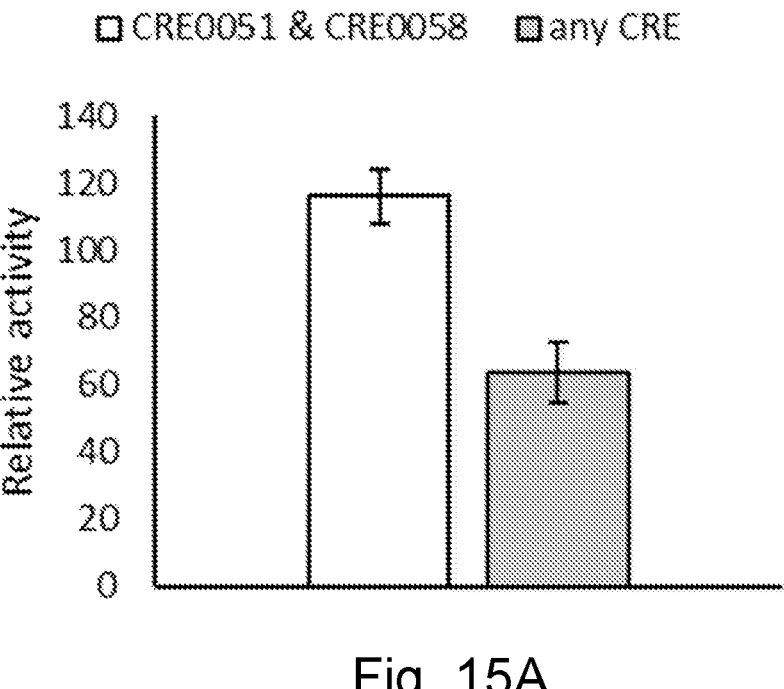

FIG. 15A shows the mean relative activity of promoters which comprise the combination of cis-regulatory elements CRE0051 and CRE0058 compared to promoters from group 'ALL' which have any two liver-specific cis-regulatory elements.

Figure 15B:
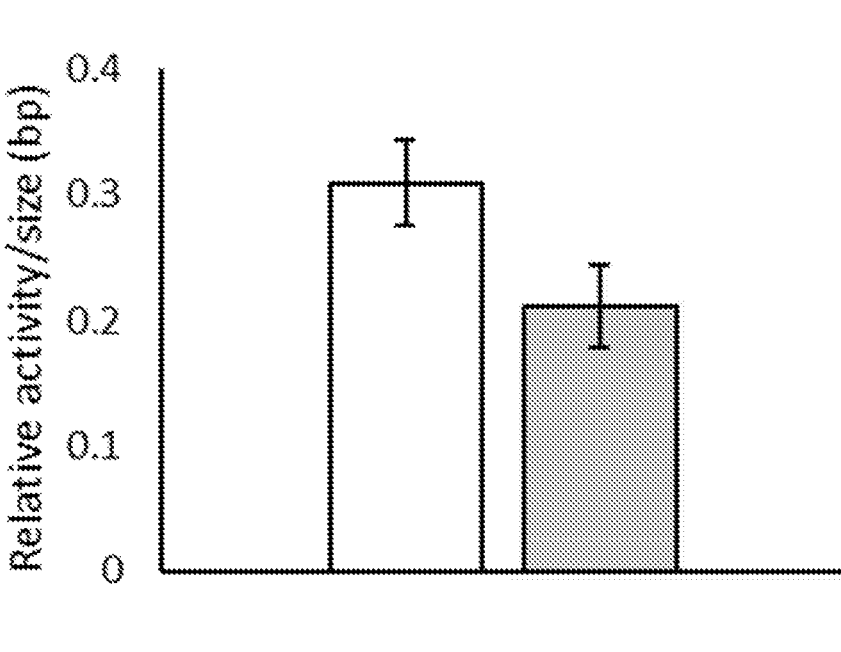

FIG. 15B shows the mean relative activity over size (in base pairs) of promoters which comprise the combination of cis-regulatory elements CRE0051 and CRE0058 compared to promoters from group 'ALL' which have any two liver-specific cis-regulatory elements. This indicates that the superior performance of promoters comprising CREs CRE0051 and CRE0058 compared to promoters comprising any two liver-specific CREs is not due to differences in promoter size.

Figure 16A:
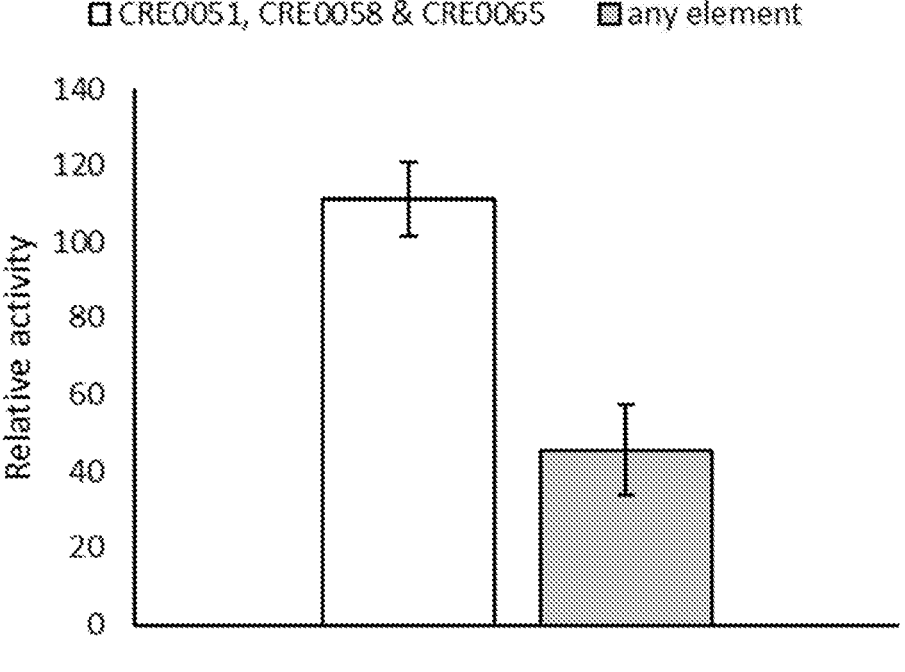

FIG. 16A shows the mean relative activity of promoters which comprise the combination of cis-regulatory elements CRE0051, CRE0058 and CRE0065 compared to promoters from group 'ALL' which have any three liver-specific cis-regulatory elements.

Figure 16B:
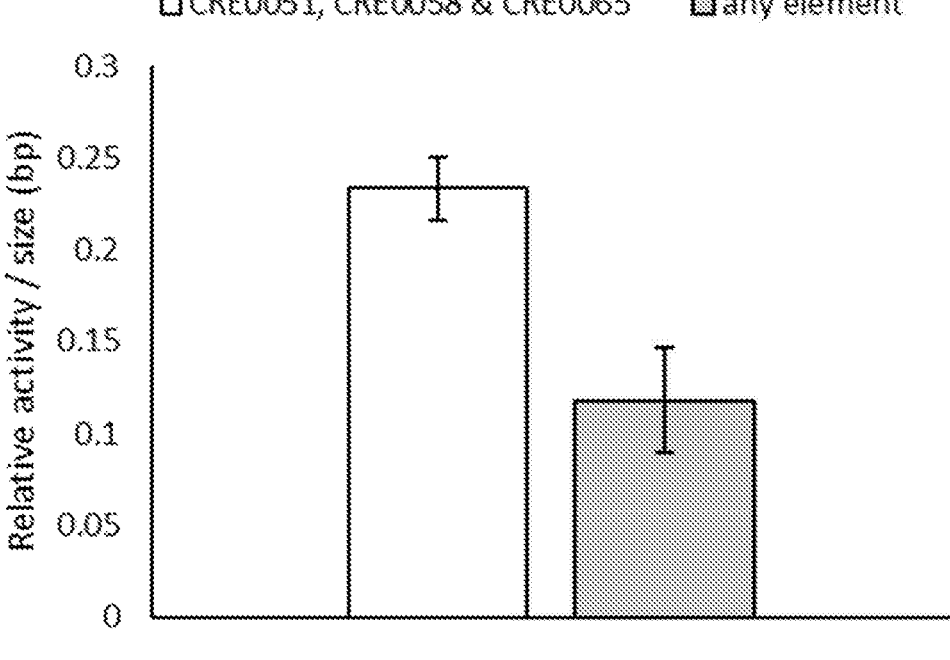

FIG. 16B shows the mean relative activity over size (in base pairs) of promoters which comprise the combination of cis-regulatory elements CRE0051, CRE0058 and CRE0065 compared to promoters from group 'ALL' which have any three liver-specific cis-regulatory elements. This indicates that the superior performance of promoters comprising CREs CRE0051, CRE0058 and CRE0065 compared to promoters comprising any three liver-specific CREs is not due to differences in promoter size.

Figure 17A:
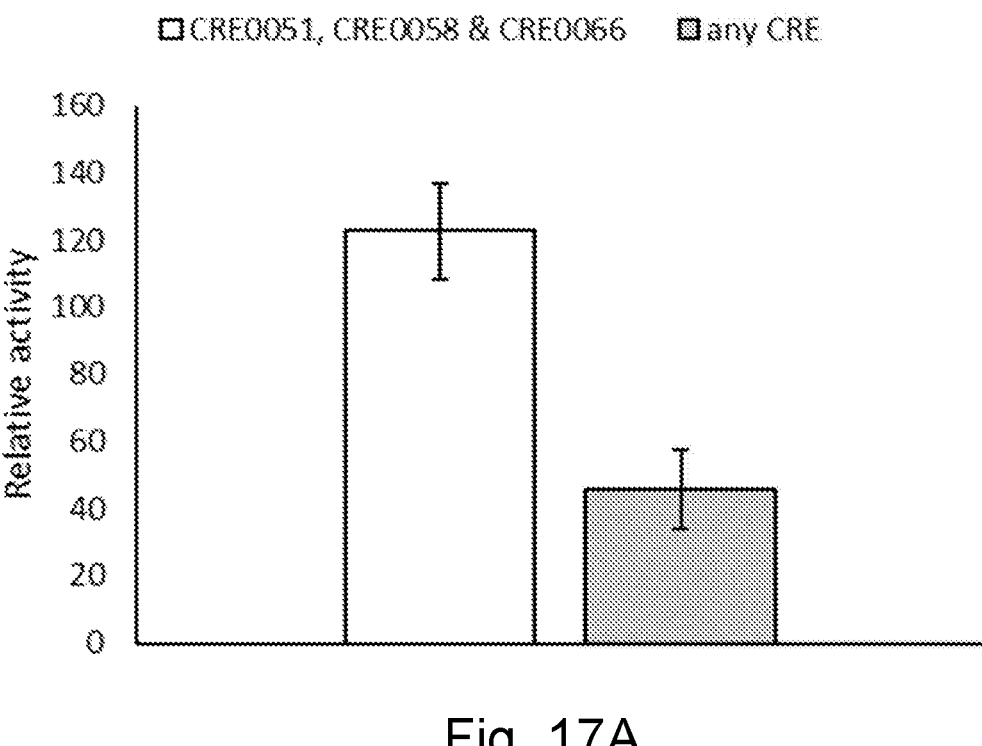

FIG. 17A shows the mean relative activity of promoters which comprise the combination of cis-regulatory elements CRE0051, CRE0058 and CRE0066 compared to promoters from group 'ALL' which have any three liver-specific cis-regulatory elements.

Figure 17B:
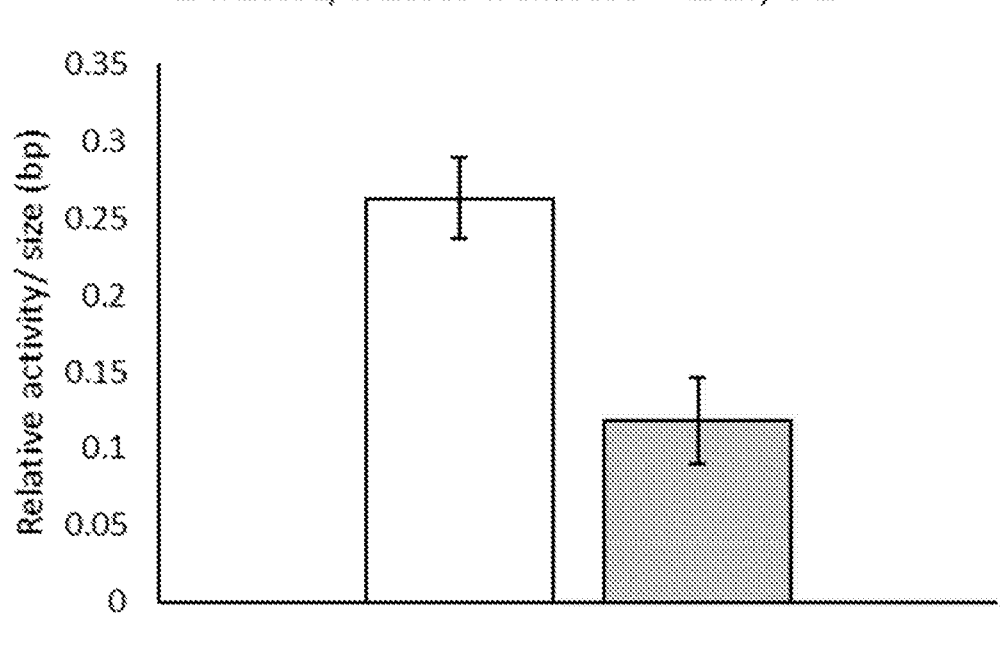

FIG. 17B shows the mean relative activity over size (in base pairs) of promoters which comprise the combination of cis-regulatory elements CRE0051, CRE0058 and CRE0066 compared to promoters from group 'ALL' which have any three liver-specific cis-regulatory elements. This indicates that the superior performance of promoters comprising CREs CRE0051, CRE0058 and CRE0066 compared to promoters comprising any three liver-specific CREs is not due to differences in promoter size.

Figure 18A:
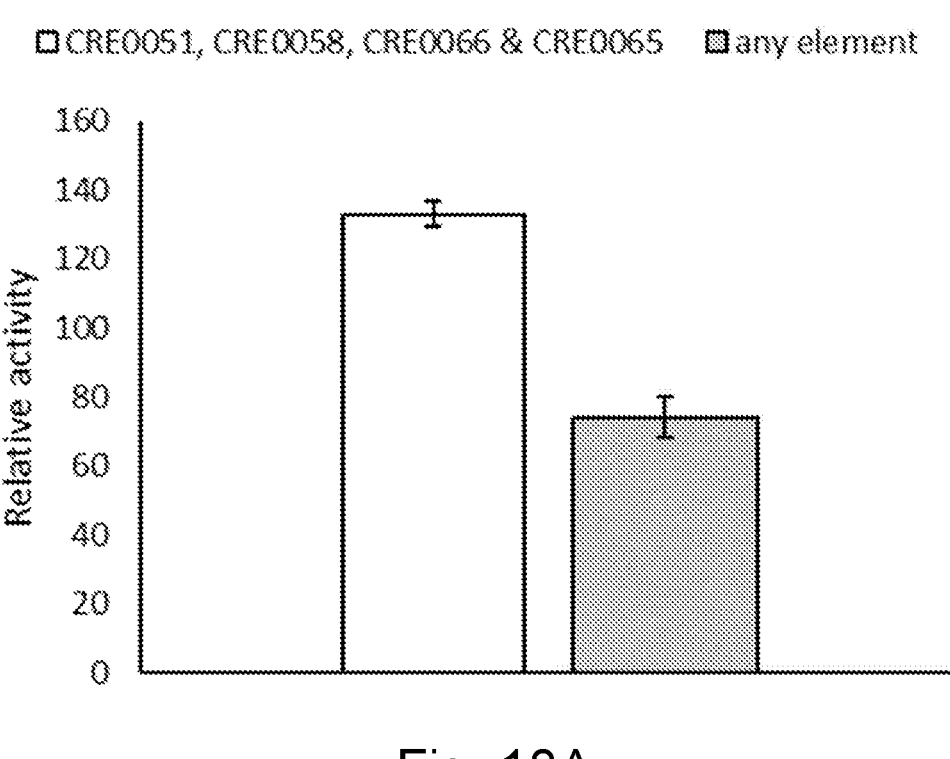

FIG. 18A shows the mean relative activity of promoters which comprise the combination of cis-regulatory elements CRE0051, CRE0058, CRE0065 and CRE0066 compared to promoters from group 'ALL' which have any four liver-specific cis-regulatory elements.

Figure 18B:
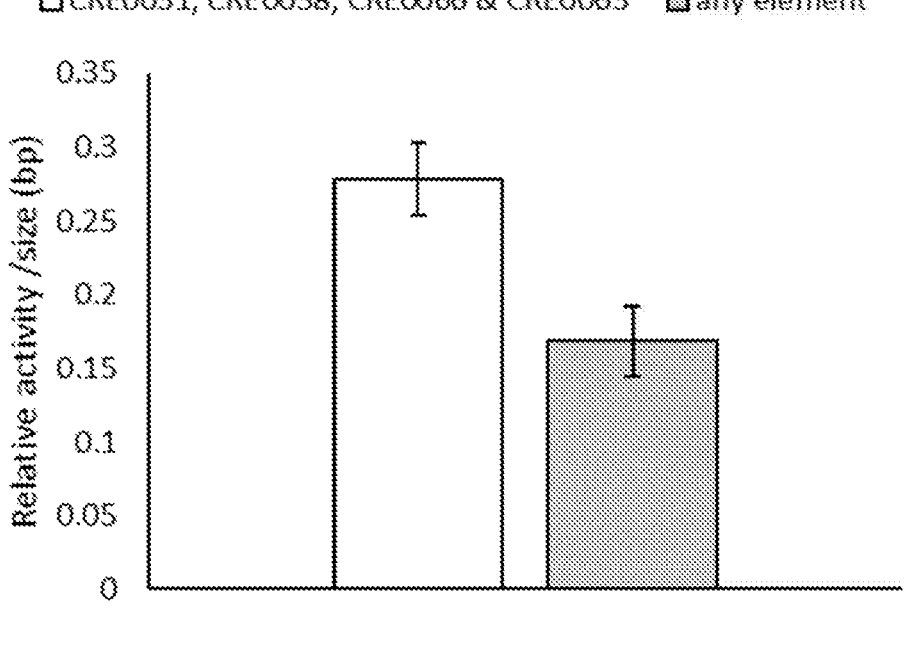

FIG. 18B shows the mean relative activity over size (in base pairs) of promoters which comprise the combination of cis-regulatory elements CRE0051, CRE0058, CRE0065 and CRE0066 compared to promoters from group 'ALL' which have any four liver-specific cis-regulatory elements. This indicates that the superior performance of promoters comprising CREs CRE0051, CRE0058, CRE0065 and CRE0066 compared to promoters comprising any four liver-specific CREs is not due to differences in promoter size.

Figure 19A:
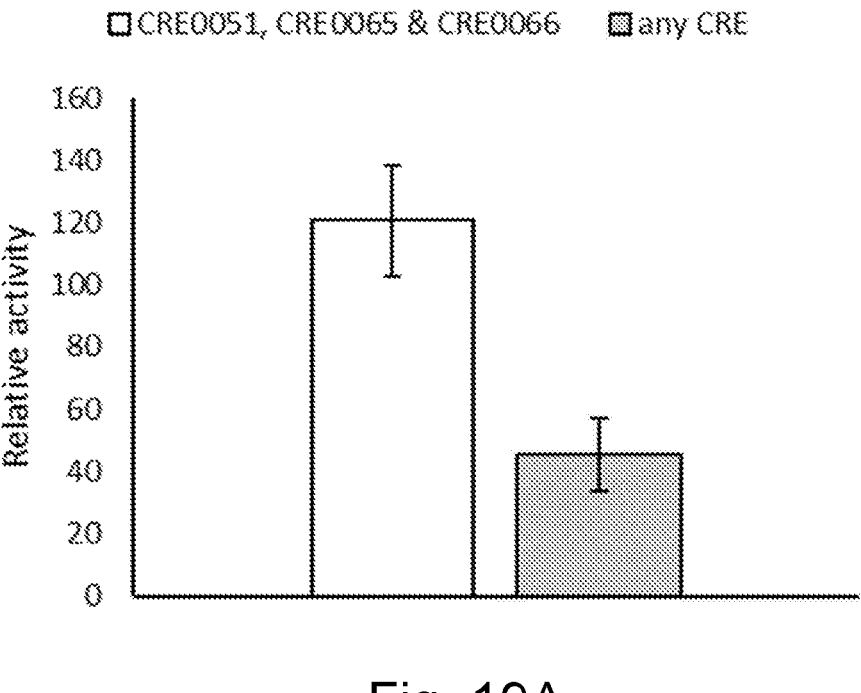

FIG. 19A shows the mean relative activity of promoters which comprise the combination of cis-regulatory elements CRE0051, CRE0065 and CRE0066 compared to promoters from group 'ALL' which have any three liver-specific cis-regulatory elements.

Figure 19B:
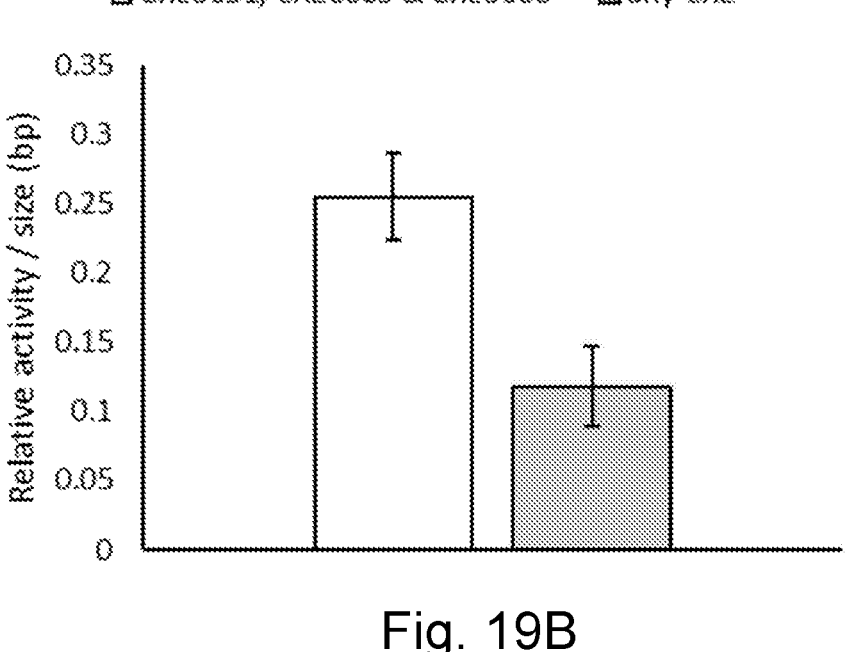

FIG. 19B shows the mean relative activity over size (in base pairs) of promoters which comprise the combination of cis-regulatory elements CRE0051, CRE0065 and CRE0066 compared to promoters from group 'ALL' which have any three liver-specific cis-regulatory elements. This indicates that the superior performance of promoters comprising cis-regulatory elements CRE0051, CRE0065 and CRE0066 compared to promoters comprising any three liver-specific cis-regulatory elements is not due to differences in promoter size.

Figure 20A:
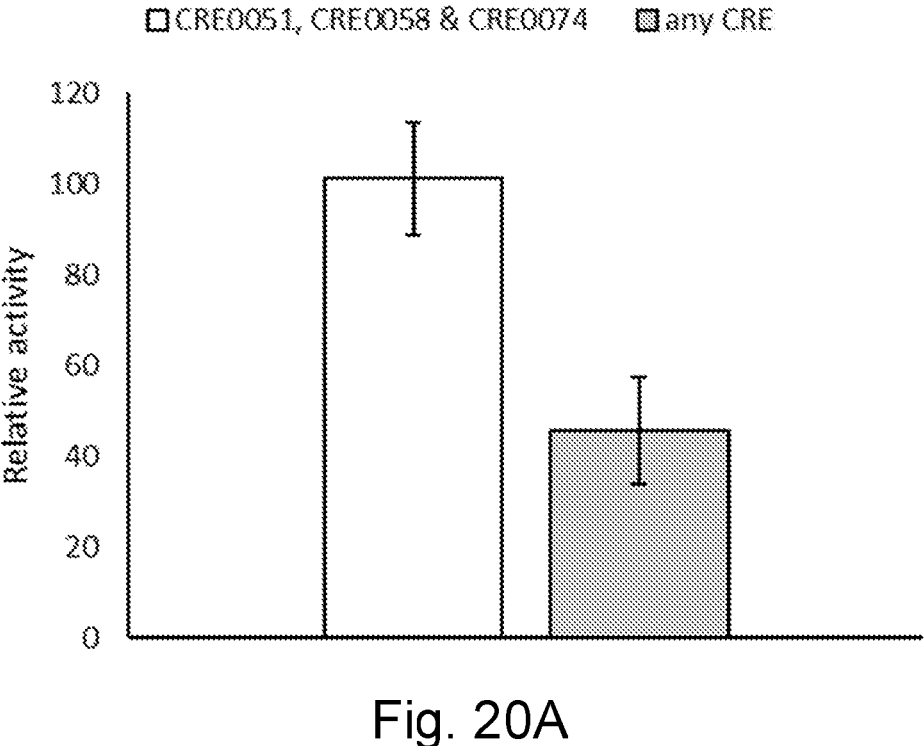

FIG. 20A shows the mean relative activity of promoters which comprise the combination of cis-regulatory elements CRE0051, CRE0058 and CRE0074 compared to promoters from group 'ALL' which have any three liver-specific cis-regulatory elements.

Figure 20B:
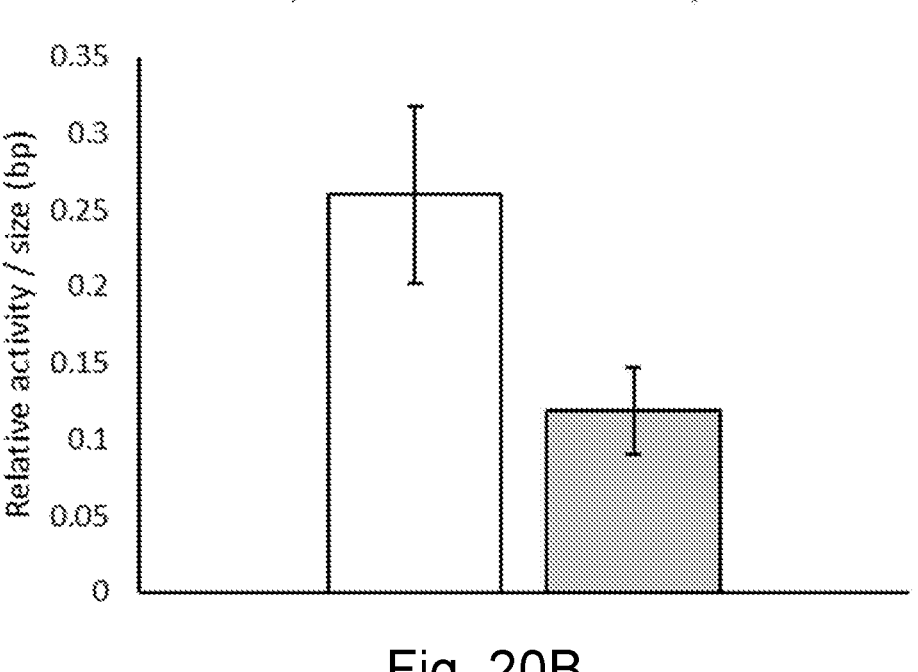

FIG. 20B shows the mean relative activity over size (in base pairs) of promoters which comprise the combination of cis-regulatory elements CRE0051, CRE0058 and CRE0074 compared to promoters from group 'ALL' which have any three liver-specific cis-regulatory elements. This indicates that the superior performance of promoters comprising cis-regulatory elements CRE0051, CRE0058 and CRE0074 compared to promoters comprising any three liver-specific cis-regulatory elements is not due to differences in promoter size.

Figure 21A:
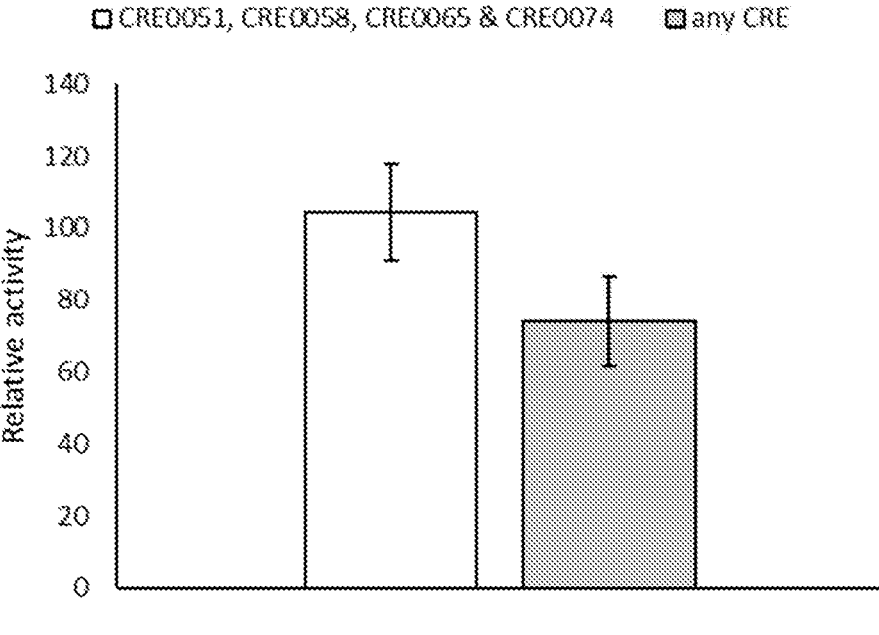

FIG. 21A shows the mean relative activity of promoters which comprise the combination of cis-regulatory elements CRE0051, CRE0058, CRE0065 and CRE0074 compared to promoters from group 'ALL' which have any four liver-specific cis-regulatory elements.

Figure 21B:
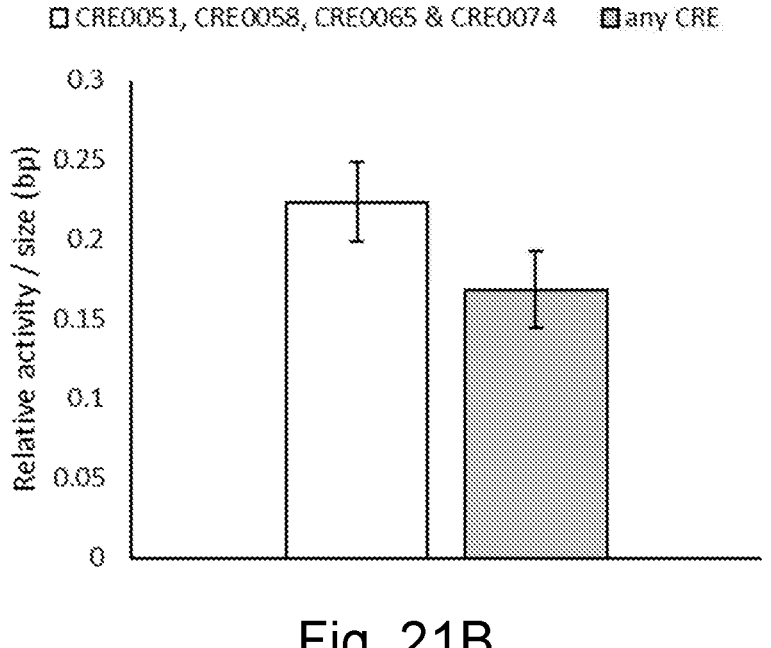

FIG. 21B shows the mean relative activity over size (in base pairs) of promoters which comprise the combination of cis-regulatory elements CRE0051, CRE0058, CRE0065 and CRE0074 compared to promoters from group 'ALL' which have any four liver-specific cis-regulatory elements. This indicates that the superior performance of promoters comprising cis-regulatory elements CRE0051, CRE0058, CRE0065 and CRE0074 compared to promoters comprising any four liver-specific cis-regulatory elements is not due to differences in promoter size.

Figure 22A:
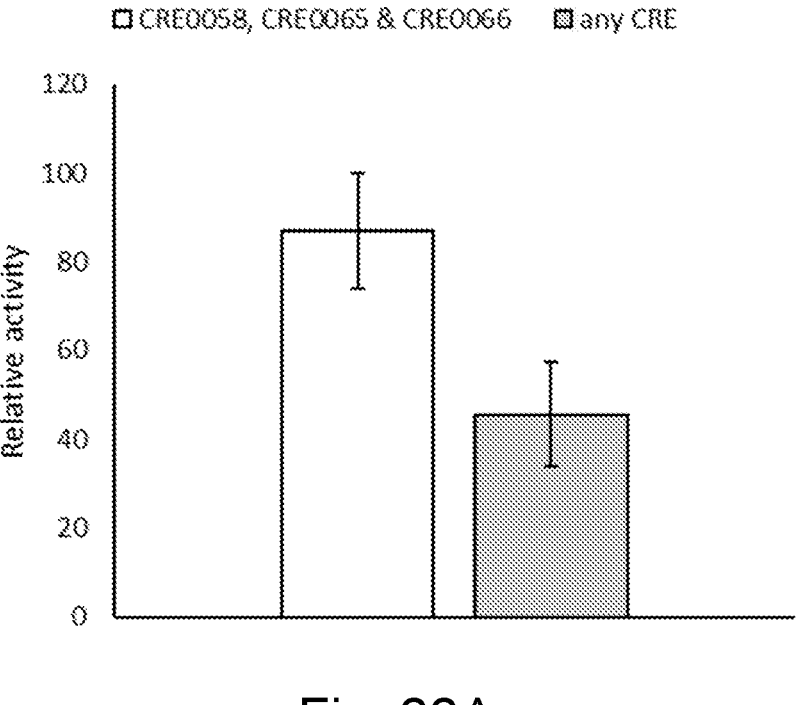

FIG. 22A shows the mean relative activity of promoters which comprise the combination of cis-regulatory elements CRE0058, CRE0065 and CRE0066 compared to promoters from group 'ALL' which have any three liver-specific cis-regulatory elements.

Figure 22B:
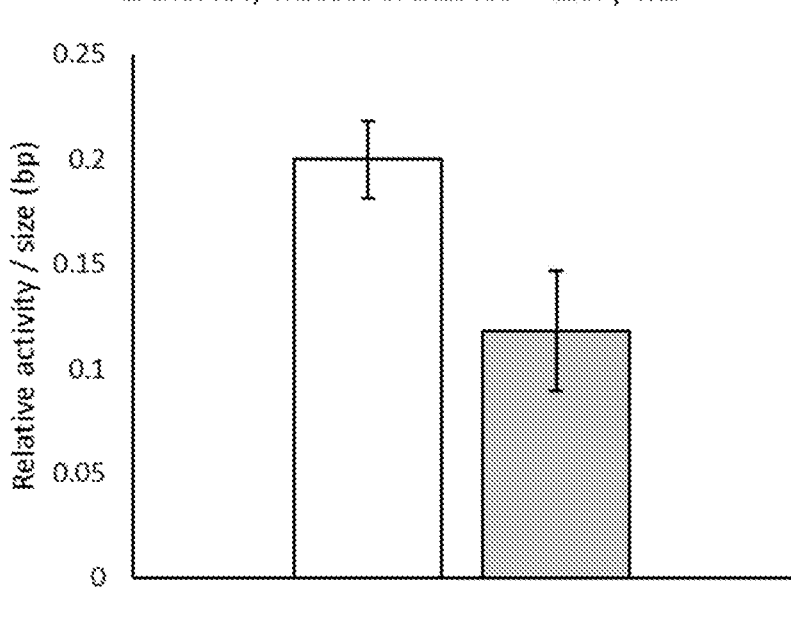

FIG. 22B shows the mean relative activity over size (in base pairs) of promoters which comprise the combination of cis-regulatory elements CRE0058, CRE0065 and CRE0066 compared to promoters from group 'ALL' which have any three liver-specific cis-regulatory elements. This indicates that the superior performance of promoters comprising cis-regulatory elements CRE0058, CRE0065 and CRE0066 compared to promoters comprising any three liver-specific cis-regulatory elements is not due to differences in promoter size.

Figure 23A:
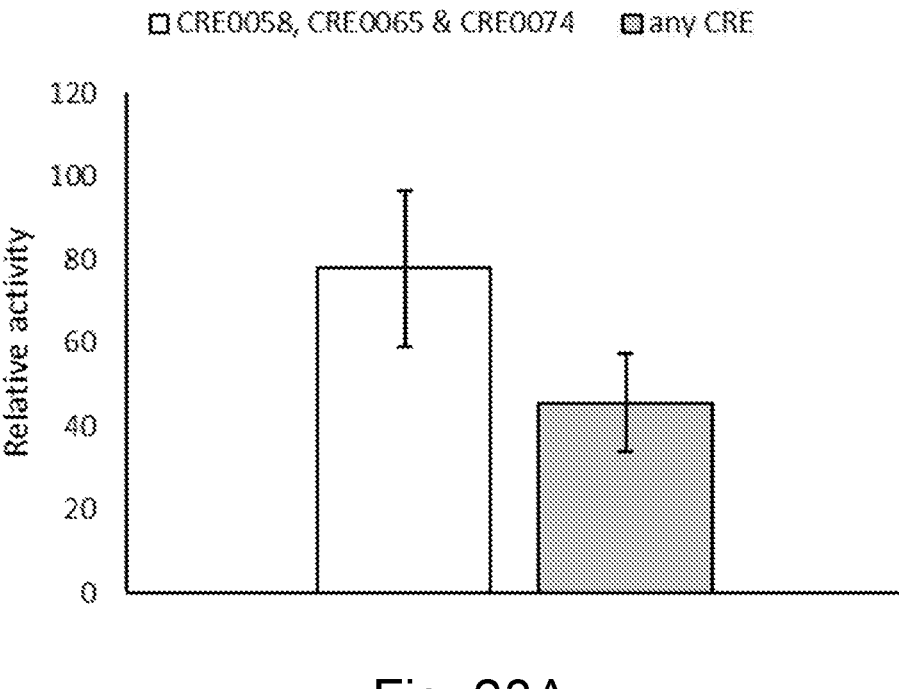

FIG. 23A shows the mean relative activity of promoters which comprise the combination of cis-regulatory elements CRE0058, CRE0065 and CRE0074 compared to promoters from group 'ALL' which have any three liver-specific cis-regulatory elements.

Figure 23B:
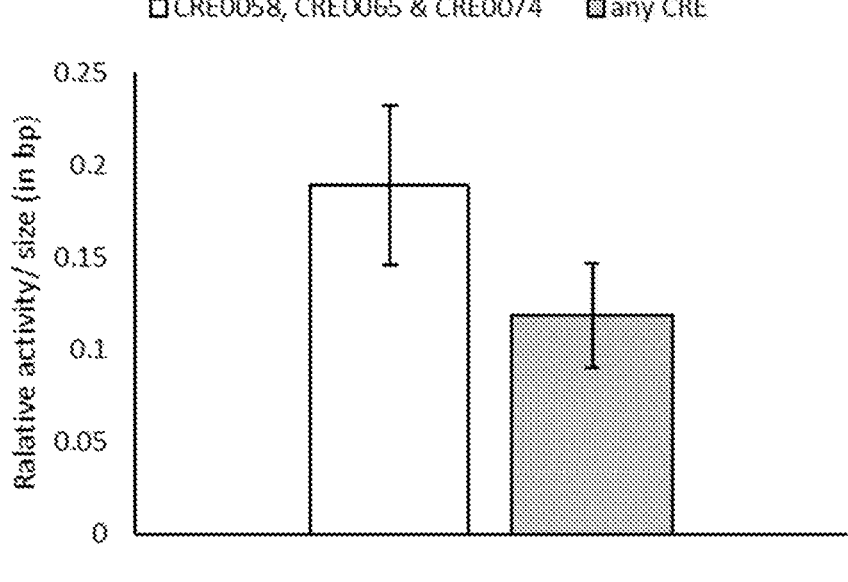

FIG. 23B shows the mean relative activity over size (in base pairs) of promoters which comprise the combination of cis-regulatory elements CRE0058, CRE0065 and CRE0074 compared to promoters from group 'ALL' which have any three liver-specific cis-regulatory elements. This indicates that the superior performance of promoters comprising cis-regulatory elements CRE0058, CRE0065 and CRE0074 compared to promoters comprising any three liver-specific cis-regulatory elements is not due to differences in promoter size.

Figure 24A:
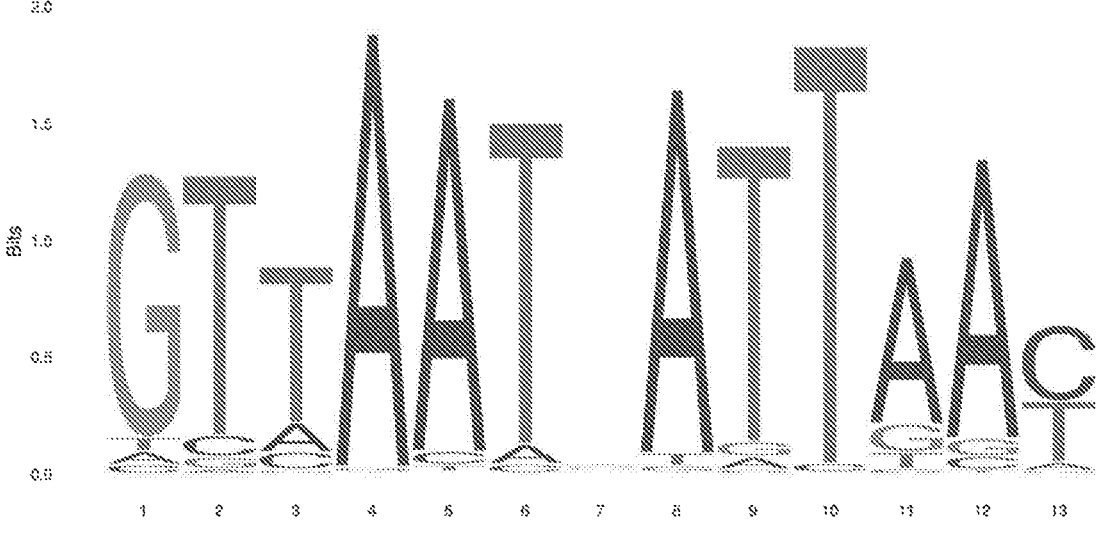
Figure 24B:
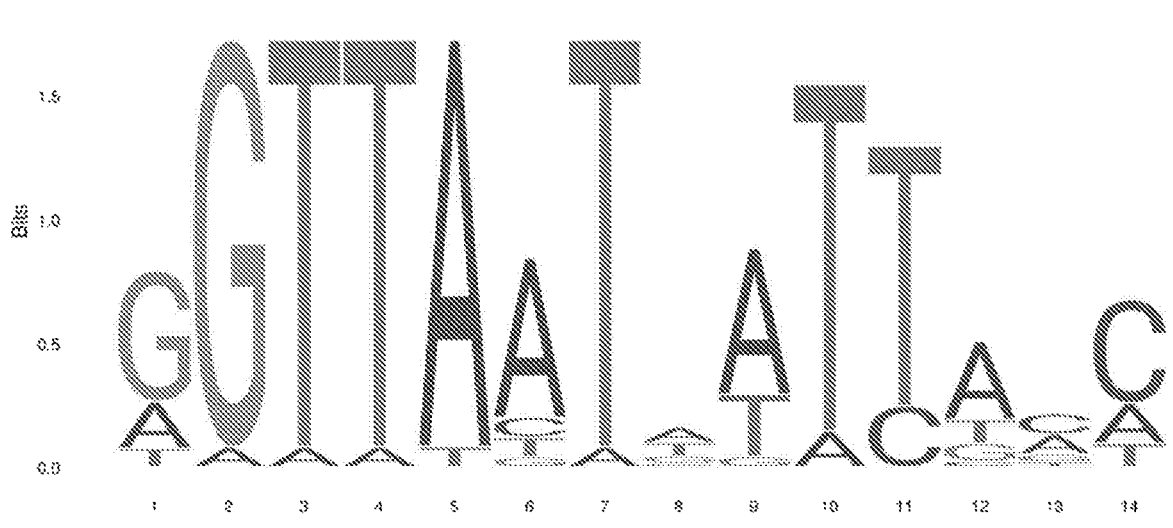

FIG. 24A shows the PWM of HNF1A and FIG. 24B shows the PWM of HNF1B.

DETAILED DESCRIPTION OF THE INVENTION

CREs and Functional Variants Thereof:

Disclosed herein are various CREs that can be used in the construction of liver-specific promoters. These CREs are generally derived from genomic promoter and enhancer sequences, but they are used herein in contexts quite different from their native genomic environment. Generally, the CREs constitute small parts of much larger genomic regulatory domains, which control expression of the genes with which they are normally associated. It has been surprisingly found that these CREs, many of which are very small, can be isolated form their normal environment and retain liver-specific regulatory activity when used to construct various synthetic promoters. This is surprising because the removal of a regulatory sequence from the complex and "three dimensional" natural context in the genome often results in a significant loss of activity, so there is no reason to expect a given CRE to retain the levels of activity observed once removed from their natural environment. Many combinations of these CREs have been tested and found to be highly effective at enhancing liver-specific promoter activity when combined with minimal and proximal promoters. It should be noted that the sequences of the CREs of the present invention can be altered without causing a substantial loss of activity. Thus, functional variants of the CREs discussed below can be prepared by modifying the sequence of the CREs, provided that modifications which are significantly detrimental to activity of the CRE are avoided. In view of the information provided in the present disclosure, modification of CREs to provide functional variants is straightforward. Moreover, the present disclosure provides methodologies for simply assessing the functionality of any given CRE variant. Functional variants for each CRE are discussed below.

The relatively small size of certain CREs according to the present invention is advantageous because it allows for the CREs, more specifically promoters containing them, to be provided in vectors while taking up the minimal amount of the payload of the vector. This is particularly important when a CRE is used in a vector with limited capacity, such as an AAV-based vector.

CRE0018, CRE0051, CRE0042, CRE0058, CRE0065, CRE0066, CRE0068 and CRE0074 (or functional variants thereof) are of particular interest in the present invention as their presence in various combinations has been shown to consistently correlate with highly active liver-specific promoters. Thus, combinations which comprise two of these elements are of particular relevance. Furthermore, combinations of one of these CREs with promoter elements CRE0006 and CRE0059 have been shown to consistently correlate with highly active liver-specific promoters. Without wishing to be bound by theory, it appears that these CREs are particularly effective in enhancing liver specific promoter activity, and in many cases they may act synergistically when combined in a CRM/promoter.

The presence of CRE0001, CRE0005, CRE0012, CRE0047, CRE0048, CRE0056, CRE0062, CRE0077, CRE0078, CRE0083.1 and CRE0089 (or functional variants thereof) have been found to also correlate with high liver-specific activity, but to a lesser degree. As such, the presence of one or more of these CREs are preferred in some cases. Without wishing to be bound by theory, it appears that these CREs are somewhat effective in enhancing liver-specific promoter activity, and they may act synergistically when combined with one or more of the above-mentioned CREs in a CRM/promoter.

As is disused in some detail below, the CREs of the present invention comprise certain liver-specific TFBS. It is generally desired that in functional variants of the CREs these liver-specific TFBS remain functional. The skilled person is well aware that TFBS sequences can vary yet retain functionality. In view of this, the sequence for a TFBS is typically illustrated by a consensus sequence from which some degree of variation is typically present. Further information about the variation that occurs in a TFBS can be illustrated using a positional weight matrix (PWM), which represents the frequency with which a given nucleotide is typically found at a given location in the consensus sequence. Details of TF consensus sequences and associated positional weight matrices can be found in, for example, the Jaspar or Transfac databases http://jaspar.genereg.net/ and http://gene-regulation.com/pub/databases.html). This information allows the skilled person to modify the sequence in any given TFBS of a CRE in a manner which retains, and in some cases even increases, CRE functionality. By way of example, if we consider the TFBS for HNF1 found in CRE0079 as set below. The TFBS for HNF1 in CRE0079 has the sequence GTTAATTTATAAC (SEQ ID NO: 98). The PMW for HNF1 is shown in FIG. 24 (HNF1 has two sub-family members, HNF1A and HNF1B, with very similar TFBS PWMs; the PWMs for both HNF1A and HNF1B isoforms are shown in FIG. 24A and 24B, respectively). In view of this the skilled person has ample guidance on how the TFBS for HNF1 can be modified, while maintaining ability to bind the desired TF; the Jaspar system will, for example, score a putative TFBS based on its similarity to a given PWM. Furthermore, CREs can be scanned against all PWM from JASPAR database to identify/analyse all TFBS. The skilled person can of course find additional guidance in the literature, and, moreover, routine experimentation can be used to confirm TF binding to a putative TFBS in any variant CRE. While HNF1 has been discussed in this example, the skilled person can do the same for the other TFs and TFBS mentioned herein. It will be apparent that significant sequence modification in a CRE, even within TFBS in a CRE, can be made while retaining function.

CRE0018 and Functional Variants Thereof:

CRE0018 has a sequence as set out in SEQ ID NO: 1.

Functional variants of CRE0018 are regulatory elements with sequences which vary from CRE0018, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE substantially non-functional.

In some embodiments, a functional variant of CRE0018 can be viewed as a CRE which, when substituted in place of CRE0018 in a CRM or promoter, substantially retains its activity. For example, a promoter which comprises a functional variant of CRE0018 substituted in place of CRE0018 preferably retains 80% of its activity, more preferably 90% of its activity, more preferably 95% of its activity, and yet more preferably 100% of its activity (compared to the reference promoter comprising CRE0018). For example, considering promoter SP0239 as an example, CRE0018 in SP0239 in can be replaced with a functional variant of CRE0018, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments the functional variant of CRE0018 comprises transcription factor binding sites (TFBS) for the same liver-specific transcription factors (TF) as CRE0018. The liver-specific TFBS present in CRE0018, listed in the order in which they are present, are: IRF, NF1, HNF3, HBLF, RXRa, EF-C, NF1, and c/EBP. The functional variant of CRE0018 thus preferably comprises all of these TFBS. Preferably, they are present in the same order that they are present in CRE0018, i.e. in the order IRF, NF1, HNF3, HBLF, RXRa, EF-C, NF1, and then c/EBP. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0018 comprises the following TFBS sequences: CTTTCACTTTC (SEQ ID NO: 34) (IRF), TCGCCAA (SEQ ID NO: 35) (NF1), TGTGTAAACA (SEQ ID NO: 36) (HNF3), TGTAAACAATA (SEQ ID NO: 37) (HBLF), CTGAACCTTTACCC (SEQ ID NO: 38) (RXRa), GTTGCCCGGCAAC (SEQ ID NO: 39) (EF-C), CAGGTCTGTGCCAAG (SEQ ID NO: 40) (NF1), TGC-CAAGTGTTTG (SEQ ID NO: 41) (c/EBP), sequences complementary thereto, or functional variants of these TFBS sequences that maintain the ability to bind to bind to their respective TF (see Table 9 for TFBS SEQ ID NOs). These may be present in the same order as CRE0018, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0018 comprises the sequence:

CTTTCACTTTCTCGCCAA-Na-TGTGTAAACAATA-
   Nb-CTGAACCTTTACCC-Nc-GTTGCCCGGCAAC-
   Nd-CAGGTCTGTGCCAAGTGTTTG (SEQ ID NO:
   268), or a sequence that is at least 70%, 80%, 90%,
   95% or 99% identical thereto,
wherein Na, Nb, Nc, and Nd represent optional spacer
   sequences. When present, Na optionally has a length of
   from 10 to 20 nucleotides, preferably from 13 to 17
   nucleotides, and more preferably 15 nucleotides. When
   present, Nb optionally has a length of from 1 to 10
   nucleotides, preferably from 1 to 5 nucleotides, more
   preferably 1 nucleotide. When present, Nc optionally
   has a length of from 1 to 10 nucleotides, preferably 1
   to 5 nucleotides, and more preferably 1 nucleotide.
   When present, Nd suitably has a length of from 1 to 10
   nucleotides, preferably from 2 to 8 nucleotides in
   length, and more preferably 3 nucleotides in length.
In some embodiments, a functional variant of CRE0018
suitably comprises a sequence that is at least 70% identical to SEQ ID NO: 1, more preferably at least 80%, 90%, 95% or 99% identical to SEQ ID NO: 1. Additionally or alternatively, a functional variant of CRE0018 suitably comprises a sequence which hybridises under stringent conditions to SEQ ID NO: 1.

In some embodiments of the invention the cis-regulatory enhancer element consists of SEQ ID NO: 1 or a functional variant thereof.

It will be noted that the CRE or functional variant thereof can be provided on either strand of a double stranded polynucleotide and can be provided in either orientation. As such, complementary and reverse complementary sequences of SEQ ID NO: 1 or a functional variant thereof fall within the scope of the invention. Single stranded nucleic acids comprising the sequence according to SEQ ID NO: 1 or a functional variant thereof also fall within the scope of the invention.

In some preferred embodiments, there is provided a CRE comprising or consisting of CRE0018 or a functional variant thereof has a length of 200 or fewer nucleotides, 150 or fewer nucleotides, 125 or fewer nucleotides, or 103 or fewer nucleotides.

CRE0042 and Functional Variants Thereof:

CRE0042 has a sequence as set out in SEQ ID NO: 2.

Functional variants of CRE0042 are regulatory elements with sequences which vary from CRE0042, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE substantially non-functional.

In some embodiments, a functional variant of CRE0042 can be viewed as a CRE which, when substituted in place of CRE0042 in a CRM or promoter, substantially retains its activity. For example, a promoter which comprises a functional variant of CRE0042 substituted in place of CRE0042 preferably retains 80% of its activity, more preferably 90% of its activity, more preferably 95% of its activity, and yet more preferably 100% of its activity (compared to the reference promoter comprising CRE0042). For example, considering promoter SP0239 as an example, CRE0042 in SP0380 can be replaced with a functional variant of CRE0042, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0042 comprises transcription factor binding sites (TFBS) for the same liver-specific transcription factors (TF) as CRE0042. The liver-specific TFBS present in CRE0042, listed in the order in which they are present, are: HNF-3, C/EBP, HNF-4 and C/EBP. The functional variant of CRE0042 thus preferably comprises all of these TFBS. Preferably, they are present in the same order that they are present in CRE0042, i.e. in the order HNF-3, C/EBP, HNF-4 and then C/EBP. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0042 comprises the following TFBS sequences: GTTCAAA-CATG (SEQ ID NO: 42) (HNF-3), CTAATACTCTG (SEQ ID NO: 43) (C/EBP), TGCAAGGGTCAT (SEQ ID NO: 44) (HNF-4), and TTACTCAACA (SEQ ID NO: 45) (C/EBP) and sequences complementary thereto, or functional variants of these TFBS sequences that maintain the ability to bind to bind to their respective TF (see Table 10 for SEQ ID NOs). These may be present in the same order as CRE0042, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0042 comprises the sequence:

GTTCAAACATG-Na-CTAATACTCTG-Nb-
    TGCAAGGGTCAT-Nc-TTACTCAACA (SEQ ID NO: 269) or a sequence that is at least 70%, 80%, 90%, 95% or 99% identical thereto, wherein Na, Nb and Nc represent optional spacer sequences. When present, Na optionally has a length of from 1 to 10 nucleotides, preferably from 1 to 5 nucleotides, and more preferably 2 nucleotides. When present, Nb optionally has a length of from 1 to 10 nucleotides, preferably from 2 to 6 nucleotides, and more preferably 4 nucleotides. When present, Nc optionally has a length of from 8 to 23 nucleotides, preferably from 10 to 20 nucleotides, and more preferably 15 nucleotides.

In some embodiments, a functional variant of CRE0042 suitably comprises a sequence that is at least 70% identical to SEQ ID NO: 2, more preferably at least 80%, 90%, 95% or 99% identical to SEQ ID NO: 2. Additionally or alternatively, a functional variant of CRE0042 suitably comprises a sequence which hybridises under stringent conditions to SEQ ID NO: 2.

In some embodiments of the invention the cis-regulatory enhancer element consists of CRE0042 or a functional variant thereof.

It will be noted that the CRE or functional variant thereof can be provided on either strand of a double stranded polynucleotide and can be provided in either orientation. As such, complementary and reverse complementary sequences of SEQ ID NO: 2 or a functional variant thereof fall within the scope of the invention. Single stranded nucleic acids comprising the sequence according to SEQ ID NO: 2 or a functional variant thereof also fall within the scope of the invention.

In some preferred embodiments, there is provided a CRE comprising or consisting of CRE0042 or a functional variant thereof has a length of 200 or fewer nucleotides, 150 or fewer nucleotides, 125 or fewer nucleotides, 100 or fewer nucleotides, or 80 or fewer nucleotides.

CRE0051 and Functional Variants Thereof:

CRE0051 (also known as Al or alpha mic/bik) has a sequence as set out in SEQ ID NO: 3.

Functional variants of CRE0051 are regulatory elements with sequences which vary from CRE0051, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE substantially non-functional.

In some embodiments, a functional variant of CRE0051 can be viewed as a CRE which, when substituted in place of CRE0051 in a CRM or promoter, substantially retains its activity. For example, a liver-promoter which comprises a functional variant of CRE0051 substituted in place of CRE0051 preferably retains 80% of its activity, more preferably 90% of its activity, more preferably 95% of its activity, and yet more preferably 100% of its activity. For example, considering promoter SP0373 as an example, CRE0051 in SP0239 can be replaced with a functional variant of CRE0051, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments the functional variant of CRE0051 comprises transcription factor binding sites (TFBS) for the same liver-specific transcription factors (TF) as CRE0051. The liver-specific TFBS present in CRE0051, listed in the order in which they are present, are: HNF1, HNF4, HNF3, HNF1 and HNF3. The functional variant of CRE0051 thus preferably comprises all of these TFBS. Preferably, they are present in the same order that they are present in CRE0051, i.e. in the order HNF1, HNF4, HNF3, HNF1 then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0051 comprises the following TFBS sequences: GTTAATTTT-TAAA (SEQ ID NO: 46) (HNF1), GTGGCCCTTGG (SEQ ID NO: 47) (HNF4), TGTTTGC (SEQ ID NO: 48) (HNF3), TGGTTAATAATCTCA (SEQ ID NO: 49) (HNF1) then ACAAACA (SEQ ID NO: 50) (HNF3), sequences complementary thereto, or functional variants of these TFBS sequences that maintain the ability to bind to bind to their respective TF (see Table 11 for TFBS SEQ ID NOs). These may be present in the same order as CRE0051, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0051 comprises the sequence:

GTTAATTTTTAAA-Na-GTGGCCCTTGG-N
    b-TGTTTGC-Nc-TGGTTAATAATCTCA-Nd-
    ACAAACA (SEQ ID NO: 270), or a sequence that is at least 70%, 80%, 90%, 95% or 99% identical thereto, wherein Na, Nb, Nc, and Nd represent optional spacer sequences. When present, Na optionally has a length of from 10 to 26 nucleotides, preferably from 14 to 22 nucleotides, and more preferably 18 nucleotides. When present, Nb optionally has a length of from 8 to 22 nucleotides, preferably from 12 to 20 nucleotides, more preferably 16 nucleotides. When present, Nc optionally has a length of from 1 to 10 nucleotides, preferably 1 to 5 nucleotides, and more preferably 2 nucleotides.

When present, Nd suitably has a length of from 1 to 13 nucleotides, preferably from 2 to 9 nucleotides in length, and more preferably 5 nucleotides in length.

In some embodiments, a functional variant of CRE0051 suitably comprises a sequence that is at least 70% identical to SEQ ID NO: 3, more preferably at least 80%, 90%, 95% or 99% identical to SEQ ID NO: 3. Additionally or alternatively, a functional variant of SEQ ID NO: 3 suitably comprises a sequence which hybridises under stringent conditions to SEQ ID NO: 3.

In some embodiments of the invention the cis-regulatory enhancer element consists of SEQ ID No: 3 or a functional variant thereof.

It will be noted that the CRE or functional variant thereof can be provided on either strand of a double stranded polynucleotide and can be provided in either orientation. As such, complementary and reverse complementary sequences of SEQ ID NO: 3 or a functional variant thereof fall within the scope of the invention. Single stranded nucleic acids comprising the sequence according to SEQ ID NO: 3 or a functional variant thereof also fall within the scope of the invention.

In some preferred embodiments, there is provided a CRE comprising or consisting of CRE0051 or a functional variant thereof has a length of 200 or fewer nucleotides, 150 or fewer nucleotides, 125 or fewer nucleotides, or 100 or fewer nucleotides.

CRE0058 and Functional Variants Thereof:

CRE0058 has a sequence as set out in SEQ ID NO: 4.

Functional variants of CRE0058 are regulatory elements with sequences which vary from CRE0058, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0058 can be viewed as a CRE which, when substituted in place of CRE0058 in a CRM or promoter, substantially retains its activity. For example, a promoter which comprises a functional variant of CRE0058 substituted in place of CRE0058 preferably retains 80% of its activity, more preferably 90% of its activity, more preferably 95% of its activity, and yet more preferably 100% of its activity (compared to the reference promoter comprising CRE0058). For example, considering promoter SP0373 as an example, CRE0058 in SP0373 can be replaced with a functional variant of CRE0058, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0058 (SEQ ID NO: 4) comprises transcription factor binding sites (TFBS) for the same liver-specific transcription factors (TF) as CRE0058. The liver-specific TFBS present in CRE0058, listed in the order in which they are present, are: HNF4 and c/EBP. The functional variant of CRE0058 thus preferably comprises all of these TFBS. Preferably, they are present in the same order that they are present in CRE0058, i.e. in the order HNF4 then c/EBP. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0058 comprises the following TFBS sequences: CGCCCTTTGGACC (SEQ ID NO: 51) (HNF4) and GACCTTTTGCAATCCTGG (SEQ ID NO: 52) (c/EBP), sequences complementary thereto, or functional variants of these TFBS sequences that maintain the ability to bind to bind to their respective TF (see Table 12 for TFBS SEQ ID NOs). These may be present in the same order as CRE0058, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0058 comprises the sequence:

GCGCCCTTTGGACCTTTTGCAATCCTGG (SEQ ID NO: 271), or a sequence that is at least 70%, 80%, 90%, 95% or 99% identical thereto.

In some embodiments, a functional variant of CRE0058 suitably comprises a sequence that is at least 70% identical to SEQ ID NO: 4, more preferably at least 80%, 90%, 95% or 99% identical to SEQ ID NO: 4. Additionally or alternatively, a functional variant of CRE0058 suitably comprises a sequence which hybridises under stringent conditions to SEQ ID NO: 4.

In some embodiments of the invention the cis-regulatory enhancer element consists of SEQ ID NO: 4 or a functional variant thereof.

It will be noted that the CRE or functional variant thereof can be provided on either strand of a double stranded polynucleotide and can be provided in either orientation. As such, complementary and reverse complementary sequences of SEQ ID NO: 4 or a functional variant thereof fall within the scope of the invention. Single stranded nucleic acids comprising the sequence according to SEQ ID NO: 4 or a functional variant thereof also fall within the scope of the invention.

In some preferred embodiments, there is provided a CRE comprising or consisting of CRE0058 or a functional variant thereof has a length of 120 or fewer nucleotides, 80 or fewer nucleotides, 60 or fewer nucleotides, or 40 or fewer nucleotides.

CRE0065 and Functional Variants Thereof:

CRE0065 (also known as LVR_CRE0065_AP0A1) has a sequence as set out in SEQ ID NO: 5.

Functional variants of CRE0065 are regulatory elements with sequences which vary from CRE0065, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0065 can be viewed as a CRE which, when substituted in place of CRE0065 in a CRM or promoter, substantially retains its activity. For example, a promoter which comprises a functional variant of CRE0065 substituted in place of CRE0065 preferably retains 80% of its activity, more preferably 90% of its activity, more preferably 95% of its activity, and yet more preferably 100% of its activity (compared to the reference promoter comprising CRE0065). For example, considering promoter SP0239 as an example, CRE0065 in SP0239 can be replaced with a functional variant of CRE0065, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0065 comprises transcription factor binding sites (TFBS) for the same liver-specific transcription factors (TF) as CRE0065. The liver-specific TFBS present in CRE0065, listed in the order in which they are present, are: RXR Alpha, HNF3 and HNF3. The functional variant of CRE0065 thus preferably comprises all of these TFBS. Preferably, they are present in the same order that they are present in CRE0065, i.e. in the order RXR Alpha, HNF3 then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0065 comprises the following TFBS sequences: ACT-GAACCCTTGACCCCTGCCCT (SEQ ID NO: 53) (RXR Alpha), CTGTTTGCCC (SEQ ID NO: 54) (HNF3), and CTATTTGCCC (SEQ ID NO: 55) (HNF3), sequences complementary thereto, or functional variants of these TFBS sequences that maintain the ability to bind to bind to their respective TF (see Table 13 for TFBS SEQ ID NOs). These may be present in the same order as CRE0065, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0065 comprises the sequence: ACTGAACCCTTGACCCCT-Na-CTGTTTGCCC-Nb-TATTTGCCC (SEQ ID NO: 272), or a sequence that is at least 70%, 80%, 90%, 95% or 99% identical thereto, wherein Na and Nb represent optional spacer sequences. When present, Na optionally has a length of from 14 to 30 nucleotides, preferably from 18 to 26 nucleotides, and more preferably 22 nucleotides. When present, Nb optionally has a length of from 1 to 10 nucleotides, preferably from 2 to 6 nucleotides, and more preferably 4 nucleotides.

In some embodiments, a functional variant of CRE0065 suitably comprises a sequence that is at least 70% identical to SEQ ID NO: 5, more preferably at least 80%, 90%, 95% or 99% identical to SEQ ID NO: 5. Additionally or alternatively, a functional variant of CRE0065 suitably comprises a sequence which hybridises under stringent conditions to SEQ ID NO: 5.

In some embodiments of the invention the cis-regulatory enhancer element consists of SEQ ID NO: 5 or a functional variant thereof.

It will be noted that the CRE or functional variant thereof can be provided on either strand of a double stranded polynucleotide and can be provided in either orientation. As such, complementary and reverse complementary sequences of SEQ ID NO: 5 or a functional variant thereof fall within the scope of the invention. Single stranded nucleic acids comprising the sequence according to SEQ ID NO: 5 or a functional variant thereof also fall within the scope of the invention.

In some preferred embodiments, there is provided a CRE comprising or consisting of CRE0065 or a functional variant thereof has a length of 200 or fewer nucleotides, 150 or fewer nucleotides, 125 or fewer nucleotides, 90 or fewer nucleotides, or 72 or fewer nucleotides.

CRE0065.1 and Functional Variants Thereof:

CRE0065.1 (also known as LVR_CRE0065_AP0A1_v1) has a sequence as set out in SEQ ID NO: 6. CRE0065.1 comprises CRE0065 in its entirety, and an additional 34 nucleotides at the 3' end. CRE0065.1 can be viewed as a longer, functional equivalent of CRE0065.

Functional variants of CRE0065.1 are regulatory elements with sequences which vary from CRE0065.1, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0065.1 can be viewed as a CRE which, when substituted in place of CRE0065.1 in a CRM or promoter, substantially retains its activity. For example, a promoter which comprises a functional variant of CRE0065.1 substituted in place of CRE0065.1 preferably retains 80% of its activity, more preferably 90% of its activity, more preferably 95% of its activity, and yet more preferably 100% of its activity (compared to the reference promoter comprising CRE0065.1). For example, considering promoter SP0127A1 as an example, CRE0065.1 in SP0127A1 can be replaced with a functional variant of CRE0065.1, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0065.1 comprises transcription factor binding sites (TFBS) for the same liver-specific transcription factors (TF) as CRE0065.1. The liver-specific TFBS present in CRE0065.1, listed in the order in which they are present, are: RXR Alpha, HNF3, HNF3 and HNF4 (i.e. it compares an additional HNF4 TFBS when compared to CRE0065). The functional variant of CRE0065.1 thus preferably comprises all of these TFBS. Preferably, they are present in the same order that they are present in CRE0065.1, i.e. in the order RXR Alpha, HNF3, HNF3 then HNF4. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0065.1 comprises the following TFBS sequences: ACT- GAACCCTTGACCCCTGCCCT (SEQ ID NO: 53) (RXR Alpha), CTGTTTGCCC (SEQ ID NO: 54) (HNF3), CTAT-TTGCCC (SEQ ID NO: 55) (HNF3) and TGATCCTT-GAACTCT (SEQ ID NO: 59) (HNF4), sequences complementary thereto, or functional variants of these TFBS sequences that maintain the ability to bind to bind to their respective TF (see Table 14 for TFBS SEQ ID NOs). These may be present in the same order as CRE0065.1, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0065.1 comprises the sequence:

ACTGAACCCTTGACCCCT-Na-CTGTTTGCCC-Nb-TATTTGCCC-Nc-TGATCCTTGAACTCT (SEQ ID NO: 273), or a sequence that is at least 70%, 80%, 90%, 95% or 99% identical thereto, wherein Na, Nb and Nc represent optional spacer sequences. When present, Na optionally has a length of from 14 to 30 nucleotides, preferably from 18 to 26 nucleotides, and more preferably 22 nucleotides. When present, Nb optionally has a length of from 1 to 10 nucleotides, preferably from 2 to 6 nucleotides, and more preferably 4 nucleotides. When present, Nc optionally has a length of from 9 to 25 nucleotides, preferably from 13 to 21 nucleotides, and more preferably 17 nucleotides.

In some embodiments, a functional variant of CRE0065.1 suitably comprises a sequence that is at least 70% identical to SEQ ID NO: 6, more preferably at least 80%, 90%, 95% or 99% identical to SEQ ID NO: 6. Additionally or alternatively, a functional variant of CRE0065.1 suitably comprises a sequence which hybridises under stringent conditions to SEQ ID NO: 6.

In some embodiments of the invention the cis-regulatory enhancer element consists of CRE0065.1 or a functional variant thereof.

It will be noted that the CRE or functional variant thereof can be provided on either strand of a double stranded polynucleotide and can be provided in either orientation. As such, complementary and reverse complementary sequences of SEQ ID NO: 6 or a functional variant thereof fall within the scope of the invention. Single stranded nucleic acids comprising the sequence according to SEQ ID NO: 6 or a functional variant thereof also fall within the scope of the invention.

In some preferred embodiments, there is provided a CRE comprising or consisting of CRE0065.1 or a functional variant thereof has a length of 200 or fewer nucleotides, 150 or fewer nucleotides, 125 or fewer nucleotides, or 106 or fewer nucleotides.

CRE0066 and Functional Variants Thereof:

CRE0066 (also known as Enh_18XS) has a sequence as set out in SEQ ID NO: 7.

Functional variants of CRE0066 are regulatory elements with sequences which vary from CRE0066, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0066 can be viewed as a CRE which, when substituted in place of CRE0066 in a CRM or promoter, substantially retains its activity. For example, a promoter which comprises a functional variant of CRE0066 substituted in place of CRE0066 preferably retains 80% of its activity, more preferably 90% of its activity, more preferably 95% of its activity, and yet more preferably 100% of its activity (compared to the reference promoter comprising CRE0066). For example, considering promoter SP0239 as an example, CRE0066 in SP0239 can be replaced with a functional variant of CRE0066, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0066 comprises transcription factor binding sites (TFBS) for the same liver-specific transcription factors (TF) as CRE0066. The liver-specific TFBS present in CRE0066, listed in the order in which they are present, are: HNF4G and FOS::JUN. The functional variant of CRE0066 thus preferably comprises all of these TFBS. Preferably, they are present in the same order that they are present in CRE0066, i.e. in the order HNF4G then FOS::JUN When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0066 comprises the following TFBS sequences: GCAGGGCAAAGTGCA (SEQ ID NO: 60) (HNF4G) and GATGACTCAG (SEQ ID NO: 61 (FOS::JUN), sequences complementary thereto, or functional variants of these TFBS sequences that maintain the ability to bind to bind to their respective TF (see Table 15 for SEQ ID NOs). These may be present in the same order as CRE0066, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0066 (SEQ ID NO: 7) comprises the sequence:

GCAGGGCAAAGTGCA-Na-GATGACTCAG (SEQ ID NO: 274) or a sequence that is at least 70%, 80%, 90%, 95% or 99% identical thereto, wherein Na represents an optional spacer sequence. When present, Na optionally has a length of from 10 to 28 nucleotides, preferably from 14 to 24 nucleotides, and more preferably 19 nucleotides.

In some embodiments, a functional variant of CRE0066 suitably comprises a sequence that is at least 70% identical to SEQ ID NO: 7, more preferably at least 80%, 90%, 95% or 99% identical to SEQ ID NO: 7. Additionally or alternatively, a functional variant of CRE0066 suitably comprises a sequence which hybridises under stringent conditions to SEQ ID NO: 7.

In some embodiments of the invention the cis-regulatory enhancer element consists of CRE0066 or a functional variant thereof.

It will be noted that the CRE or functional variant thereof can be provided on either strand of a double stranded polynucleotide and can be provided in either orientation. As such, complementary and reverse complementary sequences of SEQ ID NO: 7 or a functional variant thereof fall within the scope of the invention. Single stranded nucleic acids comprising the sequence according to SEQ ID NO: 7 or a functional variant thereof also fall within the scope of the invention.

In some preferred embodiments, there is provided a CRE comprising or consisting of CRE0066 or a functional variant thereof has a length of 200 or fewer nucleotides, 150 or fewer nucleotides, 125 or fewer nucleotides, 100 or fewer nucleotides, or 87 or fewer nucleotides.

CRE0066.2 and Functional Variants Thereof:

CRE0066.2 (also known as LVR_CRE0066_v2 or Enh_18S) has a sequence as set out in SEQ ID NO: 8. CRE0066.2 comprises CRE0066 in its entirety, with an additional 81 nucleotides present at the 3' end. CRE0066.2 can be viewed as a longer, functional variant of CRE0066.

Functional variants of CRE0066.2 are regulatory elements with sequences which vary from CRE0066.2, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0066.2 can be viewed as a CRE which, when substituted in place of CRE0066.2 in a CRM or promoter, substantially retains its activity. For example, a promoter which comprises a functional variant of CRE0066.2 substituted in place of CRE0066.2 preferably retains 80% of its activity, more preferably 90% of its activity, more preferably 95% of its activity, and yet more preferably 100% of its activity (compared to the reference promoter comprising CRE0066.2). For example, considering promoter SP0109 as an example, CRE0066.2 in SP0109 can be replaced with a functional variant of CRE0066.2, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

CRE0066.2 contains the same TFBS for liver-specific TFBS as CRE0066, and thus the same considerations apply as regards the preferable presence and location of the relevant TFBS.

In some embodiments, a functional variant of CRE0066.2 suitably comprises a sequence that is at least 70% identical to SEQ ID NO: 8, more preferably at least 80%, 90%, 95% or 99% identical to SEQ ID NO: 8. Additionally or alternatively, a functional variant of CRE0066.2 suitably comprises a sequence which hybridises under stringent conditions to SEQ ID NO: 8.

In some embodiments of the invention, the cis-regulatory enhancer element consists of SEQ ID NO: 8 or a functional variant thereof.

It will be noted that the CRE or functional variant thereof can be provided on either strand of a double stranded polynucleotide and can be provided in either orientation. As such, complementary and reverse complementary sequences of SEQ ID NO: 8 or a functional variant thereof fall within the scope of the invention. Single stranded nucleic acids comprising the sequence according to SEQ ID NO: 8 or a functional variant thereof also fall within the scope of the invention.

CRE0066.1 and Functional Variants Thereof:

CRE0066.1 (also known as LVR_CRE0066_v1 or Enh_18) has a sequence as set out in SEQ ID NO: 9. CRE0066.1 comprises both CRE0066 and CRE0066.2 in their entirety, with an additional 154 nucleotides present at the 3' end when compared to CRE0066. CRE0066.1 can be viewed as a longer, functional variant of each of CRE0066 and CRE0066.2.

Functional variants of CRE0066.1 are regulatory elements with sequences which vary from CRE0066.1, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0066.1 can be viewed as a CRE which, when substituted in place of CRE0066.1 in a CRM or promoter, substantially retains its activity. For example, a promoter which comprises a functional variant of CRE0066.1 substituted in place of CRE0066.1 preferably retains 80% of its activity, more preferably 90% of its activity, more preferably 95% of its activity, and yet more preferably 100% of its activity (compared to the reference promoter comprising CRE0066.1. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

CRE0066.1 contains the same TFBS for liver-specific TFBS as CRE0066, and thus the same considerations apply as regards the preferable presence and location of the relevant TFBS.

In some embodiments, a functional variant of CRE0066.1 suitably comprises a sequence that is at least 70% identical to SEQ ID NO: 9, more preferably at least 80%, 90%, 95% or 99% identical to SEQ ID NO: 9. Additionally or alternatively, a functional variant of CRE0066.1 suitably comprises a sequence which hybridises under stringent conditions to SEQ ID NO: 9.

In some embodiments of the invention the cis-regulatory enhancer element consists of SEQ ID NO: 9 or a functional variant thereof.

It will be noted that the CRE or functional variant thereof can be provided on either strand of a double stranded polynucleotide and can be provided in either orientation. As such, complementary and reverse complementary sequences of SEQ ID NO: 9 or a functional variant thereof fall within the scope of the invention. Single stranded nucleic acids comprising the sequence according to SEQ ID NO: 9 or a functional variant thereof also fall within the scope of the invention.

CRE0068 and Functional Variants Thereof:

CRE0068 has a sequence as set out in SEQ ID NO: 10.

Functional variants of CRE0068 are regulatory elements with sequences which vary from CRE0068, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0068 can be viewed as a CRE which, when substituted in place of CRE0068 in a CRM or promoter, substantially retains its activity. For example, a promoter which comprises a functional variant of CRE0068 substituted in place of CRE0068 preferably retains 80% of its activity, more preferably 90% of its activity, more preferably 95% of its activity, and yet more preferably 100% of its activity (compared to the reference promoter comprising CRE0068). For example, considering promoter SP0379 as an example, CRE0068 in SP0379 can be replaced with a functional variant of CRE0068, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0068 comprises transcription factor binding sites (TFBS) for the same liver-specific transcription factors (TF) as CRE0068. The liver-specific TFBS present in CRE0068, listed in the order in which they are present, are: HNF-4, HNF-1/HNF-3 and SP1. The functional variant of CRE0068 thus preferably comprises all of these TFBS. Preferably, they are present in the same order that they are present in CRE0068, i.e. in the order above. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0068 comprises the following TFBS sequences: TTCCTGCTCTTTGTCCC (SEQ ID NO: 62) (HNF4), AGACTAATATTTGCC (SEQ ID NO: 63) (HNF-1/HNF-3) and ATGGGGGAGGGACAG (SEQ ID NO: 64) (SP1), sequences complementary thereto, or functional variants of these TFBS sequences that maintain the ability to bind to bind to their respective TF (see Table 16 for TFBS SEQ ID NOs). These may be present in the same order as CRE0068, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0068 comprises the sequence:

TTCCTGCTCTTTGTCCC-Na-AGACTAATATTTGCC-Nb-ATGGGGGAGGGACAG (SEQ ID NO: 275), or a sequence that is at least 70%, 80%, 90%, 95% or 99% identical thereto, wherein Na and Nb represent optional spacer sequences. When present, Na optionally has a length of from 4 to 20 nucleotides, preferably from 8 to 16 nucleotides, and more preferably 12 nucleotides. When present, Nb optionally has a length of from 10 to 30 nucleotides, preferably from 15 to 25 nucleotides, and more preferably 20 nucleotides.

In some embodiments, a functional variant of CRE0068 suitably comprises a sequence that is at least 70% identical to SEQ ID NO: 10, more preferably at least 80%, 90%, 95% or 99% identical to SEQ ID NO: 10. Additionally or alternatively, a functional variant of CRE0068 suitably comprises a sequence which hybridises under stringent conditions to SEQ ID NO: 10.

In some embodiments of the invention the cis-regulatory enhancer element consists of CRE0068 or a functional variant thereof.

It will be noted that the CRE or functional variant thereof can be provided on either strand of a double stranded polynucleotide and can be provided in either orientation. As such, complementary and reverse complementary sequences of SEQ ID NO: 10 or a functional variant thereof fall within the scope of the invention. Single stranded nucleic acids comprising the sequence according to SEQ ID NO: 10 or a functional variant thereof also fall within the scope of the invention.

In some preferred embodiments, there is provided a CRE comprising or consisting of CRE0068 or a functional variant thereof has a length of 200 or fewer nucleotides, 150 or fewer nucleotides, 125 or fewer nucleotides, or 100 or fewer nucleotides.

CRE0074 and Functional Variants Thereof:

CRE0074 (also known as SEPP1) has a sequence as set out in SEQ ID NO: 11.

Functional variants of CRE0074 are regulatory elements with sequences which vary from CRE0074, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0068 can be viewed as a CRE which, when substituted in place of CRE0074 in a CRM or promoter, substantially retains its activity. For example, a promoter which comprises a functional variant of CRE0074 substituted in place of CRE0074 preferably retains 80% of its activity, more preferably 90% of its activity, more preferably 95% of its activity, and yet more preferably 100% of its activity (compared to the reference promoter comprising CRE0074). For example, considering promoter SP0379 as an example, CRE0074 in SP0268 can be replaced with a functional variant of CRE0074, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0074 comprises transcription factor binding sites (TFBS) for the liver-specific same transcription factors (TF) as CRE0074. The liver-specific TFBS present in CRE0074, listed in the order in which they are present, are: HNF4 and FoxO1a. The functional variant of CRE0074 thus preferably comprises all of these TFBS. Preferably, they are present in the same order that they are present in CRE0074, i.e. in the order HNF4 then FoxO1a. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0074 comprises the following TFBS sequences: AACATT-GAACTTTGGACTA (SEQ ID NO: 65) (HNF4) and GTAAACAA (SEQ ID NO: 66) (FoxO1a), sequences complementary thereto, or functional variants of these TFBS sequences that maintain the ability to bind to bind to their respective TF (see Table 17 for TFBS SEQ ID NOs). These may be present in the same order as CRE0074, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0074 comprises the sequence:

AACATTGAACTTTGGACTA-Na-GTAAACAA (SEQ ID NO: 276), or a sequence that is at least 70%, 80%, 90%, 95% or 99% identical thereto, wherein Na represents an optional spacer sequence. When present, Na optionally has a length of from 7 to 23 nucleotides, preferably from 11 to 19 nucleotides, and more preferably 15 nucleotides.

In some embodiments, a functional variant of CRE0074 suitably comprises a sequence that is at least 70% identical to SEQ ID NO: 11, more preferably at least 80%, 90%, 95% or 99% identical to SEQ ID NO: 11. Additionally or alternatively, a functional variant of SEQ ID NO: 11 suitably comprises a sequence which hybridises under stringent conditions to SEQ ID NO: 11.

In some embodiments of the invention the cis-regulatory enhancer element consists of SEQ ID No: 11 or a functional variant thereof.

It will be noted that the CRE0074 or a functional variant thereof can be provided on either strand of a double stranded polynucleotide and can be provided in either orientation. As such, complementary and reverse complementary sequences of SEQ ID NO: 11 or a functional variant thereof fall within the scope of the invention. Single stranded nucleic acids comprising the sequence according to SEQ ID NO: 11 or a functional variant thereof also fall within the scope of the invention.

In some preferred embodiments, there is provided a CRE comprising or consisting of CRE0074 or a functional variant thereof has a length of 200 or fewer nucleotides, 150 or fewer nucleotides, 100 or fewer nucleotides, 80 or fewer nucleotides, or 61 or fewer nucleotides.

CRE0001 and Functional Variants Thereof:

CRE0001 has a sequence as set out in SEQ ID NO: 12.

Functional variants of CRE0001 are regulatory elements with sequences which vary from CRE0001, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0001 can be viewed as a CRE which, when substituted in place of CRE0001 in a CRM or promoter, substantially retains its activity. For example, a promoter which comprises a functional variant of CRE0001 substituted in place of CRE0001 preferably retains 80% of its activity, more preferably 90% of its activity, more preferably 95% of its activity, and yet more preferably 100% of its activity (compared to the reference promoter comprising CRE0001). For example, considering promoter SP0250 as an example, CRE0001 in SP0250 can be replaced with a functional variant of CRE0001, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0001 comprises transcription factor binding sites (TFBS) for the same liver-specific transcription factors (TF) as CRE0001. The liver-specific TFBS present in CRE0001, listed in the order in which they are present, are: HNF-4, HNF-1, HNF-3 and HNF-4. The functional variant of CRE0018 thus preferably comprises all of these TFBS. Preferably, they are present in the same order that they are present in CRE0018, i.e. in the order set out above. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0001 comprises the following TFBS sequences: TCCAAAGTC-CAAA (SEQ ID NO: 67) (HNF-4), TGTTAATAATTAATA (SEQ ID NO: 68) (HNF-1), CAATAAACATCA (SEQ ID NO: 69) (HNF-3), TTCCCTTTGAACCTT (SEQ ID NO: 70) (HNF-4), sequences complementary thereto, or functional variants of these TFBS sequences that maintain the ability to bind to bind to their respective TF (see Table 18 for TFBS SEQ ID NOs). These may be present in the same order as CRE0018, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0001 comprises the sequence:

TCCAAAGTCCAAA-Na-TGTTAATAATTAATA-Nb-CAATAAACATCA-Nc-TTCCCTTTGAACCTT (SEQ ID NO: 277), or a sequence that is at least 70%, 80%, 90%, 95% or 99% identical thereto, wherein Na, Nb, and Nc represent optional spacer sequences. When present, Na optionally has a length of from 1 to 10 nucleotides, preferably from 2 to 6 nucleotides, and more preferably 3 nucleotides. When present, Nb optionally has a length of from 1 to 10 nucleotides, preferably from 2 to 6 nucleotides, and more preferably 3 nucleotides. When present, Nc optionally has a length of from 11 to 31 nucleotides, preferably 16 to 26 nucleotides, and more preferably 21 nucleotides.

In some embodiments, a functional variant of CRE0001 suitably comprises a sequence that is at least 70% identical to SEQ ID NO: 12, more preferably at least 80%, 90%, 95% or 99% identical to SEQ ID NO: 12. Additionally or alternatively, a functional variant of CRE0001 suitably comprises a sequence which hybridises under stringent conditions to SEQ ID NO: 12.

In some embodiments of the invention the cis-regulatory enhancer element consists of SEQ ID NO: 12 or a functional variant thereof.

It will be noted that the CRE or functional variant thereof can be provided on either strand of a double stranded polynucleotide and can be provided in either orientation. As such, complementary and reverse complementary sequences of SEQ ID NO: 12 or a functional variant thereof fall within the scope of the invention. Single stranded nucleic acids comprising the sequence according to SEQ ID NO: 12 or a functional variant thereof also fall within the scope of the invention.

In some preferred embodiments, there is provided a CRE comprising or consisting of CRE0001 or a functional variant thereof has a length of 400 or fewer nucleotides, 300 or fewer nucleotides, 250 or fewer nucleotides, or 201 or fewer nucleotides.

CRE0005 and Functional Variants Thereof:

CRE0005 has a sequence as set out in SEQ ID NO: 13.

Functional variants of CRE0005 are regulatory elements with sequences which vary from CRE0005, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0005 can be viewed as a CRE which, when substituted in place of CRE0005 in a CRM or promoter, substantially retains its activity. For example, a promoter which comprises a functional variant of CRE0005 substituted in place of CRE0005 preferably retains 80% of its activity, more preferably 90% of its activity, more preferably 95% of its activity, and yet more preferably 100% of its activity (compared to the reference promoter comprising CRE0005). For example, considering promoter SP0256 as an example, CRE0005 in SP0256 can be replaced with a functional variant of CRE0005, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Bioinformatic analysis of CRE0005 revealed that it does not apparently contain any known liver-specific TFBS. Nonetheless, the present inventors have determined that CRE0005 nonetheless contributes to liver-specific activity of promoters. Without wishing to be bound by theory, this may be through cooperative interaction with other CREs that do contain liver-specific TFBS to enhance their activity.

In some embodiments of the invention, the functional variant of CRE0005 comprises a sequence that is at least 70% identical to SEQ ID NO: 13, more preferably at least 80%, 90%, 95% or 99% identical to SEQ ID NO: 13. Additionally or alternatively, a functional variant of CRE0005 suitably comprises a sequence which hybridises under stringent conditions to SEQ ID NO: 13.

In some embodiments of the invention the CRE consists of SEQ ID NO: 13 or a functional variant thereof.

It will be noted that the CRE or functional variant thereof can be provided on either strand of a double stranded polynucleotide and can be provided in either orientation. As such, complementary and reverse complementary sequences of SEQ ID NO: 13 or a functional variant thereof fall within the scope of the invention. Single stranded nucleic acids comprising the sequence according to SEQ ID NO: 13 or a functional variant thereof also fall within the scope of the invention.

In some preferred embodiments, there is provided a CRE comprising or consisting of CRE0005 or a functional variant thereof has a length of 400 or fewer nucleotides, 325 or fewer nucleotides, 275 or fewer nucleotides, or 232 or fewer nucleotides.

CRE0012 and Functional Variants Thereof:

CRE0012 has a sequence as set out in SEQ ID NO: 14.

Functional variants of CRE0012 are regulatory elements with sequences which vary from CRE0012, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0012 can be viewed as a CRE which, when substituted in place of CRE0012 in a CRM or promoter, substantially retains its activity. For example, a promoter which comprises a functional variant of CRE0012 substituted in place of CRE0012 preferably retains 80% of its activity, more preferably 90% of its activity, more preferably 95% of its activity, and yet more preferably 100% of its activity (compared to the reference promoter comprising CRE0012). For example, considering promoter SP0243 as an example, CRE0012 in SP0243 in can be replaced with a functional variant of CRE0012, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0012 comprises transcription factor binding sites (TFBS) for the same liver-specific transcription factors (TF) as CRE0012. The liver-specific TFBS present in CRE0012, listed in the order in which they are present, are: HNF-4, HNF-3, HNF-3 and C/EBP. The functional variant of CRE0012 thus preferably comprises all of these TFBS. Preferably, they are present in the same order that they are present in CRE0012, i.e. in the order HNF-4, HNF-3, HNF-3 and then C/EBP. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0012 comprises the following TFBS sequences: AAGTC-CAAAGGTAGA (SEQ ID NO: 71) (HNF-4), GAGTCAA-CATGA (SEQ ID NO: 72) (HNF-3), AAATGTTGACTG (SEQ ID NO: 73) (HNF-3) and GGTTGCTTAAT (SEQ ID NO: 74) (C/EBP), sequences complementary thereto, or functional variants of these TFBS sequences that maintain the ability to bind to bind to their respective TF (see Table 19 for TFBS SEQ ID NOs). These may be present in the same order as CRE0012, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0012 comprises the sequence:

AAGTCCAAAGGTAGA-Na-GAGTCAACATGA-Nb-AAATGTTGACTG-Nc-GGTTGCTTAAT (SEQ ID NO: 278), or a sequence that is at least 70%, 80%, 90%, 95% or 99% identical thereto, wherein Na, Nb, and Nc represent optional spacer sequences. When present, Na optionally has a length of from 23 to 43 nucleotides, preferably from 28 to 38 nucleotides, and more preferably 33 nucleotides. When present, Nb optionally has a length of from 38 to 58 nucleotides, preferably from 42 to 53 nucleotides, more preferably 48 nucleotides. When present, Nc optionally has a length of from 8 to 28 nucleotides, preferably 13 to 23 nucleotides, and more preferably 18 nucleotides.

In some embodiments, a functional variant of CRE0012 suitably comprises a sequence that is at least 70% identical to SEQ ID NO: 14, more preferably at least 80%, 90%, 95% or 99% identical to SEQ ID NO: 14. Additionally or alternatively, a functional variant of CRE0012 suitably comprises a sequence which hybridises under stringent conditions to SEQ ID NO: 14.

In some embodiments of the invention the CRE consists of SEQ ID NO: 14 or a functional variant thereof.

It will be noted that the CRE or functional variant thereof can be provided on either strand of a double stranded polynucleotide and can be provided in either orientation. As such, complementary and reverse complementary sequences of SEQ ID NO: 14 or a functional variant thereof fall within the scope of the invention. Single stranded nucleic acids comprising the sequence according to SEQ ID NO: 14 or a functional variant thereof also fall within the scope of the invention.

In some preferred embodiments, there is provided a CRE comprising or consisting of CRE0012 or a functional variant thereof has a length of 400 or fewer nucleotides, 300 or fewer nucleotides, 250 or fewer nucleotides, or 200 or fewer nucleotides.

CRE0047 and Functional Variants Thereof:

CRE0047 has a sequence as set out in SEQ ID NO: 15.

Functional variants of CRE0047 are regulatory elements with sequences which vary from CRE0047, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0047 can be viewed as a CRE which, when substituted in place of CRE0047 in a CRM or promoter, substantially retains its activity. For example, a promoter which comprises a functional variant of CRE0047 substituted in place of CRE0047 preferably retains 80% of its activity, more preferably 90% of its activity, more preferably 95% of its activity, and yet more preferably 100% of its activity (compared to the reference promoter comprising CRE0047). For example, considering promoter SP0258 as an example, CRE0047 in SP0258 in can be replaced with a functional variant of CRE0047, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0047 comprises transcription factor binding sites (TFBS) for the same liver-specific transcription factors (TF) as CRE0047. The liver-specific TFBS present in CRE0047, listed in the order in which they are present, are: HNF-3 and C/EBP. The functional variant of CRE0047 thus preferably comprises both of these TFBS. Preferably, they are present in the same order that they are present in CRE0047, i.e. in the order HNF-3 and then C/EBP. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0047 comprises the following TFBS sequences: GCAATGTTTGCCCAT (SEQ ID NO: 75) (HNF-3), TGTTTGCCCAT (SEQ ID NO: 76) (C/EBP), sequences complementary thereto, or functional variants of these TFBS sequences that maintain the ability to bind to bind to their respective TF (see Table 20 for TFBS SEQ ID NOs). These may be present in the same order as CRE0047, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0047 comprises the sequence:

GCAATGTTTGCCCAT (SEQ ID NO: 279), or a sequence that is at least 70%, 80%, 90%, 95% or 99% identical thereto.

In some embodiments, a functional variant of CRE0047 suitably comprises a sequence that is at least 70% identical to SEQ ID NO: 15, more preferably at least 80%, 90%, 95% or 99% identical to SEQ ID NO: 15. Additionally or alternatively, a functional variant of CRE0047 suitably comprises a sequence which hybridises under stringent conditions to SEQ ID NO: 15.

In some embodiments of the invention the CRE consists of SEQ ID NO: 15 or a functional variant thereof.

It will be noted that the CRE or functional variant thereof can be provided on either strand of a double stranded polynucleotide and can be provided in either orientation. As such, complementary and reverse complementary sequences of SEQ ID NO: 15 or a functional variant thereof fall within the scope of the invention. Single stranded nucleic acids comprising the sequence according to SEQ ID NO: 15 or a functional variant thereof also fall within the scope of the invention.

In some preferred embodiments, there is provided a CRE comprising or consisting of CRE0047 or a functional variant thereof has a length of 200 or fewer nucleotides, 150 or fewer nucleotides, 100 or fewer nucleotides, 50 or fewer nucleotides, or 35 or fewer nucleotides.

CRE0048 and Functional Variants Thereof:

CRE0048 has a sequence as set out in SEQ ID NO: 16.

Functional variants of CRE0048 are regulatory elements with sequences which vary from CRE0048, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0048 can be viewed as a CRE which, when substituted in place of CRE0048 in a CRM or promoter, substantially retains its activity. For example, a promoter which comprises a functional variant of CRE0048 substituted in place of CRE0048 preferably retains 80% of its activity, more preferably 90% of its activity, more preferably 95% of its activity, and yet more preferably 100% of its activity (compared to the reference promoter comprising CRE0048). For example, considering promoter SP0378 as an example, CRE0048 in SP0378 can be replaced with a functional variant of CRE0048, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Bioinformatic analysis of CRE0048 revealed that it does not apparently contain any known liver-specific TFBS. Nonetheless, the present inventors have determined that CRE0005 nonetheless contributes to liver-specific activity of promoters. Without wishing to be bound by theory, this may be through cooperative interaction with other CREs that do contain liver-specific TFBS to enhance their activity.

In some embodiments of the invention, the functional variant of CRE0048 comprises a sequence that is at least 70% identical to SEQ ID NO: 16, more preferably at least 80%, 90%, 95% or 99% identical to SEQ ID NO: 16. Additionally or alternatively, a functional variant of CRE0048 suitably comprises a sequence which hybridises under stringent conditions to SEQ ID NO: 16.

In some embodiments of the invention the CRE consists of SEQ ID NO: 16 or a functional variant thereof.

It will be noted that the CRE or functional variant thereof can be provided on either strand of a double stranded polynucleotide and can be provided in either orientation. As such, complementary and reverse complementary sequences of SEQ ID NO: 16 or a functional variant thereof fall within the scope of the invention. Single stranded nucleic acids comprising the sequence according to SEQ ID NO: 16 or a functional variant thereof also fall within the scope of the invention.

In some preferred embodiments, there is provided a CRE comprising or consisting of CRE0048 or a functional variant thereof has a length of 200 or fewer nucleotides, 150 or fewer nucleotides, 125 or fewer nucleotides, or 92 or fewer nucleotides.

CRE0056 and Functional Variants Thereof:

CRE0056 has a sequence as set out in SEQ ID NO: 17.

Functional variants of CRE0056 are regulatory elements with sequences which vary from CRE0056, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0056 can be viewed as a CRE which, when substituted in place of CRE0056 in a CRM or promoter, substantially retains its activity. For example, a promoter which comprises a functional variant of CRE0056 substituted in place of CRE0056 preferably retains 80% of its activity, more preferably 90% of its activity, more preferably 95% of its activity, and yet more preferably 100% of its activity (compared to the reference promoter comprising CRE0056). For example, considering promoter SP0380 as an example, CRE0056 in SP0380 can be replaced with a functional variant of CRE0056, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0056 comprises transcription factor binding sites (TFBS) for the same liver-specific transcription factors (TF) as CRE0056. The liver-specific TFBS present in CRE0056, listed in the order in which they are present, are: HNF-4 and HNF-3. The functional variant of CRE0056 thus preferably comprises both of these TFBS. Preferably, they are present in the same order that they are present in CRE0056, i.e. in the order HNF-4 and then HNF-3. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0056 comprises the following TFBS sequences: ACTGAACCCTTGACCCCTGCCCT (SEQ ID NO: 53) (HNF-4) and TGCCCACTCTATTTGCCCAGCC (SEQ ID NO: 78) (HNF-3), sequences complementary thereto, or functional variants of these TFBS sequences that maintain the ability to bind to bind to their respective TF (see Table 21 for TFBS SEQ ID NOs). These may be present in the same order as CRE0056, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0056 comprises the sequence:

ACTGAACCCTTGACCCCTGCCCT-Na-TGCC-CACTCTATTTGCCCAGCC (SEQ ID NO: 280), or a sequence that is at least 70%, 80%, 90%, 95% or 99% identical thereto, wherein Na represents an optional spacer sequence. When present, Na optionally has a length of from 12 to 32 nucleotides, preferably from 17 to 27 nucleotides, and more preferably 22 nucleotides.

In some embodiments, a functional variant of CRE0056 suitably comprises a sequence that is at least 70% identical to SEQ ID NO: 17, more preferably at least 80%, 90%, 95% or 99% identical to SEQ ID NO: 17. Additionally or alternatively, a functional variant of CRE0056 suitably comprises a sequence which hybridises under stringent conditions to SEQ ID NO: 17.

In some embodiments of the invention the CRE consists of SEQ ID NO: 17 or a functional variant thereof.

It will be noted that the CRE or functional variant thereof can be provided on either strand of a double stranded polynucleotide and can be provided in either orientation. As such, complementary and reverse complementary sequences of SEQ ID NO: 17 or a functional variant thereof fall within the scope of the invention. Single stranded nucleic acids comprising the sequence according to SEQ ID NO: 17 or a functional variant thereof also fall within the scope of the invention.

In some preferred embodiments, there is provided a CRE comprising or consisting of CRE0056 or a functional variant thereof has a length of 200 or fewer nucleotides, 150 or fewer nucleotides, 125 or fewer nucleotides, 100 or fewer nucleotides, or 79 or fewer nucleotides.

CRE0062 and Functional Variants Thereof:

CRE0062 has a sequence as set out in SEQ ID NO: 18.

Functional variants of CRE0062 are regulatory elements with sequences which vary from CRE0062, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0062 can be viewed as a CRE which, when substituted in place of CRE0062 in a CRM or promoter, substantially retains its activity. For example, a promoter which comprises a functional variant of CRE0062 substituted in place of CRE0062 preferably retains 80% of its activity, more preferably 90% of its activity, more preferably 95% of its activity, and yet more preferably 100% of its activity (compared to the reference promoter comprising CRE0062). For example, considering promoter SP0381 as an example, CRE0062 in SP0381 can be replaced with a functional variant of CRE0062, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0062 comprises transcription factor binding sites (TFBS) for the same liver-specific transcription factors (TF) as CRE0062. The liver-specific TFBS present in CRE0062, listed in the order in which they are present, are: HNF-4, HNF-4, and HNF-3. The functional variant of CRE0062 thus preferably comprises all of these TFBS. Preferably, they are present in the same order that they are present in CRE0062, i.e. in the order: HNF-4, HNF-4, and then HNF-3. When the CRE is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of CRE0062 comprises the following TFBS sequences: AGATTC-CAAAGTTCA (SEQ ID NO: 79) (HNF-4), ACCAAAGTTCAGA (SEQ ID NO: 80) (HNF-4), and GTTATTTACAA (SEQ ID NO: 81) (HNF-3), sequences complementary thereto, or functional variants of these TFBS sequences that maintain the ability to bind to bind to their respective TF (see Table 22 for TFBS SEQ ID NOs). These may be present in the same order as CRE0062, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0062 comprises the sequence:

AGAGATTCCAAAGTTCA-Na-ACCAAAGTTCAGA-Nb-GTTATTTACAA (SEQ ID NO: 281), or a sequence that is at least 70%, 80%, 90%, 95% or 99% identical thereto, wherein Na and Nb represent optional spacer sequences. When present, Na optionally has a length of from 1 to 13 nucleotides, preferably from 2 to 8 nucleotides, and more preferably 3 nucleotides. When present, Nb optionally has a length of from 1 to 18 nucleotides, preferably from 3 to 13 nucleotides, more preferably 8 nucleotides.

In some embodiments, a functional variant of CRE0062 suitably comprises a sequence that is at least 70% identical to SEQ ID NO: 18, more preferably at least 80%, 90%, 95% or 99% identical to SEQ ID NO: 18. Additionally or alternatively, a functional variant of CRE0062 suitably comprises a sequence which hybridises under stringent conditions to SEQ ID NO: 18.

In some embodiments of the invention the CRE consists of SEQ ID NO: 18 or a functional variant thereof.

It will be noted that the CRE or functional variant thereof can be provided on either strand of a double stranded polynucleotide and can be provided in either orientation. As such, complementary and reverse complementary sequences of SEQ ID NO: 18 or a functional variant thereof fall within the scope of the invention. Single stranded nucleic acids comprising the sequence according to SEQ ID NO: 18 or a functional variant thereof also fall within the scope of the invention.

In some preferred embodiments, there is provided a CRE comprising or consisting of CRE0062 or a functional variant thereof has a length of 200 or fewer nucleotides, 150 or fewer nucleotides, 125 or fewer nucleotides, 100 or fewer nucleotides, or 85 or fewer nucleotides.

CRE0077 and Functional Variants Thereof:

CRE0077 has a sequence as set out in SEQ ID NO: 19.

Functional variants of CRE0077 are regulatory elements with sequences which vary from CRE0077, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0077 can be viewed as a CRE which, when substituted in place of CRE0077 in a CRM or promoter, substantially retains its activity. For example, a promoter which comprises a functional variant of CRE0077 substituted in place of CRE0077 preferably retains 80% of its activity, more preferably 90% of its activity, more preferably 95% of its activity, and yet more preferably 100% of its activity (compared to the reference promoter comprising CRE0077). For example, considering promoter SP0405 as an example, CRE0077 in SP0405 can be replaced with a functional variant of CRE0077, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0077 (SEQ ID NO: 19) comprises transcription factor binding sites (TFBS) for the same liver-specific transcription factors (TF) as CRE0077. The liver-specific TFBS present in CRE0077, listed in order (5' to 3'), are: HNF3, HNF3, HNF1, HNF3, and HNF3. A functional variant of CRE0077 thus preferably comprises all of these TFBS. Preferably, the TFBS are present in the same order that they are present in CRE0077, i.e. in the order HNF3, HNF3, HNF1, HNF3, then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some preferred embodiments the functional variant of CRE0077 comprises the following TFBS sequences: AGCAAATATTT (SEQ ID NO: 82) (HNF3), AAATAT-TTGTGG (SEQ ID NO: 83) (HNF3), GGTTATGGAT-TAACT (SEQ ID NO: 84) (HNF1), CTGTTTGCCC (SEQ ID NO: 54) (HNF3), CTATTTGCCC (SEQ ID NO: 55) (HNF3), sequences complementary thereto, or functional variants of these TFBS sequences that maintain the ability to bind to bind to their respective TF (see Table 23 for TFBS SEQ ID NOs). These may be present in the same order as CRE0077, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of CRE0077 comprises the sequence:
  AGCAAATATTTGTGGTTATGGATTAACT-Na-
    CTGTTTGCCC-Nb-CTATTTGCCC (SEQ ID NO: 282), or a sequence that is at least 70%, 80%, 90%, 95% or 99% identical thereto,
  wherein Na and Nb each represent an optional spacer sequence. Where present, the spacer sequences Na and Nb are suitably from 0 to 10 nucleotides in length. Optionally, Na is from 2 to 8 nucleotides in length, preferably from 3 to 6 nucleotides in length, and more preferably 4 nucleotides in length. Optionally Nb is from 2 to 8 nucleotides in length, preferably from 2 to 6 nucleotides in length, and more preferably 3 nucleotides in length.

In some embodiments of the invention, the functional variant of CRE0077 comprises a sequence that is at least 70% identical to SEQ ID NO: 19, more preferably at least 80%, 90%, 95% or 99% identical to SEQ ID NO: 19. Additionally or alternatively, a functional variant of CRE0077 suitably comprises a sequence which hybridises under stringent conditions to SEQ ID NO: 19.

In some embodiments of the invention the CRE consists of SEQ ID NO: 19 or a functional variant thereof.

It will be noted that the CRE or functional variant thereof can be provided on either strand of a double stranded polynucleotide and can be provided in either orientation. As such, complementary and reverse complementary sequences of SEQ ID NO: 19 or a functional variant thereof fall within the scope of the invention. Single stranded nucleic acids comprising the sequence according to SEQ ID NO: 19 or a functional variant thereof also fall within the scope of the invention.

In some preferred embodiments, there is provided a CRE comprising or consisting of CRE0077 or a functional variant thereof has a length of 150 or fewer nucleotides, 125 or fewer nucleotides, 100 or fewer nucleotides, 75 or fewer nucleotides, or 56 or fewer nucleotides.

CRE0078 and Functional Variants Thereof:

CRE0078 has a sequence as set out in SEQ ID NO: 20.

Functional variants of CRE0078 are regulatory elements with sequences which vary from CRE0078, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0078 can be viewed as a CRE which, when substituted in place of CRE0078 in a CRM or promoter, substantially retains its activity. For example, a promoter which comprises a functional variant of CRE0078 substituted in place of CRE0078 preferably retains 80% of its activity, more preferably 90% of its activity, more preferably 95% of its activity, and yet more preferably 100% of its activity (compared to the reference promoter comprising CRE0078). For example, considering promoter SP0270 as an example, CRE0078 in SP0270 can be replaced with a functional variant of CRE0078, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

In some embodiments it is preferred that the functional variant of CRE0078 (SEQ ID NO: 20) comprises transcription factor binding sites (TFBS) for the same liver-specific transcription factors (TF) as CRE0078. The liver-specific TFBS present in CRE0078, listed in order, are: HNF4, c/EBP, HNF3, and HNF3. The functional variant of CRE0078 thus preferably comprises these TFBS. Preferably, they are present in the same order that they are present in CRE0078, i.e. in the order HNF4, c/EBP, HNF3, and HNF3. When the cis-regulatory element is associated with a promoter and gene, this order is preferably considered in an upstream to downstream direction (i.e. in the direction from distal from the transcription start site (TSS) to proximal to the TSS). In some embodiments the TFBS overlap, provided they remain functional, i.e. overlapping sequences are both able to bind their respective TFs.

In some embodiments the functional variant of CRE0078 comprises the following TFBS sequences: CGCCCTTTGGACC (SEQ ID NO: 51) (HNF4), GACCTTTTGCAATCCTGG (SEQ ID NO: 52) (c/EBP), CTGTTTGCT (SEQ ID NO: 89) (HNF3), GTGTTTGCTG (SEQ ID NO: 90) (HNF3), sequences complementary thereto, or functional variants of these TFBS sequences that maintain the ability to bind to bind to their respective TF (see Table 24 for TFBS SEQ ID NOs). It is well-known in the art that there is sequence variability associated with TFBS, and that for a given TFBS a consensus sequence is typically defined based upon multiple sequence alignments, with some degree of deviation from the consensus sequence typically being present.

In some embodiments of the invention, the functional variant of CRE0078 comprises the sequence: CGCCCTTTGGACCTTTTGCAATCCTG-GAGCAAACAGCAAACAC (SEQ ID NO: 283), or a sequence that is at least 70%, 80%, 90%, 95% or 99% identical thereto.

In some embodiments of the invention, the functional variant of CRE0078 comprises a sequence that is at least 70% identical to SEQ ID NO: 20, more preferably at least 80%, 90%, 95% or 99% identical to SEQ ID NO: 20. Additionally or alternatively, a functional variant of CRE0078 suitably comprises a sequence which hybridises under stringent conditions to SEQ ID NO: 20.

In some embodiments of the invention the CRE consists of SEQ ID NO: 20 or a functional variant thereof.

It will be noted that the CRE or functional variant thereof can be provided on either strand of a double stranded polynucleotide and can be provided in either orientation. As such, complementary and reverse complementary sequences of SEQ ID NO: 20 or a functional variant thereof fall within the scope of the invention. Single stranded nucleic acids comprising the sequence according to SEQ ID NO: 20 or a functional variant thereof also fall within the scope of the invention.

In some preferred embodiments, there is provided a CRE comprising or consisting of CRE0078 or a functional variant thereof has a length of 150 or fewer nucleotides, 125 or fewer nucleotides, 100 or fewer nucleotides, 75 or fewer nucleotides, or 45 or fewer nucleotides.

CRE0083.1 and Functional Variants Thereof:

CRE0083.1 has a sequence as set out in SEQ ID NO: 21.

Functional variants of CRE0083.1 are regulatory elements with sequences which vary from CRE0083.1, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0083.1 can be viewed as a CRE which, when substituted in place of CRE0083.1 in a CRM or promoter, substantially retains its activity. For example, a promoter which comprises a functional variant of CRE0083.1 substituted in place of CRE0083.1 preferably retains 80% of its activity, more preferably 90% of its activity, more preferably 95% of its activity, and yet more preferably 100% of its activity (compared to the reference promoter comprising CRE0083.1). For example, considering promoter SP0112 as an example, CRE0083.1 in SP0112 can be replaced with a functional variant of CRE0083.1, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Bioinformatic analysis of CRE0083.1 revealed that it does not apparently contain any known liver-specific TFBS. Nonetheless, the present inventors have determined that CRE0005 nonetheless contributes to liver-specific activity of promoters. Without wishing to be bound by theory, this may be through cooperative interaction with other CREs that do contain liver-specific TFBS to enhance their activity.

In some embodiments of the invention, the functional variant of CRE0083.1 comprises a sequence that is at least 70% identical to SEQ ID NO: 21, more preferably at least 80%, 90%, 95% or 99% identical to SEQ ID NO: 21. Additionally or alternatively, a functional variant of CRE0083.1 suitably comprises a sequence which hybridises under stringent conditions to SEQ ID NO: 21.

In some embodiments of the invention the CRE consists of SEQ ID NO: 21 or a functional variant thereof.

It will be noted that the CRE or functional variant thereof can be provided on either strand of a double stranded polynucleotide and can be provided in either orientation. As such, complementary and reverse complementary sequences of SEQ ID NO: 21 or a functional variant thereof fall within the scope of the invention. Single stranded nucleic acids comprising the sequence according to SEQ ID NO: 21 or a functional variant thereof also fall within the scope of the invention.

In some preferred embodiments, there is provided a CRE comprising or consisting of CRE0083.1 or a functional variant thereof has a length of 250 or fewer nucleotides, 200 or fewer nucleotides, 150 or fewer nucleotides, 125 or fewer nucleotides, or 112 or fewer nucleotides.

CRE0089 and Functional Variants Thereof:

CRE0089 has a sequence as set out in SEQ ID NO: 22.

Functional variants of CRE0089 are regulatory elements with sequences which vary from CRE0089, but which substantially retain their activity as liver-specific CREs. It will be appreciated by the skilled person that it is possible to vary the sequence of a CRE while retaining its ability to bind to the requisite transcription factors (TFs) and enhance expression. A functional variant can comprise substitutions, deletions and/or insertions compared to a reference CRE, provided they do not render the CRE non-functional.

In some embodiments, a functional variant of CRE0089 can be viewed as a CRE which, when substituted in place of CRE0089 in a CRM or promoter, substantially retains its activity. For example, a promoter which comprises a functional variant of CRE0089 substituted in place of CRE0089 preferably retains 80% of its activity, more preferably 90% of its activity, more preferably 95% of its activity, and yet more preferably 100% of its activity (compared to the reference promoter comprising CRE0089). For example, considering promoter SP0139 as an example, CRE0089 in SP0139 can be replaced with a functional variant of CRE0089, and the promoter substantially retains its activity. Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Bioinformatic analysis of CRE0083 revealed that it does not apparently contain any known liver-specific TFBS. Nonetheless, the present inventors have determined that CRE0005 nonetheless contributes to liver-specific activity of promoters. Without wishing to be bound by theory, this may be through cooperative interaction with other CREs that do contain liver-specific TFBS to enhance their activity.

In some embodiments of the invention, the functional variant of CRE0089 comprises a sequence that is at least 70% identical to SEQ ID NO: 22, more preferably at least 80%, 90%, 95% or 99% identical to SEQ ID NO: 22. Additionally or alternatively, a functional variant of CRE0089 suitably comprises a sequence which hybridises under stringent conditions to SEQ ID NO: 22.

In some embodiments of the invention the CRE consists of SEQ ID NO: 22 or a functional variant thereof.

It will be noted that the CRE or functional variant thereof can be provided on either strand of a double stranded polynucleotide and can be provided in either orientation. As such, complementary and reverse complementary sequences of SEQ ID NO: 22 or a functional variant thereof fall within the scope of the invention. Single stranded nucleic acids comprising the sequence according to SEQ ID NO: 22 or a functional variant thereof also fall within the scope of the invention.

In some preferred embodiments, there is provided a CRE comprising or consisting of CRE0089 or a functional variant thereof has a length of 250 or fewer nucleotides, 200 or fewer nucleotides, 150 or fewer nucleotides, 125 or fewer nucleotides, or 102 or fewer nucleotides.

Promoter Elements and Functional Variants Thereof:

Various promoter elements are disclosed herein that can be used in the constructions of synthetic liver-specific promoters. These promoter elements are either minimal promoters or liver-specific proximal promoters. While the CREs and CRMs of the present invention can be used in combination with a wide range of suitable minimal promoters or liver-specific proximal promoters, some proximal promoters have been found to act synergistically with the CREs or CRMs to contribute significantly to activity of the activity of the liver-specific promoter. In addition, some liver-specific proximal promoters as disclosed herein have been found to have remarkable levels of activity even in the absence of additional CRE or CRM sequences (most notably the proximal promoters CRE0006 and CRE0059)

Functional variants of a promoter element include sequences which vary from the reference promoter element, but which substantially retain their activity liver-specific promoter elements. It will be appreciated by the skilled person that it is possible to vary the sequence of a promoter element while retaining its ability to recruit RNA polymerase II, and, where relevant, bind to liver-specific transcription factors (TFs) to enhance expression. A functional variant of a promoter element can comprise substitutions, deletions and/or insertions compared to a reference promoter element, provided they do not render the promoter element non-functional.

In some embodiments, a functional variant of a promoter element can be viewed as a promoter element which, when substituted in place of a reference promoter element in a promoter, substantially retains its activity. For example, a liver-specific promoter which comprises a functional variant of a given promoter element preferably retains at least 80% of its activity, more preferably at least 90% of its activity, more preferably at least 95% of its activity, and yet more preferably 100% of its activity (compared to the reference promoter comprising the unmodified promoter element). Suitable assays for assessing liver-specific promoter activity are disclosed herein, e.g. in examples 2 and 3.

Suitably, functional variants of a promoter element retain a significant level of sequence identity to a reference promoter element. Suitably functional variants comprise a sequence that is at least 70% identical to the reference promoter element, more preferably at least 80%, 90%, 95% or 99% identical to the reference promoter element.

In the case of promoter element that are proximal promoters, it is preferred that functional variants retain TFBS for the liver-specific TFs that bind to the reference promoter element (the above discussion regarding PWMs applies equally here). Preferably the TFBS are retained in the same order and at substantially the same location as in the reference promoter element. Furthermore, it is generally preferred that the sequence of the transcription start site (TSS) is substantially unaltered in a functional variant of a promoter element.

Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Promoter elements used in the present invention can be natural (i.e. obtained or derived from a naturally occurring gene promoter) or can be synthetic (i.e., non-naturally occurring).

CRE0006 and Functional Variants Thereof:

CRE0006 has a sequence as set out in SEQ ID NO: 25.

As discussed above, functional variants of CRE0006 substantially retain the ability of CRE0006 to act as a liver-specific promoter element. For example, when a functional variants of CRE0006 is substituted into liver-specific promoter SP0241 or SP0244, the modified retains at least 80% of its activity, more preferably at least 90% of its activity, more preferably at least 95% of its activity, and yet more preferably 100% of the activity of SP0241 or SP0244. Suitably the functional variant of CRE0006 comprises a sequence which has at least 70%, 80%, 90%, 95% or 99% identity to SEQ ID NO: 25.

CRE0006 is a proximal promoter and comprises TFBS for liver-specific TFs upstream of the TSS. The liver-specific TFBS present in CRE0006, listed in order, are HNF4, RXRa, HNF4, c/EBP, and HNF3 (see Table 25 for details). The functional variant of CRE0006 thus preferably comprises these TFBS. Preferably, they are present in the same order that they are present in CRE0006, i.e. in the order HNF4, c/EBP, HNF3, and HNF3. In some embodiments the TFBS overlap, provided they remain functional, i.e. overlapping sequences are both able to bind their respective TFs.

In some embodiments, a functional variant of CRE0006 comprises a sequence which is at least 70% identical to SEQ ID NO: 25 (preferably at least 80%, 90%, 95% or 99% identical to SEQ ID NO: 25), which contains TFBS for HNF4, RXRa, HNF4, c/EBP, and HNF3, and preferably which contains a TSS sequence which is at least 80%, 90%, 95% or completely identical to that shown in Table 25 downstream of said TFBS.

In some embodiments, a functional variant of CRE0006 comprises a sequence which has at least 70%, 80%, 90%, 95% or 99% identity to SEQ ID NO: 25, and which further comprises the following TFBS: HNF4 at or near position 25-37; RXRa at or near position 73-83; HNF4 at or near position 74-86; c/EBP at or near position 123-136; and HNF3 at or near position 129-137; and which comprises a TSS sequence which is at least 80%, 90%, 95% or completely identical to that shown in Table 25 at or near position 166-196, positions being numbered with reference to SEQ ID NO: 25. At or near in the present context suitably means within 10, 5, 4, 3, 2, or 1 nucleotide of the recited position with reference to SEQ ID NO: 25. Suitable TFBS sequences are shown in Table 25, but alternative TFBS sequences can be used.

In some preferred embodiments, a promoter comprising or consisting of CRE0006 or a functional variant thereof has a length of 400 or fewer nucleotides, 350 or fewer nucleotides, 325 or fewer nucleotides, 300 or fewer nucleotides, or 279 or fewer nucleotides.

CRE0059 and Functional Variants Thereof:

CRE0059 has a sequence as set out in SEQ ID NO: 26.

As discussed above, functional variants of CRE0059 substantially retain the ability of CRE00059 to act as a liver-specific promoter element. For example, when a functional variants of CRE0059 is substituted into liver-specific promoter SP0412 or SP0380, the modified retains at least 80% of its activity, more preferably at least 90% of its activity, more preferably at least 95% of its activity, and yet more preferably 100% of the activity of SP0412 or SP0380. Suitably the functional variant of CRE0059 comprises a sequence which has at least 70%, 80%, 90%, 95% or 99% identity to SEQ ID NO: 26.

CRE0059 is a proximal promoter and comprises a TFBS for a liver-specific TF, namely HNF1, upstream of the TSS. The functional variant of CRE0059 thus preferably comprises a TFBS for HNF1 upstream of the TSS.

In some embodiments, a functional variant of CRE0059 comprises a sequence which is at least 70% identical to SEQ ID NO: 26 (preferably at least 80%, 90%, 95% or 99% identical to SEQ ID NO: 26), which contains a TFBS for HNF1, and preferably which contains a TSS sequence which is at least 80%, 90%, 95% or completely identical to that shown in Table 27 downstream of said TFBS.

In some embodiments, a functional variant of CRE0059 comprises a sequence which has at least 70%, 80%, 90%, 95% or 99% identity to SEQ ID NO: 26, and which further comprises a TFBS for HNF3 at or near position 24-36; and which comprises the TSS sequence which is at least 80%, 90%, 95% or completely identical to that shown in Table 27 at or near position 73-93, positions being numbered with reference to SEQ ID NO: 26. At or near in the present context suitably means within 10, 5, 4, 3, 2, or 1 nucleotide of the recited position with reference to SEQ ID NO: 26. Suitable TFBS sequences are shown in Table 27, but alternative TFBS sequences can be used.

In some preferred embodiments, a promoter comprising or consisting of CRE0059 or a functional variant thereof has a length of 200 or fewer nucleotides, 150 or fewer nucleotides, 125 or fewer nucleotides, 110 or fewer nucleotides, or 95 or fewer nucleotides.

CRE0073 and Functional Variants Thereof:

CRE0073 has a sequence as set out in SEQ ID NO: 27.

As discussed above, functional variants of CRE0073 substantially retain the ability of CRE0073 to act as a liver-specific promoter element. For example, when a functional variants of CRE0073 is substituted into liver-specific promoter SP0249 or SP0116, the modified retains at least 80% of its activity, more preferably at least 90% of its activity, more preferably at least 95% of its activity, and yet more preferably 100% of the activity of SP0249 or SP0116. Suitably the functional variant of CRE0073 comprises a sequence which has at least 70%, 80%, 90%, 95% or 99% identity to SEQ ID NO: 27.

CRE0073 is a proximal promoter and comprises TFBS for liver-specific TFs upstream of the TSS. The liver-specific TFBS present in CRE0073, listed in order, are HNF3, C/EBP, HNF1 and C/EBP (see Table 28 for details). The functional variant of CRE0073 thus preferably comprises these TFBS. Preferably, they are present in the same order that they are present in CRE0073, i.e. in the order HNF3, C/EBP, HNF1 and then C/EBP. In some embodiments the TFBS overlap, provided they remain functional, i.e. overlapping sequences are both able to bind their respective TFs.

In some embodiments, a functional variant of CRE0073 comprises a sequence which is at least 70% identical to SEQ ID NO: 27 (preferably at least 80%, 90%, 95% or 99% identical to SEQ ID NO: 27), which contains TFBS for HNF3, C/EBP, HNF1 and C/EBP, and preferably which contains a TSS sequence which is at least 80%, 90%, 95% or completely identical to that shown in Table 28 downstream of said TFBS.

In some embodiments, a functional variant of CRE0073 comprises a sequence which has at least 70%, 80%, 90%, 95% or 99% identity to SEQ ID NO: 27, and which further comprises the following TFBS: HNF3 at or near position 36-42; C/EBP at or near position 38-49; HNF1 at or near position 66-83; C/EBP at or near position 75-86; and HNF3 at or near position 129-137; and which comprises a TSS sequence which is at least 80%, 90%, 95% or completely identical to that shown in Table 28 at or near position 138-156, positions being numbered with reference to SEQ ID NO: 27. At or near in the present context suitably means within 10, 5, 4, 3, 2, or 1 nucleotide of the recited position with reference to SEQ ID NO: 27. Suitable TFBS sequences are shown in Table 28, but alternative TFBS sequences can be used.

CRE0073.1 in an exemplary functional variant of CRE0073. CRE0073.1 has a deletion of 22 nucleotides from the 5' end compared with CRE0073. It is otherwise identical, and comprises the same TFBS in the same relative positions relative to CRE0073.

In some preferred embodiments, a promoter comprising or consisting of CRE0073 or a functional variant thereof has a length of 300 or fewer nucleotides, 250 or fewer nucleotides, 200 or fewer nucleotides, 175 or fewer nucleotides, or 164 or fewer nucleotides.

CRE0040 and Functional Variants Thereof:

CRE0040 has a sequence as set out in SEQ ID NO: 29.

As discussed above, functional variants of CRE0040 substantially retain the ability of CRE0040 to act as a liver-specific promoter element. For example, when a functional variants of CRE0040 is substituted into liver-specific promoter SP0254 or SP0252, the modified retains at least 80% of its activity, more preferably at least 90% of its activity, more preferably at least 95% of its activity, and yet more preferably 100% of the activity of SP0254 or SP0252. Suitably the functional variant of CRE0040 comprises a sequence which has at least 70%, 80%, 90%, 95% or 99% identity to SEQ ID NO: 29.

CRE0040 is a proximal promoter and comprises TFBS for liver-specific TFs upstream of the TSS. The liver-specific TFBS present in CRE0040, listed in order, are C/EBP and HNF1 (see Table 30 for details). The functional variant of CRE0040 thus preferably comprises these TFBS. Preferably, they are present in the same order that they are present in CRE0040, i.e. in the order C/EBP and then HNF1.

In some embodiments, a functional variant of CRE0040 comprises a sequence which is at least 70% identical to SEQ ID NO: 29 (preferably at least 80%, 90%, 95% or 99% identical to SEQ ID NO: 29), which contains TFBS for C/EBP and HNF1, and preferably which contains a TSS sequence which is at least 80%, 90%, 95% or completely identical to that shown in Table 30 downstream of said TFBS.

In some embodiments, a functional variant of CRE0040 comprises a sequence which has at least 70%, 80%, 90%, 95% or 99% identity to SEQ ID NO: 29, and which further comprises the following TFBS: C/EBP at or near position 39-52; HNF1 at or near position 120-140; and which comprises a TSS sequence which is at least 80%, 90%, 95% or completely identical to that shown in Table 30 at or near position 172-201, positions being numbered with reference to SEQ ID NO: 29. At or near in the present context suitably means within 10, 5, 4, 3, 2, or 1 nucleotide of the recited position with reference to SEQ ID NO: 29. Suitable TFBS sequences are shown in Table 30, but alternative TFBS sequences can be used.

In some preferred embodiments, a promoter comprising or consisting of CRE0006 or a functional variant thereof has a length of 400 or fewer nucleotides, 350 or fewer nucleotides, 300 or fewer nucleotides, 275 or fewer nucleotides, or 240 or fewer nucleotides.

CRE0079 and Functional Variants Thereof:

CRE0079 has a sequence as set out in SEQ ID NO: 24.

As discussed above, functional variants of CRE0079 substantially retain the ability of CRE0079 to act as a liver-specific promoter element. For example, when a functional variants of CRE0079 is substituted into liver-specific promoter SP0271 or SP0272, the modified retains at least 80% of its activity, more preferably at least 90% of its activity, more preferably at least 95% of its activity, and yet more preferably 100% of the activity of SP0271 or SP0272. Suitably the functional variant of CRE0079 comprises a sequence which has at least 70%, 80%, 90%, 95% or 99% identity to SEQ ID NO: 24.

CRE0079 is a proximal promoter and comprises TFBS for liver-specific TFs upstream of the TSS. The liver-specific TFBS present in CRE0079, listed in order, are HNF4, HNF1 and C/EBP (see Table 26 for details). The functional variant of CRE0079 thus preferably comprises these TFBS. Preferably, they are present in the same order that they are present in CRE0079, i.e. in the order HNF4, HNF1 and then C/EBP.

In some embodiments, a functional variant of CRE0079 comprises a sequence which is at least 70% identical to SEQ ID NO: 24 (preferably at least 80%, 90%, 95% or 99% identical to SEQ ID NO: 24), which contains TFBS for HNF4, HNF1 and C/EBP, and preferably which contains a TSS sequence which is at least 80%, 90%, 95% or completely identical to that shown in Table 24 downstream of said TFBS.

In some embodiments, a functional variant of CRE0079 comprises a sequence which has at least 70%, 80%, 90%, 95% or 99% identity to SEQ ID NO: 24, and which further comprises the following TFBS: HNF4 at or near position 43-55; HNF1 at or near position 138-150; C/EBP at or near position 162-175, and which comprises a TSS sequence which is at least 80%, 90%, 95% or completely identical to that shown in Table 26 at or near position 206-219, positions being numbered with reference to SEQ ID NO: 24. At or near in the present context suitably means within 10, 5, 4, 3, 2, or 1 nucleotide of the recited position with reference to SEQ ID NO: 24. Suitable TFBS sequences are shown in Table 26, but alternative TFBS sequences can be used.

In some preferred embodiments, a promoter comprising or consisting of CRE0079 or a functional variant thereof has a length of 400 or fewer nucleotides, 325 or fewer nucleotides, 275 or fewer nucleotides, 250 or fewer nucleotides, or 226 or fewer nucleotides.

CRE0052 and Functional Variants Thereof:

CRE0052 has a sequence as set out in SEQ ID NO: 23.

As discussed above, functional variants of CRE0052 substantially retain the ability of CRE0052 to act as a liver-specific promoter element. For example, when a functional variants of CRE0052 is substituted into liver-specific promoter SP0239 or SP0265, the modified retains at least 80% of its activity, more preferably at least 90% of its activity, more preferably at least 95% of its activity, and yet more preferably 100% of the activity of SP0239 or SP0265.

Suitably the functional variant of CRE0052 comprises a sequence which has at least 70%, 80%, 90%, 95% or 99% identity to SEQ ID NO: 23.

In some preferred embodiments, a promoter comprising or consisting of CRE0052 or a functional variant thereof has a length of 200 or fewer nucleotides, 150 or fewer nucleotides, 125 or fewer nucleotides, 100 or fewer nucleotides, or 76 or fewer nucleotides.

Other Promoter Elements:

Non-limiting examples of other liver-specific proximal promoters that may be used in the present invention include, but are not limited to, the ApoA-I promoter, the ApoA-I I promoter, the ApoA-IV promoter, the ApoB promoter, the ApoC-1 promoter, the ApoC-I I promoter, the ApoC-III promoter, the ApoE promoter, the albumin promoter, the a-fetoprotein promoter, the phosphoenolpyruvate carboxykinase (PCK1) promoter, the phosphoenolpyruvate carboxykinase 2 (PCK2) promoter, the transthyretin (TTR) promoter, the a-antitrypsin (AAT or SERPI NA1) promoter, the TK (thymidine kinase) promoter, the hemopexin promoter, the alcohol dehydrogenase 6 promoter, the cholesterol 7alpha-25 hydroxylase promoter, the factor IX promoter, the a-microglobulin promoter, the SV40 promoter, the CMV promoter, the Rous Sarcoma Virus-L TR promoter and the HBV promoter. Minimal promoters derived from these promoters can of course also be used.

Synthetic Liver-Specific CRMs and Functional Variants Thereof:

Various synthetic liver-specific CRMs are disclosed herein that can be used in the constructions of synthetic liver-specific promoters. CRMs of the present invention can be used in combination with a wide range of suitable minimal promoters or liver-specific proximal promoters, as discussed above.

Functional variants of a CRM include sequences which vary from the reference CRM element, but which substantially retain activity as liver-specific CRMs. It will be appreciated by the skilled person that it is possible to vary the sequence of a CRM while retaining its ability to recruit suitable liver-specific transcription factors (TFs) and thereby enhance expression. A functional variant of a CRM can comprise substitutions, deletions and/or insertions compared to a reference CRM, provided they do not render the CRM substantially non-functional.

In some embodiments, a functional variant of a CRM can be viewed as a CRM which, when substituted in place of a reference CRM in a promoter, substantially retains its activity. For example, a liver-specific promoter which comprises a functional variant of a given CRM preferably retains at least 80% of its activity, more preferably at least 90% of its activity, more preferably at least 95% of its activity, and yet more preferably 100% of its activity (compared to the reference promoter comprising the unmodified CRM).

Suitably, functional variants of a CRM retain a significant level of sequence identity to a reference CRM. Suitably functional variants comprise a sequence that is at least 70% identical to the reference CRM, more preferably at least 80%, 90%, 95% or 99% identical to the reference CRM.

Retention of activity can be assessed by comparing expression of a suitable reporter under the control of the reference promoter with an otherwise identical promoter comprising the substituted CRE under equivalent conditions. Suitable assays for assessing liver-specific promoter activity are disclosed herein, e.g. in examples 2 and 3.

Functional variants of a given CRM can, in some embodiments, comprise functional variants of one or more of the CREs present in the reference CRM. For example, functional variants of a given CRM can comprise functional variants of 1, 2, 3, 4, 5, or 6 of the CREs present in the reference CRM. Functional variants of CREs are discussed above.

Functional variants of a given CRM can, in some embodiments, comprise the same combination CREs as a reference CRM, but the CREs can be present in a different order from the reference CRM. It is usually preferred that the CREs are present in the same order as the reference CRM (thus, the functional variant of a CRM suitably comprises the same permutation of the CREs as set out in a reference CRM).

Functional variants of a given CRM can, in some embodiments, comprise one or more additional CREs to those present in a reference CRM. Additional CREs can be provided upstream of the CREs present in the reference CRM, downstream of the CREs present in the reference CRM, and/or between the CREs present in the reference CRM. The additional CREs can be CREs disclosed herein, or they can be other CREs. Generally, it is preferred that a functional variant of a given CRM comprises the same CREs (or functional variants thereof) and does not comprise additional CREs.

Functional variants of a given CRM can comprise one or more additional regulatory elements compared to a reference CRM. For example, they may comprise an inducible or repressible element, a boundary control element, an insulator, a locus control region, a response element, a binding site, a segment of a terminal repeat, a responsive site, a stabilizing element, a de-stabilizing element, and a splicing element, etc., provided that they do not render the CRM substantially non-functional.

Functional variants of a given CRM can comprise additional spacers between adjacent CREs or, if one or more spacer are present in the reference CRM, said one or more spacers can be longer or shorter than in the reference CRM.

It will be apparent that the CRMs as disclosed herein, or functional variants thereof, can be combined with any suitable promoter elements in order to provide a synthetic liver-specific promoter according to the present invention.

In many instances, shorter promoter sequences are preferred, particularly for use in situations where a vector (e.g. a viral vector such as AAV) has limited capacity. Accordingly, in some embodiments the synthetic liver-specific CRM has length of 500 or fewer nucleotides, for example 450, 400, 350, 300, 250, 200, 150, 100, 75, 60, 50 or fewer nucleotides.

Synthetic Liver-Specific Promoters and Functional Variants Thereof:

Various synthetic liver-specific promoters are disclosed herein.

A functional variant of a reference synthetic liver-specific promoter is a promoter which comprise a sequence which varies from the reference synthetic liver-specific promoter, but which substantially retains liver-specific promoter activity. It will be appreciated by the skilled person that it is possible to vary the sequence of a synthetic liver-specific promoter while retaining its ability to recruit suitable liver-specific transcription factors (TFs) and to recruit RNA polymerase II to provide liver-specific expression of an operably linked sequence (e.g. open reading frame). A functional variant of a synthetic liver-specific promoter can comprise substitutions, deletions and/or insertions compared to a reference promoter, provided such substitutions, deletions and/or insertions do not render the synthetic liver-specific promoter substantially non-functional compared to the reference promoter.

Accordingly, in some embodiments, a functional variant of a synthetic liver-specific promoter can be viewed as a variant which substantially retains the liver-specific promoter activity of the reference promoter. For example, a functional variant of a synthetic liver-specific promoter preferably retains at least 70% of the activity of the reference promoter, more preferably at least 80% of its activity, more preferably at least 90% of its activity, more preferably at least 95% of its activity, and yet more preferably 100% of its activity.

Functional variants of a synthetic liver-specific promoter often retain a significant level of sequence similarity to a reference synthetic liver-specific promoter. In some embodiments, functional variants comprise a sequence that is at least 70% identical to the reference synthetic liver-specific promoter, more preferably at least 80%, 90%, 95% or 99% identical to the reference synthetic liver-specific promoter.

Activity in a functional variant can be assessed by comparing expression of a suitable reporter under the control of the reference synthetic liver-specific promoter with the putative functional variant under equivalent conditions. Suitable assays for assessing liver-specific promoter activity are disclosed herein, e.g. in examples 2 and 3.

Functional variants of a given synthetic liver-specific promoter can comprise functional variants of one or more CREs present in the reference synthetic liver-specific promoter. For example, functional variant of a given CRM can comprise 1, 2, 3, 4, 5, or 6 of the CREs present in the reference CRM. Functional variants of CREs are discussed above.

Functional variants of a given synthetic liver-specific promoter can comprise functional variants of the promoter element, or a different promoter element when compare to the reference synthetic liver-specific promoter.

Functional variants of a given synthetic liver-specific promoter can comprise the same CREs as a reference synthetic liver-specific promoter, but the CREs can be present in a different order from the reference synthetic liver-specific promoter.

Functional variants of a given synthetic liver-specific promoter can comprise one or more additional CREs to those present in a reference synthetic liver-specific promoter. Additional CREs can be provided upstream of the CREs present in the reference CRM, downstream of the CREs present in the reference synthetic liver-specific promoter, and/or between the CREs present in the reference synthetic liver-specific promoter. The additional CREs can be CREs disclosed herein, or they can be other CREs.

Functional variants of a given CRM can comprise one or more additional regulatory elements compared to a reference CRM. For example, they may comprise an inducible elements, an intronic element, a boundary control element, an insulator, a locus control region, a response element, a binding site, a segment of a terminal repeat, a responsive site, a stabilizing element, a de-stabilizing element, and a splicing element, etc., provided that they do not render the promoter substantially non-functional.

Functional variants of a given synthetic liver-specific promoter can comprise additional spacers between adjacent CREs and promoter elements or, if one or more spacer are present in the reference synthetic liver-specific promoter, said one or more spacers can be longer or shorter than in the reference synthetic liver-specific promoter.

It will be apparent that synthetic liver-specific promoters of the present invention can comprise a CRM of the present invention and additional regulatory sequences. For example, they may comprise one or more additional CRMs, an inducible or repressible element, a boundary control element, an insulator, a locus control region, a response element, a binding site, a segment of a terminal repeat, a responsive site, a stabilizing element, a de-stabilizing element, and a splicing element, etc., provided that they do not render the promoter substantially non-functional.

Preferred synthetic liver-specific promoters of the present invention exhibit liver-specific promoter activity which is at least 15%, 20%, 25%, 30%, 40%, 50%, 60%, 70%, 80%, 90%, 100%, 125%, 150%, 175%, 200%, 250%, 300%, 350% or 400% of the activity of the TBG promoter. In some embodiments, the synthetic liver-specific promoters of the invention are suitable for promoting liver-specific transgene expression at a level at least 100% of the activity of the LP1 promoter, preferably 150%, 200%, 300% or 500% of the activity of the LP1 promoter. In many cases higher levels of promoter activity is preferred, but this is not always the case; thus, in some cases more moderate levels of expression may be preferred. Activity of a given synthetic liver-specific promoter of the present invention compared to TBG can be assessed by comparing liver-specific expression of a reporter gene under control of the synthetic liver-specific promoter with expression of the same reporter under control of the TBG promoter, when the two promoters are provided in otherwise equivalent expression constructs and under equivalent conditions.

In some embodiments a synthetic liver-specific promoter of the invention is able to increase expression of a gene (e.g. a therapeutic gene or gene of interest) in the liver of a subject or in a liver cell by at least 20%, at least 40%, at least 60%, at least 80%, at least 100%, at least 200%, at least 300%, at least 500%, at least 1000% or more relative to a known liver-specific promoter, suitably the LP-1 promoter.

Preferred synthetic liver-specific promoters of the present invention exhibit activity in non-liver cells (e.g. HEK293 cells) which is 50% or less when compared to CMV-IE, preferably 25% or less than CMV-IE, more preferably 10% or less than CMV-IE, and in some cases 5% or less than CMV-IE, or 1% or less than CMV-IE.

In many instances, shorter promoter sequences are preferred, particularly for use in situations where a vector (e.g. a viral vector such as AAV) has limited capacity. Accordingly, in some embodiments the synthetic liver-specific promoter has length of 700 or fewer nucleotides, for example, 600, 500, 450, 400, 350, 300, 250, 200, 150, 100, 75, 70, 68 or fewer nucleotides.

Particularly preferred synthetic liver-specific promoters are those that are both short and which exhibit high levels of activity.

Synthetic Liver-Specific Expression Cassettes:

The present invention also provides a synthetic liver-specific expression cassette comprising a synthetic liver-specific promoter of the present invention operably linked to a sequence encoding an expression product, suitably a gene (e.g. a transgene).

The gene typically encodes a desired gene expression product such as a polypeptide (protein) or RNA. The gene may be a full-length cDNA or genomic DNA sequence, or any fragment, subunit or mutant thereof that has at least some desired biological activity.

Where the gene encodes a protein, it can be essentially any type of protein. By way of non-limiting example, the protein can be an enzyme, an antibody or antibody fragment (e.g. a monoclonal antibody), a viral protein (e.g. REP-CAP, REV, VSV-G, or RD114), a therapeutic protein, or a toxic protein (e.g. Caspase 3, 8 or 9).

In some preferred embodiments of the present invention, the gene encodes a therapeutic expression product, preferably a therapeutic polypeptide suitable for use in treating a disease or condition associated with aberrant gene expression, optionally in the liver. The therapeutic expression product can be a protein, e.g. a secretable protein such as, e.g., a clotting factor (e.g., factor IX or factor VIII), a cytokine, a growth factor, an antibody or nanobody, a chemokine, a plasma factor, insulin, erythropoietin, lipoprotein lipase, or a toxic protein. Alternatively, the therapeutic expression product may be RNA, such as an siRNA or miRNA. A non-exhaustive list of therapeutic expression products (and sequences encoding them) envisaged for use in the present invention includes: factor VIII, factor IX, factor VII, factor X, von Willebrand factor, erythropoietin (EPO), interferon-a, interferon-B, interferon-y, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumour necrosis factor (TNF), afamin (AFM), a1-antitrypsin, a-galactosidase A, $\alpha$-L-iduronidase, ATP7b, ornithine transcarbamoylase, phenylalanine hydroxylase, lipoprotein lipase, aromatic amino acid decarboxylase (AADC), ATPase Sarcoplasmic/Endoplasmic Reticulum Ca2+ Transporting 2 (ATP2A2), cystic fibrosis transmembrane conductance regulator (CTFR), glutamic acid decarboxylase 65 kDa protein (GAD65), glutamic acid decarboxylase 67 kDa protein (GAD67), lipoprotein lipase (LPL), nerve growth factor (NGF), neurturin (NTN), porphobilinogen deaminase (PBGD), sarcoglycan alpha (SGCA), soluble fms-like tyrosine kinase-1 (sFLT-1), apoliproteins, low-density lipoprotein receptor (LDL-R), albumin, glucose-6-phosphatase, antibodies, nanobodies, aptamers, anti-viral dominant-negative proteins, and functional fragments, subunits or mutants thereof. Preferably the protein is a primate protein, more preferably a human protein.

In some embodiments of the invention, the synthetic liver-specific expression cassette comprises a gene useful for gene editing, e.g. a gene encoding a site-specific nuclease, such as a meganuclease, zinc finger nuclease (ZFN), transcription activator-like effector-based nuclease (TALEN), or the clustered regularly interspaced short palindromic repeats system (CRISPR-Cas). Suitably the site-specific nuclease is adapted to edit a desired target genomic locus by making a cut (typically a site-specific double-strand break) which is then repaired via non-homologous end-joining (NHEJ) or homology dependent repair (HDR), resulting in a desired edit. The edit can be the partial or complete repair of a gene that is dysfunctional, or the knock-down or knock-out of a functional gene.

Suitably the synthetic liver-specific expression cassette comprises sequences providing or coding for one or more of, and preferably all of, a ribosomal binding site, a start codon, a stop codon, and a transcription termination sequence. Suitably the expression cassette comprises a nucleic acid encoding a posttranscriptional regulatory element. Suitably the expression cassette comprises a nucleic acid encoding a polyA element.

Vectors and Viral Particles:

The present invention further provides a vector comprising a synthetic liver-specific CRM, synthetic liver-specific promoter, or expression cassette according to the present invention.

In some embodiments of the invention, the vector is a plasmid. Such a plasmid may include a variety of other functional nucleic acid sequences, such as one or more selectable markers, one or more origins of replication, multiple cloning sites and the like. In some embodiments of the invention, the vector is a viral vector.

In some embodiments of the invention, the vector is an expression vector for expression in eukaryotic cells. Examples of eukaryotic expression vectors include, but are not limited to, pW-LNEO, pSV2CAT, pOG44, pXTI and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available. For mammalian cells adenoviral vectors, the pSV and the pCMV series of vectors are particularly well-known non-limiting examples. There are many well-known yeast expression vectors including, without limitation, yeast integrative plasmids (Ylp) and yeast replicative plasmids (YRp). For plants the Ti plasmid of agrobacterium is an exemplary expression vector, and plant viruses also provide suitable expression vectors, e.g. tobacco mosaic virus (TMV), potato virus X, and cowpea mosaic virus.

In some preferred embodiments, the vector is a gene therapy vector. Various gene therapy vectors are known in the art, and mention can be made of AAV vectors, adenoviral vectors, retroviral vectors and lentiviral vectors. Where the vector is a gene therapy vector the vector preferably comprises a nucleic acid sequence operably linked to the synthetic liver-specific promoter of the invention that encodes a therapeutic product, suitably a therapeutic protein. The therapeutic protein may be a secretable protein. Non-limiting examples of secretable proteins are discussed above, and exemplary secretable therapeutic proteins, include clotting factors, such as factor VIII or factor IX, insulin, erythropoietin, lipoprotein lipase, antibodies or nanobodies, growth factors, cytokines, chemokines, plasma factors, toxic proteins, etc.

In some embodiments of the invention, the vector is a viral vector, such as a retroviral, lentiviral, adenoviral, or adeno-associated viral (AAV) vector. In some preferred embodiments the vector is an AAV vector. In some preferred embodiments the AAV has a serotype suitable for liver transduction. In some embodiments, the AAV is selected from the group consisting of: AAV2, AAV5, AAV6, AAV7, AAV8, AAV9, or derivatives thereof. AAV vectors are preferably used as self-complementary, double-stranded AAV vectors (scAAV) in order to overcome one of the limiting steps in AAV transduction (i.e. single-stranded to double-stranded AAV conversion), although the use of single-stranded AAV vectors (ssAAV) is also encompassed herein. In some embodiments of the invention, the AAV vector is chimeric, meaning it comprises components from at least two AAV serotypes, such as the ITRs of an AAV2 and the capsid protein of an AAV5.

The invention further provides recombinant virions (viral particles) comprising a vector as described above.

Pharmaceutical Compositions:

The vectors or virions of the present invention may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

Accordingly, a further aspect of the invention provides a pharmaceutical composition comprising a vector or virion as described herein.

Therapeutic and Other Methods and Uses:

The present invention also provides a synthetic liver-specific CRM, synthetic liver-specific promoter, expression cassette, vector, virion or pharmaceutical composition according to various aspects of the present invention for use in the treatment of a disease, preferably a disease associated with aberrant gene expression, optionally in the liver (e.g. a genetic liver disease). Various diseases associated with aberrant gene expression in the liver are discussed above, and these include but are not limited to haemophilia (including haemophilia A or B), familial hypercholesterolemia, ornithine transcarbamylase deficiency, phenylketonuria, ornithine transcarbamylase deficiency, glycogen storage disease, α1-antitrypsin deficiency, hereditary hemochromatosis, tyrosinemia type 1, argininosuccinic aciduria, hepatitis virus infection, non-viral hepatitis, liver cancer, genetic cholestasis, Wilson's disease, and various other liver diseases (such as non-alcoholic fatty liver disease (NAFLD), alcohol-related liver disease (ARLD), and lysosomal storage disorders. Use for the treatment of haemophilia A or B represent preferred embodiments of the invention.

The present invention also provides a synthetic liver-specific CRM, synthetic liver-specific promoter, expression cassette, vector, virion according to the various aspects of the present invention for use the manufacture of a pharmaceutical composition for treatment of any condition or disease mentioned herein.

The present invention further provides a cell comprising a synthetic liver-specific CRM, synthetic liver-specific promoter, expression cassette, vector, virion according to the various aspects of the invention. Suitably the cell is a eukaryotic cell. The eukaryotic cell can suitably be a fungal cell (e.g. yeast cell), an animal (metazoan) cell (e.g. a mammalian cell), or a plant cell. Alternatively, the cell may be a prokaryotic cell.

In some embodiments of the invention, the cell is ex vivo, e.g. in cell culture. In other embodiments of the invention the cell may be part of a tissue or multicellular organism.

In a preferred embodiment, the cell is a liver cell (hepatocyte), which may be ex vivo or in vivo. The liver cell may be a primary liver cell or a cell of a liver-derived cell line, e.g. an immortalised cell line. The cell may be present within a liver tissue environment (e.g. within a liver of an animal) or may be isolated from liver tissue, e.g. it may be in cell culture. Suitably the cell is a human cell.

The liver-specific CRM, synthetic liver-specific promoter, expression cassette, or vector, according to the invention may be inserted into the genome of the cell, or it may be episomal (e.g. present in an episomal vector).

In a further aspect the present invention provides a method for producing an expression product, the method comprising providing a synthetic liver-specific expression cassette according to the present invention (preferably in a vector as set out above) in a cell, preferably a liver cell and expressing the gene present in the synthetic liver-specific expression cassette. The method suitably comprises maintaining said liver cell under suitable conditions for expression of the gene. In culture this may comprise incubating the cell, or tissue comprising the cell, under suitable culture conditions. The expression may of course be in vivo, e.g. in one or more cells in the liver of a subject.

Suitably the method comprises the step of introducing the synthetic liver-specific expression cassette into the liver cell. A wide range of methods of transfecting liver cells are well-known in the art. A preferred method of transfecting liver cells is transducing the cells with a viral vector comprising the synthetic liver-specific expression cassette, e.g. an AAV vector.

It will be evident to the skilled person that a synthetic liver-specific CRM, synthetic liver-specific promoter, expression cassette, vector or virion according to various aspects of the invention may be used for gene therapy. Accordingly, the use of the such nucleic acid constructs in gene therapy forms part of the present invention.

The invention thus provides, in some embodiments, an expression cassettes, vectors or virion according to the present for use in gene therapy in a subject, preferably gene therapy through liver-specific expression of a therapeutic gene. The therapy may involve treatment of a disease through secretion of a therapeutic product from liver cells, suitable, a disease involving aberrant gene expression in the liver (for example, haemophilia A or B).

The present invention also provides a method of expressing a therapeutic transgene in a liver cell, the method comprising introducing into the liver cell an expression cassette or vector according to the present invention. The liver cell can be in vivo or ex vivo.

The present invention also provides a method of gene therapy of a subject, preferably a human, in need thereof, the method comprising:

administering to the subject (suitably introducing into the liver of the subject) a synthetic liver-specific expression cassette, vector, virion or pharmaceutical composition of the present invention, which comprises a gene encoding a therapeutic product.

The method suitably comprises expressing a therapeutic amount of the therapeutic product from the gene in the liver of said subject.

Genes encoding suitable therapeutic products are discussed above. However, specific mention may be made of therapeutic proteins, such as factor VIII and IX for the treatment of haemophilia.

The method suitably comprises administering a vector or virion according to the present invention to the subject. Suitably the vector is a viral gene therapy vector, for example an AAV vector.

In some embodiments, the method comprises administering the viral gene therapy vector systemically. Systemic administration may be enteral (e.g. oral, sublingual, and rectal) or parenteral (e.g. injection). Preferred routes of injection include intravenous, intramuscular, subcutaneous, intra-arterial, intra-articular, intrathecal, and intradermal injections.

In some embodiments, the viral gene therapy vector may be administered concurrently or sequentially with one or more additional therapeutic agents or with one or more saturating agents designed to prevent clearance of the vectors by the reticular endothelial system.

Where the vector is an AAV vector, the dosage of the vector may be from $1 \times 10^{10}$ gc/kg to $1 \times 10^{15}$ gc/kg or more, suitably from $1 \times 10^{12}$ gc/kg to $1 \times 10^{14}$ gc/kg, suitably from $5 \times 10^{12}$ gc/kg to $5 \times 10^{13}$ gc/kg.

In general, the subject in need thereof will be a mammal, and preferably primate, more preferably a human. Typically, the subject in need thereof will display symptoms characteristic of a disease. The method typically comprises ameliorating the symptoms displayed by the subject in need thereof, by expressing the therapeutic amount of the therapeutic product.

Gene therapy protocols for therapeutic gene expression in target cells in vitro and in vivo, are well-known in the art and will not be discussed in detail here. Briefly, they include intramuscular injection, interstitial injection, instillation in airways, application to endothelium, intra-hepatic parenchyme, and intravenous or intra-arterial administration (e.g. intra-hepatic artery, intra-hepatic vein) of plasmid DNA vectors (naked or in liposomes) or viral vectors. Various devices have been developed for enhancing the availability of DNA to the target cell. While a simple approach is to contact the target cell physically with catheters or implantable materials containing the relevant vector, more complex approaches can use jet injection devices an suchlike. Gene transfer into mammalian liver cells has been performed using both ex vivo and in vivo procedures. The ex vivo approach typically requires harvesting of the liver cells, in vitro transduction with suitable expression vectors, followed by reintroduction of the transduced hepatocytes the liver. In vivo gene transfer has been achieved by injecting DNA or viral vectors into the liver parenchyma, hepatic artery, or portal vein.

According to some preferred embodiments, the methods set out above may be used for the treatment of a subject with haemophilia, e.g. haemophilia A or B. Accordingly, the invention provides a method of treating a subject with haemophilia A or B, the method comprising the steps of:

administering to the subject (suitably introducing into the liver of the subject) a synthetic liver-specific expression cassette, vector, virion or pharmaceutical composition of the present invention which comprises a gene encoding a suitable clotting factor (in particular, factor VIII in the case of haemophilia A or factor IX in the case of haemophilia B); and expressing a therapeutic amount of the clotting factor in the liver of said subject.

In some cases, the synthetic liver-specific expression cassette is provided in a gene therapy vector, suitably an AAV vector.

Preferably the method comprises expressing a suitable amount of the relevant clotting factor in the liver of the subject to alleviate or ameliorate the symptoms of haemophilia A or B.

Additional Matters:

In some embodiments of the invention, the CRM or synthetic liver-specific promoter does not comprise both CR0077 (or a functional variant thereof) and CR0078 (or a functional variant thereof). In some embodiments of the invention, where a CRE, CRM or synthetic liver-specific promoter comprises either CR0077 or CR0078 (or a functional variant thereof), it does not comprise a further CRE selected from the group consisting of: CR0077 (or a functional variant thereof) and CR0078 (or a functional variant thereof). In some embodiments of the invention, the CRM or synthetic liver-specific promoter does not comprise more than one CRE selected from the group consisting of: CR0077 (or a functional variant thereof) or CR0078 (or a functional variant thereof).

In some embodiments of the invention, the CRE, CRM or synthetic liver-specific promoter does not comprise CR0077 or a functional variant thereof or CR0078 or a functional variant thereof.

In some embodiments of the invention, the CRM or synthetic liver-specific promoter does not comprise the sequence GGACTTAGCCCCTGTTTGCTCCTCCGA- TAACTGGGGTGACCTTGGTTAATATTCACCA (SEQ ID NO: 284), or GCCCCTGTTTGCTCCTCCGA-TAACTGGGGTGACCTTGGTTAATATTCACCA (SEQ ID NO: 285), or a functional variant of either thereof. These sequences are portions the SEPRINA1 promoter.

In some embodiments of the invention, where the CRM or synthetic liver-specific promoter comprises either CR0077 or CR0078 (or functional variants of any thereof), it does not contain SEQ ID NO: 284 or SEQ ID NO: 285 (or functional variants of any thereof). Thus, in some embodiments, the CRM or synthetic liver-specific promoter contains not more than one of sequences V1, V2, SEQ ID NO: 284 and SEQ ID NO: 285.

In some embodiments of the invention, the CRM or synthetic liver-specific promoter comprises not more than two of the following elements: LVR_CRE0080_PROC, LVR_CRE0081_APOA1, LVR_CRE0061_APOB, LVR_CRE0082_APOC4, SEQ ID NO: 284 and SEQ ID NO: 285, or functional variants of any thereof. In some embodiments of the invention, the CRM or synthetic liver-specific promoter comprises not more than one of said elements, or functional variants of any thereof. In some embodiments of the invention, the CRM or synthetic liver-specific promoter does not comprise any of said elements, or functional variants of any thereof. LVR_CRE0080_PROC, and LVR_CRE0081_APOA1 are components of CR0077, and LVR_CRE0061_APOB, LVR_CRE0082_APOC4 are components of CR0078 (see Tables 7 and 8 for further details).

In some embodiments of the invention, the synthetic liver-specific promoter does not comprise the CRE0052 minimal promoter or a functional variant thereof.

In some embodiments of the invention, the CRM or synthetic liver-specific promoter does not comprise a sequence as disclosed in European patent application no 18207027.6.

The functional variants of the any of the sequences in these disclaimers and embodiments discussed above can have, for example, a sequence having 60%, 70%, 80%, 90%, 95% or 99% identity to any of the reference sequences.

Definitions and General Points

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

The practice of the present invention will employ, unless otherwise indicated, conventional techniques of cell biology, cell culture, molecular biology, transgenic biology, micro-biology, recombinant DNA, and immunology, which are within the skill of the art. Such techniques are explained fully in the literature. See, for example, Current Protocols in Molecular Biology (Ausubel, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); U.S. Pat. No. 4,683,195; Nucleic Acid Hybridization (Harries and Higgins eds. 1984); Transcription and Translation (Hames and Higgins eds. 1984); Culture of Animal Cells (Freshney, Alan R. Liss, Inc., 1987); Immobilized Cells and Enzymes (IRL Press, 1986); Perbal, A Practical Guide to Molecular Cloning (1984); the series, Methods in Enzymology (Abelson and Simon, eds. -in-chief, Academic Press, Inc., New York), specifically, Vols. 154 and 155 (Wu et al. eds.) and Vol. 185, "Gene Expression Technology" (Goeddel, ed.); Gene Transfer Vectors For Mammalian Cells (Miller and Calos eds., 1987, Cold Spring Harbor Laboratory); Immunochemical Methods in Cell and Molecular Biology (Mayer and Walker, eds., Academic Press, London, 1987); Handbook of Experimental Immunology, Vols. I-IV (Weir and Blackwell, eds., 1986); and Manipulating the Mouse Embryo, (Cold Spring Harbor Laboratory Press, Cold Spring Harbor, N.Y., 1986).

To facilitate the understanding of this invention, a number of terms are defined or explained below. Terms used herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "cis-regulatory element" or "CRE", is a term well-known to the skilled person, and means a nucleic acid sequence such as an enhancer, promoter, insulator, or silencer, that can regulate or modulate the transcription of a neighbouring gene (i.e. in cis). CREs are found in the vicinity of the genes that they regulate. CREs typically regulate gene transcription by binding to TFs, i.e. they include TFBS. A single TF may bind to many CREs, and hence control the expression of many genes (pleiotropy). CREs are usually, but not always, located upstream of the transcription start site (TSS) of the gene that they regulate. "Enhancers" are CREs that enhance (i.e. upregulate) the transcription of genes that they are operably associated with, and can be found upstream, downstream, and even within the introns of the gene that they regulate. Multiple enhancers can act in a coordinated fashion to regulate transcription of one gene. "Silencers" in this context relates to CREs that bind TFs called repressors, which act to prevent or down-regulate transcription of a gene. The term "silencer" can also refer to a region in the 3' untranslated region of messenger RNA, that bind proteins which suppress translation of that mRNA molecule, but this usage is distinct from its use in describing a CRE. Generally, the CREs of the present invention are liver-specific enhancer elements (often referred to as liver-specific CREs, or liver-specific CRE enhancers, or suchlike). In the present context, it is preferred that the CRE is located 1500 nucleotides or less from the transcription start site (TSS), more preferably 1000 nucleotides or less from the TSS, more preferably 500 nucleotides or less from the TSS, and suitably 250, 200, 150, or 100 nucleotides or less from the TSS. CREs of the present invention are preferably comparatively short in length, preferably 250 nucleotides or less in length, for example they may be 200, 175, 150, 90, 80, 70, 60 or 50 nucleotides or less in length. The CREs of the present invention are typically provided in combination with an operably linked promoter element, which ca be a minimal promoter or proximal promoter; the CREs of the present invention enhance liver-specific activity of the promoter element.

The term "cis-regulatory module" or "CRM" means a functional regulatory nucleic acid module, which usually comprises two or more CREs; in the present invention the CREs are typically liver-specific enhancers and thus the CRM is a synthetic liver-specific regulatory nucleic acid. Thus, in the present application a CRM typically comprises a plurality of liver-specific CREs. Typically, the multiple CREs within the CRM act together (e.g. additively or synergistically) to enhance the transcription of a gene that a promoter comprising the CRM is operably associated with. There is considerable scope to shuffle (i.e. reorder), invert (i.e. reverse orientation), and alter spacing of CREs within a CRM. Accordingly, functional variants of CRMs of the present invention include, inter alia, variants of the referenced CRMs wherein CREs within them have been shuffled and/or inverted, and/or the spacing between CREs has been altered.

As used herein, the phrase "promoter" refers to a region of DNA that generally is located upstream of a nucleic acid sequence to be transcribed that is needed for transcription to occur, i.e. which initiates transcription. Promoters permit the proper activation or repression of transcription of a coding sequence under their control. A promoter typically contains specific sequences that are recognized and bound by plurality of TFs. TFs bind to the promoter sequences and result in the recruitment of RNA polymerase, an enzyme that synthesizes RNA from the coding region of the gene. Many diverse promoters are known in the art.

The term "synthetic promoter" as used herein relates to a promoter that does not occur in nature. In the present context it typically comprises a CRE and/or CRM of the present invention operably linked to a minimal (or core) promoter or liver-specific proximal promoter (promoter element). The CREs and/or CRMs of the present invention serve to enhance liver-specific transcription of a gene operably linked to the synthetic promoter. Parts of the synthetic promoter may be naturally occurring (e.g. the minimal promoter or one or more CREs in the promoter), but the synthetic promoter as a complete entity is not naturally occurring.

As used herein, "minimal promoter" (also known as the "core promoter") refers to a short DNA segment which is inactive or largely inactive by itself, but can mediate transcription when combined with other transcription regulatory elements. Minimum promoter sequence can be derived from various different sources, including prokaryotic and eukaryotic genes. Examples of minimal promoters are discussed above, and include the dopamine beta-hydroxylase gene minimum promoter, cytomegalovirus (CMV) immediate early gene minimum promoter (CMV-MP), and the herpes thymidine kinase minimal promoter (MinTK). A minimal promoter typically comprises the transcription start site (TSS) and elements directly upstream, a binding site for RNA polymerase II, and general transcription factor binding sites (often a TATA box). A minimal promoter may also include some elements downstream of the TSS, but these typically have little functionality absent additional regulatory elements.

As used herein, "proximal promoter" relates to the minimal promoter plus the proximal sequence upstream of the gene that tends to contain primary regulatory elements. It often extends approximately 250 base pairs upstream of the TSS, and includes specific TFBS. A proximal promoter may also include one or more regulatory elements downstream of the TSS, for example a UTR or an intron. In the present case, the proximal promoter may suitably be a naturally occurring liver-specific proximal promoter that can be combined with one or more CREs or CRMs of the present invention. However, the proximal promoter can be synthetic.

As used herein, "promoter element" refers to either a minimal promoter or proximal promoter as defined above. In the context of the present invention a promoter element is typically combined with one or more CREs in order to provide a synthetic liver-specific promoter of the present invention.

A "functional variant" of a CRE, CRM, promoter element, promoter or other nucleic acid construct in the context of the present invention is a variant of a reference sequence that retains the ability to function in the same way as the reference sequence, e.g. as a liver-specific CRE, liver-specific CRM or liver-specific promoter. Alternative terms for such functional variants include "biological equivalents" or "equivalents".

It will be appreciated that the ability of a given CRE to function as a liver-specific enhancer is determined principally by the ability of the sequence to bind the same liver-specific TFs that bind to the reference sequence. Accordingly, in most cases, a functional variant of a CRE or CRM will contain TFBS for the most or all of same TFs as the reference CRE or CRM. It is preferred, but not essential, that the TFBS of a functional variant are in the same relative positions (i.e. order and general position) as the reference CRE or CRM. It is also preferred, but not essential, that the TFBS of a functional variant are in the same orientation as the reference sequence (it will be noted that TFBS can in some cases be present in reverse orientation, e.g. as the reverse complement vis-à-vis the sequence in the reference sequence). It is also preferred, but not essential, that the TFBS of a functional variant are on the same strand as the reference sequence. Thus, in preferred embodiments, the functional variant comprises TFBS for the same TFs, in the same order, the same position, in the same orientation and on the same strand as the reference sequence. It will also be appreciated that the sequences lying between TFBS (referred to in some cases as spacer sequences, or suchlike) are of less consequence to the function of the CRE or CRM. Such sequences can typically be varied considerably, and their lengths can be altered. However, in preferred embodiments the spacing (i.e. the distance between adjacent TFBS) is substantially the same (e.g. it does not vary by more than 20%, preferably by not more than 10%, and more preferably it is approximately the same) in a functional variant as it is in the reference sequence. It will be apparent that in some cases a functional variant of a CRE can be present in the reverse orientation, e.g. it can be the reverse complement of a CRE as described above, or a variant thereof.

Levels of sequence identity between a functional variant and the reference sequence can also be an indicator or retained functionality. High levels of sequence identity in the TFBS of the CRE is of generally higher importance than sequence identity in the spacer sequences (where there is little or no requirement for any conservation of sequence). However, it will be appreciated that even within the TFBS, a considerable degree of sequence variation can be accommodated, given that the sequence of a functional TFBS does not need to exactly match the consensus sequence.

The ability of one or more TFs to bind to a TFBS in a given functional variant can determined by any relevant means known in the art, including, but not limited to, electromobility shift assays (EMSA), binding assays, chromatin immunoprecipitation (ChIP), and ChIP-sequencing (ChI P-seq). In a preferred embodiment the ability of one or more TFs to bind a given functional variant is determined by EMSA. Methods of performing EMSA are well-known in the art. Suitable approaches are described in Sambrook et al. cited above. Many relevant articles describing this procedure are available, e.g. Hellman and Fried, Nat Protoc. 2007; 2(8): 1849-1861.

"Liver-specific" or "liver-specific expression" refers to the ability of a cis-regulatory element, cis-regulatory module or promoter to enhance or drive expression of a gene in the liver (or in liver-derived cells) in a preferential or predominant manner as compared to other tissues (e.g. spleen, muscle, heart, lung, and brain). Expression of the gene can be in the form of mRNA or protein. In preferred embodiments, liver-specific expression is such that there is negligible expression in other (i.e. non-liver) tissues or cells, i.e. expression is highly liver-specific.

The ability of a CRE, CRM or promoter to function as a liver-specific CRE, CRM or promoter can be readily assessed by the skilled person. The skilled person can thus easily determine whether any variant of the specific CRE, CRM or promoter recited above remains functional (i.e. it is a functional variant as defined above). For example, any given CRM to be assessed can be operably linked to a minimal promoter (e.g. positioned upstream of CMV-MP) and the ability of the cis-regulatory element to drive liver-specific expression of a gene (typically a reporter gene) is measured. Alternatively, a variant of a CRE can be substituted into a synthetic liver-specific promoter in place of a reference CRE, and the effects on liver-specific expression driven by said modified promoter can be determined and compared to the unmodified form. Similarly, the ability of a CRM or promoter to drive liver-specific expression can be readily assessed by the skilled person (e.g. as described in the examples below). Expression levels of a gene driven by a variant of a reference promoter can be compared to the expression levels driven by the reference sequence. In some embodiments, where liver-specific expression levels driven by a variant promoter are at least 50%, at least 60%, at least 70%, at least 80%, at least 90%, or at least 100% of the expression levels driven by the reference promoter, it can be said that the variant remains functional. Suitable nucleic acid constructs and reporter assays to assess liver-specific expression enhancement can easily constructed, and the examples set out below give suitable methodologies.

Liver-specificity can be identified wherein the expression of a gene (e.g. a therapeutic or reporter gene) occurs preferentially or predominantly in liver-derived cells. Preferential or predominant expression can be defined, for example, where the level of expression is significantly greater in liver-derived cells than in other types of cells (i.e. non-liver-derived cells). For example, expression in liver-derived cells is suitably at least 5-fold higher than in non-liver cells, preferably at least 10-fold higher than in non-liver cells, and it may be 50-fold higher or more in some cases. For convenience, liver-specific expression can suitably be demonstrated via a comparison of expression levels in a hepatic cell line (e.g. liver-derived cell line such as Huh7 and/or HepG2 cells) or liver primary cells, compared with expression levels in a kidney-derived cell line (e.g. HEK-293), a cervical tissue-derived cell line (e.g. HeLa) and/or a lung-derived cell line (e.g. A549).

The synthetic liver-specific promoters of the present invention preferably exhibit reduced expression in non-liver-derived cells, suitably in HEK-293, HeLa, and/or A549 cells when compared to a non-tissue specific promoter such as CMV-IE. The synthetic liver-specific promoters of the present invention preferably have an activity of 50% or less than the CMV-IE promoter in non-liver-derived cells (suitably in HEK-293, HeLa, and/or A549 cells), suitably 25% or less, 20% or less, 15% or less, 10% or less, 5% or less or 1% or less. Generally, it is preferred that expression in non-liver-derived cells is minimized, but in some cases this may not be necessary. In some embodiments, the synthetic liver-specific promoters of the present invention are suitable for promoting gene expression at a level of at 50% or less than an LP1 promoter in non-liver-derived cells (e.g. HEK-293, HeLa, and/or A549 cells).

The synthetic liver-specific promoters of the present invention are preferably suitable for promoting expression in the liver of a subject, e.g. driving liver-specific expression of a transgene, preferably a therapeutic transgene. Preferred synthetic liver-specific promoters of the present invention are suitable for promoting liver-specific transgene expression and have an activity in liver cells which is at least 15%, 20%, 30%, 40%, 50%, 60%, 70%, 80%, 90%, 100%, 125%, 150%, 175%, 200%, 250%, 300%, 350% or 400% of the activity of the TBG promoter. In some embodiments, the synthetic liver-specific promoters of the invention are suitable for promoting liver-specific transgene expression at a level at least 100% of the activity of the LP1 promoter, preferably 150%, 200%, 300% or 500% of the activity of the LP1 promoter. Such liver-specific expression is suitably determined in liver-derived cells, e.g. in Huh7, and/or HepG2 cells or primary liver cells (suitably primary human hepatocytes).

Synthetic liver-specific promoters of the present invention may also be able to promote liver-specific expression of a gene at a level at least 150% compared to CMV-IE in liver-derived cells (e.g. Huh7 and/or HepG2 cells), preferably at least 200% CMV-IE promoter in liver-derived cells The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA RNA hybrid molecules, specifically including hnRNA, pre-mRNA, mRNA, cDNA, genomic DNA, amplification products, oligonucleotides, and synthetic (e.g., chemically synthesised) DNA, RNA or DNA RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

The terms "identity" and "identical" and the like refer to the sequence similarity between two polymeric molecules, e.g., between two nucleic acid molecules, such as between two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method. Typically, the percentage sequence identity is calculated over the entire length of the sequence.

For example, a global optimal alignment is suitably found by the Needleman-Wunsch algorithm with the following scoring parameters: Match score: +2, Mismatch score: −3; Gap penalties: gap open 5, gap extension 2. The percentage identity of the resulting optimal global alignment is suitably calculated by the ratio of the number of aligned bases to the total length of the alignment, where the alignment length includes both matches and mismatches, multiplied by 100.

The term "hybridising" means annealing to two at least partially complementary nucleotide sequences in a hybridization process. In order to allow hybridisation to occur complementary nucleic acid molecules are generally thermally or chemically denatured to melt a double strand into two single strands and/or to remove hairpins or other secondary structures from single-stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and Na-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. By way of non-limiting example, representative salt and temperature conditions for stringent hybridization are: 1×SSC, 0.5% SDS at 65° C. The abbreviation SSC refers to a buffer used in nucleic acid hybridization solutions. One litre of a 20× (twenty times concentrate) stock SSC buffer solution (pH 7.0) contains 175.3 g sodium chloride and 88.2 g sodium citrate. A representative time period for achieving hybridisation is 12 hours.

The term "transcription factor binding site" (TFBS) is well known in the art. Disclosed herein are various specific TFBS sequences. It will be apparent to the skilled person that alternative TFBS sequences can be used, provided that they are bound by the intended TF. Consensus sequences for the various TFBS disclosed herein are known in the art, and the skilled person can readily use this information to determine alternative TFBS. Furthermore, the ability of a TF to bind to a given putative sequence can readily be determined experimentally by the skilled person (e.g. by EMSA and other approaches well known in the art and discussed herein).

The meaning of "consensus sequence" is well-known in the art. In the present application, the following notation is used for the consensus sequences, unless the context dictates otherwise. Considering the following exemplary DNA sequence:

A[CT]N{A}YR

A means that an A is always found in that position; [CT] stands for either C or T in that position; N stands for any base in that position; and {A} means any base except A is found in that position. Y represents any pyrimidine, and R indicates any purine.

"Synthetic" in the present application means a nucleic acid molecule that does not occur in nature. Synthetic nucleic acid expression constructs of the present invention are produced artificially, typically by recombinant technologies. Such synthetic nucleic acids may contain naturally occurring sequences (e.g. promoter, enhancer, intron, and other such regulatory sequences), but these are present in a non-naturally occurring context. For example, a synthetic gene (or portion of a gene) typically contains one or more nucleic acid sequences that are not contiguous in nature (chimeric sequences), and/or may encompass substitutions, insertions, and deletions and combinations thereof.

"Complementary" or "complementarity", as used herein, refers to the Watson-Crick base-pairing of two nucleic acid sequences. For example, for the sequence 5'-AGT-3' binds to the complementary sequence 3'-TCA-5'. Complementarity between two nucleic acid sequences may be "partial", in which only some of the bases bind to their complement, or it may be complete as when every base in the sequence binds to its complementary base. The degree of complementarity between nucleic acid strands has significant effects on the efficiency and strength of hybridisation between nucleic acid strands.

"Transfection" in the present application refers broadly to any process of deliberately introducing nucleic acids into cells, and covers introduction of viral and non-viral vectors, and includes transformation, transduction and like terms and processes. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); Agrobacterium-mediated transfer (Fraley et al. (1983) Proc. Natl. Acad. Sci. USA 80:4803-7); direct DNA uptake; whiskers-mediated transformation; and micropro-jectile bombardment (Klein et al. (1987) Nature 327:70).

As used herein, the phrase "transgene" refers to an exogenous nucleic acid sequence. In one example, a transgene is a gene encoding an industrially or pharmaceutically useful compound, or a gene encoding a desirable trait. In yet another example, the transgene encodes an antisense nucleic acid sequence, wherein expression of the antisense nucleic acid sequence inhibits expression of a target nucleic acid sequence. The transgene preferably encodes a therapeutic product, e.g. a protein.

The term "vector" is well known in the art, and as used herein refers to a nucleic acid molecule, e.g. double-stranded DNA, which may have inserted into it a nucleic acid sequence according to the present invention. A vector is suitably used to transport an inserted nucleic acid molecule into a suitable host cell. A vector typically contains all of the necessary elements that permit transcribing the insert nucleic acid molecule, and, preferably, translating the transcript into a polypeptide. A vector typically contains all of the necessary elements such that, once the vector is in a host cell, the vector can replicate independently of, or coincidental with, the host chromosomal DNA; several copies of the vector and its inserted nucleic acid molecule may be generated. Vectors of the present invention can be episomal vectors (i.e., that do not integrate into the genome of a host cell), or can be vectors that integrate into the host cell genome. This definition includes both non-viral and viral vectors. Non-viral vectors include but are not limited to plasmid vectors (e.g. pMA-RQ, pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Larger vectors such as artificial chromosomes (bacteria (BAC), yeast (YAC), or human (HAC)) may be used to accommodate larger inserts. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

The term "operably linked", "operably connected" or equivalent expressions as used herein refer to the arrangement of various nucleic acid elements relative to each other such that the elements are functionally connected and are able to interact with each other in the manner intended. Such elements may include, without limitation, a promoter, a CRE (e.g. enhancer or other regulatory element), a polyade-nylation sequence, one or more introns and/or exons, and a coding sequence of a gene of interest to be expressed. The nucleic acid sequence elements, when properly oriented or operably linked, act together to modulate the activity of one another, and ultimately may affect the level of expression of an expression product. By modulate is meant increasing, decreasing, or maintaining the level of activity of a particular element. The position of each element relative to other elements may be expressed in terms of the 5' terminus and the 3' terminus of each element or their position upstream or downstream of another element or position (such as a TSS or promoter element), and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, CREs will typically be located immediately upstream of the promoter element (although this is generally the case, it should definitely not be interpreted as a limitation or exclusion of positions within the nucleic acid expression cassette), but this needs not be the case in vivo, e.g., a regulatory element sequence naturally occurring downstream of a gene whose transcription it affects is able to function in the same way when located upstream of the promoter. Hence, according to a specific embodiment, the regulatory or enhancing effect of the regulatory element can be position-independent.

A "spacer sequence" or "spacer" as used herein is a nucleic acid sequence that separates two functional nucleic acid sequences (e.g. TFBS, CREs, CRMs, promoter element, etc.). It can have essentially any sequence, provided it does not prevent the functional nucleic acid sequence (e.g. cis-regulatory element) from functioning as desired (e.g. this could happen if it includes a silencer sequence, prevents binding of the desired transcription factor, or suchlike). Typically, it is non-functional, as in it is present only to space adjacent functional nucleic acid sequences from one another. In some embodiments, spacers may have a length of 75, 50, 40, 30, 30 or 10 nucleotides or fewer.

The term "pharmaceutically acceptable" as used herein is consistent with the art and means compatible with the other ingredients of the pharmaceutical composition and not deleterious to the recipient thereof.

"Therapeutically effective amount" and like phrases mean a dose or plasma concentration in a subject that provides the desired specific pharmacological effect, e.g. to express a therapeutic gene in the liver. A therapeutically effective amount may not always be effective in treating the conditions described herein, even though such dosage is deemed to be a therapeutically effective amount by those of skill in the art. The therapeutically effective amount may vary based on the route of administration and dosage form, the age and weight of the subject, and/or the disease or condition being treated.

The terms "treatment" or "treating" refer to reducing, ameliorating or eliminating one or more signs, symptoms, or effects of a disease or condition.

The "administration" of an agent to a subject includes any route of introducing or delivering to a subject the agent to perform its intended function. Administration can be carried out by any suitable route, including orally, intranasally, intraocularly, ophthalmically, parenterally (intravenously, intramuscularly, intraperitoneally, or subcutaneously), or topically. Administration includes self-administration and the administration by another.

The terms "individual," "subject," and "patient" are used interchangeably, and refer to any individual subject with a disease or condition in need of treatment. For the purposes of the present disclosure, the subject may be a primate, preferably a human, or another mammal, such as a dog, cat, horse, pig, goat, or bovine, and the like.

EXAMPLES

Example 1—Sequences

The following sequences are of relevance to the present disclosure:

TABLE 5

Cis-regulatory elements (CREs):

| Name (also known as) | Sequence |
|---|---|
| CRE0018 (HBV) | CAGGCTTTCACTTTCTCGCCAACTTACAAGGC CTTTCTGTGTAAACAATACCTGAACCTTTACC CCGTTGCCCGGCAACGGCCAGGTCTGTGCCAA GTGTTTG (SEQ ID NO: 1) |
| CRE0042 (TTR) | CCCTGTTCAAACATGTCCTAATACTCTGTCTC TGCAAGGGTCATCAGTAGTTTTCCATCTTACT CAACATCCTCCCAGTG (SEQ ID NO: 2) |
| CRE0051 (A1; alpha mic/ bik) | AGGTTAATTTTTAAAAAGCAGTCAAAAGTCCA AGTGGCCCTTGGCAGCATTTACTCTCTCTGTT TGCTCTGGTTAATAATCTCAGGAGCACAAACA TTCC (SEQ ID NO: 3) |
| CRE0058 (APOB) | GGCCCGGGAGGCGCCCTTTGGACCTTTTGCAA TCCTGGCG (SEQ ID NO: 4) |
| CRE0065 (APOA1) | CACTGAACCCTTGACCCCTGCCCTGCAGCCCC CGCAGCTTGCTGTTTGCCCACTCTATTTGCCC AGCCCCAG (SEQ ID NO: 5) |
| CRE0065.1 (APOA1_v1) | CACTGAACCCTTGACCCCTGCCCTGCAGCCCC CGCAGCTTGCTGTTTGCCCACTCTATTTGCCC AGCCCCAGGGACAGAGCTGATCCTTGAACTCT TAAGTTCCAC (SEQ ID NO: 6) |
| CRE0066 (NR1l2 or Enh_18XS) | CCCTGGAGAGTCCTTTAGCAGGGCAAAGTGCA ACATAGGCAGACCTTAAGGGATGACTCAGTAA CAGATAAGCTTTGTGTGCCTGCA (SEQ ID NO: 7) |
| CRE0066.2 (Enh_18S) | CCCTGGAGAGTCCTTTAGCAGGGCAAAGTGCA ACATAGGCAGACCTTAAGGGATGACTCAGTAA CAGATAAGCTTTGTGTGCCTGCAGGGGGATGG GAAGAGGGTGGGGCAGGAGAGGGACATAAAAG GGCTCTGAGGCATTGTACTGTGAATTCCTTCA GTCTCCTG (SEQ ID NO: 8) |
| CRE0066.1 (Enh_18) | CCCTGGAGAGTCCTTTAGCAGGGCAAAGTGCA ACATAGGCAGACCTTAAGGGATGACTCAGTAA CAGATAAGCTTTGTGTGCCTGCAGGGGGATGG GAAGAGGGTGGGGCAGGAGAGGGACATAAAAG GGCTCTGAGGCATTGTACTGTGAATTCCTTCA GTCTCCTGCTCTGCTCAGCCAGTCAGCCCTGC CTCCCTTGTTTAGGACCACACAGCACTGCTGG GTGTCTGCCTTTCCTTG (SEQ ID NO: 9) |
| CRE0068 (F2) | CCTCCCCGTGTTCCTGCTCTTTGTCCCTCTGT CCTACTTAGACTAATATTTGCCTTGGGTACTG CAAACAGGAAATGGGGGAGGGACAGGAGTAGG GCGG (SEQ ID NO: 10) |

TABLE 5-continued

Cis-regulatory elements (CREs):

| Name (also known as) | Sequence |
|---|---|
| CRE0074 (SEPP1) | AGAATGAACATTGAACTTTGGACTATACCTGA GGGGTGAGGTAAACAACAGGACTATAAAT (SEQ ID NO: 11) |
| CRE0001 (AKR1C4) | GCTGGTTTCTTATAAAACTGATGGAAGATACA AACACTATTAAAGAACTGTTTGCATGTTGCAA ATGATGTCCAAAGTCCAAACATTGTTAATAAT TAATACTCCAATAAACATCATGTCAGAATTTC TGTTTTCTTTTCCCTTTGAACCTTTGCAGGAT TGCCACATCATCAGGACCACACCTTCATCAGG AATGAATAT (SEQ ID NO: 12) |
| CRE0005 (LIPC) | ATTGGCATCTTCTATTGCTTTTCCTGGTGACT TCATTTTTCACTCTTGGCTAAAAATGGGTCTC TGATGATTTATTCTATCCTGGGTGTTGACAAG CTGAAGAAGTTGTGTGGGGCCTGCTGCCAGTA ACCCTGGGTGACGAAGCGTGACTCACCACTCC GAGGTCAGTGGGGGGATGGAAGGCAGGGGAGT CAGCTGACAAGATCTGCTGCTTTGTCACCAGG CCTTCTGC (SEQ ID NO: 13) |
| CRE0012 (ALB) | TGAAATGCCTGCCATATATTAGTGCCCTGAAG TCCAAAGGTAGAGGAACCGAGTGTTTAAAAAT TACTGTGGCTGTGGAGTCAACATGATGTAAAA AAACAAACATTTGGATAACACCAAGAAGCCAG ATATGGTTGAAATGTTGACTGGTTGACAAAAA TAATTTGGGTTGCTTAATGGTGCACAAAGGTA ATGCAAAA (SEQ ID NO: 14) |
| CRE0047 (APOC1P1) | CTGTTTGCTGCTTGCAATGTTTGCCCATTTTA GGG (SEQ ID NO: 15) |
| CRE0048 (F9) | TGCTCTCTGACAAAGATACGGTGGGTCCCACT GATGAACTGTGCTGCCACAGTAAATGTAGCCA CTATGCCTATCTCCATTCTGAAGATGTG (SEQ ID NO: 16) |
| CRE0056 (APOA1) | CCGCCCCCACTGAACCCTTGACCCCTGCCCTG CAGCCCCCGCAGCTTGCTGTTTGCCCACTCTA TTTGCCCAGCCCCAG (SEQ ID NO: 17) |
| CRE0062 (ALB) | AAGCTTTCTGAACAGCCAAACAGAGATTCCAA AGTTCAGGCACCAAAGTTCAGACCCTAACAGT TATTTACAAGGGTCAGTTAAC (SEQ ID NO: 18) |
| CRE0077 (V1) | AAGCAAATATTTGTGGTTATGGATTAACTCGA ACTGTTTGCCCACTCTATTTGCCC (SEQ ID NO: 19) |
| CRE0078 (V2) | GGCGCCCTTTGGACCTTTTGCAATCCTGGAGC AAACAGCAAACAC (SEQ ID NO: 20) |
| CRE0083.1 (Enh_27s) | TTTGGAGAAGACAGAGCCAATGAGGCCCTCGT TCCAGGGAAACAGAATATGCTCAGCATGACGC AGCACTCCCTGAACTTTCCGGTTACATCACCC AATAGCTGAGATCAGA (SEQ ID NO: 21) |
| CRE0089 (ECR9) | TTGGTGGAATATCTTTATGTCTTTTGCTAGCC ACTTGTCACATGTTATCATATTTGGTTTAATG AGAAGTCAGATATACCTTAATGATAACTTATG TCTGGA (SEQ ID NO: 22) |

TABLE 6

Minimal/Proximal Promoters:

| Name | Sequence |
|---|---|
| CRE0052 (G6PC) | GGGCATATAAAACAGGGGCAAGGCACAGACTCATA GCAGAGCAATCACCACCAAGCCTGGAATAACTGCA GCCACC (SEQ ID NO: 23) |

TABLE 6-continued

Minimal/Proximal Promoters:

| Name | Sequence |
|---|---|
| CRE0079 (SERPINA7 proximal promoter) | CTCTTTTGTTTTACATGAAGGGTCTGGCAGCCAAA GCAATCACTCAAAGTTCAAACCTTATCATTTTTTG CTTTGTTCCTCTTGGCCTTGGTTTTGTACATCAGC TTTGAAAATACCATCCCAGGGTTAATGCTGGGGTT AATTTATAACTAAGAGTGCTCTAGTTTTGCAATAC AGGACATGCTATAAAAATGGAAAGATGTTGCTTTC TGAGAGATGCGCCACC (SEQ ID NO: 288) |
| CRE0006 (VTN proximal promoter) | CCGATGACCTAATGATTCTGAGCTTGGCAAAGGTC TTATCTCCCAGCTCGCCCAGGCCCAGTGTTCCAGG AATGTGACCTTTGCTGCAGCAGCCGCTGGAGGGGG CAGAGGGGATGGGCTGGAGGTTGAGCAAACAGAGC AGCAGAAAAGGCAGTTCCTCTTCTCCAGTGCCCTC CTTCCCTGTCTCTGCCTCTCCCTCCCTTCCTCAGG CATCAGAGCGGAGACTTCAGGGAGACCAGAGCCCA GCTTGCCAGGCACTGAGCTAGAAGCCCTGCCATG (SEQ ID NO: 25) |
| CRE0059 (AFP minimal promoter) | AGTCATATGTTTGCTCACTGAAGGTTACTAGTTAA CAGGCATCCCTTAAACAGGATATAAAAGGACTTCA GCAGGACTGCTCGAAACATCCCACT (SEQ ID NO: 26) |
| CRE0073 (SERPINA1 proximal promoter) | GGGCGACTCAGATCCCAGCCAGTGGACTTAGCCCC TGTTTGCTCCTCCGATAACTGGGGTGACCTTGGTT AATATTCACCAGCAGCCTCCCCCGTTGCCCCTCTG GATCCACTGCTTAAATACGGACGAGGACAGGGCCC TGTCTCCTCAGCTTCAGGCACCACCACTGACCTGG GACAGTGAATC (SEQ ID NO: 27) |
| CRE0073.1 (SERPINA1 proximal promoterV1) | TGGACTTAGCCCCTGTTTGCTCCTCCGATAACTGG GGTGACCTTGGTTAATATTCACCAGCAGCCTCCCC CGTTGCCCCTCTGGATCCACTGCTTAAATACGGAC GAGGACAGGGCCCTGTCTCCTCAGCTTCAGGCACC ACCACTGACCTGGGACAGTGAATC (SEQ ID NO: 28) |
| CRE0040 (FGA proximal promoter) | CCTTTGCAACAGCTTATCGGAAGCAAACAAGCTGA GGGGAATTGAGCAAGAATTTCTGGGATACCAACAG CATAGGAGGAACAAAGGACGTAGAGGGAGGGTTGA CTGTCTACACAGGACAAAGCCAATGATTAACCAAA CCTCTTGCAGATTTAAATAGGATGGGAACTAGGAG TGGCAGCAATCCTTTCTTTCAGCTGGAGTGCTCCT CAGGAGCCAGCCCCACCCTTAGAAAAGATG (SEQ ID NO: 29) |

TABLE 7

Component parts of V1 (LVR_CRE0077_V1):

| Name | Sequence |
|---|---|
| LVR_CRE0080_PROC | AAGCAAATATTTGTGGTTATGGA TTAACTCGAA (SEQ ID NO: 30) |
| LVR_CRE0081_APOA1 | CTGTTTGCCCACTCTATTTGCCC (SEQ ID NO: 31) |

TABLE 8

Component parts of V2 (LVR_CRE0078_V2):

| Name | Sequence |
|---|---|
| LVR_CRE0061_APOB | GGCGCCCTTTGGACCT TTTGCAATCCTGG (SEQ ID NO: 32) |
| LVR_CRE0082_APOC4 | AGCAAACAGCAAACAC (SEQ ID NO: 33) |

TABLE 9

TFBS in CRE0018 (TFBS shown in bold):

| CRE0018 | CAGGCTTTCACTTTCTCGCCAACTTACAAGGCCTT TCTGTGTAAACAATACCTGAACCTTTACCCCGTTG CCCGGCAACGGCCAGGTCTGTGCCAAGTGTTTG (SEQ ID NO: 1) |
|---|---|

| TF | Position | TFBS sequence (SEQ ID NO:) |
|---|---|---|
| IRF | 5..15 | CTTTCACTTTC (34) |
| NF1 | 16..22 | TCGCCAA (35) |
| HNF3 | 38..47 | TGTGTAAACA (36) |
| HBLF | 40..50 | TGTAAACAATA (37) |
| RXRa | 52..65 | CTGAACCTTTACCC (38) |
| EF-C | 67..79 | GTTGCCCGGCAAC (39) |
| NF1 | 83..97 | CAGGTCTGTGCCAAG (40) |
| c/EBP | 91..103 | TGCCAAGTGTTTG (41) |

TABLE 10

TFBS in CRE0042 (TFBS shown in bold):

| CRE0042 | CCCTGTTCAAACATGTCCTAATACTCTGTC TCTGCAAGGGTCATCAGTAGTTTTCCATCT TACTCAACATCCTCCCAGTG (SEQ ID NO: 2) |
|---|---|

| TF | Position | TFBS sequence (SEQ ID NO:) |
|---|---|---|
| HNF-3 | 5..15 | GTTCAAACATG (42) |
| C/EBP | 18..28 | CTAATACTCTG (43) |
| HNF-4 | 33..44 | TGCAAGGGTCAT (44) |
| C/EBP | 60..69 | TTACTCAACA (45) |

TABLE 11

TFBS in CRE0051 (TFBS shown in bold):

| CRE0051 | AGGTTAATTTTTAAAAAGCAGTCAAAAGTCCAAGTGGCCC TTGGCAGCATTTACTCTCTCTGTTTGCTCTGGTTAATAAT CTCAGGAGCACAAACATTCC (SEQ ID NO: 3) |
|---|---|

| TF | Position | TFBS sequence (SEQ ID NO:) |
|---|---|---|
| HNF1 | 3 . . . 15 | GTTAATTTTTAAA (46) |
| HNF4 | 34 . . . 44 | GTGGCCCTTGG (47) |

TABLE 11-continued

| TFBS in CRE0051 (TFBS shown in bold): | | | |
|---|---|---|---|
| HNF3 | 61 . . . 67 | TGTTTGC (48) | |
| HNF1 | 70 . . . 84 | TGGTTAATAATCTCA (49) | |
| HNF3 | 90 . . . 96 | ACAAACA (50) | |

TABLE 12

| TFBS in CRE0058 (TFBS shown in bold): | |
|---|---|
| LVR_CRE0058_APOB | GGCCCGGGAGGCGCCCTTTGGACCTTTT GCAATCCTGGCG (SEQ ID NO: 4) |

| TF | Position | TFBS sequence (SEQ ID NO: |
|---|---|---|
| HNF4 | 12 . . . 24 | CGCCCTTTGGACC (51) |
| c/EBP | 21 . . . 38 | GACCTTTTGCAATCCTGG (52) |

TABLE 13

| TFBS in CRE0065 (TFBS shown in bold): | |
|---|---|
| LVR_CRE0065_APOA1 | CACTGAACCCTTGACCCCTGCCCTGCAG CCCCCGCAGCTTGCTGTTTGCCCACTCT ATTTGCCCAGCCCCAG (SEQ ID NO: 5) |

| TF | Position | TFBS sequence (SEQ ID NO:) |
|---|---|---|
| RXR Alpha | 2 . . . 24 | ACTGAACCCTTGACCCCTG CCCT (53) |
| HNF3 | 42 . . . 51 | CTGTTTGCCC (54) |
| HNF3 | 55 . . . 64 | CTATTTGCCC (55) |

TABLE 14

| TFBS in CRE0065.1 (TFBS shown in bold): | |
|---|---|
| LVR_CRE0065_APOA1_v1 | CACTGAACCCTTGACCCCTGCCCTGCAG CCCCCGCAGCTTGCTGTTTGCCCACTCT ATTTGCCCAGCCCCAGGGACAGAGCTGA TCCTTGAACTCTTAAGTTCCAC (SEQ ID NO: 6) |

| TF | Position | TFBS sequence (SEQ ID NO:) |
|---|---|---|
| RXR Alpha | 2 . . . 24 | ACTGAACCCTTGACCCCT GCCCT (56) |
| HNF3 | 42 . . . 51 | CTGTTTGCCC (57) |
| HNF3 | 55 . . . 64 | CTATTTGCCC (58) |
| HNF4 | 82 . . . 96 | TGATCCTTGAACTCT (59) |

TABLE 15

| TFBS in CRE0066 (TFBS shown in bold) - the same TFBS are present in CRE0066.1 and CRE0066.2: | |
|---|---|
| LVR_CRE0066_NR1I2 | CCCTGGAGAGTCCTTTAGCAGGGCAAAGTG CAACATAGGCAGACCTTAAGGGATGACTCA GTAACAGATAAGCTTTGTGTGCCTGCA (SEQ ID NO: 7) |

| TF | Position | TFBS sequence (SEQ ID NO:) |
|---|---|---|
| HNF4 | 18 . . . 32 | GCAGGGCAAAGTGCA (SEQ ID NO: 60) |
| FOS::JUN | 52 . . . 61 | GATGACTCAG (SEQ ID NO: 61) |

TABLE 16

| TFBS in CRE0068 (TFBS shown in bold): | |
|---|---|
| CRE0068 | CCTCCCCGTGTTCCTGCTCTTTGTCCCTCTGTCCTAC TTAGACTAATATTTGCCTTGGGTACTGCAAACAGGAA ATGGGGGAGGGACAGGAGTAGGGCGG (SEQ ID NO: 10) |

| TF | Position | TFBS sequence (SEQ ID NO:) |
|---|---|---|
| HNF-4 | 11 . . . 27 | TTCCTGCTCTTTGTCCC (62) |
| HNF-1/HNF-3 | 40 . . . 54 | AGACTAATATTTGCC (63) |
| SP1 | 75 . . . 89 | ATGGGGGAGGGACAG (64) |

TABLE 17

| TFBS in CRE0074 (TFBS shown in bold): | |
|---|---|
| LVR_CRE0074_SEPP1 | AGAATGAACATTGAACTTTGGACTATACC TGAGGGGTGAGGTAAACAACAGGACTATA AAT (SEQ ID NO: 11) |

| TF | Position | TFBS sequence (SEQ ID NO:) |
|---|---|---|
| HNF4 | 7 . . . 25 | AACATTGAACTTTGGAC TA (65) |
| FoxO1a | 41 . . . 48 | GTAAACAA (66) |

TABLE 18

| TFBS in CRE0001 (TFBS shown in bold): | | |
|---|---|---|
| CRE0001 | GCTGGTTTCTTATAAAACTGATGGAAGATACAAACACTATT AAAGAACTGTTTGCATGTTGCAAATGATGTCCAAAGTCCAA ACATTGTTAATAATTAATACTCCAATAAACATCATGTCAGA ATTTCTGTTTTCTTTTCCCTTTGAACCTTTGCAGGATTGCC ACATCATCAGGACCACACCTTCATCAGGAATGAATAT (SEQ ID NO: 12) | |

| TF | Position | TFBS sequence (SEQ ID NO:) |
|---|---|---|
| HNF-4 | 71 . . . 83 | TCCAAAGTCCAAA (67) |
| HNF-1 | 87 . . . 101 | TGTTAATAATTAATA (68) |
| HNF-3 | 105 . . . 116 | CAATAAACATCA (69) |
| HNF-4 | 138 . . . 152 | TTCCCTTTGAACCTT (70) |

TABLE 19

TFBS in CRE0012 (TFBS shown in bold):

TGAAATGCCTGCCATATATTAGTGCCCTGAAGTCCAAAGGT
AGAGGAACCGAGTGTTTAAAAATTACTGTGGCTGTGGAGTC
AACATGATGTAAAAAAACAAACATTTGGATAACACCAAGAA
GCCAGATATGGTTGAAATGTTGACTGGTTGACAAAAATAAT
TTGGGTTGCTTAATGGTGCACAAAGGTAATGCAAAA
CRE0012 (SEQ ID NO: 14)

| TF | Position | TFBS sequence (SEQ ID NO:) |
|---|---|---|
| HNF-4 | 30 . . . 44 | AAGTCCAAAGGTAGA (71) |
| HNF-3 | 78 . . . 89 | GAGTCAACATGA (72) |
| HNF-3 | 138 . . . 149 | AAATGTTGACTG (73) |
| C/EBP | 168 . . . 178 | GGTTGCTTAAT (74) |

TABLE 20

TFBS in CRE0047 (TFBS shown in bold):

CTGTTTGCTGCTTGCAATGTTTGCCCATTTTAGGG
CRE0047 (SEQ ID NO: 15)

| TF | Position | TFBS sequence (SEQ ID NO:) |
|---|---|---|
| HNF-3 | 14 . . . 28 | GCAATGTTTGCCCAT (75) |
| C/EBP | 18 . . . 28 | TGTTTGCCCAT (76) |

TABLE 21

TFBS in CRE005 (TFBS shown in bold):

CCGCCCCCACTGAACCCTTGACCCCTGCCCTGCAGCCCCCG
CAGCTTGCTGTTTGCCCACTCTATTTGCCCAGCCCCAG
CRE0056 (SEQ ID NO: 17)

| TF | Position | TFBS sequence (SEQ ID NO:) |
|---|---|---|
| HNF-4 | 9 . . . 31 | ACTGAACCCTTGACCCCTGCCCT (77) |
| HNF-3 | 54 . . . 75 | TGCCCACTCTATTTGCCCAGCC (78) |

TABLE 22

TFBS in CRE0062 (TFBS shown in bold):

AAGCTTTCTGAACAGCCAAACAGAGATTCCAAAGTTCAGG
CACCAAAGTTCAGACCCTAACAGTTATTTACAAGGGTCAG
CRE0062 TTAAC (SEQ ID NO: 18)

| TF | Position | TFBS sequence (SEQ ID NO:) |
|---|---|---|
| HNF-4 | 24 . . . 38 | AGATTCCAAAGTTCA (79) |
| HNF-4 | 42 . . . 54 | ACCAAAGTTCAGA (80) |
| HNF-3 | 63 . . . 73 | GTTATTTACAA (81) |

TABLE 23

TFBS in CRE0077 (TFBS shown in bold):

| | AAGCAAATATTTGTGGTTATGGATTAACTCGAACTG |
|---|---|
| CRE0077 (V1) | TTTGCCCACTCTATTTGCCCTGTACC (SEQ ID NO: 286) |

| TF | Position | TFBS sequence (SEQ ID NO:) |
|---|---|---|
| HNF3 | 2 . . . 12 | AGCAAATATTT (82) |
| HNF3 | 5 . . . 16 | AAATATTTGTGG (83) |
| HNF1 | 15 . . . 29 | GGTTATGGATTAACT (84) |
| HNF3 | 34 . . . 43 | CTGTTTGCCC (85) |
| HNF3 | 47 . . . 56 | CTATTTGCCC (86) |

TABLE 24

TFBS in CRE0078 (TFBS shown in bold):

| CRE0078 (V2) | GGCGCCCTTTGGACCTTTTGCAATCCTGGAGCAAACAGCA AACACTGTACC (SEQ ID NO: 287) |
|---|---|

| TF | TFBS sequence | Position |
|---|---|---|
| HNF4 | 3 . . . 15 | CGCCCTTTGGACC (87) |
| c/EBP | 12 . . . 29 | GACCTTTTGCAATCCTGG (88) |
| HNF3 | 30 . . . 38 | CTGTTTGCT (89) |
| HNF3 | 36 . . . 45 | GTGTTTGCTG (90) |

TABLE 25

TFBS and TSS sequences in promoter element CRE0006 (TFBS shown in bold):

| | CCGATGACCTAATGATTCTGAGCTTGGCAAAGGTCTTAT CTCCCAGCTCGCCCAGGCCCAGTGTTCCAGGAATGTGAC CTTTGCTGCAGCAGCCGCTGGAGGGGGCAGAGGGGATGG GCTGGAGGTTGAGCAAACAGAGCAGCAGAAAAGGCAGTT CCTCTTCTCCAGTGCCCTCCTTCCCTGTCTCTGCCTCTC CCTCCCTTCCTCAGGCATCAGAGCGGAGACTTCAGGGAG <u>ACCAGAGCCCAGCTTGCCAGGCACTGAGCTAGAAG</u>CCCT |
|---|---|
| CRE0006 | <u>GCCATG</u> (SEQ ID NO: 25) |

| TF | Position | TFBS sequence (SEQ ID NO:) |
|---|---|---|
| HNF4 | 25 . . . 37 | TGGCAAAGGTCTT (91) |
| RXRa | 73 . . . 83 | TGTGACCTTTG (92) |
| HNF4 | 74 . . . 86 | GTGACCTTTGCTG (93) |
| c/EBP | 123 . . . 136 | AGGTTGAGCAAACA (94) |
| HNF3 | 129 . . . 137 | AGCAAACAG (95) |
| p1@VTN | 166 . . . 196 | GGAGAGGCAGAGACAGGGAAGGAG GGCACTG (96) | p1@VTN, underlined, represents the transcription start site (TSS) in CRE0006, as determined by Cap Analysis of Gene Expression (CAGE).
NB CRE0006 can also be considered as synthetic liver-specific promoter due to its high level of liver-specific activity even absent additional CREs (SP0154).

TABLE 26

TFBS and TSS sequences in promoter element
CRE0079 (TFBS shown in bold):

CRE0079  CTCTTTTGTTTTACATGAAGGGTCTGGCAGCCA
AAGCAATCACTCAAAGTTCAAACCTTATCATTT
TTTGCTTTGTTCCTCTTGGCCTTGGTTTTGTAC
ATCAGCTTTGAAAATACCATCCCAGGGTTAATG
CTGGGGTTAATTTATAACTAAGAGTGCTCTAGT
TTTGCAATACAGGACATGCTATAAAAATGGAAA
GATGTTG<u>CTTTCTGAGAGATGC</u>
(SEQ ID NO: 24)

| TF | Position | TFBS sequence (SEQ ID NO:) |
|---|---|---|
| HNF4 | 43 . . . 55 | CTCAAAGTTCAAA (97) |
| HNF1 | 138 . . . 150 | GTTAATTTATAAC (98) |
| C/EBP | 162 . . . 175 | TAGTTTTGCAATAC (99) |
| p1@SERPINA7 | 206 . . . 219 | CTTTCTGAGAGATG (100) | p1@SERPINA7, underlined, represents the TSS in CRE0079, as
determined by CAGE.

TABLE 27

TFBS and TSS sequences in promoter element
CRE0059 (TFBS shown in bold):

CRE0059  AGTCATATGTTTGCTCACTGAAGGTT
ACTAGTTAACAGGCATCCCTTAAACA
GGATATAAAAGGACTTCAGCAGGACT
<u>GCTCGAAACATCCCACT</u>
(SEQ ID NO: 26)

| TF | Position | TFBS sequence (SEQ ID NO:) |
|---|---|---|
| HNF1 | 24 . . . 36 | GTTACTAGTTAAC (101) |
| p1@SERPINA1 | 73 . . . 93 | GCTCGAAACATCCCA (102) | p1@AFP, underlined, represents the TSS in CRE0059 as determined
by CAGE.

TABLE 28

TFBS and TSS sequences in promoter element
CRE0073 (TFBS shown in bold):

CRE0073  GGGCGACTCAGATCCCAGCCAGTGGA
CTTAGCCCCTGTTTGCTCCTCCGATA
ACTGGGGTGACCTTGGTTAATATTCA
CCAGCAGCCTCCCCCGTTGCCCCTCT
GGATCCACTGCTTAAATACGGACGAG
GACAGGGCCCTGTCTCCTCAGCTTCA
GGCACCACCACTGACCTGGGACAGTG
AATC (SEQ ID NO: 27)

| TF | Position | TFBS sequence (SEQ ID NO:) |
|---|---|---|
| HNF3 | 36 . . . 42 | TGTTTGC (103) |
| C/EBP | 38 . . . 49 | TTTGCTCCTCCG (104) |
| HNF1 | 66 . . . 83 | TGGTTAATATTCACCAGC (105) |

TABLE 28 -continued

TFBS and TSS sequences in promoter element
CRE0073 (TFBS shown in bold):

| C/EBP | 75 . . . 86 | TTCACCAGCAGC (106) |
|---|---|---|
| p1@SERPINA1 | 138 . . . 156 | CCCTGTCTCCTCAGCTTC (107) | p1@SERPINA1, underlined, represents the TSS in CRE0073, as
determined by CAGE.

TABLE 29

TFBS and TSS sequences in promoter element
CRE0073.1 (TFBS shown in bold):

CRE0073.1  TGGACTTAGCCCCTGTTTGCTCCTCCG
ATAACTGGGGTGACCTTGGTTAATATT
CACCAGCAGCCTCCCCCGTTGCCCCTC
TGGATCCACTGCTTAAATACGGACGAG
GACAGGGCCCTGTCTCCTCAGCTTCAG
GCACCACCACTGACCTGGGACAGTGAA
TC (SEQ ID NO: 28)

| TF | Position | TFBS sequence (SEQ ID NO:) |
|---|---|---|
| HNF3 | 14 . . . 20 | TGTTTGC (108) |
| C/EBP | 36 . . . 27 | TTTGCTCCTCCG (109) |
| HNF1 | 44 . . . 61 | TGGTTAATATTCACCAGC (110) |
| C/EBP | 53 . . . 64 | TTCACCAGCAGC (111) |
| p1@SERPINA1 | 116 . . . 134 | CCCTGTCTCCTCAGCTTC (112) | p1@SERPINA1, underlined, represents the TSS in CRE0073.1, as
determined by CAGE.

TABLE 30

TFBS and TSS sequences in promoter element
CRE0040 (TFBS shown in bold):

CRE0040  CCTTTGCAACAGCTTATCGGAAGCAA
ACAAGCTGAGGGGAATTGAGCAAGAA
TTTCTGGGATACCAACAGCATAGGAG
GAACAAAGGACGTAGAGGGAGGGGTTG
ACTGTCTACACAGGACAAAGCCAATG
ATTAACCAAACCTCTTGCAGATTTAA
ATAGGATGGGAACTAGGAGTGGCAGC
<u>AATCCTTTCTTTCAGCTGGAGTGCTC</u>
CTCAGGAGCCAGCCCCACCCTTAGAA
AAGATG (SEQ ID NO: 29)

| TF | Position | TFBS sequence (SEQ ID NO:) |
|---|---|---|
| C/EBP | 39 . . . 52 | GAATTGAGCAAGAA (113) |
| HNF1 | 120 . . . 140 | CAAAGCCAATGATTAACCAAA (114) |
| p1@FGA | 172 . . . 201 | GGAGTGGCAGCAATCCTTTCTTTCAGCTGG (115) | p1@FGA, underlined, represents the TSS in CRE0040, as deter-
mined by CAGE.

TABLE 31

Cis-regulatory modules (CRMs):

| CRM NAME | SEQUENCE |
| --- | --- |
| CRM_SP0107 | CCCTGGAGAGTCCTTTAGCA GGGCAAAGTGCAACATAGGC AGACCTTAAGGGATGACTCA GTAACAGATAAGCTTTGTGT GCCTGCAGGGGGATGGGAAG AGGGTGGGGCAGGAGAGGGA CATAAAAGGGCTCTGAGGCA TTGTACTGTGAATTCCTTCA GTCTCCTGTTTGGAGAAGAC AGAGCCAATGAGGCCCTCGT TCCAGGGAAACAGAATATGC TCAGCATGACGCAGCACTCC CTGAACTTTCCGGTTACATC ACCCAATAGCTGAGATCAGA (SEQ ID NO: 116) |
| CRM_SP0109 | CCCTGGAGAGTCCTTTAGCA GGGCAAAGTGCAACATAGGC AGACCTTAAGGGATGACTCA GTAACAGATAAGCTTTGTGT GCCTGCAGGGGGATGGGAAG AGGGTGGGGCAGGAGAGGGA CATAAAAGGGCTCTGAGGCA TTGTACTGTGAATTCCTTCA GTCTCCTGCTCTGCTCAGCC AGTCAGCCCTGCCTCCCTTG TTTAGGACCACACAGCACTG CTGGGTGTCTGCCTTTCCTT G (SEQ ID NO: 117) |
| CRM_SP0111 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TTTGGAGAAGACAGAGCCAA TGAGGCCCTCGTTCCAGGGA AACAGAATATGCTCAGCATG ACGCAGCACTCCCTGAACTT TCCGGTTACATCACCCAATA GCTGAGATCAGA (SEQ ID NO: 118) |
| CRM_SP0112 | CACTGAACCCTTGACCCCTG CCCTGCAGCCCCCGCAGCTT GCTGTTTGCCCACTCTATTT GCCCAGCCCCAGAGGTTAAT TTTTAAAAAGCAGTCAAAAG TCCAAGTGGCCCTTGGCAGC ATTTACTCTCTGTTTGCT CTGGTTAATAATCTCAGGAG CACAAACATTCCTTTGGAGA AGACAGAGCCAATGAGGCCC TCGTTCCAGGGAAACAGAAT ATGCTCAGCATGACGCAGCA CTCCCTGAACTTTCCGGTTA CATCACCCAATAGCTGAGAT CAGA (SEQ ID NO: 119) |
| CRM_SP0113 | CACTGAACCCTTGACCCCTG CCCTGCAGCCCCCGCAGCTT GCTGTTTGCCCACTCTATTT GCCCAGCCCCAGCCCTGGAG AGTCCTTTAGCAGGGCAAAG TGCAACATAGGCAGACCTTA AGGGATGACTCAGTAACAGA TAAGCTTTGTGTGCCTGCAG GGGGATGGGAAGAGGGTGGG GCAGGAGAGGGACATAAAAG GGCTCTGAGGCATTGTACTG TGAATTCCTTCAGTCTCCTG (SEQ ID NO: 120) |

TABLE 31-continued

Cis-regulatory modules (CRMs):

| CRM NAME | SEQUENCE |
| --- | --- |
| CRM_SP0115 | CCCTGGAGAGTCCTTTAGCA GGGCAAAGTGCAACATAGGC AGACCTTAAGGGATGACTCA GTAACAGATAAGCTTTGTGT GCCTGCAGGGGGATGGGAAG AGGGTGGGGCAGGAGAGGGA CATAAAAGGGCTCTGAGGCA TTGTACTGTGAATTCCTTCA GTCTCCTGCTCTGCTCAGCC AGTCAGCCCTGCCTCCCTTG TTTAGGACCACACAGCACTG CTGGGTGTCTGCCTTTCCTT G (SEQ ID NO: 121) |
| CRM_SP0116 | CCCTGGAGAGTCCTTTAGCA GGGCAAAGTGCAACATAGGC AGACCTTAAGGGATGACTCA GTAACAGATAAGCTTTGTGT GCCTGCAGGGGGATGGGAAG AGGGTGGGGCAGGAGAGGGA CATAAAAGGGCTCTGAGGCA TTGTACTGTGAATTCCTTCA GTCTCCTG (SEQ ID NO: 122) |
| CRM_SP0121 | CCCTGGAGAGTCCTTTAGCA GGGCAAAGTGCAACATAGGC AGACCTTAAGGGATGACTCA GTAACAGATAAGCTTTGTGT GCCTGCACCCTGGAGAGTCC TTTAGCAGGGCAAAGTGCAA CATAGGCAGACCTTAAGGGA TGACTCAGTAACAGATAAGC TTTGTGTGCCTGCA (SEQ ID NO: 123) |
| CRM_SP0124 | CACTGAACCCTTGACCCCTG CCCTGCAGCCCCCGCAGCTT GCTGTTTGCCCACTCTATTT GCCCAGCCCCAGCCCTGGAG AGTCCTTTAGCAGGGCAAAG TGCAACATAGGCAGACCTTA AGGGATGACTCAGTAACAGA TAAGCTTTGTGTGCCTGCA (SEQ ID NO: 124) |
| CRM_SP0127 (CRM_LVR_127) | AGAATGAACATTGAACTTTG GACTATACCTGAGGGGTGAG GTAAACAACAGGACTATAAA TGGCCCGGGAGGCGCCCTTT GGACCTTTTGCAATCCTGGC GCACTGAACCCTTGACCCCT GCCCTGCAGCCCCCGCAGCT TGCTGTTTGCCCACTCTATT TGCCCAGCCCCAGGGACAGA GCTGATCCTTGAACTCTTAA GTTCCAC (SEQ ID NO: 125) |
| CRM_SP0127A1 (CRM_LVR_127_ A1) | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCAGAATGAACATTGA ACTTTGGACTATACCTGAGG GGTGAGGTAAACAACAGGAC TATAAATGGCCCGGGAGGCG CCCTTTGGACCTTTTGCAAT |

TABLE 31-continued

Cis-regulatory modules (CRMs):

| CRM NAME | SEQUENCE |
|---|---|
| | CCTGGCGCACTGAACCCTTG ACCCCTGCCCTGCAGCC CCCGCAGCTTGCTGTTTGCC CACTCTATTTGCCCAGCCCC AGGGACAGAGCTGATCCTTG AACTCTTAAGTTCCAC (SEQ ID NO: 126) |
| CRM_SP0127V1 (CRM_LVR_127_ V1) | AAGCAAATATTTGTGGTTAT GGATTAACTCGAACTGTTTG CCCACTCTATTTGCCCTGTA CCAGAATGAACATTGAACTT TGGACTATACCTGAGGGGTG AGGTAAACAACAGGACTATA AATGGCCCGGGAGGCGCCCT TTGGACCTTTTGCAATCCTG GCGCACTGAACCCTTGACCC CTGCCCTGCAGCCCCCGCAG CTTGCTGTTTGCCCACTCTA TTTGCCCAGCCCCAGGGACA GAGCTGATCCTTGAACTCTT AAGTTCCAC (SEQ ID NO: 127) |
| CRM_SP0127V2 (CRM_LVR_127_ V2) | GGCGCCCTTTGGACCTTTTG CAATCCTGGAGCAAACAGCA AACACTGTACCAGAATGAAC ATTGAACTTTGGACTATACC TGAGGGGTGAGGTAAACAAC AGGACTATAAATGGCCCGGG AGGCGCCCTTTGGACCTTTT GCAATCCTGGCGCACTGAAC CCTTGACCCCTGCCCTGCAG CCCCCGCAGCTTGCTGTTTG CCCACTCTATTTGCCCAGCC CCAGGGACAGAGCTGATCCT TGAACTCTTAAGTTCCAC (SEQ ID NO: 128) |
| CRM_SP0128 | AGAATGAACATTGAACTTTG GACTATACCTGAGGGGTGAG GTAAACAACAGGACTATAAA TAGAATGAACATTGAACTTT GGACTATACCTGAGGGGTGA GGTAAACAACAGGACTATAA ATCACTGAACCCTTGACCCC TGCCCTGCAGCCCCCGCAGC TTGCTGTTTGCCCACTCTAT TTGCCCAGCCCCAG (SEQ ID NO: 129) |
| CRM_SP0131 (CRM_LVR_131) | GGCCCGGGAGGCGCCCTTTG GACCTTTTGCAATCCTGGCG CACTGAACCCTTGACCCCTG CCCTGCAGCCCCCGCAGCTT GCTGTTTGCCCACTCTATTT GCCCAGCCCCAGCCTGGAG AGTCCTTTAGCAGGGCAAAG TGCAACATAGGCAGACCTTA AGGGATGACTCAGTAACAGA TAAGCTTTGTGTGCCTGCA (SEQ ID NO: 130) |
| CRM_SP0132 (CRM_LVR_132) | AGAATGAACATTGAACTTTG GACTATACCTGAGGGGTGAG GTAAACAACAGGACTATAAA TGGCCCGGGAGGCGCCCTTT GGACCTTTTGCAATCCTGGC GCACTGAACCCTTGACCCCT GCCCTGCAGCCCCCGCAGCT TGCTGTTTGCCCACTCTATT TGCCCAGCCCCAGCCCTGGA GAGTCCTTTAGCAGGGCAAA |

TABLE 31-continued

Cis-regulatory modules (CRMs):

| CRM NAME | SEQUENCE |
|---|---|
| | GTGCAACATAGGCAGACCTT AAGGGATGACTCAGTAACAG ATAAGCTTTGTGTGCCTGCA (SEQ ID NO: 131) |
| CRM_SP0133 (CRM_LVR_133) | AGAATGAACATTGAACTTTG GACTATACCTGAGGGGTGAG GTAAACAACAGGACTATAAA TGGCCCGGGAGGCGCCCTTT GGACCTTTTGCAATCCTGGC G (SEQ ID NO: 132) |
| CRM_SP0155 | GCTGGTTTCTTATAAAACTG ATGGAAGATACAAACACTAT TAAAGAACTGTTTGCATGTT GCAAATGATGTCCAAAGTCC AAACATTGTTAATAATTAAT ACTCCAATAAACATCATGTC AGAATTTCTGTTTTCTTTTC CCTTTGAACCTTTGCAGGAT TGCCACATCATCAGGACCAC ACCTTCATCAGGAATGAATA T (SEQ ID NO: 133) |
| CRM_SP0158 | ATTGGCATCTTCTATTGCTT TTCCTGGTGACTTCATTTTT CACTCTTGGCTAAAAATGGG TCTCTGATGATTTATTCTAT CCTGGGTGTTGACAAGCTGA AGAAGTTGTGTGGGGCCTGC TGCCAGTAACCCTGGGTGAC GAAGCGTGACTCACCACTCC GAGGTCAGTGGGGGGATGGA AGGCAGGGGAGTCAGCTGAC AAGATCTGCTGCTTTGTCAC CAGGCCTTCTGC (SEQ ID NO: 134) |
| CRM_SP0163 | TGAAATGCCTGCCATATATT AGTGCCCTGAAGTCCAAAGG TAGAGGAACCGAGTGTTTAA AAATTACTGTGGCTGTGGAG TCAACATGATGTAAAAAAAC AAACATTTGGATAACACCAA GAAGCCAGATATGGTTGAAA TGTTGACTGGTTGACAAAAA TAATTTGGGTTGCTTAATGG TGCACAAAGGTAATGCAAAA (SEQ ID NO: 135) |
| CRM_SP0236 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTG (SEQ ID NO: 136) |
| CRM_SP0239 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAGGTTAATTTTTAAAAA GCAGTCAAAAGTCCAAGTGG CCCTTGGCAGCATTTACTCT CTCTGTTTGCTCTGGTTAAT AATCTCAGGAGCACAAACAT TCCGGCCCGGGAGGCGCCCT TTGGACCTTTTGCAATCCTG GCGCACTGAACCCTTGACCC CTGCCCTGCAGCCCCCGCAG CTTGCTGTTTGCCCACTCTA TTTGCCCAGCCCCAGCCCTG |

TABLE 31-continued

Cis-regulatory modules (CRMs):

| CRM NAME | SEQUENCE |
|---|---|
| | GAGAGTCCTTTAGCAGGGCA<br>AAGTGCAACATAGGCAGACC<br>TTAAGGGATGACTCAGTAAC<br>AGATAAGCTTTGTGTGCCTG<br>CA<br>(SEQ ID NO: 137) |
| CRM_SP0240 | CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTG<br>(SEQ ID NO: 138) |
| CRM_SP0241 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCCCTGGAG<br>AGTCCTTTAGCAGGGC<br>AAAGTGCAACATAGGCAGAC<br>CTTAAGGGATGACTCAGTAA<br>CAGATAAGCTTTGTGTGCCT<br>GCA<br>(SEQ ID NO: 139) |
| CRM_SP0242 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAG<br>(SEQ ID NO: 140) |
| CRM_SP0243 | TGAAATGCCTGCCATATATT<br>AGTGCCCTGAAGTCCAAAGG<br>TAGAGGAACCGAGTGTTTAA<br>AAATTACTGTGGCTGTGGAG<br>TCAACATGATGTAAAAAAAC<br>AAACATTTGGATAACACCAA<br>GAAGCCAGATATGGTTGAAA<br>TGTTGACTGGTTGACAAAAA<br>TAATTTGGGTTGCTTAATGG<br>TGCACAAAGGTAATGCAAAA<br>AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCCCTGGAG<br>AGTCCTTTAGCAGGGCAAAG<br>TGCAACATAGGCAGACCTTA<br>AGGGATGACTCAGTAACAGA<br>TAAGCTTTGTGTGCCTGCA<br>(SEQ ID NO: 141) |
| CRM_SP0244 | CTTTGGACCTTTTGCAATCC<br>TGGCGCACTGAACCCTTGAC<br>CCCTGCCCTGCAGCCCCCGC |

TABLE 31-continued

Cis-regulatory modules (CRMs):

| CRM NAME | SEQUENCE |
|---|---|
| | AGCTTGCTGTTTGCCCACTC<br>TATTTGCCCAGCCCCAGTGA<br>AATGCCTGCCATATATTAGT<br>GCCCTGAAGTCCAAAGGTAG<br>AGGAACCGAGTGTTTAAAAA<br>TTACTGTGGCTGTGGAGTCA<br>ACATGATGTAAAAAAACAAA<br>CATTTGGATAACACCAAGAA<br>GCCAGATATGGTTGAAATGT<br>TGACTGGTTGACAAAAATAA<br>TTTGGGTTGCTTAATGGTGC<br>ACAAAGGTAATGCAAAA<br>(SEQ ID NO: 142) |
| CRM_SP0246 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAG<br>(SEQ ID NO: 143) |
| CRM_SP0247 | GCTGGTTTCTTATAAAACTG<br>ATGGAAGATACAAACACTAT<br>TAAAGAACTGTTTGCATGTT<br>GCAAATGATGTCCAAAGTCC<br>AAACATTGTTAATAATTAAT<br>ACTCCAATAAACATCATGTC<br>AGAATTTCTGTTTTCTTTTC<br>CCTTTGAACCTTTGCAGGAT<br>TGCCACATCATCAGGACCAC<br>ACCTTCATCAGGAATGAATA<br>TCAGGCTTTCACTTTCTCGC<br>CAACTTACAAGGCCTTTCTG<br>TGTAAACAATACCTGAACCT<br>TTACCCCGTTGCCCGGCAAC<br>GGCCAGGTCTGTGCCAAGTG<br>TTTG<br>(SEQ ID NO: 144) |
| CRM_SP0248 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCAGGCTTT<br>CACTTTCTCGCCAACTTACA<br>AGGCCTTTCTGTGTAAACAA<br>TACCTGAACCTTTACCCCGT<br>TGCCCGGCAACGGCCAGGTC<br>TGTGCCAAGTGTTTG<br>(SEQ ID NO: 145) |
| CRM_SP0249 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCAGGCTTT<br>CACTTTCTCGCCAACTTACA<br>AGGCCTTTCTGTGTAAACAA |

TABLE 31-continued

Cis-regulatory modules (CRMs):

| CRM NAME | SEQUENCE |
|---|---|
| | TACCTGAACCTTTACCCCGT<br>TGCCCGGCAACGGCCAGGTC<br>TGTGCCAAGTGTTTG<br>(SEQ ID NO: 146) |
| CRM_SP0250 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGGCTGGTTT<br>CTTATAAAACTGATGGAAGA<br>TACAAACACTATTAAAGAAC<br>TGTTTGCATGTTGCAAATGA<br>TGTCCAAAGTCCAAACATTG<br>TTAATAATTAATACTCCAAT<br>AAACATCATGTCAGAATTTC<br>TGTTTTCTTTTCCCTTTGAA<br>CCTTTGCAGGATTGCCACAT<br>CATCAGGACCACACCTTCAT<br>CAGGAATGAATAT<br>(SEQ ID NO: 147) |
| CRM_SP0251 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGAAGCAAAT<br>ATTTGTGGTTATGGATTAAC<br>TCGAACTGTTTGCCCACTCT<br>ATTTGCCC<br>(SEQ ID NO: 148) |
| CRM_SP0252 | AAGCAAATATTTGTGGTTAT<br>GGATTAACTCGAACTGTTTG<br>CCCACTCTATTTGCCCCAGG<br>CTTTCACTTTCTCGCCAACT<br>TACAAGGCCTTTCTGTGTAA<br>ACAATACCTGAACCTTTACC<br>CCGTTGCCCGGCAACGGCCA<br>GGTCTGTGCCAAGTGTTTG<br>(SEQ ID NO: 149) |
| CRM_SP0253 | AAGCAAATATTTGTGGTTAT<br>GGATTAACTCGAACTGTTTG<br>CCCACTCTATTTGCCCCAGG<br>CTTTCACTTTCTCGCCAACT<br>TACAAGGCCTTTCTGTGTAA<br>ACAATACCTGAACCTTTACC<br>CCGTTGCCCGGCAACGGCCA<br>GGTCTGTGCCAAGTGTTTG<br>(SEQ ID NO: 150) |
| CRM_SP0254 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CAGGCTTTCACTTTCTCGCC<br>AACTTACAAGGCCTTTCTGT |

TABLE 31-continued

Cis-regulatory modules (CRMs):

| CRM NAME | SEQUENCE |
|---|---|
| | GTAAACAATACCTGAACCTT<br>TACCCCGTTGCCCGGCAACG<br>GCCAGGTCTGTGCCAAGTGT<br>TTG<br>(SEQ ID NO: 151) |
| CRM_SP0255 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTG<br>(SEQ ID NO: 152) |
| CRM_SP0256 | ATTGGCATCTTCTATTGCTT<br>TTCCTGGTGACTTCATTTTT<br>CACTCTTGGCTAAAAATGGG<br>TCTCTGATGATTTATTCTAT<br>CCTGGGTGTTGACAAGCTGA<br>AGAAGTTGTGTGGGGCCTGC<br>TGCCAGTAACCCTGGGTGAC<br>GAAGCGTGACTCACCACTCC<br>GAGGTCAGTGGGGGGATGGA<br>AGGCAGGGGAGTCAGCTGAC<br>AAGATCTGCTGCTTTGTCAC<br>CAGGCCTTCTGCCAGGCTTT<br>CACTTTCTCGCCAACTTACA<br>AGGCCTTTCTGTGTAAACAA<br>TACCTGAACCTTTACCCCGT<br>TGCCCGGCAACGGCCAGGTC<br>TGTGCCAAGTGTTTG<br>(SEQ ID NO: 153) |
| CRM_SP0257 | CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTGGCTGGTTTCTTATAAAA<br>CTGATGGAAGATACAAACAC<br>TATTAAAGAACTGTTTGCAT<br>GTTGCAAATGATGTCCAAAG<br>TCCAAACATTGTTAATAATT<br>AATACTCCAATAAACATCAT<br>GTCAGAATTTCTGTTTTCTT<br>TTCCCTTTGAACCTTTGCAG<br>GATTGCCACATCATCAGGAC<br>CACACCTTCATCAGGAATGA<br>ATAT<br>(SEQ ID NO: 154) |
| CRM_SP0258 | CTGTTTGCTGCTTGCAATGT<br>TTGCCCATTTTAGGGAGGTT<br>AATTTTTAAAAAGCAGTCAA<br>AAGTCCAAGTGGCCCTTGGC<br>AGCATTTACTCTCTCTGTTT<br>GCTCTGGTTAATAATCTCAG<br>GAGCACAAACATTCCGGCCC<br>GGGAGGCGCCCTTTGGACCT<br>TTTGCAATCCTGGCGCACTG<br>AACCCTTGACCCCTGCCCTG<br>CAGCCCCCGCAGCTTGCTGT<br>TTGCCCACTCTATTTGCCCA<br>GCCCCAGCCTGGAGAGTCC<br>TTTAGCAGGGCAAAGTGCAA<br>CATAGGCAGACCTTAAGGGA<br>TGACTCAGTAACAGATAAGC<br>TTTGTGTGCCTGCA<br>(SEQ ID NO: 155) |

TABLE 31-continued

| Cis-regulatory modules (CRMs): | |
|---|---|
| CRM NAME | SEQUENCE |
| CRM_SP0259 | CTGTTTGCTGCTTGCAATGT<br>TTGCCCATTTTAGGGGCTGG<br>TTTCTTATAAAACTGATGGA<br>AGATACAAACACTATTAAAG<br>AACTGTTTGCATGTTGCAAA<br>TGATGTCCAAAGTCCAAACA<br>TTGTTAATAATTAATACTCC<br>AATAAACATCATGTCAGAAT<br>TTCTGTTTTCTTTTCCCTTT<br>GAACCTTTGCAGGATTGCCA<br>CATCATCAGGACCACACCTT<br>CATCAGGAATGAATAT<br>(SEQ ID NO: 156) |
| CRM_SP0264 | CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTG<br>(SEQ ID NO: 157) |
| CRM_SP0265<br>(CRM_LVR_131_<br>A1) | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>TGTACCGGCCCGGGAGGCGC<br>CCTTTGGACCTTTTGCAATC<br>CTGGCGCACTGAACCCTTGA<br>CCCCTGCCCTGCAGCCCCCG<br>CAGCTTGCTGTTTGCCCACT<br>CTATTTGCCCAGCCCCAGCC<br>CTGGAGAGTCCTTTAGCAGG<br>GCAAAGTGCAACATAGGCAG<br>ACCTTAAGGGATGACTCAGT<br>AACAGATAAGCTTTGTGTGC<br>CTGCA<br>(SEQ ID NO: 158) |
| CRM_SP0266<br>(CRM_LVR_131_<br>V1) | AAGCAAATATTTGTGGTTAT<br>GGATTAACTCGAACTGTTTG<br>CCCACTCTATTTGCCCTGTA<br>CCGGCCCGGGAGGCGCCCTT<br>TGGACCTTTTGCAATCCTGG<br>CGCACTGAACCCTTGACCCC<br>TGCCCTGCAGCCCCCGCAGC<br>TTGCTGTTTGCCCACTCTAT<br>TTGCCCAGCCCCAGCCCTGG<br>AGAGTCCTTTAGCAGGGCAA<br>AGTGCAACATAGGCAGACCT<br>TAAGGGATGACTCAGTAACA<br>GATAAGCTTTGTGTGCCTGC<br>A<br>(SEQ ID NO: 159) |
| CRM_SP0267<br>(CRM_LVR_131_<br>V2) | GGCGCCCTTTGGACCTTTTG<br>CAATCCTGGAGCAAACAGCA<br>AACACTGTACCGGCCCGGGA<br>GGCGCCCTTTGGACCTTTTG<br>CAATCCTGGCGCACTGAACC<br>CTTGACCCCTGCCCTGCAGC<br>CCCCGCAGCTTGCTGTTTGC<br>CCACTCTATTTGCCCAGCCC<br>CAGCCCTGGAGAGTCCTTTA<br>GCAGGGCAAAGTGCAACATA<br>GGCAGACCTTAAGGGATGAC<br>TCAGTAACAGATAAGCTTTG<br>TGTGCCTGCA<br>(SEQ ID NO: 160) |
| CRM_SP0268<br>(CRM_LVR_132_<br>A1) | AGGTTAATTTTTAAAAAGCA<br>GTCAAAAGTCCAAGTGGCCC<br>TTGGCAGCATTTACTCTCTC<br>TGTTTGCTCTGGTTAATAAT |

TABLE 31-continued

| Cis-regulatory modules (CRMs): | |
|---|---|
| CRM NAME | SEQUENCE |
| | CTCAGGAGCACAAACATTCC<br>TGTACCAGAATGAACATTGA<br>ACTTTGGACTATACCTGAGG<br>GGTGAGGTAAACAACAGGAC<br>TATAAATGGCCCGGGAGGCG<br>CCCTTTGGACCTTTTGCAAT<br>CCTGGCGCACTGAACCCTTG<br>ACCCCTGCCCTGCAGCCCCC<br>GCAGCTTGCTGTTTGCCCAC<br>TCTATTTGCCCAGCCCCAGC<br>CCTGGAGAGTCCTTTAGCAG<br>GGCAAAGTGCAACATAGGCA<br>GACCTTAAGGGATGACTCAG<br>TAACAGATAAGCTTTGTGTG<br>CCTGCA<br>(SEQ ID NO: 161) |
| CRM_SP0269<br>(CRM_LVR_132_<br>V1) | AAGCAAATATTTGTGGTTAT<br>GGATTAACTCGAACTGTTTG<br>CCCACTCTATTTGCCCTGTA<br>CCAGAATGAACATTGAACTT<br>TGGACTATACCTGAGGGGTG<br>AGGTAAACAACAGGACTATA<br>AATGGCCCGGGAGGCGCCCT<br>TTGGACCTTTTGCAATCCTG<br>GCGCACTGAACCCTTGACCC<br>CTGCCCTGCAGCCCCCGCAG<br>CTTGCTGTTTGCCCACTCTA<br>TTTGCCCAGCCCCAGCCCTG<br>GAGAGTCCTTTAGCAGGGCA<br>AAGTGCAACATAGGCAGACC<br>TTAAGGGATGACTCAGTAAC<br>AGATAAGCTTTGTGTGCCTG<br>CA<br>(SEQ ID NO: 162) |
| CRM_SP0270<br>(CRM_LVR_132_<br>V2) | GGCGCCCTTTGGACCTTTTG<br>CAATCCTGGAGCAAACAGCA<br>AACACTGTACCAGAATGAAC<br>ATTGAACTTTGGACTATACC<br>TGAGGGGTGAGGTAAACAAC<br>AGGACTATAAATGGCCCGGG<br>AGGCGCCCTTTGGACCTTTT<br>GCAATCCTGGCGCACTGAAC<br>CCTTGACCCCTGCCCTGCAG<br>CCCCCGCAGCTTGCTGTTTG<br>CCCACTCTATTTGCCCAGCC<br>CCAGCCCTGGAGAGTCCTTT<br>AGCAGGGCAAAGTGCAACAT<br>AGGCAGACCTTAAGGGATGA<br>CTCAGTAACAGATAAGCTTT<br>GTGTGCCTGCA<br>(SEQ ID NO: 163) |
| CRM_SP0271<br>(CRM_LVR_133_<br>A1) | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>TGTACCAGAATGAACATTGA<br>ACTTTGGACTATACCTGAGG<br>GGTGAGGTAAACAACAGGAC<br>TATAAATGGCCCGGGAGGCG<br>CCCTTTGGACCTTTTGCAAT<br>CCTGGCG<br>(SEQ ID NO: 164) |
| CRM_SP0272<br>(CRM_LVR_133_<br>V1) | AAGCAAATATTTGTGGTTAT<br>GGATTAACTCGAACTGTTTG<br>CCCACTCTATTTGCCCTGTA<br>CCAGAATGAACATTGAACTT<br>TGGACTATACCTGAGGGGTG |

TABLE 31-continued

Cis-regulatory modules (CRMs):

| CRM NAME | SEQUENCE |
|---|---|
| | AGGTAAACAACAGGACTATA AATGGCCCGGGAGGCGCCCT TTGGACCTTTTGCAATCCTG GCG (SEQ ID NO: 165) |
| CRM_SP0273 (CRM_LVR_133_ V2) | GGCGCCCTTTGGACCTTTTG CAATCCTGGAGCAAACAGCA AACACTGTACCAGAATGAAC ATTGAACTTTGGACTATACC TGAGGGGTGAGGTAAACAAC AGGACTATAAATGGCCCGGG AGGCGCCCTTTGGACCTTTT GCAATCCTGGCG (SEQ ID NO: 166) |
| CRM_SP0368 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC (SEQ ID NO: 167) |
| CRM_SP0373 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCGGCCCGGGAGGCGC CCTTTGGACCTTTTGCAATC CTGGCG (SEQ ID NO: 168) |
| CRM_SP0378 | TGCTCTCTGACAAAGATACG GTGGGTCCCACTGATGAACT GTGCTGCCACAGTAAATGTA GCCACTATGCCTATCTCCAT TCTGAAGATGTGCCCTGTTC AAACATGTCCTAATACTCTG TCTCTGCAAGGGTCATCAGT AGTTTTCCATCTTACTCAAC ATCCTCCAGTG (SEQ ID NO: 169) |
| CRM_SP0379 | CCTCCCCGTGTTCCTGCTCT TTGTCCCTCTGTCCTACTTA GACTAATATTTGCCTTGGGT ACTGCAAACAGGAAATGGGG GAGGGACAGGAGTAGGGCGG CCCTGTTCAAACATGTCCTA ATACTCTGTCTCTGCAAGGG TCATCAGTAGTTTTCCATCT TACTCAACATCCTCCAGTG (SEQ ID NO: 170) |
| CRM_SP0380 | CCGCCCCCACTGAACCCTTG ACCCCTGCCCTGCAGCCCCC GCAGCTTGCTGTTTGCCCAC TCTATTTGCCCAGCCCCAGC CCTGTTCAAACATGTCCTAA TACTCTGTCTCTGCAAGGGT CATCAGTAGTTTTCCATCTT ACTCAACATCCTCCCAGTG (SEQ ID NO: 171) |
| CRM_SP0381 | AAGCTTTCTGAACAGCCAAA CAGAGATTCCAAAGTTCAGG CACCAAAGTTCAGACCCTAA CAGTTATTTACAAGGGTCAG TTAACCCCTGTTCAAACATG TCCTAATACTCTGTCTCTGC AAGGGTCATCAGTAGTTTTC CATCTTACTCAACATCCTCC CAGTG (SEQ ID NO: 172) |

TABLE 31-continued

Cis-regulatory modules (CRMs):

| CRM NAME | SEQUENCE |
|---|---|
| CRM_SP0384 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC GGCCCGGGAGGCGCCCTTTG GACCTTTTGCAATCCTGGCG (SEQ ID NO: 173) |
| CRM_SP0388 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC (SEQ ID NO: 174) |
| CRM_SP0396 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCGGCCCGGGAGGCGC CCTTTGGACCTTTTGCAATC CTGGCGCCCTGGAGAGTCCT TTAGCAGGGCAAAGTGCA ACATAGGCAGACCTTAAGGG ATGACTCAGTAACAGATAAG CTTTGTGTGCCTGCA (SEQ ID NO: 175) |
| CRM_SP0397 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCCACTGAACCCTTGA CCCCTGCCCTGCAGCCCCCG CAGCTTGCTGTTTGCCCACT CTATTTGCCCAGCCCCAGCC CTGGAGAGTCCTTTAGCAGG GCAAAGTGCAACATAGGCAG ACCTTAAGGGATGACTCAGT AACAGATAAGCTTTGTGTGC CTGCA (SEQ ID NO: 176) |
| CRM_SP0398 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAGGTTAATTTTTAAAAA GCAGTCAAAAGTCCAAGTGG CCCTTGGCAGCATTTACTCT CTCTGTTTGCTCTGGTTAAT AATCTCAGGAGCACAAACAT TCCTGTACCAGAATGAACAT TGAACTTTGGACTATACCTG AGGGGTGAGGTAAACAACAG GACTATAAATGGCCCGGGAG GCGCCCTTTGGACCTTTTGC AATCCTGGCGCACTGAACCC TTGACCCCTGCCCTGCAGCC CCCGCAGCTTGCTGTTTGCC CACTCTATTTGCCCAGCCCC AGCCCTGGAGAGTCCTTTAG CAGGGCAAAGTGCAACATAG GCAGACCTTAAGGGATGACT CAGTAACAGATAAGCTTTGT GTGCCTGCA (SEQ ID NO: 177) |

TABLE 31-continued

Cis-regulatory modules (CRMs):

| CRM NAME | SEQUENCE |
|---|---|
| CRM_SP0399 | AGAATGAACATTGAACTTTG GACTATACCTGAGGGGTGAG GTAAACAACAGGACTATAAA T (SEQ ID NO: 178) |
| CRM_SP0403 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT TATGGATTAACTCGAACTGT TTGCCCACTCTATTTGCCCT GTACCGGCCCGGGAGGCGCC CTTTGGACCTTTTGCAATCC TGGCGCACTGAACCCTTGAC CCCTGCCCTGCAGCCCCCGC AGCTTGCTGTTTGCCCACTC TATTTGCCCAGCCCCAGCCC TGGAGAGTCCTTTAGCAGGG CAAAGTGCAACATAGGCAGA CCTTAAGGGATGACTCAGTA ACAGATAAGCTTTGTGTGCC TGCA (SEQ ID NO: 179) |
| CRM_SP0404 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT TATGGATTAACTCGAACTGT TTGCCCACTCTATTTGCCCT GTACCAGAATGAACATTGAA CTTTGGACTATACCTGAGGG GTGAGGTAAACAACAGGACT ATAAATGGCCCGGGAGGCGC CCTTTGGACCTTTTGCAATC CTGGCGCACTGAACCCTTGA CCCCTGCCCTGCAGCCCCCG CAGCTTGCTGTTTGCCCACT CTATTTGCCCAGCCCCAGCC CTGGAGAGTCCTTTAGCAGG GCAAAGTGCAACATAGGCAG ACCTTAAGGGATGACTCAGT AACAGATAAGCTTTGTGTGC CTGCA (SEQ ID NO: 180) |
| CRM_SP0405 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT TATGGATTAACTCGAACTGT TTGCCCACTCTATTTGCCCT GTACCAGAATGAACATTGAA CTTTGGACTATACCTGAGGG GTGAGGTAAACAACAGGACT ATAAATGGCCCGGGAGGCGC CCTTTGGACCTTTTGCAATC CTGGCGCACTGAACCCTTGA CCCCTGCCCTGCAGCCCCCG CAGCTTGCTGTTTGCCCACT CTATTTGCCCAGCCCCAG (SEQ ID NO: 181) |
| CRM_SP0406 | AGGTTAATTTTTAAAAAGCA GTCAAAGTCCAAGTGGCCC TTGGCAGCATTTACTCTCTC |

TABLE 31-continued

Cis-regulatory modules (CRMs):

| CRM NAME | SEQUENCE |
|---|---|
| | TGTTTGCTCTGGTTAATAAT CTCAGGAGCACAAACATTCC GGCCCGGGAGGCGCCCTTTG GACCTTTTGCAATCCTGGCG (SEQ ID NO: 182) |
| CRM_SP0407 | AGGTTAATTTTTAAAAAGCA GTCAAAGTCCAAGTGGCCC TTGGCAGCATTTACTCTCTC TGTTTGCTCTGGTTAATAAT CTCAGGAGCACAAACATTCC CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTG (SEQ ID NO: 183) |
| CRM_SP0409 | AGGTTAATTTTTAAAAAGCA GTCAAAGTCCAAGTGGCCC TTGGCAGCATTTACTCTCTC TGTTTGCTCTGGTTAATAAT CTCAGGAGCACAAACATTCC CCCTGTTCAAACATGTCCTA ATACTCTGTCTCTGCAAGGG TCATCAGTAGTTTTCCATCT TACTCAACATCCTCCCAGTG (SEQ ID NO: 184) |
| CRM_SP0411 | CCCTGTTCAAACATGTCCTA ATACTCTGTCTCTGCAAGGG TCATCAGTAGTTTTCCATCT TACTCAACATCCTCCCAGTG (SEQ ID NO: 185) |
| CRM_SP0412 | AGGTTAATTTTTAAAAAGCA GTCAAAGTCCAAGTGGCCC TTGGCAGCATTTACTCTCTC TGTTTGCTCTGGTTAATAAT CTCAGGAGCACAAACATTCC CCCTGTTCAAACATGTCCTA ATACTCTGTCTCTGCAAGGG TCATCAGTAGTTTTCCATCT TACTCAACATCCTCCCAGTG (SEQ ID NO: 186) |
| CRM_SP0413 | AGGTTAATTTTTAAAAAGCA GTCAAAGTCCAAGTGGCCC TTGGCAGCATTTACTCTCTC TGTTTGCTCTGGTTAATAAT CTCAGGAGCACAAACATTCC TGTACCGGCCCGGGAGGCGC CCTTTGGACCTTTTGCAATC CTGGCG (SEQ ID NO: 187) |

TABLE 32

Synthetic Promoters:

| NAME | SEQUENCE | LENGTH |
|---|---|---|
| SP0107 | CCCTGGAGAGTCCTTTAGCA GGGCAAAGTGCAACATAGGC AGACCTTAAGGGATGACTCA GTAACAGATAAGCTTTGTGT GCCTGCAGGGGGATGGGAAG AGGGTGGGGCAGGAGAGGGA CATAAAAGGGCTCTGAGGCA TTGTACTGTGAATTCCTTCA GTCTCCTGTTTGGAGAAGAC AGAGCCAATGAGGCCCTCGT | 356 |

TABLE 32-continued

Synthetic Promoters:

| NAME | SEQUENCE | LENGTH |
|------|----------|--------|
| | TCCAGGGAAACAGAATATGC | |
| | TCAGCATGACGCAGCACTCC | |
| | CTGAACTTTCCGGTTACATC | |
| | ACCCAATAGCTGAGATCAGA | |
| | GGGCATATAAAACAGGGGCA | |
| | AGGCACAGACTCATAGCAGA | |
| | GCAATCACCACCAAGCCTGG | |
| | AATAACTGCAGCCACC | |
| | (SEQ ID NO: 188) | |
| SP0109 | CCTGGAGAGTCCTTTAGCAG | 344 |
| | GGCAAAGTGCAACATAGGCA | |
| | GACCTTAAGGGATGACTCAG | |
| | TAACAGATAAGCTTTGTGTG | |
| | CCTGCAGGGGGATGGGAAGA | |
| | GGGTGGGGCAGGAGAGGGAC | |
| | ATAAAAGGGCTCTGAGGCAT | |
| | TGTACTGTGAATTCCTTCAG | |
| | TCTCCTGCTCTGCTCAGCCA | |
| | GTCAGCCCTGCCTCCCTTGT | |
| | TTAGGACCACACAGCACTGC | |
| | TGGGTGTCTGCCTTTCCTTG | |
| | GGTAATTTTTTTTTCTGGTT | |
| | AATATTTAGCAAGAATTCTG | |
| | CAGAGTGATCAAAAAAATCA | |
| | AATACTCAGTATTTCAGAAA | |
| | TAGATTAAATAGGTTACTTT | |
| | TTTACTGATAATGTGAAAGA | |
| | ATGATATAAAAACTTGATTT | |
| | TCCTCAACAACATTACTTTC | |
| | TTTTGTAAATGTGGTTTCTA | |
| | CAAAGATGAAACTACTAAAA | |
| | CTTACAGGCCACC | |
| | (SEQ ID NO: 189) | |
| SP0111 | AGGTTAATTTTTAAAAAGCA | 288 |
| | GTCAAAAGTCCAAGTGGCCC | |
| | TTGGCAGCATTTACTCTCTC | |
| | TGTTTGCTCTGGTTAATAAT | |
| | CTCAGGAGCACAAACATTCC | |
| | TTTGGAGAAGACAGAGCCAA | |
| | TGAGGCCCTCGTTCCAGGGA | |
| | AACAGAATATGCTCAGCATG | |
| | ACGCAGCACTCCCTGAACTT | |
| | TCCGGTTACATCACCCAATA | |
| | GCTGAGATCAGAGGGCATAT | |
| | AAAACAGGGGCAAGGCACAG | |
| | ACTCATAGCAGAGCAATCAC | |
| | CACCAAGCCTGGAATAACTG | |
| | CAGCCACC | |
| | (SEQ ID NO: 190) | |
| SP0112 | CACTGAACCCTTGACCCCTG | 360 |
| | CCCTGCAGCCCCCGCAGCTT | |
| | GCTGTTTGCCCACTCTATTT | |
| | GCCCAGCCCCAGAGGTTAAT | |
| | TTTTAAAAAGCAGTCAAAAG | |
| | TCCAAGTGGCCCTTGGCAGC | |
| | ATTTACTCTCTCTGTTTGCT | |
| | CTGGTTAATAATCTCAGGAG | |
| | CACAAACATTCCTTTGGAGA | |
| | AGACAGAGCCAATGAGGCCC | |
| | TCGTTCCAGGGAAACAGAAT | |
| | ATGCTCAGCATGACGCAGCA | |
| | CTCCCTGAACTTTCCGGTTA | |
| | CATCACCCAATAGCTGAGAT | |
| | CAGAGGGCATATAAAACAGG | |
| | GGCAAGGCACAGACTCATAG | |
| | CAGAGCAATCACCACCAAGC | |
| | CTGGAATAACTGCAGCCACC | |
| | (SEQ ID NO: 191) | |
| SP0113 | CACTGAACCCTTGACCCCTG | 316 |
| | CCCTGCAGCCCCCGCAGCTT | |
| | GCTGTTTGCCCACTCTATTT | |
| | GCCCAGCCCCAGCCCTGGAG | |

TABLE 32-continued

Synthetic Promoters:

| NAME | SEQUENCE | LENGTH |
|------|----------|--------|
| | AGTCCTTTAGCAGGGCAAAG | |
| | TGCAACATAGGCAGACCTTA | |
| | AGGGATGACTCAGTAACAGA | |
| | TAAGCTTTGTGTGCCTGCAG | |
| | GGGGATGGGAAGAGGGTGGG | |
| | GCAGGAGAGGGACATAAAAG | |
| | GGCTCTGAGGCATTGTACTG | |
| | TGAATTCCTTCAGTCTCCTG | |
| | GGGCATATAAAACAGGGGCA | |
| | AGGCACAGACTCATAGCAGA | |
| | GCAATCACCACCAAGCCTGG | |
| | AATAACTGCAGCCACC | |
| | (SEQ ID NO: 192) | |
| SP0115 | CCCTGGAGAGTCCTTTAGCA | 411 |
| | GGGCAAAGTGCAACATAGGC | |
| | AGACCTTAAGGGATGACTCA | |
| | GTAACAGATAAGCTTTGTGT | |
| | GCCTGCAGGGGGATGGGAAG | |
| | AGGGTGGGGCAGGAGAGGGA | |
| | CATAAAAGGGCTCTGAGGCA | |
| | TTGTACTGTGAATTCCTTCA | |
| | GTCTCCTGCTCTGCTCAGCC | |
| | AGTCAGCCCTGCCTCCCTTG | |
| | TTTAGGACCACACAGCACTG | |
| | CTGGGTGTCTGCCTTTCCTT | |
| | GTGGACTTAGCCCCTGTTTG | |
| | CTCCTCCGATAACTGGGGTG | |
| | ACCTTGGTTAATATTCACCA | |
| | GCAGCCTCCCCCGTTGCCCC | |
| | TCTGGATCCACTGCTTAAAT | |
| | ACGGACGAGGACAGGGCCCT | |
| | GTCTCCTCAGCTTCAGGCAC | |
| | CACCACTGACCTGGGACAGT | |
| | GAATCGCCACC | |
| | (SEQ ID NO: 193) | |
| SP0116 | CCCTGGAGAGTCCTTTAGCA | 338 |
| | GGGCAAAGTGCAACATAGGC | |
| | AGACCTTAAGGGATGACTCA | |
| | GTAACAGATAAGCTTTGTGT | |
| | GCCTGCAGGGGGATGGGAAG | |
| | AGGGTGGGGCAGGAGAGGGA | |
| | CATAAAAGGGCTCTGAGGCA | |
| | TTGTACTGTGAATTCCTTCA | |
| | GTCTCCTGTGGACTTAGCCC | |
| | CTGTTTGCTCCTCCGATAAC | |
| | TG | |
| | GGGTGACCTTGGTTAATATT | |
| | CACCAGCAGCCTCCCCCGTT | |
| | GCCCCTCTGGATCCACTGCT | |
| | TAAATACGGACGAGGACAGG | |
| | GCCCTGTCTCCTCAGCTTCA | |
| | GGCACCACCACTGACCTGGG | |
| | ACAGTGAATCGCCACC | |
| | (SEQ ID NO: 194) | |
| SP0121 | CCCTGGAGAGTCCTTTAGCA | 250 |
| | GGGCAAAGTGCAACATAGGC | |
| | AGACCTTAAGGGATGACTCA | |
| | GTAACAGATAAGCTTTGTGT | |
| | GCCTGCACCCTGGAGAGTCC | |
| | TTTAGCAGGGCAAAGTGCAA | |
| | CATAGGCAGACCTTAAGGGA | |
| | TGACTCAGTAACAGATAAGC | |
| | TTTGTGTGCCTGCAGGGCAT | |
| | ATAAAACAGGGGCAAGGCAC | |
| | AGACTCATAGCAGAGCAATC | |
| | ACCACCAAGCCTGGAATAAC | |
| | TGCAGCCACC | |
| | (SEQ ID NO: 195) | |
| SP0124 | CACTGAACCCTTGACCCCTG | 385 |
| | CCCTGCAGCCCCCGCAGCTT | |
| | GCTGTTTGCCCACTCTATTT | |
| | GCCCAGCCCCAGCCCTGGAG | |

TABLE 32-continued

Synthetic Promoters:

| NAME | SEQUENCE | LENGTH |
|---|---|---|
| | AGTCCTTTAGCAGGGCAAAG TGCAACATAGGCAGACCTTA AGGGATGACTCAGTAACAGA TAAGCTTTGTGTGCCTGCAC TCTTTTGTTTTACATGAAGG GTCTGGCAGCCAAAGCAATC ACTCAAAGTTCAAACCTTAT CATTTTTTGCTTTGTTCCTC TTGGCCTTGGTTTTGTACAT CAGCTTTGAAAATACCATCC CAGGGTTAATGCTGGGGTTA ATTTATAACTAAGAGTGCTC TAGTTTTGCAATACAGGACA TGCTATAAAAATGGAAAGAT GTTGCTTTCTGAGAGATGCG CCACC (SEQ ID NO: 196) | |
| SP0127 (LVR_SP127) | AGAATGAACATTGAACTTTG GACTATACCTGAGGGGTGAG GTAAACAACAGGACTATAAA TGGCCCGGGAGGCGCCCTTT GGACCTTTTGCAATCCTGGC GCACTGAACCCTTGACCCCT GCCCTGCAGCCCCCGCAGCT TGCTGTTTGCCCACTCTATT TGCCCAGCCCCAGGGACAGA GCTGATCCTTGAACTCTTAA GTTCCACGGGCATATAAAAC AGGGGCAAGGCACAGACTCA TAGCAGAGCAATCACCACCA AGCCTGGAATAACTGCAGCC ACC (SEQ ID NO: 197) | 283 |
| SP0127A1 (LVR_SP127_A1) | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCAGAATGAACATTGA ACTTTGGACTATACCTGAGG GGTGAGGTAAACAACAGGAC TATAAATGGCCCGGGAGGCG CCCTTTGGACCTTTTGCAAT CCTGGCGCACTGAACCCTTG ACCCCTGCCCTGCAGCCCCC GCAGCTTGCTGTTTGCCCAC TCTATTTGCCCAGCCCCAGG GACAGAGCTGATCCTTGAAC TCTTAAGTTCCACGGGCATA TAAAACAGGGGCAAGGCACA GACTCATAGCAGAGCAATCA CCACCAAGCCTGGAATAACT GCAGCCACC (SEQ ID NO: 198) | 387 |
| SP0127V1 (LVR_SP127_V1) | AAGCAAATATTTGTGGTTAT GGATTAACTCGAACTGTTTG CCCACTCTATTTGCCCTGTA CCAGAATGAACATTGAACTT TGGACTATACCTGAGGGGTG AGGTAAACAACAGGACTATA AATGGCCCGGGAGGCGCCCT TTGGACCTTTTGCAATCCTG GCGCACTGAACCCTTGACCC CTGCCCTGCAGCCCCCGCAG CTTGCTGTTTGCCCACTCTA TTTGCCCAGCCCCAGGGACA GAGCTGATCCTTGAACTCTT AAGTTCCACGGGCATATAAA ACAGGGGCAAGGCACAGACT CATAGCAGAGCAATCACCAC CAAGCCTGGAATAACTGCAG CCACC (SEQ ID NO: 199) | 345 |

TABLE 32-continued

Synthetic Promoters:

| NAME | SEQUENCE | LENGTH |
|---|---|---|
| SP0127V2 (LVR_SP127_V2) | GGCGCCCTTTGGACCTTTTG CAATCCTGGAGCAAACAGCA AACACTGTACCAGAATGAAC ATTGAACTTTGGACTATACC TGAGGGGTGAGGTAAACAAC AGGACTATAAATGGCCCGGG AGGCGCCCTTTGGACCTTTT GCAATCCTGGCGCACTGAAC CCTTGACCCCTGCCCTGCAG CCCCCGCAGCTTGCTGTTTG CCCACTCTATTTGCCCAGCC CCAGGGACAGAGCTGATCCT TGAACTCTTAAGTTCCACGG GCATATAAAACAGGGGCAAG GCACAGACTCATAGCAGAGC AATCACCACCAAGCCTGGAA TAACTGCAGCCACC (SEQ ID NO: 200) | 334 |
| SP0128 | AGAATGAACATTGAACTTTG GACTATACCTGAGGGGTGAG GTAAACAACAGGACTATAAA TAGAATGAACATTGAACTTT GGACTATACCTGAGGGGTGA GGTAAACAACAGGACTATAA ATCACTGAACCCTTGACCCC TGCCCTGCAGCCCCCGCAGC TTGCTGTTTGCCCACTCTAT TTGCCCAGCCCCAGGGGCAT ATAAAACAGGGGCAAGGCAC AGACTCATAGCAGAGCAATC ACCACCAAGCCTGGAATAAC TGCAGCCACC (SEQ ID NO: 201) | 270 |
| SP0131 (LVR_SP131) | GGCCCGGGAGGCGCCCTTTG GACCTTTTGCAATCCTGGCG CACTGAACCCTTGACCCCTG CCCTGCAGCCCCCGCAGCTT GCTGTTTGCCCACTCTATTT GCCCAGCCCCAGCCCTGGAG AGTCCTTTAGCAGGGCAAAG TGCAACATAGGCAGACCTTA AGGGATGACTCAGTAACAGA TAAGCTTTGTGTGCCTGCAG GGCATATAAAACAGGGGCAA GGCACAGACTCATAGCAGAG CAATCACCACCAAGCCTGGA ATAACTGCAGCCACC (SEQ ID NO: 202) | 275 |
| SP0132 (LVR_SP132) | AGAATGAACATTGAACTTTG GACTATACCTGAGGGGTGAG GTAAACAACAGGACTATAAA TGGCCCGGGAGGCGCCCTTT GGACCTTTTGCAATCCTGGC GCACTGAACCCTTGACCCCT GCCCTGCAGCCCCCGCAGCT TGCTGTTTGCCCACTCTATT TGCCCAGCCCCAGCCCTGGA GAGTCCTTTAGCAGGGCAAA GTGCAACATAGGCAGACCTT AAGGGATGACTCAGTAACAG ATAAGCTTTGTGTGCCTGCA GGGCATATAAAACAGGGGCA AGGCACAGACTCATAGCAGA GCAATCACCACCAAGCCTGG AATAACTGCAGCCACC (SEQ ID NO: 203) | 336 |
| SP0133 (LVR_SP133) | AGAATGAACATTGAACTTTG GACTATACCTGAGGGGTGAG GTAAACAACAGGACTATAAA TGGCCCGGGAGGCGCCCTTT GGACCTTTTGCAATCCTGGC | 327 |

TABLE 32-continued

Synthetic Promoters:

| NAME | SEQUENCE | LENGTH |
|------|----------|--------|
| | GCTCTTTTGTTTTACATGAA GGGTCTGGCAGCCAAAGCAA TCACTCAAAGTTCAAACCTT ATCATTTTTTGCTTTGTTCC TCTTGGCCTTGGTTTTGTAC ATCAGCTTTGAAAATACCAT CCCAGGGTTAATGCTGGGGT TAATTTATAACTAAGAGTGC TCTAGTTTTGCAATACAGGA CATGCTATAAAAATGGAAAG ATGTTGCTTTCTGAGAGATG CGCCACC (SEQ ID NO: 204) | |
| SP0155 | GCTGGTTTCTTATAAAACTG ATGGAAGATACAAACACTAT TAAAGAACTGTTTGCATGTT GCAAATGATGTCCAAAGTCC AAACATTGTTAATAATTAAT ACTCCAATAAACATCATGTC AGAATTTCTGTTTTCTTTTC CCTTTGAACCTTTGCAGGAT TGCCACATCATCAGGACCAC ACCTTCATCAGGAATGAATA TCCGATGACCTAATGATTCT GAGCTTGGCAAAGGTCTTAT CTCCCAGCTCGCCCAGGCCC AGTGTTCCAGGAATGTGACC TTTGCTGCAGCAGCCGCTGG AGGGGGCAGAGGGGATGGGC TGGAGGTTGAGCAAACAGAG CAGCAGAAAAGGCAGTTCCT CTTCTCCAGTGCCCTCCTTC CCTGTCTCTGCCTCTCCCTC CCTTCCTCAGGCATCAGAGC GGAGACTTCAGGGAGACCAG AGCCCAGCTTGCCAGGCACT GAGCTAGAAGCCCTGCCATG (SEQ ID NO: 205) | 480 |
| SP0158 | ATTGGCATCTTCTATTGCTT TTCCTGGTGACTTCATTTTT CACTCTTGGCTAAAAATGGG TCTCTGATGATTTATTCTAT CCTGGGTGTTGACAAGCTGA AGAAGTTGTGTGGGGCCTGC TGCCAGTAACCCTGGGTGAC GAAGCGTGACTCACCACTCC GAGGTCAGTGGGGGGATGGA AGGCAGGGGAGTCAGCTGAC AAGATCTGCTGCTTTGTCAC CAGGCCTTCTGCCCGATGAC CTAATGATTCTGAGCTTGGC AAAGGTCTTATCTCCCAGCT CGCCCAGGCCCAGTGTTCCA GGAATGTGACCTTTGCTGCA GCAGCCGCTGGAGGGGGCAG AGGGGATGGGCTGGAGGTTG AGCAAACAGAGCAGCAGAAA AGGCAGTTCCTCTTCTCCAG TGCCCTCCTTCCCTGTCTCT GCCTCTCCCTCCCTTCCTCA GGCATCAGAGCGGAGACTTC AGGGAGACCAGAGCCCAGCT TGCCAGGCACTGAGCTAGAA GCCCTGCCATG (SEQ ID NO: 206) | 511 |
| SP0163 | TGAAATGCCTGCCATATATT AGTGCCCTGAAGTCCAAAGG TAGAGGAACCGAGTGTTTAA AAATTACTGTGGCTGTGGAG TCAACATGATGTAAAAAAAC AAACATTTGGATAACACCAA GAAGCCAGATATGGTTGAAA TGTTGACTGGTTGACAAAAA | 479 |

TABLE 32-continued

Synthetic Promoters:

| NAME | SEQUENCE | LENGTH |
|------|----------|--------|
| | TAATTTGGGTTGCTTAATGG TGCACAAAGGTAATGCAAAA CCGATGACCTAATGATTCTG AGCTTGGCAAAGGTCTTATC TCCCAGCTCGCCCAGGCCCA GTGTTCCAGGAATGTGACCT TTGCTGCAGCAGCCGCTGGA GGGGGCAGAGGGGATGGGCT GGAGGTTGAGCAAACAGAGC AGCAGAAAAGGCAGTTCCTC TTCTCCAGTGCCCTCCTTCC CTGTCTCTGCCTCTCCCTCC CTTCCTCAGGCATCAGAGCC GAGACTTCAGGGAGACCAGA GCCCAGCTTGCCAGGCACTG AGCTAGAAGCCCTGCCATG (SEQ ID NO: 207) | |
| SP0236 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGCCTTTGCAACAGCTTAT CGGAAGCAAACAAGCTGAGG GGAATTGAGCAAGAATTTCT GGGATACCAACAGCATAGGA GGAACAAAGGACGTAGAGGG AGGGTTGACTGTCTACACAG GACAAAGCCAATGATTAACC AAACCTCTTGCAGATTTAAA TAGGATGGGAACTAGGAGTG GCAGCAATCCTTTCTTTCAG CTGGAGTGCTCCTCAGGAGC CAGCCCCACCCTTAGAAAAG (SEQ ID NO: 208) | 340 |
| SP0239 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAGGTTAATTTTTAAAAA GCAGTCAAAAGTCCAAGTGG CCCTTGGCAGCATTTACTCT CTCTGTTTGCTCTGGTTAAT AATCTCAGGAGCACAAACAT TCCGGCCCGGGAGGCGCCCT TTGGACCTTTTGCAATCCTG GCGCACTGAACCCTTGACCC CTGCCCTGCAGCCCCCGCAG CTTGCTGTTTGCCCACTCTA TTTGCCCAGCCCCAGCCCTG GAGAGTCCTTTAGCAGGGCA AAGTGCAACATAGGCAGACC TTAAGGGATGACTCAGTAAC AGATAAGCTTTGTGTGCCTG CAGGGCATA TAAAACAGGGGCAAGGCACA GACTCATAGCAGAGCAATCA CCACCAAGCCTGGAATAACT GCAGCCACC (SEQ ID NO: 209) | 478 |
| SP0240 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGCCGATGACCTAATGATT CTGAGCTTGGCAAAGGTCTT ATCTCCCAGCTCGCCCAGGC CCAGTGTTCCAGGAATGTGA CCTTTGCTGCAGCAGCCGCT GGAGGGGGCAGAGGGGATGG GCTGGAGGTTGAGCAAACAG | 379 |

TABLE 32-continued

Synthetic Promoters:

| NAME | SEQUENCE | LENGTH |
|------|----------|--------|
|  | AGCAGCAGAAAAGGCAGTTC<br>CTCTTCTCCAGTGCCCTCCT<br>TCCCTGTCTCTGCCTCTCCC<br>TCCCTTCCTCAGGCATCAGA<br>GCGGAGACTTCAGGGAGACC<br>AGAGCCCAGCTTGCCAGGCA<br>CTGAGCTAGAAGCCCTGCC<br>(SEQ ID NO: 210) |  |
| SP0241 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCCCTGGAG<br>AGTCCTTTAGCAGGGCAAAG<br>TGCAACATAGGCAGACCTTA<br>AGGGATGACTCAGTAACAGA<br>TAAGCTTTGTGTGCCTGCAC<br>CGATGACCTAATGATTCTGA<br>GCTTGGCAAAGGTCTTATCT<br>CCCAGCTCGCCCAGGCCCAG<br>TGTTCCAGGAATGTGACCTT<br>TGCTGCAGCAGCCGCTGGAG<br>GGGGCAGAGGGGATGGGCTG<br>GAGGTTGAGCAAACAGAGCA<br>GCAGAAAAGGCAGTTCCTCT<br>TCTCCAGTGCCCTCCTTCCC<br>TGTCTCTGCCTCTCCCTCCC<br>TTCCTCAGGCATCAGAGCGG<br>AGACTTCAGGGAGACCAGAG<br>CCCAGCTTGCCAGGCACTGA<br>GCTAGAAGCCCTGCC<br>(SEQ ID NO: 211) | 575 |
| SP0242 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCCGATGAC<br>CTAATGATTCTGAGCTTGGC<br>AAAGGTCTTATCTCCCAGCT<br>CGCCCAGGCCCAGTGTTCCA<br>GGAATGTGACCTTTGCTGCA<br>GCAGCCGCTGGAGGGGGCAG<br>AGGGGATGGGCTGGAGGTTG<br>AGCAAACAGAGCAGCAGAAA<br>AGGCAGTTCCTCTTCTCCAG<br>TGCCCTCCTTCCCTGTCTCT<br>GCCTCTCCCTCCCTTCCTCA<br>GGCATCAGAGCGGAGACTTC<br>AGGGAGACCAGAGCCCAGCT<br>TGCCAGGCACTGAGCTAGAA<br>GCCCTGCC<br>(SEQ ID NO: 212) | 488 |
| SP0243 | TGAAATGCCTGCCATATATT<br>AGTGCCCTGAAGTCCAAAGG<br>TAGAGGAACCGAGTGTTTAA<br>AAATTACTGTGGCTGTGGAG<br>TCAACATGATGTAAAAAAAC<br>AAACATTTGGATAACACCAA<br>GAAGCCAGATATGGTTGAAA<br>TGTTGACTGGTTGACAAAAA<br>TAATTTGGGTTGCTTAATGG | 575 |

TABLE 32-continued

Synthetic Promoters:

| NAME | SEQUENCE | LENGTH |
|------|----------|--------|
|  | TGCACAAAGGTAATGCAAAA<br>AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCCCTGGAG<br>AGTCCTTTAGCAGGGCAAAG<br>TGCAACATAGGCAGACCTTA<br>AGGGATGACTCAGTAACAGA<br>TAAGCTTTGTGTGCCTGCAG<br>GGCATATAAAACAGGGGCAA<br>GGCACAGACTCATAGCAGAG<br>CAATCACCACCAAGCCTGGA<br>ATAACTGCAGCCACC<br>(SEQ ID NO: 213) |  |
| SP0244 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGTGAAATGC<br>CTGCCATATATTAGTGCCCT<br>GAAGTCCAAAGGTAGAGGAA<br>CCGAGTGTTTAAAAATTACT<br>GTGGCTGTGGAGTCAACATG<br>ATGTAAAAAAACAAACATTT<br>GGATAACACCAAGAAGCCAG<br>ATATGGTTGAAATGTTGACT<br>GGTTGACAAAAATAATTTGG<br>GTTGCTTAATGGTGCACAAA<br>GGTAATGCAAAACCGATGAC<br>CTAATGATTCTGAGCTTGGC<br>AAAGGTCTTATCTCCCAGCT<br>CGCCCAGGCCCAGTGTTCCA<br>GGAATGTGACCTTTGCTGCA<br>GCAGCCGCTGGAGGGGGCAG<br>AGGGGATGGGCTGGAGGTTG<br>AGCAAACAGAGCAGCAGAAA<br>AGGCAGTTCCTCTTCTCCAG<br>TGCCCTCCTTCCCTGTCTCT<br>GCCTCTCCCTCCCTTCCTCA<br>GGCATCAGAGCGGAGACTTC<br>AGGGAGACCAGAGCCCAGCT<br>TGCCAGGCACTGAGCTAGAA<br>GCCCTGCC<br>(SEQ ID NO: 214) | 688 |
| SP0246 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCC<br>CGGGAGGCGCCCTTTGGACC<br>TTTTGCAATCCTGGCGCACT<br>GAACCCTTGACCCCTGCCCT<br>GCAGCCCCCGCAGCTTGCTG<br>TTTGCCCACTCTATTTGCCC<br>AGCCCCAGGGGCATATAAAA<br>CAGGGGCAAGGCACAGACTC<br>ATAGCAGAGCAATCACCACC<br>AAGCCTGGAATAACTGCAGC<br>CACC<br>(SEQ ID NO: 215) | 288 |

TABLE 32-continued

Synthetic Promoters:

| NAME | SEQUENCE | LENGTH |
|------|----------|--------|
| SP0247 | GCTGGTTTCTTATAAAACTG<br>ATGGAAGATACAAACACTAT<br>TAAAGAACTGTTTGCATGTT<br>GCAAATGATGTCCAAAGTCC<br>AAACATTGTTAATAATTAAT<br>ACTCCAATAAACATCATGTC<br>AGAATTTCTGTTTTCTTTTC<br>CCTTTGAACCTTTGCAGGAT<br>TGCCACATCATCAGGACCAC<br>ACCTTCATCAGGAATGAATA<br>TCAGGCTTTCACTTTCTCGC<br>CAACTTACAAGGCCTTTCTG<br>TGTAAACAATACCTGAACCT<br>TTACCCCGTTGCCCGGCAAC<br>GGCCAGGTCTGTGCCAAGTG<br>TTTGCCGATGACCTAATGAT<br>TCTGAGCTTGGCAAAGGTCT<br>TATCTCCCAGCTCGCCCAGG<br>CCCAGTGTTCCAGGAATGTG<br>ACCTTTGCTGCAGCAGCCGC<br>TGGAGGGGGCAGAGGGGATG<br>GGCTGGAGGTTGAGCAAACA<br>GAGCAGCAGAAAAGGCAGTT<br>CCTCTTCTCCAGTGCCCTCC<br>TTCCCTGTCTCTGCCTCTCC<br>CTCCCTTCCTCAGGCATCAG<br>AGCGGAGACTTCAGGGAGAC<br>CAGAGCCCAGCTTGCCAGGC<br>ACTGAGCTAGAAGCCCTGCC<br>(SEQ ID NO: 216) | 580 |
| SP0248 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCAGGCTTT<br>CACTTTCTCGCCAACTTACA<br>AGGCCTTTCTGTGTAAACAA<br>TACCTGAACCTTTACCCCGT<br>TGCCCGGCAACGGCCAGGTC<br>TGTGCCAAGTGTTTGGGGCA<br>TATAAAACAGGGGCAAGGCA<br>CAGACTCATAGCAGAGCAAT<br>CACCACCAAGCCTGGAATAA<br>CTGCAGCCACC<br>(SEQ ID NO: 217) | 391 |
| SP0249 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGCAGGCTTT<br>CACTTTCTCGCCAACTTACA<br>AGGCCTTTCTGTGTAAACAA<br>TACCTGAACCTTTACCCCGT<br>TGCCCGGCAACGGCCAGGTC<br>TGTGCCAAGTGTTTGGGGCG<br>ACTCAGATCCCAGCCAGTGG<br>ACTTAGCCCTGTTTGCTCC<br>TCCGATAACTGGGGTGACCT<br>TGGTTAATATTCACCAGCAG<br>CCTCCCCCGTTGCCCCTCTG<br>GATCCACTGCTTAAATACGG | 507 |

TABLE 32-continued

Synthetic Promoters:

| NAME | SEQUENCE | LENGTH |
|------|----------|--------|
| | ACGAGGACAGGGCCCTGTCT<br>CCTCAGCTTCAGGCACCACC<br>ACTGACCTGGGACAGTGAAT<br>CGCCACC<br>(SEQ ID NO: 218) | |
| SP0250 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGGCTGGTTT<br>CTTATAAAACTGATGGAAGA<br>TACAAACACTATTAAAGAAC<br>TGTTTGCATGTTGCAAATGA<br>TGTCCAAAGTCCAAACATTG<br>TTAATAATTAATACTCCAAT<br>AAACATCATGTCAGAATTTC<br>TGTTTTCTTTTCCCTTTGAA<br>CCTTTGCAGGATTGCCACAT<br>CATCAGGACCACACCTTCAT<br>CAGGAATGAATATCCGATGA<br>CCTAATGATTCTGAGCTTGG<br>CAAAGGTCTTATCTCCCAGC<br>TCGCCCAGGCCCAGTGTTCC<br>AGGAATGTGACCTTTGCTGC<br>AGCAGCCGCTGGAGGGGGCA<br>GAGGGGATGGGCTGGAGGTT<br>GAGCAAACAGAGCAGCAGAA<br>AAGGCAGTTCCTCTTCTCCA<br>GTGCCCTCCTTCCCTGTCTC<br>TGCCTCTCCCTCCCTTCCTC<br>AGGCATCAGAGCGGAGACTT<br>CAGGGAGACCAGAGCCCAGC<br>TTGCCAGGCACTGAGCTAGA<br>AGCCCTGCC<br>(SEQ ID NO: 219) | 689 |
| SP0251 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CACTGAACCCTTGACCCCTG<br>CCCTGCAGCCCCCGCAGCTT<br>GCTGTTTGCCCACTCTATTT<br>GCCCAGCCCCAGAAGCAAAT<br>ATTTGTGGTTATGGATTAAC<br>TCGAACTGTTTGCCCACTCT<br>ATTTGCCCGGGCATATAAAA<br>CAGGGGCAAGGCACAGACTC<br>ATAGCAGAGCAATCACCACC<br>AAGCCTGGAATAACTGCAGC<br>CACC<br>(SEQ ID NO: 220) | 344 |
| SP0252 | AAGCAAATATTTGTGGTTAT<br>GGATTAACTCGAACTGTTTG<br>CCCACTCTATTTGCCCCAGG<br>CTTTCACTTTCTCGCCAACT<br>TACAAGGCCTTTCTGTGTAA<br>ACAATACCTGAACCTTTACC<br>CCGTTGCCCGGCAACGGCCA<br>GGTCTGTGCCAAGTGTTTGC<br>CTTTGCAACAGCTTATCGGA<br>AGCAAACAAGCTGAGGGGAA<br>TTGAG<br>CAAGAATTTCTGGGATACCA<br>ACAGCATAGGAGGAACAAAG | 401 |

TABLE 32-continued

Synthetic Promoters:

| NAME | SEQUENCE | LENGTH |
|---|---|---|
| | GACGTAGAGGGAGGGTTGAC<br>TGTCTACACAGGACAAAGCC<br>AATGATTAACCAAACCTCTT<br>GCAGATTTAAATAGGATGGG<br>AACTAGGAGTGGCAGCAATC<br>CTTTCTTTCAGCTGGAGTGC<br>TCCTCAGGAGCCAGCCCCAC<br>CCTTAGAAAAGCCACC<br>(SEQ ID NO: 221) | |
| SP0253 | AAGCAAATATTTGTGGTTAT<br>GGATTAACTCGAACTGTTTG<br>CCCACTCTATTTGCCCCAGG<br>CTTTCACTTTCTCGCCAACT<br>TACAAGGCCTTTCTGTGTAA<br>ACAATACCTGAACCTTTACC<br>CCGTTGCCCGGCAACGGCCA<br>GGTCTGTGCCAAGTGTTTGC<br>CGATGACCTAATGATTCTGA<br>GCTTGGCAAAGGTCTTATCT<br>CCCAGCTCGCCCAGGCCCAG<br>TGTTCCAGGAATGTGACCTT<br>TGCTGCAGCAGCCGCTGGAG<br>GGGGCAGAGGGGATGGGCTG<br>GAGGTTGAGCAAACAGAGCA<br>GCAGAAAAGGCAGTTCCTCT<br>TCTCCAGTGCCCTCCTTCCC<br>TGTCTCTGCCTCTCCCTCCC<br>TTCCTCAGGCATCAGAGCGG<br>AGACTTCAGGGAGACCAGAG<br>CCCAGCTTGCCAGGCACTGA<br>GCTAGAAGCCCTGCC<br>(SEQ ID NO: 222) | 435 |
| SP0254 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTGCCTTTGCAACAGCTTAT<br>CGGAAGCAAACAAGCTGAGG<br>GGAATTGAGCAAGAATTTCT<br>GGGATACCAACAGCATAGGA<br>GGAACAAAGGACGTAGAGGG<br>AGGGTTGACTGTCTACACAG<br>GACAAAGCCAATGATTAACC<br>AAACCTCTTGCAGATTTAAA<br>TAGGATGGGAACTAGGAGTG<br>GCAGCAATCCTTTCTTTCAG<br>CTGGAGTGCTCCTCAGGAGC<br>CAGCCCCACCCTTAGAAAAG<br>CCACC<br>(SEQ ID NO: 223) | 485 |
| SP0255 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>GGCCCGGGAGGCGCCCTTTG<br>GACCTTTTGCAATCCTGGCG<br>CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTGCCGATGACCTAATGATT<br>CTGAGCTTGGCAAAGGTCTT<br>ATCTCCCAGCTCGCCCAGGC | 519 |

TABLE 32-continued

Synthetic Promoters:

| NAME | SEQUENCE | LENGTH |
|---|---|---|
| | CCAGTGTTCCAGGAATGTGA<br>CCTTTGCTGCAGCAGCCGCT<br>GGAGGGGGCAGAGGGGATGG<br>GCTGGAGGTTGAGCAAACAG<br>AGCAGCAGAAAAGGCAGTTC<br>CTCTTCTCCAGTGCCCTCCT<br>TCCCTGTCTCTGCCTCTCCC<br>TCCCTTCCTCAGGCATCAGA<br>GCGGAGACTTCAGGGAGACC<br>AGAGCCCAGCTTGCCAGGCA<br>CTGAGCTAGAAGCCCTGCC<br>(SEQ ID NO: 224) | |
| SP0256 | ATTGGCATCTTCTATTGCTT<br>TTCCTGGTGACTTCATTTTT<br>CACTCTTGGCTAAAAATGGG<br>TCTCTGATGATTTATTCTAT<br>CCTGGGTGTTGACAAGCTGA<br>AGAAGTTGTGTGGGGCCTGC<br>TGCCAGTAACCCTGGGTGAC<br>GAAGCGTGACTCACCACTCC<br>GAGGTCAGTGGGGGGATGGA<br>AGGCAGGGGAGTCAGCTGAC<br>AAGATCTGCTGCTTTGTCAC<br>CAGGCCTTCTGCCAGGCTTT<br>CACTTTCTCGCCAACTTACA<br>AGGCCTTTCTGTGTAAACAA<br>TACCTGAACCTTTACCCCGT<br>TGCCCGGCAACGGCCAGGTC<br>TGTGCCAAGTGTTTGCCGAT<br>GACCTAATGATTCTGAGCTT<br>GGCAAAGGTCTTATCTCCCA<br>GCTCGCCCAGGCCCAGTGTT<br>CCAGGAATGTGACCTTTGCT<br>GCAGCAGCCGCTGGAGGGGG<br>CAGAGGGGATGGGCTGGAGG<br>TTGAGCAAACAGAGCAGCAG<br>AAAAGGCAGTTCCTCTTCTC<br>CAGTGCCCTCCTTCCCTGTC<br>TCTGCCTCTCCCTCCCTTCC<br>TCAGGCATCAGAGCGGAGAC<br>TTCAGGGAGACCAGAGCCCA<br>GCTTGCCAGGCACTGAGCTA<br>GAAGCCCTGCC<br>(SEQ ID NO: 225) | 611 |
| SP0257 | CAGGCTTTCACTTTCTCGCC<br>AACTTACAAGGCCTTTCTGT<br>GTAAACAATACCTGAACCTT<br>TACCCCGTTGCCCGGCAACG<br>GCCAGGTCTGTGCCAAGTGT<br>TTGGCTGGTTTCTTATAAAA<br>CTGATGGAAGATACAAACAC<br>TATTAAAGAACTGTTTGCAT<br>GTTGCAAATGATGTCCAAAG<br>TCCAAACATTGTTAATAATT<br>AATACTCCAATAAACATCAT<br>GTCAGAATTTCTGTTTTCTT<br>TTCCCTTTGAACCTTTGCAG<br>GATTGCCACATCATCAGGAC<br>CACACCTTCATCAGGAATGA<br>ATATCCGATGACCTAATGAT<br>TCTGAGCTTGGCAAAGGTCT<br>TATCTCCCAGCTCGCCCAGG<br>CCCAGTGTTCCAGGAATGTG<br>ACCTTTGCTGCAGCAGCCGC<br>TGGAGGGGGCAGAGGGGATG<br>GGCTGGAGGTTGAGCAAACA<br>GAGCAGCAGAAAAGGCAGTT<br>CCTCTTCTCCAGTGCCCTCC<br>TTCCCTGTCTCTGCCTCTCC<br>CTCCCTTCCTCAGGCATCAG<br>AGCGGAGACTTCAGGGAGAC<br>CAGAGCCCAGCTTGCCAGGC<br>ACTGAGCTAGAAGCCCTGCC<br>(SEQ ID NO: 226) | 580 |

TABLE 32-continued

| Synthetic Promoters: | | |
| --- | --- | --- |
| NAME | SEQUENCE | LENGTH |
| SP0258 | CTGTTTGCTGCTTGCAATGT TTGCCCATTTTAGGGAGGTT AATTTTTAAAAAGCAGTCAA AAGTCCAAGTGGCCCTTGGC AGCATTTACTCTCTCTGTTT GCTCTGGTTAATAATCTCAG GAGCACAAACATTCCGGCCC GGGAGGCGCCCTTTGGACCT TTTGCAATCCTGGCGCACTG AACCCTTGACCCCTGCCCTG CAGCCCCGCAGCTTGCTGT TTGCCCACTCTATTTGCCCA GCCCCAGCCCTGGAGAGTCC TTTAGCAGGGCAAAGTGCAA CATAGGCAGACCTTAAGGGA TGACTCAGTAACAGATAAGC TTTGTGTGCCTGCAGGGCAT ATAAAACAGGGGCAAGGCAC AGACTCATAGCAGAGCAATC ACCACCAAGCCTGGAATAAC TGCAGCCACC (SEQ ID NO: 227) | 410 |
| SP0259 | CTGTTTGCTGCTTGCAATGT TTGCCCATTTTAGGGGCTGG TTTCTTATAAAACTGATGGA AGATACAAACACTATTAAAG AACTGTTTGCATGTTGCAAA TGATGTCCAAAGTCCAAACA TTGTTAATAATTAATACTCC AATAAACATCATGTCAGAAT TTCTGTTTTCTTTTCCCTTT GAACCTTTGCAGGATTGCCA CATCATCAGGACCACACCTT CATCAGGAATGAATATCCGA TGACCTAATGATTCTGAGCT TGGCAAAGGTCTTATCTCCA AGCTCGCCCAGGCCCAGTGT TCCAGGAATGTGACCTTTGC TGCAGCAGCCGCTGGAGGGG GCAGAGGGGATGGGCTGGAG GTTGAGCAAACAGAGCAGCA GAAAAGGCAGTTCCTCTTCT CCAGTGCCCTCCTTCCCTGT CTCTGCCTCTCCCTCCCTTC CTCAGGCATCAGAGCGGAGA CTTCAGGGAGACCAGAGCCC AGCTTGCCAGGCACTGAGCT AGAAGCCCTGCC (SEQ ID NO: 228) | 512 |
| SP0264 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGCCTTTGCAACAGCTTAT CGGAAGCAAACAAGCTGAGG GGAATTGAGCAAGAATTTCT GGGATACCAACAGCATAGGA GGAACAAAGGACGTAGAGGG AGGGTTGACTGTCTACACAG GACAAAGCCAATGATTAACC AAACCTCTTGCAGATTTAAA TAGGATGGGAACTAGGAGTG GCAGCAATCCTTTCTTTCAG CTGGAGTGCTCCTCAGGAGC CAGCCCCACCCTTAGAAAAG CCACC (SEQ ID NO: 229) | 345 |
| SP0265(LVR SP 131_A1) | AGGTTAATTTTTAAAAAGCA GTCAAAAGTCCAAGTGGCCC TTGGCAGCATTTACTCTCTC TGTTTGCTCTGGTTAATAAT | 381 |
| | CTCAGGAGCACAAACATTCC TGTACCGGCCCGGGAGGCGC CCTTTGGACCTTTTGCAATC CTGGCGCACTGAACCCTTGA CCCCTGCCCTGCAGCCCCG CAGCTTGCTGTTTGCCCACT CTATTTGCCCAGCCCCAGCC CTGGAGAGTCCTTTAGCAGG GCAAAGTGCAACATAGGCAG ACCTTAAGGGATGACTCAGT AACAGATAAGCTTTGTGTGC CTGCAGGGCATATAAAACAG GGGCAAGGCACAGACTCATA GCAGAGCAATCACCACCAAG CCTGGAATAACTGCAGCCAC C (SEQ ID NO: 230) | |
| SP0266(LVR_SP 131_V1) | AAGCAAATATTTGTGGTTAT GGATTAACTCGAACTGTTTG CCCACTCTATTTGCCCTGTA CCGGCCCGGGAGGCGCCCTT TGGACCTTTTGCAATCCTGG CGCACTGAACCCTTGACCCC TGCCCTGCAGCCCCCGCAGC TTGCTGTTTGCCCACTCTAT TTGCCCAGCCCCAGCCCTGG AGAGTCCTTTAGCAGGGCAA AGTGCAACATAGGCAGACCT TAAGGGATGACTCAGTAACA GATAAGCTTTGTGTGCCTGC AGGGCATATAAAACAGGGGC AAGGCACAGACTCATAGCAG AGCAATCACCACCAAGCCTG GAATAACTGCAGCCACC (SEQ ID NO: 231) | 337 |
| SP0267(LVR_SP 131_V2) | GGCGCCCTTTGGACCTTTTG CAATCCTGGAGCAAACAGCA AACACTGTACCGGCCCGGGA GGCGCCCTTTGGACCTTTTG CAATCCTGGCGCACTGAACC CTTGACCCCTGCCCTGCAGC CCCCGCAGCTTGCTGTTTGC CCACTCTATTTGCCCAGCCC CAGCCCTGGAGAGTCCTTTA GCAGGGCAAAGTGCAACATA GGCAGACCTTAAGGGATGAC TCAGTAACAGATAAGCTTTG TGTGCCTGCAGGGCATATAA AACAGGGGCAAGGCACAGAC TCATAGCAGAGCAATCACCA CCAAGCCTGGAATAACTGCA GCCACC (SEQ ID NO: 232) | 326 |
| SP0268 (LVR_132_A1) | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCAGAATGAACATTGA ACTTTGGACTATACCTGAGG GGTGAGGTAAACAACAGGAC TATAAATGGCCCGGGAGGCG CCCTTTGGACCTTTTGCAAT CCTGGCGCACTGAACCCTTG ACCCCTGCCCTGCAGCCCCC GCAGCTTGCTGTTTGCCCAC TCTATTTGCCCAGCCCCAGC CCTGGAGAGTCCTTTAGCAG GGCAAAGTGCAACATAGGCA GACCTTAAGGGATGACTCAG TAACAGATAAGCTTTGTGTG CCTGCAGGGCATATAAAACA GGGGCAAGGCACAGACTCAT | 442 |

TABLE 32-continued

Synthetic Promoters:

| NAME | SEQUENCE | LENGTH |
|---|---|---|
| | AGCAGAGCAATCACCACCAA GCCTGGAATAACTGCAGCCA CC (SEQ ID NO: 233) | |
| SP0269 (LVR_132_V1) | AAGCAAATATTTGTGGTTAT GGATTAACTCGAACTGTTTG CCCACTCTATTT GCCCTGTACCAGAATGAACA TTGAACTTTGGACTATACCT GAGGGGTGAGGTAAACAACA GGACTATAAATGGCCCGGGA GGCGCCCTTTGGACCTTTTG CAATCCTGGCGCACTGAACC CTTGACCCCTGCCCTGCAGC CCCCGCAGCTTGCTGTTTGC CCACTCTATTTGCCCAGCCC CAGCCCTGGAGAGTCCTTTA GCAGGGCAAAGTGCAACATA GGCAGACCTTAAGGGATGAC TCAGTAACAGATAAGCTTTG TGTGCCTGCAGGGCATATAA AACAGGGGCAAGGCACAGAC TCATAGCAGAGCAATCACCA CCAAGCCTGGAATAACTGCA GCCACC (SEQ ID NO: 234) | 398 |
| SP0270 (LVR_132_V2) | GGCGCCCTTTGGACCTTTTG CAATCCTGGAGCAAACAGCA AACACTGTACCAGAATGAAC ATTGAACTTTGGACTATACC TGAGGGGTGAGGTAAACAAC AGGACTATAAATGGCCCGGG AGGCGCCCTTTGGACCTTTT GCAATCCTGGCGCACTGAAC CCTTGACCCCTGCCCTGCAG CCCCCGCAGCTTGCTGTTTG CCCACTCTATTTGCCCAGCC CCAGCCCTGGAGAGTCCTTT AGCAGGGCAAAGTGCAACAT AGGCAGACCTTAAGGGATGA CTCAGTAACAGATAAGCTTT GTGTGCCTGCAGGGCATATA AAACAGGGGCAAGGCACAGA CTCATAGCAGAGCAATCACC ACCAAGCCTGGAATAACTGC AGCCACC (SEQ ID NO: 235) | 387 |
| SP0271 (LVR_133_A1) | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCAGAATGAACATTGA ACTTTGGACTATACCTGAGG GGTGAGGTAAACAACAGGAC TATAAATGGCCCGGGAGGCG CCCTTTGGACCTTTTGCAAT CCTGGCGCTCTTTTGTTTTA CATGAAGGGTCTGGCAGCCA AAGCAATCACTCAAAGTTCA AACCTTATCATTTTTTGCTT TGTTCCTCTTGGCCTTGGTT TTGTACATCAGCTTTGAAAA TACCATCCCAGGGTTAATGC TGGGGTTAATTTATAACTAA GAGTGCTCTAGTTTTGCAAT ACAGGACATGCTATAAAAAT GGAAAGATGTTGCTTTCTGA GAGATGCGCCACC (SEQ ID NO: 236) | 433 |
| SP0272 (LVR_133_V1) | AAGCAAATATTTGTGGTTAT GGATTAACTCGAACTGTTTG | 389 |

TABLE 32-continued

Synthetic Promoters:

| NAME | SEQUENCE | LENGTH |
|---|---|---|
| | CCCACTCTATTTGCCCTGTA CCAGAATGAACATTGAACTT TGGACTATACCTGAGGGGTG AGGTAAACAACAGGACTATA AATGGCCCGGGAGGCGCCCT TTGGACCTTTTGCAATCCTG GCGCTCTTTTGTTTTACATG AAGGGTCTGGCAGCCAAAGC AATCACTCAAAGTTCAAACC TTATCATTTTTTGCTTTGTT CCTCTTGGCCTTGGTTTTGT ACATCAGCTTTGAAAATACC ATCCCAGGGTTAATGCTGGG GTTAATTTATAACTAAGAGT GCTCTAGTTTTGCAATACAG GACATGCTATAAAAATGGAA AGATGTTGCTTTCTGAGAGA TGCGCCACC (SEQ ID NO: 237) | |
| SP0273 (LVR_133_V2) | GGCGCCCTTTGGACCTTTTG CAATCCTGGAGCAAACAGCA AACACTGTACCAGAATGAAC ATTGAACTTTGGACTATACC TGAGGGGTGAGGTAAACAAC AGGACTATAAATGGCCCGGG AGGCGCCCTTTGGACCTTTT GCAATCCTGGCGCTCTTTTG TTTTACATGAAGGGTCTGGC AGCCAAAGCAATCACTCAAA GTTCAAACCTTATCATTTTT TGCTTTGTTCCTCTTGGCCT TGGTTTTGTACATCAGCTTT GAAAATACCATCCCAGGGTT AATGCTGGGGTTAATTTATA ACTAAGAGTGCTCTAGTTTT GCAATACAGGACATGCTATA AAAATGGAAAGATGTTGCTT TCTGAGAGATGCGCCACC (SEQ ID NO: 238) | 378 |
| SP0368 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC AGTCATATGTTTGCTCACTG AAGGTTACTAGTTAACAGGC ATCCCTTAAACAGGATATAA AAGGACTTCAGCAGGACTGC TCGAAACATCCCACTCAGCC ACC (SEQ ID NO: 239) | 203 |
| SP0373 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCGGCCCGGGAGGCGC CCTTTGGACCTTTTGCAATC CTGGCGGGGCATATAAAACA GGGCAAGGCACAGACTCAT AGCAGAGCAATCACCACCAA GCCTGGAATAACTGCAGCCA CC (SEQ ID NO: 240) | 222 |
| SP0378 | TGCTCTCTGACAAAGATACG GTGGGTCCCACTGATGAACT GTGCTGCCACAGTAAATGTA GCCACTATGCCTATCTCCAT TCTGAAGATGTGCCCTGTTC AAACATGTCCTAATACTCTG TCTCTGCAAGGGTCATCAGT AGTTTTCCATCTTACTCAAC | 275 |

TABLE 32-continued

Synthetic Promoters:

| NAME | SEQUENCE | LENGTH |
|------|----------|--------|
|  | ATCCTCCCAGTGAGTCATAT GTTTGCTCACTGAAGGTTAC TAGTTAACAGGCATCCCTTA AACAGGATATAAAAGGACTT CAGCAGGACTGCTCGAAACA TCCCACTCAGCCACC (SEQ ID NO: 241) |  |
| SP0379 | CCTCCCCGTGTTCCTGCTCT TTGTCCCTCTGTCCTACTTA GACTAATATTTGCCTTGGGT ACTGCAAACAGGAAATGGGG GAGGGACAGGAGTAGGGCGG C CCTGTTCAAACATGTCCTAA TACTCTGTCTCTGCAAGGGT CATCAGTAGTTTTCCATCTT ACTCAACATCCTCCCAGTGA GTCATATGTTTGCTCACTGA AGGTTACTAGTTAACAGGCA TCCCTTAAACAGGATATAAA AGGACTTCAGCAGGACTGCT CGAAACATCCCACTCAGCCA CC (SEQ ID NO: 242) | 283 |
| SP0380 | CCGCCCCCACTGAACCCTTG ACCCCTGCCCTGCAGCCCCC GCAGCTTGCTGTTTGCCCAC TCTATTTGCCCAGCCCCAGC CCTGTTCAAACATGTCCTAA TACTCTGTCTCTGCAAGGGT CATCAGTAGTTTTCCATCTT ACTCAACATCCTCCCAGTGA GTCATATGTTTGCTCACTGA AGGTTACTAGTTAACAGGCA TCCCTTAAACAGGATATAAA AGGACTTCAGCAGGACTGCT CGAAACATCCCACTCAGCCA CC (SEQ ID NO: 243) | 262 |
| SP0381 | AAGCTTTCTGAACAGCCAAA CAGAGATTCCAAAGTTCAGG CACCAAAGTTCAGACCCTAA CAGTTATTTACAAGGGTCAG TTAACCCCTGTTCAAACATG TCCTAATACTCTGTCTCTGC AAGGGTCATCAGTAGTTTTC CATCTTACTCAACATCCTCC CAGTGAGTCATATGTTTGCT CACTGAAGGTTACTAGTTAA CAGGCATCCCTTAAACAGGA TATAAAAGGACTTCAGCAGG ACTGCTCGAAACATCCCACT CAGCCACC (SEQ ID NO: 244) | 268 |
| SP0384 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC GGCCCGGGAGGCGCCCTTTG GACCTTTTGCAATCCTGGCG CCGATGACCTAATGATTCTG AGCTTGGCAAAGGTCTTATC TCCCAGCTCGCCCAGGCCCA GTGTTCCAGGAATGTGACCT TTGCTGCAGCAGCCGCTGGA GGGGGCAGAGGGGATGGGCT GGAGGTTGAGCAAACAGAGC AGCAGAAAAGGCAGTTCCTC TTCTCCAGTGCCCTCCTTCC CTGTCTCTGCCTCTCCCTCC CTTCCTCAGGCATCAGAGCG | 422 |

TABLE 32-continued

Synthetic Promoters:

| NAME | SEQUENCE | LENGTH |
|------|----------|--------|
|  | GAGACTTCAGGGAGACCAGA GCCCAGCTTGCCAGGCACTG AGCTAGAAGCCCTGCCGCCA CC (SEQ ID NO: 245) |  |
| SP0388 | AGGTTAATTTTTAAAAAGCAG TCAAAAGTCCAAGTGGCCCT TGGCAGCATTTACTCTCTCT GTTTGCTCTGGTTAATAATC TCAGGAGCACAAACATTCCG GGCATATAAAACAGGGGCAA GGCACAGACTCATAGCAGAG CAATCACCACCAAGCCTGGA ATAACTGCAGCCACC (SEQ ID NO: 246) | 176 |
| SP0396 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCGGCCCGGGAGGCGC CCTTTGGACCTTTTGCAATC CTGGCGCCCTGGAGAGTCCT TTAGCAGGGCAAAGTGCAAC ATAGGCAGACCTTAAGGGAT GACTCAGTAACAGATAAGCT TTGTGTGCCTGCAGGGCATA TAAAACAGGGGCAAGGCACA GACTCATAGCAGAGCAATCA CCACCAAGCCTGGAATAACT GCAGCCACC (SEQ ID NO: 247) | 309 |
| SP0397 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC TGTACCCACTGAACCCTTGA CCCCTGCCCTGCAGCCCCCG CAGCTTGCTGTTTGCCCACT CTATTTGCCCAGCCCCAGCC CTGGAGAGTCCTTTAGCAGG GCAAAGTGCAACATAGGCAG ACCTTAAGGGATGACTCAGT AACAGATAAGCTTTGTGTGC CTGCAGGGCATATAAAACAG GGGCAAGGCACAGACTCATA GCAGAGCAATCACCACCAAG CCTGGAATAACTGCAGCCAC C (SEQ ID NO: 248) | 341 |
| SP0398 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAGGTTAATTTTTAAAAA GCAGTCAAAAGTCCAAGTGG CCCTTGGCAGCATTTACTCT CTCTGTTTGCTCTGGTTAAT AATCTCAGGAGCACAAACAT TCCTGTACCAGAATGAACAT TGAACTTTGGACTATACCTG AGGGGTGAGGTAAACAACAG GACTATAAATGGCCCGGGAG GCGCCCTTTGGACCTTTTGC AATCTGGCGCACTGAACCC TTGACCCCTGCCCTGCAGCC CCCGCAGCTTGCTGTTTGCC CACTCTATTTGCCCAGCCCC AGCCCTGGAGAGTCCTTTAG CAGGGCAAAGTGCAACATAG | 545 |

TABLE 32-continued

Synthetic Promoters:

| NAME | SEQUENCE | LENGTH |
|---|---|---|
| | GCAGACCTTAAGGGATGACT CAGTAACAGATAAGCTTTGT GTGCCTGCAGGGCATATAAA ACAGGGGCAAGGCACAGACT CATAGCAGAGCAATCACCAC CAAGCCTGGAATAACTGCAG CCACC (SEQ ID NO: 249) | |
| SP0399 | AGAATGAACATTGAACTTTG GACTATACCTGAGGGGTGAG GTAAACAACAGGACTATAAA TGGGCATATAAAACAGGGGC AAGGCACAGACTCATAGCAG AGCAATCACCACCAAGCCTG GAATAACTGCAGCCACC (SEQ ID NO: 250) | 137 |
| SP0403 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT TATGGATTAACTCGAACTGT TTGCCCACTCTATTTGCCCT GTACCGGCCCGGGAGGCGCC CTTTGGACCTTTTGCAATCC TGGCGCACTGAACCCTTGAC CCCTGCCCTGCAGCCCCCGC AGCTTGCTGTTTGCCCACTC TATTTGCCCAGCCCCAGCCC TGGAGAGTCCTTTAGCAGGG CAAAGTGCAACATAGGCAGA CCTTAAGGGATGACTCAGTA ACAGATAAGCTTTGTGTGCC TGCAGGGCATATAAAACAGG GGCAAGGCACAGACTCATAG CAGAGCAATCACCACCAAGC CTGGAATAACTGCAGCCACC (SEQ ID NO: 251) | 440 |
| SP0404 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT TATGGATTAACTCGAACTGT TTGCCCACTCTATTTGCCCT GTACCAGAATGAACATTGAA CTTTGGACTATACCTGAGGG GTGAGGTAAACAACAGGACT ATAAATGGCCCGGGAGGCGC CCTTTGGACCTTTTGCAATC CTGGCGCACTGAACCCTTGA CCCCTGCCCTGCAGCCCCCG CAGCTTGCTGTTTGCCCACT CTATTTGCCCAGCCCCAGCC CTGGAGAGTCCTTTAGCAGG GCAAAGTGCAACATAGGCAG ACCTTAAGGGATGACTCAGT AACAGATAAGCTTTGTGTGC CTGCAGGGCATATAAAACAG GGGCAAGGCACAGACTCATA GCAGAGCAATCACCACCAAG CCTGGAATAACTGCAGCCAC C (SEQ ID NO: 252) | 501 |
| SP0405 | CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGAAGCAAATATTTGTGGT | 414 |

TABLE 32-continued

Synthetic Promoters:

| NAME | SEQUENCE | LENGTH |
|---|---|---|
| | TATGGATTAACTCGAACTGT TTGCCCACTCTATTTGCCCT GTACCAGAATGAACATTGAA CTTTGGACTATACCTGAGGG GTGAGGTAAACAACAGGACT ATAAATGGCCCGGGAGGCGC CCTTTGGACCTTTTGCAATC CTGGCGCACTGAACCCTTGA CCCCTGCCCTGCAGCCCCCG CAGCTTGCTGTTTGCCCACT CTATTTGCCCAGCCCCAGGG GCATATAAAACAGGGGCAAG GCACAGACTCATAGCAGAGC AATCACCACCAAGCCTGGAA TAACTGCAGCCACC (SEQ ID NO: 253) | |
| SP0406 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC GGCCCGGGAGGCGCCCTTTG GACCTTTTGCAATCCTGGCG AGTCATATGTTTGCTCACTG AAGGTTACTAGTTAACAGGC ATCCCTTAAACAGGATATAA AAGGACTTCAGCAGGACTGC TCGAAACATCCCACTCAGCC ACC (SEQ ID NO: 254) | 243 |
| SP0407 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC CAGGCTTTCACTTTCTCGCC AACTTACAAGGCCTTTCTGT GTAAACAATACCTGAACCTT TACCCCGTTGCCCGGCAACG GCCAGGTCTGTGCCAAGTGT TTGGGGCATATAAAACAGGG GCAAGGCACAGACTCATAGC AGAGCAATCACCACCAAGCC TGGAATAACTGCAGCCACC (SEQ ID NO: 255) | 279 |
| SP0409 | AGGTTAATTTTTAAAAAGCA GTCAAAAGTCCAAGTGGCCC TTGGCAGCATTTACTCTCTC TGTTTGCTCTGGTTAATAAT CTCAGGAGCACAAACATTCC CCCTGTTCAAACATGTCCTA ATACTCTGTCTCTGCAAGGG TCATCAGTAGTTTTCCATCT TACTCAACATCCTCCCAGTG GGGCATATAAAACAGGGGCA AGGCACAGACTCATAGCAGA GCAATCACCACCAAGCCTGG AATAACTGCAGCCACC (SEQ ID NO: 256) | 256 |
| SP0411 | CCCTGTTCAAACATGTCCTA ATACTCTGTCTCTGCAAGGG TCATCAGTAGTTTTCCATCT TACTCAACATCCTCCCAGTG AGTCATATGTTTGCTCACTG AAGGTTACTAGTTAACAGGC ATCCCTTAAACAGGATATAA AAGGACTTCAGCAGGACTGC TCGAAACATCCCACTCAGCC ACC (SEQ ID NO: 257) | 183 |

TABLE 32-continued

| | Synthetic Promoters: | |
| --- | --- | --- |
| NAME | SEQUENCE | LENGTH |
| SP0412 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>CCCTGTTCAAACATGTCCTA<br>ATACTCTGTCTCTGCAAGGG<br>TCATCAGTAGTTTTCCATCT<br>TACTCAACATCCTCCCAGTG<br>AGTCATATGTTTGCTCACTG<br>AAGGTTACTAGTTAACAGGC<br>ATCCCTTAAACAGGATATAA<br>AAGGACTTCAGCAGGACTGC<br>TCGAAACATCCCACTCAGCC<br>ACC<br>(SEQ ID NO: 258) | 283 |
| SP0413 | AGGTTAATTTTTAAAAAGCA<br>GTCAAAAGTCCAAGTGGCCC<br>TTGGCAGCATTTACTCTCTC<br>TGTTTGCTCTGGTTAATAAT<br>CTCAGGAGCACAAACATTCC<br>TGTACCGGCCCGGGAGGCGC<br>CCTTTGGACCTTTTGCAATC<br>CTGGCGAGTCATATGTTTGC<br>TCACTGAAGGTTACTAGTTA<br>ACAGGCATCCCTTAAACAGG<br>ATATAAAAGGACTTCAGCAG<br>GACTGCTCGAAACATCCCAC<br>TCAGCCACC<br>(SEQ ID NO: 259) | 249 |

TABLE 33

| | Prior art promoters: |
| --- | --- |
| LP1 | CCCTAAAATGGGCAAACATT<br>GCAAGCAGCAAACAGCAAAC<br>ACACAGCCCTCCCTGCCTGC<br>TGACCTTGGAGCTGGGGCAG<br>AGGTCAGAGACCTCTCTGGG<br>CCCATGCCACCTCCAACATC<br>CACTCGACCCCTTGGAATTT<br>CGGTGGAGAGGAGCAGAGGT<br>TGTCCTGGCGTGGTTTAGGT<br>AGTGTGAGAGGGGAATGACT<br>CCTTTCGGTAAGTGCAGTGG<br>AAGCTGTACACTGCCCAGGC<br>AAAGCGTCCGGGCAGCGTAG<br>GCGGGCGACTCAGATCCCAG<br>CCAGTGGACTTAGCCCCTGT<br>TTGCTCCTCCGATAACTGGG<br>GTGACCTTGGTTAATATTCA<br>CCAGCAGCCTCCCCCGTTGC<br>CCCTCTGGATCCACTGCTTA<br>AATACGGACGAGGACAGGGC<br>CCTGTCTCCTCAGCTTCAGG<br>CACCACCACTGACCTGGGAC<br>AGTGAATCCGGACTCTAAGG<br>TAAATATAAAATTTTTAAGT<br>GTATAATGTGTTAAACTACT<br>GATTCTAATTGTTTCTCTCT<br>TTTAGATTCCAACCTTTGGA<br>ACTGAATTCTAGACCACC<br>(SEQ ID NO: 260) |
| CMV-IE | ATAGTAATCAATTACGGGGT<br>CATTAGTTCATAGCCCATAT<br>ATGGAGTTCCGCGTTACATA<br>ACTTACGGTAAATGGCCCGC<br>CTGGCTGACCGCCCAACGAC<br>CCCCGCCCATTGACGTCAAT<br>AATGACGTATGTTCCCATAG |

TABLE 33-continued

| | Prior art promoters: |
| --- | --- |
| | TAACGCCAATAGGGACTTTC<br>CATTGACGTCAATGGGTGGA<br>GTATTTACGGTAAACTGCCC<br>ACTTGGCAGTACATCAAGTG<br>TATCATATGCCAAGTACGCC<br>CCCTATTGACGTCAATGACG<br>GTAAATGGCCCGCCTGGCAT<br>TATGCCCAGTACATGACCTT<br>ATGGGACTTTCCTACTTGGC<br>AGTACATCTACGTATTAGTC<br>ATCGCTATTACCATGGTGAT<br>GCGGTTTTGGCAGTACATCA<br>ATGGGCGTGGATAGCGGTTT<br>GACTCACGGGGATTTCCAAG<br>TCTCCACCCCATTGACGTCA<br>ATGGGAGTTTGTTTTGGCAC<br>CAAAATCAACGGGACTTTCC<br>AAAATGTCGTAACAACTCCG<br>CCCCATTGACGCAAATGGGC<br>GGTAGGCGTGTACGGTGGGA<br>GGTCTATATAAGCAGAGCTG<br>GTTTAGTGAACCGTCAGATC<br>(SEQ ID NO: 261) |
| CBA | AGATCTGAATTCGGTACCTA<br>GTTATTAATAGTAATCAATT<br>ACGGGGTCATTAGTTCATAG<br>CCCATATATGGAGTTCCGCG<br>TTACATAACTTACGGTAAAT<br>GGCCCGCCTGGCTGACCGCC<br>CAACGACCCCCGCCCATTGA<br>CGTCAATAATGACGTATGTT<br>CCCATAGTAACGCCAATAGG<br>GACTTTCCATTGACGTCAAT<br>GGGTGGAGTATTTACGGTAA<br>ACTGCCCACTTGGCAGTACA<br>TCAAGTGTATCATATGCCAA<br>GTACGCCCCCTATTGACGTC<br>AATGACGGTAAATGGCCCGC<br>CTGGCATTATGCCCAGTACA<br>TGACCTTATGGGACTTTCCT<br>ACTTGGCAGTACATCTACGT<br>ATTAGTCATCGCTATTACCA<br>TGGTCGAGGTGAGCCCCACG<br>TTCTGCTTCACTCTCCCCAT<br>CTCCCCCCCCTCCCCACCCC<br>CAATTTTGTATTTATTTATT<br>TTTAATTATTTTGTGCAGC<br>GATGGGGGCGGGGGGGGGGG<br>GGGGGCGCGCGCCAGGCGGG<br>GCGGGGCGGGGCGAGGGGCG<br>GGGCGGGGCGAGGCGGAGAG<br>GTGCGGCGGCAGCCAATCAG<br>AGCGGCGCGCTCCGAAAGTT<br>TCCTTTTATGGCGAGGCGGC<br>GGCGGCGGCGGCCCTATAAA<br>AAGCGAAGCGCGCGGCGGGC<br>GGGAGTCGCTGCGCGCTGCC<br>TTCGCCCCGTGCCCCGCTCC<br>GCCGCCGCCTCGCGCCGCCC<br>GCCCCGGCTCTGACTGACCG<br>CGTTACTCCCACAGGTGAGC<br>GGGCGGGACGGCCCTTCTCC<br>TCCGGGCTGTAATTAGCGCT<br>TGGTTTAATGACGGCTTGTT<br>TCTTTTCTGTGGCTGCGTGA<br>AAGCCTTGAGGGGCTCCGGG<br>AGGGCCCTTTGTGCGGGGGG<br>AGCGGCTCGGGGGGTGCGTG<br>CGTGTGTGTGTGCGTGGGGA<br>GCGCCGCGTGCGGCTCCGCG<br>CTGCCCGGCGGCTGTGAGCG<br>CTGCGGGCGCGGCGCGGGGC<br>TTTGTGCGCTCCGCAGTGTG<br>CGCGAGGGGAGCGCGGCCGG<br>GGGCGGTGCCCCGCGGTGCG<br>GGGGGGGCTGCGAGGGGAAC<br>AAAGGCTGCGTGCGGGGTGT |

TABLE 33-continued

| Prior art promoters: |
| --- |

```
        GTGCGTGGGGGGGTGAGCAG
        GGGGTGTGGGCGCGTCGGTC
        GGGCTGCAACCCCCCCTGCA
        CCCCCCTCCCCGAGTTGCTG
        AGCACGGCCCGGCTTCGGGT
        GCGGGGCTCCGTACGGGGCG
        TGGCGCGGGGCTCGCCGTGC
        CGGGCGGGGGGTGGCGGCAG
        GTGGGGGTGCCGGGCGGGGC
        GGGGCCGCCTCGGGCCGGGG
        AGGGCTCGGGGGAGGGGCGC
        GGCGGCCCCCGGAGCGCCGG
        CGGCTGTCGAGGCGCGGCGA
        GCCGCAGCCATTGCCTTTTA
        TGGTAATCGTGCGAGAGGGC
        GCAGGGACTTCCTTTGTCCC
        AAATCTGTGCGGAGCCGAAA
        TCTGGGAGGCGCCGCCGCAC
        CCCCTCTAGCGGGCGCGGGG
        CGAAGCGGTGCGGCGCCGGC
        AGGAAGGAAATGGGCGGGGA
        GGGCCTTCGTGCGTCGCCGC
        GCCGCCGTCCCCTTCTCCCT
        CTCCAGCCTCGGGGCTGTCC
        GCGGGGGGACGGCTGCCTTC
        GGGGGGGACGGGGCAGGGCG
        GGGTTCGGCTTCTGGCGTGT
        GACCGGCGGCTCTAGAGCCT
        CTGCTAACCATGTTCATGCC
        TTCTTCTTTTTCCTACAGCT
        CCTGGGCAACGTGCTGGTTA
        TTGTGCTGTCTCATCATTTT
        GGCAAAGAATTCCTCGAAGA
        TCTAGGCAACGCGTCTCGAG
        GCGGCCGCCGCCACC
        (SEQ ID NO: 262)
```

TBG
```
        AGGTTAATTTTTAAAAAGCA
        GTCAAAAGTCCAAGTGGCCC
        TTGGCAGCATTTACTCTCTC
        TGTTTGCTCTGGTTAATAAT
        CTCAGGAGCACAAACATTCC
        AGATCCAGGTTAATTTTTAA
        AAAGCAGTCAAAAGTCCAAG
        TGGCCCTTGGCAGCATTTAC
        TCTCTCTGTTTGCTCTGGTT
        AATAATCTCAGGAGCACAAA
        CATTCCAGATCCGGCGCGCC
        AGGGCTGGAAGCTACCTTTG
        ACATCATTTCCTCTGCGAAT
        GCATGTATAATTTCTACAGA
        ACCTATTAGAAAGGATCACC
        CAGCCTCTGCTTTTGTACAA
        CTTTCCCTTAAAAAACTGCC
        AATTCCACTGCTGTTTGGCC
        CAATAGTGAGAACTTTTTCC
        TGCTGCCTCTTGGTGCTTTT
        GCCTATGGCCCCTATTCTGC
        CTGCTGAAGACACTCTTGCC
        AGCATGGACTTAAACCCCTC
        CAGCTCTGACAATCCTCTTT
        CTCTTTTGTTTTACATGAAG
        GGTCTGGCAGCCAAAGCAAT
        CACTCAAAGTTCAAACCTTA
        TCATTTTTTGCTTTGTTCCT
        CTTGGCCTTGGTTTTGTACA
        TCAGCTTTGAAAATACCATC
        CCAGGGTTAATGCTGGGGTT
        AATTTATAACTAAGAGTGCT
        CTAGTTTTGCAATACAGGAC
        ATGCTATAAAAATGGAAAGA
        TGTTGCTTTCTGAGAGACTG
        CAGAAGTTGGTCGTGAGGCA
        CTGGGCAGGTAAGTATCAAG
        GTTACAAGACAGGTTTAAGG
        AGACCAATAGAAACTGGGCT
        TGTCGAGACAGAGAAGACTC
        TTGCGTTTCTGATAGGCACC
```

TABLE 33-continued

| Prior art promoters: |
| --- |

```
        TATTGGTCTTACTGACATCC
        ACTTTGCCTTTCTCTCCACA
        GGGCAATCCGGTACTGTTGG
        TAAAGCCACC
        (SEQ ID NO: 263)
```

Example 2

Materials and Methods

Promoters were designed using Synpromics' proprietary platform PROMPT® and synthesised by GeneArt®. This involved an analysis of liver gene expression datasets to identify candidate genes, including microarray and NGS datasets and scientific literature reviews to identify genes expressed to very high levels in liver cells. Cis-regulatory element selection and analysis was performed. TFBS within the CREs were identified.

Synthetic promoters comprising the CRMs linked to minimal/proximal promoters as discussed herein, were cloned upstream of the luciferase reporter gene followed by SV40 late PolyA signal into a vector with a backbone having properties essentially identical to pUC19. DNA preparations were transfected into either Huh7 (a hepato-cellular carcinoma cell line), HeLa (an immortal cell line derived from cervical cancer) or HEK293 (human embryonic kidney cells) to asses transcriptional activity. Huh-7 cells were sourced from JCRB Cell Bank (JCRB0403), HeLa and HEK293 were sourced from ECACC cell bank. All cell lines were grown and maintained according to the cell banks' recommendations.

Transfections were performed in 48 well plates in triplicate using FuGene HD Transfection Reagent (Promega #E2311) at a DNA:FuGene HD ratio of 1:1.1. Luciferase activity was measured 24 hours after transfection. Cells were washed with phosphate buffered saline (PBS), lysed in 100 pl Passive Lysis Buffer (Promega #E194A) and stored at −80° C. overnight. Luciferase activity was quantified using the Luciferase Reporter 1000 assay system (Promega #E4550) following manufacturer's guidelines in 10 µl of lysate using 96 well flat bottom solid white Microplate FluoroNunc plates (ThermoFisher #236105) and luminescence quantified in a FLUOstar Omega plate reader (BMG Labtech) machine.

The above luciferase methods are conventional in the art, and similar techniques have been described extensively in the literature, e.g. in Alam and Cook, "*Reporter Genes: Application to the Study of Mammalian Gene Transcription*", ANALYTICAL BIOCHEMISTRY 188, 245-254 (1990).

Discussion and Results

Figure 1:
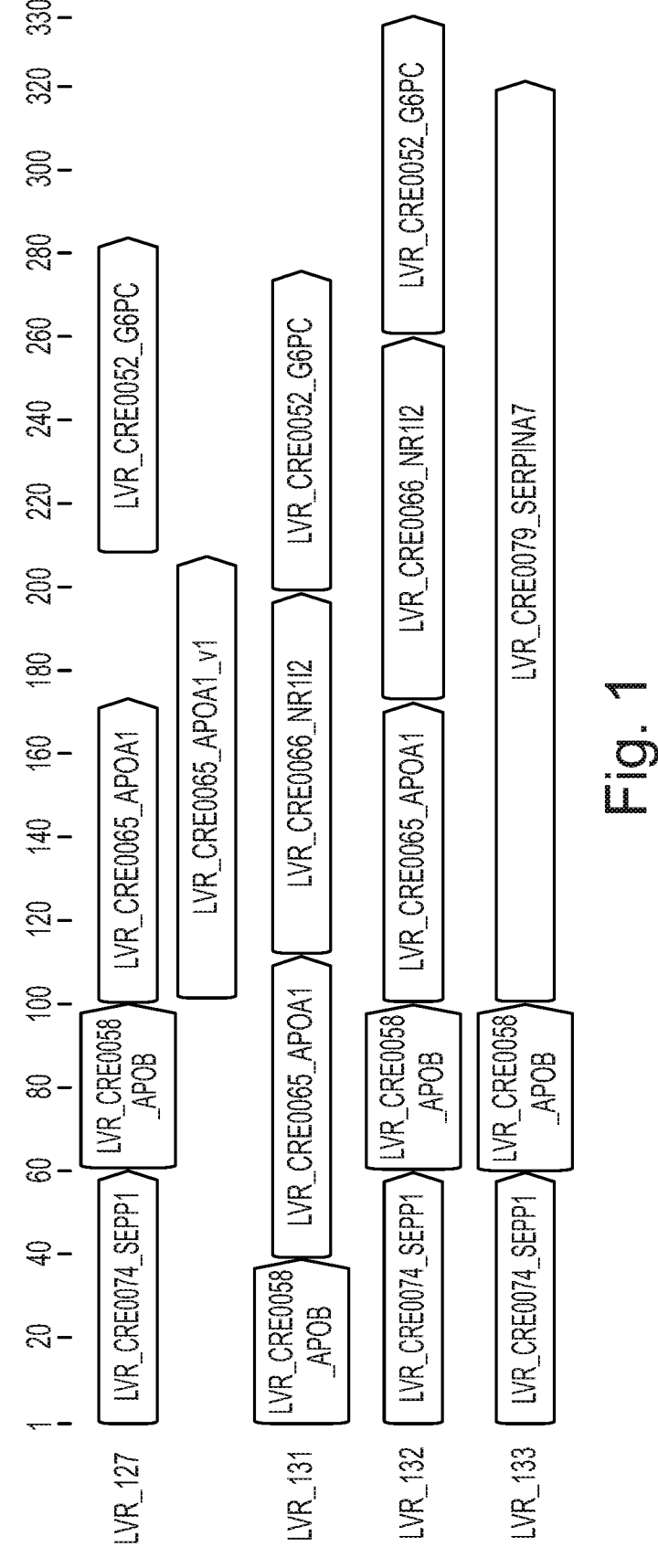
FIG. 1 shows a schematic illustration of synthetic liver-specific promoters according to the present invention, with the CRE enhancer elements indicated.

Bioinformatic analysis of large genomic data sets led to the discovery of cis-regulatory elements (CRE) expected to be useful to enhance liver-specific gene expression. The top 12 CREs were selected for the design of four synthetic liver-specific promoters. These promoters were named LVR_127, LVR_131, LVR_132 and LVR_133 respectively. The structure of these promoters is shown in FIG. 1, including the CRE and minimal/proximal promoter elements that are present in each promoter.

The sequences of these promoters are shown in Table 32, and the CRMs comprised in these promoters are shown in Table 31. The sequences of the component parts (CREs) of these CRMs/promoters are set out in Table 5, and the minimal/proximal promoters that are operably linked to thee CRMs are set out in Table 6. For the promoters LVR_127, LVR_131, LVR_132 the CRMs comprising the various combinations of CREs (Table 31) were positioned upstream of the minimal promoter LVR_CRE0052_G6PC (see Table 6). For LVR_133 the CRM was placed upstream of the SERPINA7 proximal promoter (LVR_CRE0079_SERPINA7, see Table 6).

Figure 2:
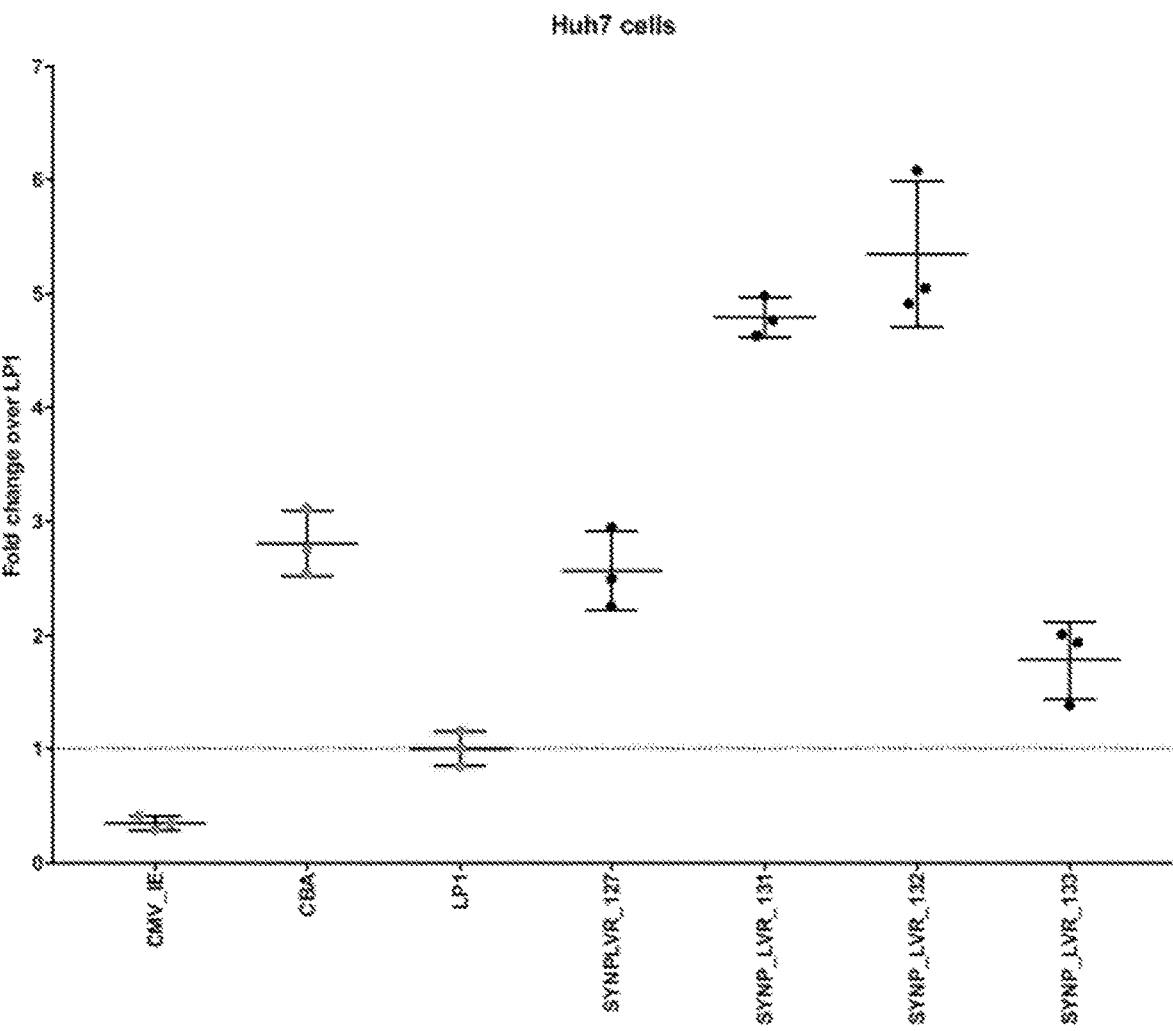
FIG. 2 shows a graph of expression levels of a luciferase reporter protein driven by various synthetic liver-specific promoters in the liver-derived cell line Huh7 relative to expression levels driven by the known liver-specific promoter LP1 and the ubiquitous CMV-IE and CBA promoters.

The ability of these synthetic promoters to drive expression in liver cells was benchmarked against the ubiquitous CMV_IE and CBA promoters, and also against the known liver specific promoter LP1. The sequences of these promoters are provided in Table 14. The results of this experiment are shown in FIG. 2, which shows a mean of 3 replicates. The bars show standard deviation.

All of the synthetic promoters according to the invention showed higher activity than the LP1 promoter in Huh7 cells (FIG. 2). When these promoters were counter-screened in non-liver-derived HEK293 and HeLa cells, they showed negligible activity compared to the ubiquitously active promoters CMV IE and CBA (see FIG. 5 and FIG. 6). This indicates that the LVR_127, LVR_131, LVR_132 and LVR_133 promoters are highly-specific for activity in liver cell lines.

Subsequently, two candidate enhancers were designed based on bioinformatic predictions using the following CREs LVR_CRE0080_PROC, LVR_CRE0081_AP0A1, LVR_CRE0061_APOB and LVR_CRE0082_APOC4. These synthetic enhancers were designated as "V1" (or LVR_CRE0077_V1, SEQ ID NO: 19) and "V2" (or LVR_CRE0078_V2, SEQ ID NO: 20), respectively (FIG. 3). The effects of these candidate enhancers were tested by adding them to the previously described LVR_127, LVR_131, LVR_132 and LVR_133 liver-specific promoters. The known human alpha(1)-microglobulin/bikunin precursor (AMBP) enhancer, designated herein as "V1" (or LVR_CRE0051_AMBP, SEQ ID NO: 3) (Rouet et al., 1992) was also adding them to the LVR_127, LVR_131, LVR_132 and LVR_133 liver-specific promoters. These new promoters with the additional enhancer element were tested in Huh7 cells, as previously described for the LVR_127, LVR_131, LVR_132 and LVR_133 liver-specific promoters.

As shown in FIGS. 4a to 4d, addition of any one of V1 or V2 enhancer significantly enhanced promoter activity of LVR_127, LVR_132 and LVR_133. The only exception observed was combining LVR_131 with V2. Moreover, addition of V1 and V2 enhancer sequences retained promoter liver-specificity, which was confirmed when the promoters were counter-screened in HEK293 and HeLa cells (FIG. 5).

The SYNP_LVR_131 family of promoters (SEQ ID NO: 202, and SEQ ID NO: 230 to 232), and in particular SYNP_LVR_131_A1 (SEQ ID NO: 230), appears to be especially powerful. Thus, these promoters, and the CRMs that they comprise (SEQ ID NO: 130, and SEQ ID NO: 158 to 160, and especially SEQ ID NO: 158), and functional variants thereof, are of particular interest. However, all of the synthetic promoters according to the present invention appear to be both powerful and liver-specific.

It is expected that the CREs used in the specifically exemplified CRMs and promoters can be rearranged (for example, shuffled or inverted) and liver-specific promoter activity will be remained. Furthermore, it is expected that the sequence of the CREs, CRMs and promoters can be altered considerably while retaining liver-specific promoter activity. Generally, the TFBS within CREs should be preserved to the extent that the CRE is still able bind the same TFs, and preferably in the same order and approximate spacing as the reference CRE, in order to maintain function. Generally, the disclosed CREs (i.e. enhancers) themselves are self-contained regulatory units, and they can be moved, and/or orientation altered, without loss of function. The skilled person can readily determine the effects of any alteration to a CRE, CRM or promoter (e.g. in absolute terms or in comparison to a reference CRE, CRM or promoter) using the methodologies described herein. Furthermore, the CREs can be incorporated in other promoters in order to drive liver-specific expression (especially V1 and V2, which are believed to have particularly broad utility, but also the other CREs disclosed herein).

In summary, these new synthetic promoters and enhancers are valuable tools for gene therapy through lever specific gene expression and for the design of liver-specific gene therapies.

Example 3

Bioinformatic analysis of large genomic data sets and literature analysis led to the identification of additional cis-regulatory elements (CREs) expected to be useful to enhance liver-specific gene expression. These CREs were used in the design of further liver-specific promoters.

The activity of the resultant liver-specific promoters (i.e. all of the promoters set out in Table 32) was tested in Huh7 cells using the materials and methods essentially as described in Example 2. However, in this case the activity of the liver-specific promoters was compared to the activity of the promoter TBG, as TBG was found to have higher and more consistent in vitro expression than LP1.

The specificity of the liver-specific promoters for liver cells was also tested using non-liver HEK293 cells, using the materials and methods described in Example 2. The activity of the liver-specific promoters is expressed compared to the activity of CMV-IE (TBG and LP1 are liver-specific and thus not particularly active in HEK293 cells). 'Relative activity' in the graphs showing the specificity of the liver-specific promoters tested in HEK293 cells is the activity of the named promoter expressed as a ratio to the activity of CMV-IE, wherein 1 is the same activity as CMV-IE, more than 1 is higher activity compared to CMV-IE and lower than 1 is lower activity compared to CMV-IE.

Activity

The average activity of the promoters according to this invention is shown in FIG. 8A, FIG. 9A, FIG. 10A and FIG. 11A. The mean relative activity of different experiments is shown for each promoter, wherein each experiment is itself a mean value of technical repeats. The error bar is a standard error of the mean. If no error bar is present, the data arises from a single experiment. 'Relative activity' in these graphs showing the activity of the liver-specific promoters tested in Huh7 cells is the activity of the named promoter expressed as a percentage of the activity of TBG (i.e. wherein 100 is the same activity as TBG, more than 100 is higher activity compared to TBG, and less than 100 is lower activity compared to TBG). It should be noted that TBG is an extremely powerful liver-specific promoter, and thus a promoter which shows expression which is less than TBG may still be extremely useful. In particular, promoters which are shorter than TBG, but which still demonstrate high levels of activity (e.g. 15%, more preferably 25%, 50%, or 75% of the activity of TBG or higher) are of particular interest.

It can be seen that the synthetic liver-specific promoters of the present invention are all highly active in liver cells.

The average activity of two promoters comprising only promoter elements CRE0006 (SP0154) and CRE0040 (SP0235) are shown in FIG. 11B as a comparison.

FIG. 11B shows the activity of SP0154, which contains only promoter element CRE0006. SP0154 has a comparatively low activity compared to TBG, but it is actually surprisingly high considering the lack of any additional CREs. However, when an additional CRE is combined with the promoter element CRE0006, such as in promoters SP0155 (CRE0006 and CRE0001), SP0158 (CRE0006 and CRE0005) and SP0163 (CRE0006 and CRE0012), the activity of the resultant synthetic liver-specific promoters is increased 5-fold, 3-fold and 6-fold respectively, as shown in FIG. 11A. Similarly, when promoter element CRE0006 is combined with a combination of CREs, such as in promoter SP259 (CRE0006 in combination with CRE0001 and CRE0047), the activity of the resultant synthetic promoters is increased 4-fold, as shown in FIG. 11A. This indicates that the individual CREs CRE0001, CRE0005, CRE0012 and the combination of CRE0001 and CRE0047 can provide considerable enhancement activity when added to a promoter element such as CRE0006.

FIG. 11B also shows the activity of SP0235, which contains only promoter element CRE0040. SP0235 has a minimal relative activity. However, when an additional CRE is combined with promoter element CRE0040, such as in promoters SP0236 and SP264 (both containing CRE0040 and CRE0018), the activity of the resultant synthetic promoters is increased around 50-fold, as shown in FIG. 11A. Similarly, when promoter element CRE0040 is combined with a combination of multiple CREs, such as in promoter SP0252 (CRE0040 in combination with CRE0018 and CRE0077), the activity of the resultant synthetic promoters is increased around 40-fold, as shown in FIG. 11A. This indicates that the individual CRE CRE0018 and the combination of CRE0018 and CRE0077 can provide considerable enhancement activity when added to a promoter element such as CRE0040. In FIG. 11A, promoters SP0236 and SP0264 contain the same CRE and promoter element but SP0236 does not have a consensus Kozak sequence while SP0264 has a consensus Kozak sequence. The presence of a consensus Kozak sequence does not appear to impact the activity of a promoter.

Liver Specificity

The activity of promoters in HEK293 cells relative to CMV-IE is shown in FIG. 8B, FIG. 9B, FIG. 10B and FIG. 11C. The mean relative activity of different experiments is shown for each promoter. If no error bar is present, the results arise from a single experiment. The specificity of the majority, but not all, promoters has been tested experimentally. Many of the promoters according to the present invention have low expression in HEK293 cells, as indicated by activity in HEK293 cells of less than 50% of the activity of CMV-IE. The majority of the promoters have activity in HEK293 cells of less than 10% of the activity of CMV-IE which indicates that their activity is very liver specific.

Identifying High-Performance CREs and Promoter Elements

A large group of more than 200 promoters comprising various combinations of CREs and/or promoter elements expected to be useful to enhance liver-specific gene expression was assembled (this included all of the synthetic promoters used in Example 3 as well as additional liver specific promoters and liver-specific CRE). These promoters represent a large group of liver-specific promoters which is useful for assessing the contribution made to expression by various CREs. This large group of promoters is referred to in FIGS. 12A and 12B as 'ALL'.

The group was analysed to identify individual CREs and groups of CREs that correlate particularly strongly with high levels of liver-specific expression.

Out of the group of all tested promoters, a particular subset of liver-specific promoters comprising two or more operably linked "core" CREs selected from the group consisting of CRE0018, CRE0042, CRE0051, CRE0058, CRE0065, CRE0066, CRE0068 and CRE0074 was found to correlate particularly well with high levels of activity. This preferred group of promoters is referred to in FIGS. 12A and 12B as 'Group 1'.

Additionally, a further subset of liver-specific promoters comprising at least one of the abovementioned Core CREs operably linked to one of promoter elements CRE0059 and CRE0006 was found to correlate particularly well with high activity. This preferred group of promoters is referred to in FIGS. 12A and 12B as 'Group 2'. It should be noted that some promoters fall both within 'Group 1' and 'Group 2' (i.e. where they contain two or more Core CREs and either CRE0059 or CRE0006).

To illustrate the particularly high activity of promoters of 'Group 1' and 'Group 2', the average relative activity of groups 'ALL' (n=217), 'Group 1' (n=49) and 'Group 2' (n=20) is shown in FIG. 12A (Note, 'ALL' contains the promoters of 'Group 1' and 'Group 2' plus additional promoters). As can be seen from this figure, the average relative activity of 'Group 1' is around two times higher than the average relative activity of group 'ALL'. Additionally, the average relative activity of 'Group 2' is around three times higher than the average relative activity of group 'ALL'. This does not appear to be a result of differences in length between the groups as 'Group 1' and 'Group 2' still perform superior to group 'ALL' when the relative activity of each promoter was divided by its size (in base pairs) and the mean of this value for each of the group is presented in FIG. 12B.

Without wishing to be bound by theory, the superior performance of 'Group 1' and 'Group 2' may be due to the presence of one or more of the core CREs and the preferred promoter elements. In the group of all tested promoters (group 'ALL'), the number of CRE present in each promoter was counted. Additionally, the number of core CRE present in each promoter was counted, wherein again the core CREs are the CRE0018, CRE0042, CRE0051, CRE0058, CRE0065, CRE0066, CRE0068 and CRE0074. The mean activity of promoters which have a specific number of core CREs versus any CREs was calculated and is presented in FIG. 13A. This figure shows that the presence of the specified number of Core CREs in a promoter is associated with increased activity compared to promoters with the specified number of CREs, wherein the CRE is any CRE. This is not because of difference in size between the group of promoters which contain the specified number of core CREs and the group of promoters which have the specified number of any CRE as comparison of the activity over size shows a similar trend, as indicated in FIG. 13B.

When one or more Core CREs is combined with a preferred promoter element, such as CRE0059 or CRE0006, the activity of the resultant synthetic promoter is even higher as can be seen from the higher mean relative activity of 'Group 2' (promoters comprising at least one Core CRE and a preferred promoter element) compared to 'Group 1' (promoters comprising at least two Core CREs).

The presence of various subset of CREs within the group of core CREs in a promoter is also associated with high levels of activity. For example, the mean activity and the mean activity over size (in base pairs) of promoters which comprise both CRE0051 and CRE0058 (n=25) is higher than the mean activity of promoters from group 'ALL' which have two CREs (n=50), as can be seen in FIG. 15A and FIG. 15B. Similarly, the mean activity and the mean activity over size (in base pairs) of promoters which comprise CRE0051, CRE0058 and CRE0065 (n=15) is higher than the mean activity of promoters from group 'ALL' which have three CREs (n=19), as can be seen in FIG. 16A and FIG. 16B. The mean activity and the mean activity over size (in base pairs) of promoters which comprise CRE0051, CRE0058 and CRE0066 (n=8) is higher than the mean activity of promoters from group 'ALL' which have three CREs (n=19), as can be seen in FIG. 17A and FIG. 17B. The mean activity and the mean activity over size (in base pairs) of promoters which comprise CRE0051, CRE0058, CRE0065 and CRE0066 (n=7) is higher than the mean activity of promoters from group 'ALL' which have four CREs (n=15), as can be seen in FIG. 18A and FIG. 18B. The mean activity and the mean activity over size (in base pairs) of promoters which comprise CRE0051, CRE0065 and CRE0066 (n=19) is higher than the mean activity of promoters from group 'ALL' which have three CREs (n=19), as can be seen in FIG. 19A and FIG. 19B. The mean activity and the mean activity over size (in base pairs) of promoters which comprise CRE0051, CRE0058 and CRE0074 (n=6) is higher than the mean activity of promoters from group 'ALL' which have three CREs (n=19), as can be seen in FIG. 20A and FIG. 20B. The mean activity and the mean activity over size (in base pairs) of promoters which comprise CRE0051, CRE0058, CRE0065 and CRE0074 (n=4) is higher than the mean activity of promoters from group 'ALL' which have four CREs (n=15), as can be seen in FIG. 21A and FIG. 21B. The mean activity and the mean activity over size (in base pairs) of promoters which comprise CRE0058, CRE0065 and CRE0066 (n=19) is higher than the mean activity of promoters from group 'ALL' which have three CREs (n=50), as can be seen in FIG. 22A and FIG. 22B. Finally, the mean activity and the mean activity over size (in base pairs) of promoters which comprise CRE0058, CRE0065 and CRE0074 (n=14) is higher than the mean activity of promoters from group 'ALL' which have two CREs (n=19), as can be seen in FIG. 23A and FIG. 23B. Overall, the presence of the abovementioned combinations of CREs are associated with higher activity. This is not due to differences in size between the groups as normalisation of the activity over size (in base pairs) reveals similar superior performance of the promoters comprising the abovementioned combinations of CREs.

Example 4

AAV Production

The activity of a subset of the promoters according to this invention were tested in vivo. The synthetic promoters included in this study were LVR-239 (SP0239), LVR-244 (SP0244) and the positive control LP1. The reporter gene used was fLUC-T2A-EGFP, i.e. fLUC (firefly Luciferase) fused to mEGFP (mutant green fluorescent protein) via T2A signal (two-way self-cleaving peptides). pAAV_SYN-P_Luc-T2A-GFP destination vector is derived from pAAV ZsGreenl (purchased from Clontech) in which the ZsGreenl reporter was replaced by the Luc-T2A-GFP dual reporter. All DNA plasmids were prepared using QIAGEN Plasmid Mega Kit (Qiagen #12181, Germany) according to manufacturer instructions.

HEK293T cells were cultured in Culture dish, Tissue culture treated, 145 mm (Greiner Bio-One Ltd # 639160, UK) in Dulbecco's modified Eagle's medium, high glucose, GlutaMAX supplement (Gibco (Life Technologies)# 61965-059, UK) supplemented with 10% (v/v) fetal bovine serum (Sigma # F7524, UK), and incubated at 37° C. and 5% $CO_2$. Other reagents for cell culture were purchased from Invitrogen-UK and plasticware form Life Technologies.

All AAV vectors that were used in this study were pseudotyped in AAV9 capsid. The HEK293T cells were used as a producer cells where they were co-transfected with plasmids wherein the reporter gene was controlled by different promoters alongside a plasmid encoding the helper functions to allow virus propagation (pDG9). HEK293T cells were transfected using Polyethylenimine (PEI) (Sigma-Aldrich # 764604, UK) at stock concentration of (1 ug/ul) using molar ratio of 1:3 (DNA:PEI).

AAV Purification and Titration

After 72 hr of transfection, cells were lysed and crude lysate was filtered then purified by HPLC columns containing POROSTM CaptureSelectTM AAV Resin (Thermo Scientific, #A36739) and using AKTAprime plus (High performance liquid chromatography-HPLC system (GE Healthcare, #11001313).

The number of vector genomes was determined by qPCR titration to target LUC cassettes with forward primer (ACGCTGGGCTACTTGATC—SEQ ID NO: 265), reverse primer (CGAGGAGGAGCTATTCTTG—SEQ ID NO: 266) and probe (TTTCGGGTCGTGCTCATG—SEQ ID NO: 267) following manufacturer instructions of Luna® Universal qPCR Master Mix (NEB # M3003, UK) in QuantStudioTM 3 System Real-Time PCR (Thermo Fisher Scientific, UK) and data analysed by QuantStudio design and analysis software V1.4.1.

Animal Procedures

Outbred 6 weeks old CD1 male mice were purchased from Charles River-UK. They were kept in quarantine for one week and then moved to their closed ventilation cages and maintained in minimal-disease facilities. They were caged at 5 mice/cage and normalized into their weights with food and water ad libitum. Newly housed mice were given another week for acclimatization before carrying out any experiments. This study was conducted under statutory Home Office recommendation; regulatory, ethics, and licensing procedures; and the Animals (Scientific Procedures) Act 1986 and following the institutional guidelines at University College London.

Animal Injections

AAV was administered to 8-week-old young adult male CD1 mice anaesthetised with 2%-4% isoflurane supplied in medical air (21% oxygen) (Abbotts Laboratories, UK) in warm chamber (Thermo Fisher Scientific, UK). The mice were injected intravenously into lateral tail vein using an Insulin syringe: 27 G ½ in., 1.0 ml (Fisher Scientific, UK). Each mouse is injected with AAV vectors dose of 8E+10 AAV viral genome per mouse in a final volume of 200 µl of physiological saline solution. The mice were then allowed to return to normal temperature before placing them back into their cages.

Bioluminescence Imaging

Mice were subjected to weekly whole-body bioluminescence imaging. Where appropriate, mice were anaesthetised with 2%-4% isoflurane supplied in medical air (21% oxygen) and received an intraperitoneal injection of 300 µl of 15 mg/mL of D-luciferin potassium salt (Syd Labs # MB000102, US) using an Insulin syringe (Fisher Scientific, UK). D-luciferin stock was prepared in physiological saline (Gibco #14190-094, UK). Mice were imaged after 5 minutes using a cooled charged-coupled device camera, (IVIS Lumina II machine, Perkin Elmer, UK) for between 1 second and 10 seconds. The regions of interest (ROI) were measured using IVIS Lumina Living image 4.5.5 (Perkin Elmer) and expressed as photons per second per centimetre squared per steradian (photons/second/cm²/sr).

Data

The results of this study are shown in FIG. 13B. The results are expressed as the mean of the luciferase biolumi-nescence intensity, total flux (in photons per second), for all tested animals in each group. Error bars are standard error of the mean.

In group 'Saline' (n=10), the animals were injected with saline only and no luciferase bioluminescence is detected. This group is a negative control and indicates that no luciferase bioluminescence is detected if no luciferase oper-ably linked to a promoter is injected.

In group 'LP1' (n=9), the animals were injected with luciferase operably linked to the LP1 promoter and lucifer-ase bioluminescence is detected. This group is a positive control and indicates that luciferase is expressed under the control of the LP1 promoter and can be detected.

To test the activity of the liver-specific promoters accord-ing to this invention, animals were injected with a construct comprising luciferase under operably linked to two promot-ers. In group 'SP0244' (n=8), luciferase is operably linked to the SP0244 promoter. In group 'SP0239' (n=10), luciferase is operably linked to the SP0239 promoter.

As can be seen from FIG. 13B, groups 'SP0244' and 'SP0239' have higher bioluminescence intensity than group 'LP1'. Promoters SP0244 and SP0239 show high activity in vivo and their activity is higher than the activity of LP1.

This experiment demonstrates that the in vitro results obtained in Example 3 corelate with results obtained in vivo. Furthermore, consistent with the data presented in Example 3 indicating that there is a relationship between the presence of core CREs and preferred promoter elements (CRE0006 an CRE0059), promoter SP0239, which shows high expres-sion in vivo, is a member 'Group 1' as discussed above and comprises 5 Core CREs. Promoter SP0244, which also shows high expression, is a member of both 'Group 1' and 'Group 2', which comprises 3 Core CREs and a preferred promoter element, namely CRE0006. This data indicates that the presence of Core CREs and the combination of Core CREs with a preferred promoter element is not only asso-ciated with high expression in vitro but also in vivo.

A range of liver-specific promoters with varying strength is provided by this invention which can be very useful to provide the desired level of liver-specific expression in a therapeutic setting.

While the present inventions have been described and illustrated in conjunction with a number of specific embodi-ments, those skilled in the art will appreciate that variations and modifications may be made without departing from the principles of the inventions as herein illustrated, as described and claimed. The present inventions may be embodied in other specific forms without departing from their spirit or essential characteristics. The described embodiments are considered in all respects to be illustrative and not restrictive.

pAAV_SYNP_Luc_2A_GFP (SEQ ID NO: 264)

```
AGCGCCCAATACGCAAACCGCCTCTCCCCGCGCGTT

GGCCGATTCATTAATGCAGCTGGCACGACAGGTTT

CCCGACTGGAAAGCGGGCAGTGAGCGCAACGCAAT

TAATGTGAGTTAGCTCACTCATTAGGCACCCCAGG

CTTTACACTTTATGCTTCCGGCTCGTATGTTGTGT

GGAATTGTGAGCGGATAACAATTTCACACAGGAAA

CAGCTATGACCATGATTACGAATTGCCTGCAGGCA

GCTGCGCGCTCGCTCGCTCACTGAGGCCGCCCGGG

CAAAGCCCGGGCGTCGGGCGACCTTTGGTCGCCCG

GCCTCAGTGAGCGAGCGAGCGCGCAGAGAGGGAGT

GGCCAACTCCATCACTAGGGGTTCCTATCGATATC

AAGCTTGGTACCGAGTCTGATCGTAGCGGCCGCCA

CCATGGAAGATGCCAAAAACATTAAGAAGGGCCCA

GCGCCATTCTACCCACTCGAAGACGGGACCGCCGG

CGAGCAGCTGCACAAAGCCATGAAGCGCTACGCCC

TGGTGCCCGGCACCATCGCCTTTACCGACGCACAT

ATCGAGGTGGACATTACCTACGCCGAGTACTTCGA

GATGAGCGTTCGGCTGGCAGAAGCTATGAAGCGCT

ATGGGCTGAATACAAACCATCGGATCGTGGTGTGC

AGCGAGAATAGCTTGCAGTTCTTCATGCCCGTGTT

GGGTGCCCTGTTCATCGGTGTGGCTGTGGCCCCAG

CTAACGACATCTACAACGAGCGCGAGCTGCTGAAC

AGCATGGGCATCAGCCAGCCCACCGTCGTATTCGT

GAGCAAGAAAGGGCTGCAAAAGATCCTCAACGTGC

AAAAGAAGCTACCGATCATACAAAAGATCATCATC

ATGGATAGCAAGACCGACTACCAGGGCTTCCAAAG

CATGTACACCTTCGTGACTTCCCATTTGCCACCCG

GCTTCAACGAGTACGACTTCGTGCCCGAGAGCTTC

GACCGGGACAAAACCATCGCCCTGATCATGAACAG

TAGTGGCAGTACCGGATTGCCCAAGGGCGTAGCCC

TACCGCACCGCACCGCTTGTGTCCGATTCAGTCAT

GCCCGCGACCCCATCTTCGGCAACCAGATCATCCC

CGACACCGCTATCCTCAGCGTGGTGCCATTTCACC

ACGGCTTCGGCATGTTCACCACGCTGGGCTACTTG

ATCTGCGGCTTTCGGGTCGTGCTCATGTACCGCTT

CGAGGAGGAGCTATTCTTGCGCAGCTTGCAAGACT

ATAAGATTCAATCTGCCCTGCTGGTGCCCACACTA

TTTAGCTTCTTCGCTAAGAGCACTCTCATCGACAA

GTACGACCTAAGCAACTTGCACGAGATCGCCAGCG

GCGGGGCGCCGCTCAGCAAGGAGGTAGGTGAGGCC
```

-continued

-continued

GTGGCCAAACGCTTCCACCTACCAGGCATCCGCCA

GGGCTACGGCCTGACAGAAACAACCAGCGCCATTC

TGATCACCCCCGAAGGGGACGACAAGCCTGGCGCA

GTAGGCAAGGTGGTGCCCTTCTTCGAGGCTAAGGT

GGTGGACTTGGACACCGGTAAGACACTGGGTGTGA

ACCAGCGCGGCGAGCTGTGCGTCCGTGGCCCCATG

ATCATGAGCGGCTACGTTAACAACCCCGAGGCTAC

AAACGCTCTCATCGACAAGGACGGCTGGCTGCACA

GCGGCGACATCGCCTACTGGGACGAGGACGAGCAC

TTCTTCATCGTGGACCGGCTGAAGAGCCTGATCAA

ATACAAGGGCTACCAGGTAGCCCCAGCCGAACTGG

AGAGCATCCTGCTGCAACACCCCAACATCTTCGAC

GCCGGGGTCGCCGGCCTGCCCGACGACGATGCCGG

CGAGCTGCCCGCCGCAGTCGTCGTGCTGGAACACG

GTAAAACCATGACCGAGAAGGAGATCGTGGACTAT

GTGGCCAGCCAGGTTACAACCGCCAAGAAGCTGCG

CGGTGGTGTTGTGTTCGTGGACGAGGTGCCTAAAG

GACTGACCGGCAAGTTGGACGCCCGCAAGATCCGC

GAGATTCTCATTAAGGCCAAGAAGGGCGGCAAGAT

CGCCGTGGGATCCGGAGAGGGCAGAGGAAGTCTTC

TAACATGCGGTGACGTGGAGGAGAATCCCGGCCCT

ATGGTGAGCAAGGGCGAGGAGCTGTTCACCGGGGT

GGTGCCCATCCTGGTCGAGCTGGACGGCGACGTAA

ACGGCCACAAGTTCAGCGTGTCCGGCGAGGGCGAG

GGCGATGCCACCTACGGCAAGCTGACCCTGAAGTT

CATCTGCACCACCGGCAAGCTGCCCGTGCCCTGGC

CCACCCTCGTGACCACCCTGACCTACGGCGTGCAG

TGCTTCAGCCGCTACCCCGACCACATGAAGCAGCA

CGACTTCTTCAAGTCCGCCATGCCCGAAGGCTACG

TCCAGGAGCGCACCATCTTCTTCAAGGACGACGGC

AACTACAAGACCCGCGCCGAGGTGAAGTTCGAGGG

CGACACCCTGGTGAACCGCATCGAGCTGAAGGGCA

TCGACTTCAAGGAGGACGGCAACATCCTGGGGCAC

AAGCTGGAGTACAACTACAACAGCCACAACGTCTA

TATCATGGCCGACAAGCAGAAGAACGGCATCAAGG

TGAACTTCAAGATCCGCCACAACATCGAGGACGGC

AGCGTGCAGCTCGCCGACCACTACCAGCAGAACAC

CCCCATCGGCGACGGCCCCGTGCTGCTGCCCGACA

ACCACTACCTGAGCACCCAGTCCAAGCTGAGCAAA

GACCCCAACGAGAAGCGCGATCACATGGTCCTGCT

GGAGTTCGTGACCGCCGCCGGGATCACTCTCGGCA

TGGACGAGCTGTACAAGTAATGAATCGATGGTCTC

TACGAGTAATAGACGCCCAGTTGAATTCCTTCGAG

CAGACATGATAAGATACATTGATGAGTTTGGACAA

ACCACAACTAGAATGCAGTGAAAAAAATGCTTTAT

TTGTGAAATTTGTGATGCTATTGCTTTATTTGTAA

CCATTATAAGCTGCAATAAACAAGTTAACAACAAC

AATTGCATTCATTTTATGTTTCAGGTTCAGGGGGA

GGTGTGGGAGGTTTTTTAAAGCAAGTAAAACCTCT

ACAAATGTGGTAAAATCGATAAGGATCCGTCGACA

GATCTAGGAACCCCTAGTGATGGAGTTGGCCACTC

CCTCTCTGCGCGCTCGCTCGCTCACTGAGGCCGGG

CGACCAAAGGTCGCCCGACGCCCGGGCTTTGCCCG

GGCGGCCTCAGTGAGCGAGCGAGCGCGCAGCTGCC

TGCAGGCAGCTTGGCACTGGCCGTCGTTTTACAAC

GTCGTGACTGGGAAAACCCTGGCGTTACCCAACTT

AATCGCCTTGCAGCACATCCCCCTTTCGCCAGCTG

GCGTAATAGCGAAGAGGCCCGCACCGATCGCCCTT

CCCAACAGTTGCGCAGCCTGAATGGCGAATGGCGC

CTGATGCGGTATTTTCTCCTTACGCATCTGTGCGG

TATTTCACACCGCATACGTCAAAGCAACCATAGTA

CGCGCCCTGTAGCGGCGCATTAAGCGCGGCGGGTG

TGGTGGTTACGCGCAGCGTGACCGCTACACTTGCC

AGCGCCCTAGCGCCCGCTCCTTTCGCTTTCTTCCC

TTCCTTTCTCGCCACGTTCGCCGGCTTTCCCCGTC

AAGCTCTAAATCGGGGGCTCCCTTTAGGGTTCCGA

TTTAGTGCTTTACGGCACCTCGACCCCAAAAAACT

TGATTTGGGTGATGGTTCACGTAGTGGGCCATCGC

CCTGATAGACGGTTTTTCGCCCTTTGACGTTGGAG

TCCACGTTCTTTAATAGTGGACTCTTGTTCCAAAC

TGGAACAACACTCAACCCTATCTCGGGCTATTCTT

TTGATTTATAAGGGATTTTGCCGATTTCGGCCTAT

TGGTTAAAAAATGAGCTGATTTAACAAAAATTTAA

CGCGAATTTTAACAAAATATTAACGTTTACAATTT

TATGGTGCACTCTCAGTACAATCTGCTCTGATGCC

GCATAGTTAAGCCAGCCCCGACACCCGCCAACACC

CGCTGACGCGCCCTGACGGGCTTGTCTGCTCCCGG

CATCCGCTTACAGACAAGCTGTGACCGTCTCCGGG

AGCTGCATGTGTCAGAGGTTTTCACCGTCATCACC

GAAACGCGCGAGACGAAAGGGCCTCGTGATACGCC

TATTTTTATAGGTTAATGTCATGATAATAATGGTT

-continued

-continued

TCTTAGACGTCAGGTGGCACTTTTCGGGGAAATGT

GCGCGGAACCCCTATTTGTTTATTTTTCTAAATAC

ATTCAAATATGTATCCGCTCATGAGACAATAACCC

TGATAAATGCTTCAATAATATTGAAAAAGGAAGAG

TATGAGTATTCAACATTTCCGTGTCGCCCTTATTC

CCTTTTTTGCGGCATTTTGCCTTCCTGTTTTTGCT

CACCCAGAAACGCTGGTGAAAGTAAAAGATGCTGA

AGATCAGTTGGGTGCACGAGTGGGTTACATCGAAC

TGGATCTCAACAGCGGTAAGATCCTTGAGAGTTTT

CGCCCCGAAGAACGTTTTCCAATGATGAGCACTTT

TAAAGTTCTGCTATGTGGCGCGGTATTATCCCGTA

TTGACGCCGGGCAAGAGCAACTCGGTCGCCGCATA

CACTATTCTCAGAATGACTTGGTTGAGTACTCACC

AGTCACAGAAAAGCATCTTACGGATGGCATGACAG

TAAGAGAATTATGCAGTGCTGCCATAACCATGAGT

GATAACACTGCGGCCAACTTACTTCTGACAACGAT

CGGAGGACCGAAGGAGCTAACCGCTTTTTTGCACA

ACATGGGGGATCATGTAACTCGCCTTGATCGTTGG

GAACCGGAGCTGAATGAAGCCATACCAAACGACGA

GCGTGACACCACGATGCCTGTAGCAATGGCAACAA

CGTTGCGCAAACTATTAACTGGCGAACTACTTACT

CTAGCTTCCCGGCAACAATTAATAGACTGGATGGA

GGCGGATAAAGTTGCAGGACCACTTCTGCGCTCGG

CCCTTCCGGCTGGCTGGTTTATTGCTGATAAATCT

GGAGCCGGTGAGCGTGGGTCTCGCGGTATCATTGC

AGCACTGGGGCCAGATGGTAAGCCCTCCCGTATCG

TAGTTATCTACACGACGGGGAGTCAGGCAACTATG

GATGAACGAAATAGACAGATCGCTGAGATAGGTGC

CTCACTGATTAAGCATTGGTAACTGTCAGACCAAG

TTTACTCATATATACTTTAGATTGATTTAAAACTT

CATTTTTAATTTAAAAGGATCTAGGTGAAGATCCT

TTTTGATAATCTCATGACCAAAATCCCTTAACGTG

AGTTTTCGTTCCACTGAGCGTCAGACCCCGTAGAA

AAGATCAAAGGATCTTCTTGAGATCCTTTTTTTCT

GCGCGTAATCTGCTGCTTGCAAACAAAAAAACCAC

CGCTACCAGCGGTGGTTTGTTTGCCGGATCAAGAG

CTACCAACTCTTTTTTCCGAAGGTAACTGGCTTCAG

CAGAGCGCAGATACCAAATACTGTTCTTCTAGTGT

AGCCGTAGTTAGGCCACCACTTCAAGAACTCTGTA

GCACCGCCTACATACCTCGCTCTGCTAATCCTGTT

ACCAGTGGCTGCTGCCAGTGGCGATAAGTCGTGTC

TTACCGGGTTGGACTCAAGACGATAGTTACCGGAT

AAGGCGCAGCGGTCGGGCTGAACGGGGGGTTCGTG

CACACAGCCCAGCTTGGAGCGAACGACCTACACCG

AACTGAGATACCTACAGCGTGAGCTATGAGAAAGC

GCCACGCTTCCCGAAGGGAGAAAGGCGGACAGGTA

TCCGGTAAGCGGCAGGGTCGGAACAGGAGAGCGCA

CGAGGGAGCTTCCAGGGGGAAACGCCTGGTATCTT

TATAGTCCTGTCGGGTTTCGCCACCTCTGACTTGA

GCGTCGATTTTTGTGATGCTCGTCAGGGGGGCGGA

GCCTATGGAAAAACGCCAGCAACGCGGCCTTTTTA

CGGTTCCTGGCCTTTTGCTGGCCTTTTGCTCACAT

GTTCTTTCCTGCGTTATCCCCTGATTCTGTGGATA

ACCGTATTACCGCCTTTGAGTGAGCTGATACCGCT

CGCCGCAGCCGAACGACCGAGCGCAGCGAGTCAGT

GAGCGAGGAAGCGGAAG

The invention claimed is:

1. A synthetic liver-specific cis-regulatory module (CRM) comprising two or more operably linked cis-regulatory elements (CREs) selected from the group consisting of:
SEQ ID NO: 1;
SEQ ID NO: 2;
SEQ ID NO: 3;
SEQ ID NO: 4;
SEQ ID NO: 5;
SEQ ID NO: 7;
SEQ ID NO: 10; and
SEQ ID NO: 11.

2. The synthetic liver-specific CRM of claim 1 comprising three or more, four or more, five or more, or six or more of said CREs.

3. The synthetic liver-specific CRM of claim 1 comprising a combination of CREs selected from the group consisting of:
CRE0051 and CRE0058;
CRE0051 and CRE0042;
CRE0051, CRE0058 and CRE0065;
CRE0051, CRE0058 and CRE0066;
CRE0051, CRE0058, CRE0065 and CRE0066;
CRE0018, CRE0051, CRE0058, CRE0065 and CRE0066
CRE0051, CRE0065 and CRE0066;
CRE0051, CRE0074 and CRE0058;
CRE0051, CRE0074, CRE0058 and CRE0065;
CRE0051, CRE0074, CRE0058, CRE0065 and CRE0066;
CRE0058 and CRE0065;
CRE0068 and CRE0042;
CRE0058, CRE0065 and CRE0066;
CRE0074, CRE0058 and CRE0065; and
CRE0074, CRE0058, CRE0065 and CRE0066, wherein the CREs are present in the CRM in the recited order, and wherein they are adjacent to one another.

4. The synthetic liver-specific CRM of claim 1 comprising two, three, four or more CREs selected from the group consisting of:
CRE0051;
CRE0058;

CRE0065;

CRE0066; and

CRE0074.

5. The synthetic liver-specific CRM of claim 1 further comprising one or more CREs selected from the group consisting of:

SEQ ID NO: 12;

SEQ ID NO: 13;

SEQ ID NO: 14;

SEQ ID NO: 15;

SEQ ID NO: 16;

SEQ ID NO: 17;

SEQ ID NO: 18;

SEQ ID NO: 19;

SEQ ID NO: 20;

SEQ ID NO: 21; and

SEQ ID NO: 22.

6. The synthetic liver-specific CRM of claim 1 comprising a combination of CREs selected from the group consisting of:

CRE0018, CRE0077, CRE0074, CRE0058, CRE0065;

CRE0068, CRE0042;

CRE0051, CRE0058;

CRE0051, CRE0042;

CRE0065, CRE0051, CRE0083.1;

CRE0018, CRE0051, CRE0058, CRE0065, CRE0066;

CRE0012, CRE0051, CRE0058, CRE0065, CRE0066;

CRE0051, CRE0058, CRE0065, CRE0066;

CRE0051, CRE0058, CRE0018;

CRE0051, CRE0058, CRE0065, CRE0018;

CRE0051, CRE0058, CRE0065, CRE0012;

CRE0047, CRE0051, CRE0058, CRE0065, CRE0066;

CRE0051, CRE0074, CRE0058, CRE0065, CRE0066;

CRE0051, CRE0058, CRE0065, CRE0001;

CRE0051, CRE0058, CRE0065; and

CRE0051, CRE0066.2, wherein the CREs are present in the CRM in the recited order, and wherein they are adjacent to one another.

7. The synthetic liver-specific CRM of claim 1 comprising a combination of CREs selected from the group consisting of: CRE0051, CRE0066.2; CRE0065, CRE0051, CRE0083.1; CRE0065, CRE0066.2; CRE0066, CRE0066; CRE0065, CRE0066; CRE0074, CRE0058, CRE0065.1; CRE0051, CRE0074, CRE0058, CRE0065.1; CRE0077, CRE0074, CRE0058, CRE0065.1; CRE0078, CRE0074, CRE0058, CRE0065.1; CRE0074, CRE0074, CRE0065; CRE0058, CRE0065, CRE0066; CRE0074, CRE0058, CRE0065, CRE0066; CRE0074, CRE0058; CRE0018, CRE0051, CRE0058, CRE0065, CRE0066; CRE0051, CRE0058, CRE0065, CRE0066; CRE0051, CRE0058, CRE0065; CRE0012, CRE0051, CRE0058, CRE0065, CRE0066; CRE0051, CRE0058, CRE0065, CRE0012; CRE0051, CRE0058, CRE0065, CRE0018; CRE0051, CRE0058, CRE0065, CRE0001; CRE0051, CRE0058, CRE0065, CRE0077; CRE0051, CRE0058, CRE0018; CRE0047, CRE0051, CRE0058, CRE0065, CRE0066; CRE0051, CRE0058, CRE0065, CRE0066; CRE0077, CRE0058, CRE0065, CRE0066; CRE0078, CRE0058, CRE0065, CRE0066; CRE0051, CRE0074, CRE0058, CRE0065, CRE0066; CRE0077, CRE0074, CRE0058, CRE0065, CRE0066; CRE0078, CRE0074, CRE0058, CRE0065, CRE0066; CRE0051, CRE0074, CRE0058, CRE0077, CRE0074, CRE0058; CRE0078, CRE0074, CRE0058; CRE0051, CRE0058, CRE0068, CRE0042; CRE0051, CRE0058, CRE0066; CRE0051, CRE0065, CRE0066; CRE0018, CRE0051, CRE0074, CRE0058, CRE0065, CRE0066; CRE0018, CRE0077, CRE0058, CRE0065, CRE0066; CRE0018, CRE0077, CRE0074, CRE0058, CRE0065, CRE0066; CRE0018, CRE0077, CRE0074, CRE0058, CRE0065; and CRE0051, CRE0042, wherein the CREs are present in the CRM in the recited order, and wherein they are adjacent to one another.

8. The synthetic liver-specific CRM of claim 1 comprising a combination of CREs selected from the group consisting of:

CRE0018, CRE0051, CRE0058, CRE0065, CRE0066;

CRE0051 CRE0058, CRE0065, CRE0012;

CRE0051, CRE0058, CRE0065, CRE0066; and

CRE0051, CRE0042, wherein the CREs are present in the CRM in the recited order, and wherein they are adjacent to one another.

9. The synthetic liver-specific CRM of claim 1 comprising a CRM selected from the group consisting of: CRM_SP0109, CRM_SP0112, CRM_SP0113, CRM SP0121, CRM SP0124, CRM SP0127, CRM SP0127A1, CRM SP0127V1, CRM_SP0127V2, CRM_SP0128, CRM_SP0131, CRM_SP0132, CRM_SP0133, CRM_SP0239, CRM_SP0240, CRM_SP0241, CRM_SP0242, CRM_SP0243, CRM_SP0244, CRM_SP0246, CRM_SP0247, CRM_SP0248, CRM_SP0249, CRM_SP0250, CRM_SP0251, CRM_SP0253, CRM_SP0254, CRM_SP0255, CRM_SP0256, CRM_SP0257, CRM_SP0258, CRM_SP0265, CRM_SP0266, CRM_SP0267, CRM_SP0268, CRM_SP0269, CRM_SP0270, CRM_SP0271, CRM_SP0272, CRM_SP0273, CRM_SP0368, CRM_SP0373, CRM_SP0378, CRM_SP0379, CRM_SP0380, CRM_SP0381, CRM_SP0384, CRM_SP0396, CRM_SP0397, CRM_SP0398, CRM_SP0403, CRM_SP0404, CRM_SP0405, CRM_SP0406, CRM_SP0407, CRM_SP0409, CRM_SP0411, CRM_SP0412, CRM_SP0413.

10. The synthetic liver-specific CRM of claim 9 wherein the CRM is CRM_SP0239, CRM_SP0244, CRM_SP0265 or CRM_SP0412, or wherein the CRM has a length of 450, 400, 350, 300, 250, 200, 150, 100, 75, 60, 50 or fewer nucleotides.

11. A synthetic liver-specific promoter comprising:

a) a CRM according to claim 1 operably linked to a promoter element; or b) at least one of the following CREs;

CRE0018;

CRE0042;

CRE0051;

CRE0058;

CRE0065;

CRE0066;

CRE0068; and

CRE0074, operably linked to a promoter element selected from CRE0059 and CRE0006.

12. The synthetic liver-specific promoter of claim 11 comprising a combination of CREs selected from the group consisting of: CRE0051, CRE0066.2; CRE0065, CRE0051, CRE0083.1; CRE0065, CRE0066.2; CRE0066, CRE0066; CRE0065, CRE0066; CRE0074, CRE0058, CRE0065.1; CRE0051, CRE0074, CRE0058, CRE0065.1; CRE0077, CRE0074, CRE0058, CRE0065.1; CRE0078, CRE0074, CRE0058, CRE0065.1; CRE0074, CRE0074, CRE0065; CRE0058, CRE0065, CRE0066; CRE0074, CRE0058, CRE0065, CRE0066; CRE0074, CRE0058; CRE0018, CRE0051, CRE0058, CRE0065, CRE0066; CRE0051, CRE0058, CRE0065, CRE0066; CRE0051, CRE0058, CRE0065, CRE0066; CRE0051, CRE0058, CRE0065; CRE0012, CRE0051, CRE0058, CRE0065, CRE0066; CRE0051, CRE0058, CRE0065, CRE0012; CRE0051, CRE0058, CRE0065, CRE0018; CRE0051, CRE0058, CRE0065, CRE0001; CRE0051, CRE0058, CRE0065, CRE0077; CRE0051, CRE0058, CRE0018; CRE0047, CRE0051, CRE0058, CRE0065, CRE0066; CRE0051, CRE0058, CRE0065, CRE0066; CRE0077, CRE0058, CRE0065, CRE0066; CRE0078, CRE0058, CRE0065, CRE0066; CRE0051, CRE0074, CRE0058, CRE0065, CRE0066; CRE0077, CRE0074, CRE0058, CRE0065, CRE0066; CRE0078, CRE0074, CRE0058, CRE0065, CRE0066; CRE0051, CRE0074, CRE0058, CRE0077, CRE0074, CRE0058; CRE0078, CRE0074, CRE0058; CRE0051, CRE0058; CRE0068, CRE0042; CRE0051, CRE0058, CRE0066; CRE0051, CRE0065, CRE0066; CRE0018, CRE0051, CRE0074, CRE0058, CRE0065, CRE0066; CRE0018, CRE0077, CRE0058, CRE0065, CRE0066; CRE0018, CRE0077, CRE0074, CRE0058, CRE0065, CRE0066; CRE0018, CRE0077, CRE0074, CRE0058, CRE0065; and CRE0051, CRE0042,
wherein the CREs are present in the CRM in the recited order, and wherein they are adjacent to one another, or wherein the promoter element is selected from CRE0006, CRE0059, CRE0052, CRE0079, CRE0073, or CRE0073.1.

13. The synthetic liver-specific promoter of claim 11 comprising an individual CREs or combinations of CREs selected from the group consisting of: CRE0051, CRE0066.2; CRE0065, CRE0051, CRE0083.1; CRE0065, CRE0066.2; CRE0066, CRE0066; CRE0065, CRE0066; CRE0074, CRE0058, CRE0065.1; CRE0051, CRE0074, CRE0058, CRE0065.1; CRE0077, CRE0074, CRE0058, CRE0065.1; CRE0078, CRE0074, CRE0058, CRE0065.1; CRE0074, CRE0074, CRE0065; CRE0058, CRE0065, CRE0066; CRE0074, CRE0058, CRE0065, CRE0066; CRE0074, CRE0058; CRE0018, CRE0051, CRE0058, CRE0065, CRE0066; CRE0018; CRE0051, CRE0058, CRE0065, CRE0065, CRE0066; CRE0051, CRE0058, CRE0065; CRE0012, CRE0051, CRE0058, CRE0065, CRE0066; CRE0051, CRE0058, CRE0065, CRE0012; CRE0001, CRE0018; CRE0051, CRE0058, CRE0065, CRE0018; CRE0051, CRE0058, CRE0065, CRE0001; CRE0051, CRE0058, CRE0065, CRE0077; CRE0077, CRE0018; CRE0051, CRE0058, CRE0018; CRE0005, CRE0018; CRE0018, CRE0001; CRE0047, CRE0051, CRE0058, CRE0065, CRE0066; CRE0051, CRE0058, CRE0065, CRE0066; CRE0077, CRE0058, CRE0065, CRE0066; CRE0078, CRE0058, CRE0065, CRE0066; CRE0051, CRE0074, CRE0058, CRE0065, CRE0066; CRE0077, CRE0074, CRE0058, CRE0065, CRE0066; CRE0078, CRE0074, CRE0058, CRE0065, CRE0066; CRE0051, CRE0074, CRE0058; CRE0077, CRE0074, CRE0058; CRE0078, CRE0074, CRE0058; CRE0051; CRE0051, CRE0058; CRE0048, CRE0042; CRE0068, CRE0042; CRE0056, CRE0042; CRE0062, CRE0042; CRE0051, CRE0058, CRE0066; CRE0051, CRE0065, CRE0066;

CRE0018, CRE0051, CRE0074, CRE0058, CRE0065, CRE0066; CRE0018, CRE0077, CRE0058, CRE0065, CRE0066; CRE0018, CRE0077, CRE0074, CRE0058, CRE0065, CRE0066; CRE0018, CRE0077, CRE0074, CRE0058, CRE0065; CRE0051, CRE0018; CRE0051, CRE0042; and CRE0042, wherein the CREs are present in the recited order, and wherein they are adjacent to one another.

14. The synthetic liver-specific promoter according claim 11 selected from the group consisting of: SP0109, SP0112, SP0113, SP0121, SP0124, SP0127, SP0127A1, SP0127V1, SP0127V2, SP0128, SP0131, SP0132, SP0133, SP0239, SP0240, SP0241, SP0242, SP0243, SP0244, SP0246, SP0247, SP0248, SP0249, SP0250, SP0251, SP0253, SP0254, SP0255, SP0256, SP0257, SP0258, SP0265, SP0266, SP0267, SP0268, SP0269, SP0270, SP0271, SP0272, SP0273, SP0368, SP0373, SP0378, SP0379, SP0380, SP0381, SP0384, SP0396, SP0397, SP0398, SP0403, SP0404, SP0405, SP0406, SP0407, SP0409, SP0411, SP0412, and SP0413,
wherein the synthetic liver-specific promoter has length 600, 500, 450, 400, 350, 300, 250, 200, 150, 100, 75, 70 or 68 or fewer nucleotides, and/or
wherein the liver-specific promoter exhibits activity which is at least 25%, 50%, 75% or 100% of the activity of a TBG promoter, and/or
wherein the liver-specific promoter exhibits activity in non-liver cells which is 50%, 10%, 1% or less than CMV-IE.

15. An expression cassette comprising a synthetic liver-specific promoter according to claim 11 operably linked to a sequence encoding an expression product wherein sequence encoding an expression product is a transgene encoding a therapeutic protein.

16. A vector comprising a synthetic liver-specific CRM according to claim 1, wherein the vector is a viral vector, an AAV vector, or a gene therapy vector.

17. A virion comprising a vector of claim 16.

18. A pharmaceutical composition comprising a synthetic liver-specific CRM according to claim 1.

19. A isolated cell comprising a synthetic liver-specific CRM according to claim 1, wherein the isolated cell is an isolated liver cell.

20. A method for producing an expression product, the method comprising providing an expression cassette according to claim 15 in a liver cell and expressing an expression product from the sequence encoding the expression product.

21. A method of expressing a therapeutic gene in a liver cell, the method comprising introducing into the liver cell an expression cassette according to claim 15.

22. A method of therapy of a subject in need thereof, the method comprising:
administering to the subject an expression cassette according to claim 15.

* * * * *